(12) United States Patent
Attenni et al.

(10) Patent No.: US 7,863,294 B2
(45) Date of Patent: Jan. 4, 2011

(54) HETEROCYCLE DERIVATIVES AS HISTONE DEACETYLASE (HDAC) INHIBITORS

(75) Inventors: Barbara Attenni, Rome (IT); Federica Ferrigno, Rome (IT); Philip Jones, Rome (IT); Raffaele Ingenito, Rome (IT); Olaf Kinzel, Rome (IT); Laura Llauger Bufi, Rome (IT); Jesus Maria Ontoria, Rome (IT); Giovanna Pescatore, Rome (IT); Michael Rowley, Rome (IT); Rita Scarpelli, Rome (IT); Carsten Schultz, Rome (IT)

(73) Assignee: Instituto Di Ricerche Di Biologia Molecolare P. Angeletti SpA, Rome (IT)

( * ) Notice: Subject to any disclaimer, the term of this patent is extended or adjusted under 35 U.S.C. 154(b) by 305 days.

(21) Appl. No.: 11/792,294

(22) PCT Filed: Dec. 9, 2005

(86) PCT No.: PCT/GB2005/004743

§ 371 (c)(1),
(2), (4) Date: Feb. 14, 2008

(87) PCT Pub. No.: WO2006/061638

PCT Pub. Date: Jun. 15, 2006

(65) Prior Publication Data

US 2009/0048228 A1     Feb. 19, 2009

(30) Foreign Application Priority Data

Dec. 10, 2004  (GB) ................................ 0427138.3
Aug. 11, 2005  (GB) ................................ 0516435.5

(51) Int. Cl.
*A61K 31/4709*  (2006.01)
*C07D 215/227*  (2006.01)

(52) U.S. Cl. ...................................... 514/312; 546/157

(58) Field of Classification Search ............ 514/210.21, 514/326, 399, 397, 254.05, 365, 378, 316, 514/256, 318, 235.8, 383, 364, 363, 277.8, 514/249; 546/210, 187, 193, 152; 548/340.1, 548/312.1, 146, 240, 312.7, 266.4, 143, 131, 548/136

See application file for complete search history.

(56) References Cited

FOREIGN PATENT DOCUMENTS

| WO | WO 98/27108 | * | 6/1998 |
|---|---|---|---|
| WO | WO 99/64401 | | 12/1999 |
| WO | WO 02/10140 | | 2/2002 |
| WO | WO 2004/072047 | | 8/2004 |
| WO | WO 2006/005941 | | 1/2006 |
| WO | WO 2006/005955 | | 1/2006 |
| WO | WO2007/052073 | | 5/2007 |
| WO | WO2007/072080 | | 6/2007 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*

* cited by examiner

*Primary Examiner*—Kamal A Saeed
*Assistant Examiner*—Kristin Bianchi
(74) *Attorney, Agent, or Firm*—Li Su; David A. Muthard

(57) ABSTRACT

The present invention relates to compounds of formula I:

(I)

$$R^1-D-\underset{\underset{R^4}{\overset{\underset{|}{N}}{|}}}{\overset{\text{Het}}{\underset{|}{C}}}-(\ )_q-\overset{O}{\underset{R^2}{\overset{\|}{C}}}$$
$$\underset{(NR^5)_t(CR^6R^8)_p-R^3}{X=O}$$

or pharmaceutically acceptable salts or tautomers thereof, which are inhibitors of histone deacetylase (HDAC). The compounds of the present invention are useful for treating cellular proliferative diseases, including cancer. Further, the compounds of the present invention are useful for treating neurodegenerative diseases, schizophrenia and stroke among other diseases.

18 Claims, No Drawings

HETEROCYCLE DERIVATIVES AS HISTONE DEACETYLASE (HDAC) INHIBITORS

PRIORITY CLAIM

This application is a §371 National Stage Application of PCT/GB2005/004743, filed on Dec. 9, 2005, which claims priority from GB Provisional Application Serial Numbers 0516435.5, filed on Aug. 11, 2005, and 0427138.3, filed on Dec. 10, 2004.

The present invention relates to heterocycle derivatives that are inhibitors of histone deacetylase (HDAC). The compounds of the present invention are useful for treating cellular proliferative diseases, including cancer. Further, the compounds of the present invention are useful for treating neurodegenerative diseases, schizophrenia and stroke among other diseases.

DNA in the nucleus of the cell exists as a hierarchy of compacted chromatin structures. The basic repeating unit in chromatin is the nucleosome. The nucleosome consists of a histone octamer of proteins in the nucleus of the cell around which DNA is wrapped twice. The orderly packaging of DNA in the nucleus plays an important role in the functional aspects of gene regulation. Covalent modifications of the histones have a key role in altering chromatin higher order structure and function and ultimately gene expression. The covalent modification of histones, such as acetylation, occurs by enzymatically mediated processes.

Regulation of gene expression through the inhibition of the nuclear enzyme histone deacetylase (HDAC) is one of several possible regulatory mechanisms whereby chromatin activity can be affected. The dynamic homeostasis of the nuclear acetylation of histones can be regulated by the opposing activity of the enzymes histone acetyl transferase (HAT) and histone deacetylase (HDAC). Transcriptionally silent chromatin can be characterized by nucleosomes with low levels of acetylated histones. Acetylation reduces the positive charge of histones, thereby expanding the structure of the nucleosome and facilitating the interaction of transcription factors with the DNA. Removal of the acetyl group restores the positive charge, condensing the structure of the nucleosome. Histone acetylation can activate DNA transcription, enhancing gene expression. Histone deacetylase can reverse the process and can serve to repress gene expression. See, for example, Grunstein, *Nature* 389, 349-352 (1997); Pazin et al., *Cell* 89, 325-328 (1997); Wade et al., *Trends Biochem. Sci.* 22, 128-132 (1997); and Wolffe, *Science* 272, 371-372 (1996).

WO 04/072047, published on 26 Aug. 2004, discloses indoles, benzimidazoles and naphthimidazoles as HDAC inhibitors, which compounds differ in structure to the compounds of the present invention.

WO 99/64401 and WO 02/10140 disclose structurally related imidazolyl derivatives as somatostatin receptor agonists and antagonists.

SUMMARY OF THE INVENTION

The present invention relates to heterocycle derivatives that are inhibitors of histone deacetylase (HDAC). The compounds of the present invention are useful for treating cellular proliferative diseases, including cancer. Further, the compounds of the present invention are useful for treating neurodegenerative diseases, schizophrenia and stroke among other diseases.

The present invention provides compounds of formula (I):

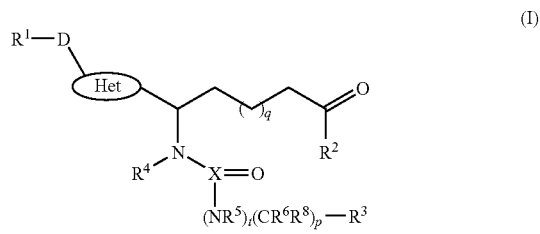

DETAILED DESCRIPTION OF THE INVENTION

The compounds of this invention are useful in the inhibition of histone deacetylase. The present invention provides compounds of formula (I):

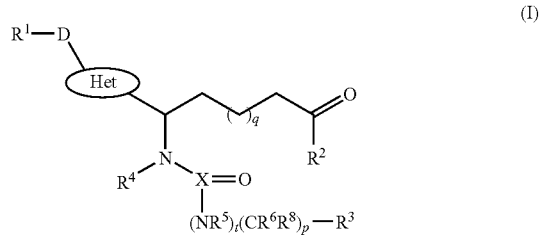

p is 0, 1, 2, 3, 4 or 5;
q is 1, 2, 3 or 4;
t is 0 or 1;
D is absent, $(CH_2)_b$ or $(CH=CH)_c$;
b is 1, 2 or 3;
c is 1, 2 or 3;
X is C or S=O;
Het is a 5 membered unsaturated heterocycle containing 1, 2, 3 or 4 heteroatoms independently selected from N, O and S, but not more than one of which is O or S, or a 6 membered unsaturated heterocycle containing 1, 2, 3 or 4 heteroatoms independently selected from N and O; optionally substituted by one or more groups independently chosen from cyano, halogen, hydroxy, oxo, nitro, amino, $C_{1-6}$alkylamino, di($C_{1-6}$alkyl)amino, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl and $C_{6-10}$aryl;
$R^1$ is hydrogen, hydroxy, halogen, $C_{1-6}$alkylcarbonyl, $C_{1-6}$alkoxycarbonyl, $C_{1-6}$alkyl, halo$C_{1-6}$alkyl, $N(R^h)_2$ wherein $R^h$ is independently selected from hydrogen, $C_{1-6}$alkyl, $C_{6-10}$aryl and $C_{6-10}$aryl$C_{1-6}$alkyl; $C_{3-10}$cycloalkyl, $C_{6-10}$aryl, 5 or 6 membered saturated or partially saturated heterocycle containing 1, 2 or 3 heteroatoms independently selected from N, O and S, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-13 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkylN$(R^a)_2$ and $(CO)_dR^k$ wherein d is 0 or 1 and $R^k$ is as defined below;

$R^2$ is hydrogen, hydroxy, $C_{1-6}$alkyl, halo$C_{1-6}$alkyl, $C_{1-6}$alkoxy, $C_{3-10}$cycloalkyl, hydroxy$C_{1-6}$alkyl, $N(R^b)_2$, —(C=O)—N$(R^c)_2$ wherein $R^c$ is independently selected from hydrogen and $C_{1-6}$alkyl; $C_{1-6}$alkylS(O)$_w R^g$ wherein $R^g$ is as defined below and w is zero, one or two; a 5 membered unsaturated heterocycle containing 1, 2, 3 or 4 heteroatoms independently selected from N, O and S, but not more than one of which is O or S, or a 6 membered unsaturated heterocycle containing 1, 2, or 3 heteroatoms independently selected from N and O; any of which rings being optionally substituted by one or more groups independently chosen from cyano, halogen, hydroxy, oxo, nitro, amino, $C_{1-6}$alkylamino, di($C_{1-6}$alkyl)amino, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl and $C_{6-10}$aryl;

$R^3$ is hydrogen, halogen, hydroxy, cyano, $C_{1-6}$alkyl, halo$C_{1-6}$alkyl, hydroxy$C_{1-6}$alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, amino, $C_{1-6}$alkylamino, di($C_{1-6}$alkyl)amino, $C_{6-10}$aryl, $C_{6-10}$aryl$C_{1-6}$alkyl, $C_{6-10}$aryl$C_{1-6}$alkoxy; 6-13 membered partially saturated hydrocarbon ring; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-15 membered saturated, partially saturated or unsaturated heterocycle containing heteroatoms independently selected from N, O or S; any of which rings being optionally substituted by one or more groups independently chosen from $(CH_2)_m(CO)_nR^d$;

m is 0, 1, 2 or 3;

n is 0, 1 or 2;

$R^4$ and $R^5$ are independently selected from hydrogen and $C_{1-6}$alkyl;

$R^6$ and $R^8$ are independently hydrogen, $C_{1-6}$alkyl, a 5 or 6 membered saturated or partially saturated heterocycle containing 1, 2 or 3 heteroatoms independently selected from N, O and S or a 6 membered unsaturated heterocycle containing 1, 2 or 3 nitrogen atoms; each of which rings being optionally substituted by one or more groups independently chosen from halogen, nitro, amino, cyano, oxo, hydroxy, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl and $C_{2-6}$alkynyl; or $R^6$ and $R^8$ together represent an oxo group;

each $R^b$ is independently hydrogen, $C_{1-6}$alkyl, hydroxy, $C_{1-6}$alkoxy, $C_{1-6}$alkylS(O)$_w R^g$ wherein $R^g$ is as defined below and w is zero, one or two; SO$_2R^g$ wherein $R^g$ is $C_{1-6}$alkyl, halo$C_{1-6}$alkyl, amino, $C_{1-6}$alkylamino or di($C_{1-6}$alkyl)amino; or a ring which is $C_{6-10}$aryl, $C_{6-10}$aryl$C_{1-6}$alkyl or a 5 membered unsaturated heterocycle containing 1, 2, 3 or 4 heteroatoms independently selected from N, O and S, but not more than one of which is O or S, the ring being optionally substituted by one or more groups independently selected from amino, hydroxy, nitro, cyano, halogen, $C_{1-6}$alkyl, halo$C_{1-6}$alkyl, $C_{1-6}$alkoxy and halo$C_{1-6}$alkoxy;

each $R^d$ is halogen, hydroxy, cyano, $C_{1-6}$alkyl, halo$C_{1-6}$alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, oxo, SO$_2N(R^e)_2$, $N(R^e)_2$ wherein $R^e$ is independently selected from hydrogen, $C_{1-6}$alkyl, $C_{1-6}$alkylcarbonyl, carboxy and $C_{1-6}$alkyloxycarbonyl; $C_{1-6}$alkylN$(R^e)_2$, $C_{6-10}$aryl; $C_{6-10}$aryl$C_{1-6}$alkoxy, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; a 5 or 6 membered spiro ring containing zero, one or two heteroatoms independently selected from N, O or S, or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy;

$R^k$ is NSO$_2R^g$, 5 or 6 membered saturated or partially saturated heterocycle containing 1, 2 or 3 heteroatoms independently selected from N, O and S or a 5 membered unsaturated heterocycle containing 1, 2, 3 or 4 heteroatoms independently selected from N, O and S, but not more than one of which is O or S; any of which rings being optionally substituted by one or more groups independently selected from halogen and $C_{1-6}$alkyl:

or a pharmaceutically acceptable salt or tautomer thereof.

In an embodiment:

D is absent;

p is 0, 1, 2 or 3;

q is 1, 2, 3 or 4;

t is 0 or 1;

X is C or S=O;

Het is a 5 membered unsaturated heterocycle containing 1, 2, 3 or 4 heteroatoms independently selected from N, O and S, but not more than one of which is O or S, or a 6 membered unsaturated heterocycle containing 1, 2, 3 or 4 heteroatoms independently selected from N and O; optionally substituted by one or more groups independently chosen from cyano, halogen, hydroxy, oxo, nitro, amino, $C_{1-6}$alkylamino, di($C_{1-6}$alkyl)amino, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl and $C_{6-10}$aryl;

$R^1$ is hydrogen, $C_{1-6}$alkyl, halo$C_{1-6}$alkyl, $C_{6-10}$aryl, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-10 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-10}$aryl, $C_{6-10}$aryloxy, $C_{6-10}$arylcarbonyl and $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl;

$R^2$ is hydrogen, hydroxy, $C_{1-6}$alkyl, halo$C_{1-6}$alkyl, hydroxy$C_{1-6}$alkyl, $N(R^b)_2$, —(C=O)—N$(R^c)_2$ wherein $R^c$ is independently selected from hydrogen and $C_{1-6}$alkyl; a 5 membered unsaturated heterocycle containing 1, 2, 3 or 4 heteroatoms independently selected from N, O and S, but not more than one of which is O or S, or a 6 membered unsaturated heterocycle containing 1, 2, or 3 heteroatoms independently selected from N and O; any of which rings being optionally substituted by one or more groups independently chosen from cyano, halogen, hydroxy, oxo, nitro, amino, $C_{1-6}$alkylamino, di($C_{1-6}$alkyl)amino, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl and $C_{6-10}$aryl;

$R^3$ is hydrogen, halogen, hydroxy, cyano, $C_{1-6}$alkyl, halo$C_{1-6}$alkyl, hydroxy$C_{1-6}$alkyl, $C_{1-6}$alkoxy, halo$C_{1-6}$ alkoxy, $C_{3-10}$cycloalkyl, halo$C_{3-10}$cycloalkyl, $C_{2-10}$alkenyl, $C_{2-10}$alkynyl, nitro, amino, $C_{1-6}$alkylamino, di($C_{1-6}$alkyl)amino, $C_{6-10}$aryl, $C_{6-10}$aryl$C_{1-6}$alkyl, $C_{6-10}$aryl$C_{1-6}$alkoxy; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, O or S; any of which rings being optionally substituted by one or more groups independently chosen from $R^d$;

$R^4$ and $R^5$ are independently selected from hydrogen and $C_{1-6}$alkyl;

$R^6$ and $R^8$ are independently hydrogen, $C_{1-6}$alkyl, a 5 or 6 membered saturated or partially saturated heterocycle containing 1, 2 or 3 heteroatoms independently selected from N, O and S or a 6 membered unsaturated heterocycle containing 1, 2 or 3 nitrogen atoms; each of which rings being optionally substituted by one or more groups independently chosen from halogen, nitro, amino, cyano, oxo, hydroxy, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl and $C_{2-6}$alkynyl; or $R^6$ and $R^8$ together represent an oxo group;

each $R^b$ is independently hydrogen, $C_{1-6}$alkyl, hydroxy, $C_{1-6}$alkoxy, $SO_2R^g$ wherein $R^g$ is $C_{1-6}$alkyl or halo$C_{1-6}$alkyl; or a ring which is $C_{6-10}$aryl, $C_{6-10}$aryl$C_{1-6}$alkyl or a 5 membered unsaturated heterocycle containing 1, 2, 3 or 4 heteroatoms independently selected from N, O and S, but not more than one of which is O or S, the ring being optionally substituted by one or more groups independently selected from amino, hydroxy, nitro, cyano, halogen, $C_{1-6}$alkyl, halo$C_{1-6}$alkyl, $C_{1-6}$alkoxy and halo$C_{1-6}$alkoxy;

$R^d$ is halogen, hydroxy, cyano, $C_{1-6}$alkyl, halo$C_{1-6}$alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, oxo, $SO_2N(R^e)_2$, $N(R^e)_2$ wherein $R^e$ is independently selected from hydrogen, $C_{1-6}$alkyl, $C_{1-6}$alkylcarbonyl, carboxy and $C_{1-6}$alkyloxycarbonyl; or $C_{1-10}$aryl; 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy;

or a pharmaceutically acceptable salt thereof.

In an embodiment of the previous embodiment:

$R^1$ is hydrogen, $C_{1-6}$alkyl, halo$C_{1-6}$alkyl, $C_{6-10}$aryl, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-10 membered unsaturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$aryl, $C_{6-10}$aryloxy, $C_{6-10}$arylcarbonyl and $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl;

$R^2$ is hydrogen, hydroxy, $C_{1-6}$alkyl, halo$C_{1-6}$alkyl, hydroxy$C_{1-6}$alkyl or $N(R^b)_2$ wherein $R^b$ is independently selected from hydrogen, $C_{1-6}$alkyl, hydroxy and phenyl optionally substituted by amino, hydroxy, nitro, cyano, halogen or $C_{1-6}$alkyl; —(C=O)—$N(R^c)_2$ wherein $R^c$ is independently selected from hydrogen and $C_{1-6}$alkyl; a 5 membered unsaturated heterocycle containing 1, 2, 3 or 4 heteroatoms independently selected from N, O and S, but not more than one of which is O or S, or a 6 membered unsaturated heterocycle containing 1, 2, or 3 heteroatoms independently selected from N and O; any of which rings being optionally substituted by one or more groups independently chosen from cyano, halogen, hydroxy, oxo, nitro, amino, $C_{1-6}$alkylamino, di($C_{1-6}$alkyl)amino, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl and $C_{6-10}$aryl;

$R^3$ is hydrogen, halogen, hydroxy, cyano, $C_{1-6}$alkyl, halo$C_{1-6}$alkyl; hydroxy$C_{1-6}$alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, amino, $C_{1-6}$alkylamino, di($C_{1-6}$alkyl)amino; $C_{6-10}$aryl; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-10 membered saturated, partially saturated or unsaturated heterocycle containing heteroatoms independently selected from N, O or S; any of which rings being optionally substituted by one or more groups independently chosen from $R^d$;

$R^4$ and $R^5$ are independently selected from hydrogen and $C_{1-6}$alkyl;

$R^6$ is hydrogen, $C_{1-6}$alkyl, a 5 or 6 membered saturated or partially saturated heterocycle containing 1, 2 or 3 heteroatoms independently selected from N, O and S or a 6 membered unsaturated heterocycle containing 1, 2 or 3 nitrogen atoms; each of which rings being optionally substituted by one or more groups independently chosen from halogen, nitro, amino, cyano, oxo, hydroxy, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl and $C_{2-6}$alkynyl;

$R^8$ is hydrogen;

$R^d$ is halogen, hydroxy, cyano, $C_{1-6}$alkyl, halo$C_{1-6}$alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, $SO_2N(R^e)_2$, $N(R^e)_2$ wherein $R^e$ is independently selected from hydrogen, $C_{1-6}$alkyl, $C_{1-6}$alkylcarbonyl, carboxy and $C_{1-6}$alkyloxycarbonyl; or $C_{1-10}$aryl; 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy; and p, q, t, X and Het are as defined above;

or a pharmaceutically acceptable salt thereof.

b is preferably 1 or 2.

c is preferably 1.

Preferably, D is absent, $CH_2$, $CH_2CH_2$ or $CH=CH$.

In an embodiment D is absent.

p is preferably 0, 1, 2, 3 or 4.

p is preferably 0, 1 or 2. In one embodiment p is 0.

q is preferably 2, 3 or 4, especially 3 or 4, and most especially 3.

In one embodiment t is 0.

In another embodiment t is 1 and $R^5$ is hydrogen or methyl, preferably methyl.

In an embodiment of the present invention X is C.

In another embodiment X is S=O.

Preferably, Het is an optionally substituted 5 membered unsaturated heterocycle containing 1, 2 or 3 heteroatoms independently selected from N, O and S, but not more than one of which is O or S, or an optionally substituted 6 membered unsaturated heterocycle containing 1, 2 or 3 nitrogen atoms.

In one embodiment Het is an optionally substituted 5 membered unsaturated heterocycle containing 1, 2, 3 or 4 heteroatoms independently selected from N, O and S, but not more than one of which is O or S.

More particularly Het is an optionally substituted imidazolyl, oxazolyl, triazolyl or thienyl. Further particular Het groups include an optionally substituted furyl, oxadiazolyl, thiazolyl, pyrazolyl and pyridinyl.

Preferably Het is unsubstituted or substituted by one, two or three groups. More particularly Het is unsubstituted or monosubstituted. Favoured optional substituents include $C_{1-4}$alkyl and $C_{6-10}$aryl, especially methyl and phenyl.

In one embodiment Het is unsubstituted.

For the avoidance of doubt $R^1$ may be attached to any substitutable position of Het as may any optional substituent on Het.

Thus, particular preferred Het groups include imidazolyl, methylimidazolyl, phenylimidazolyl, phenyloxazolyl, triazolyl and thienyl. Further preferred Het groups include furyl, oxadiazolyl, thiazolyl, oxazolyl, pyrazolyl and pyridinyl.

Specific Het groups are imidazol-2-yl, 4-methylimidazol-2-yl, 4-phenylimidazol-2-yl, 4-phenyloxazol-2-yl, 1,2,4-triazol-3-yl, 1-methylimidazol-2-yl and 2-thienyl. Further specific Het groups are 2-furyl, 1,3,4-oxadiazol-2-yl, 1,3-thiazol-2-yl, 1,2,4-oxadiazol-5-yl, 1,3-thiazol-5-yl, 1,2,4-oxadiazol-3-yl, 1,3-oxazol-2-yl, imidazol-4-yl, pyrazol-5-yl and pyridin-2-yl.

Preferably $R^1$ is hydrogen, hydroxy, halogen, $C_{1-6}$alkylcarbonyl, $C_{1-6}$alkoxycarbonyl, di($C_{1-6}$alkyl)amino, ($C_{6-10}$aryl$C_{1-6}$alkyl)($C_{1-6}$alkyl)amino or an optionally substituted ring selected from $C_{3-7}$cycloalkyl, $C_{6-10}$aryl, 5 or 6 membered saturated or partially saturated heterocycle, a 5 membered unsaturated heterocycle containing 1, 2 or 3 heteroatoms independently selected from N, O and S, but not more than one of which is O or S, a 6 membered unsaturated heterocycle contains 1, 2 or 3 nitrogen atoms, or a 8, 9, 10, 11, 12 or 13 membered unsaturated or partially saturated heterocycle containing 1, 2, 3 or 4 heteroatoms independently selected from O, N and S.

Preferably, $R^1$ is an optionally substituted ring selected from $C_{6-10}$aryl, a 5 membered unsaturated heterocycle containing 1, 2 or 3 heteroatoms independently selected from N, O and S, but not more than one of which is O or S, a 6 membered unsaturated heterocycle containing 1, 2 or 3 nitrogen atoms, or a 8, 9 or 10 membered unsaturated or partially saturated heterocycle containing 1, 2, 3 or 4 heteroatoms independently selected from O, N and S.

More particularly, $R^1$ is an optionally substituted phenyl, naphthyl, thienyl, isoxazolyl, pyridinyl, benzothienyl or thiazolotriazolyl. Further particular $R^1$ groups include an optionally substituted dihydrobenzodioxinyl, benzothiazolyl, quinolinyl or isoquinolinyl. Further particular $R^1$ groups include hydroxy, (benzyl)(methyl)amino, dimethylamino, methoxycarbonyl, hydrogen, acetyl, cyclohexyl, bromine and an optionally substituted quinoxalinyl, morpholinyl, tetrahydroisoquinolinyl, indolyl, dibenzo[b,d]furanyl, naphthyridinyl or dihydroquinolinyl.

Favourably $R^1$ is unsubstituted or substituted by one, two or three groups. More particularly $R^1$ is unsubstituted, monosubstituted or disubstituted. In an embodiment $R^1$ is monosubstituted. Favoured optional substituents include cyano, halogen, $C_{1-4}$alkyl, halo$C_{1-4}$alkyl, $C_{1-4}$alkoxy, halo$C_{1-4}$alkoxy and $C_{6-10}$aryl. Further favoured optional substituents include pyrazolyl, di($C_{1-6}$alkyl)amino, carboxy, piperidinylcarbonyl, morpholinyl, nitro, ($C_{1-6}$alkylcarbonyl)amino, $C_{1-6}$alkoxycarbonyl, amino, amino$C_{1-6}$alkyl, tetrazolyl, [($C_{1-6}$ alkylsulfonyl)amino]carbonyl, hydroxy, [di($C_{1-6}$alkyl)amino]$C_{1-6}$alkyl and oxo; any of which rings being optionally substituted by one, two or three $C_{1-6}$alkyl groups. Examples of typical optional substituents include cyano, bromine, chlorine, fluorine, methyl, trifluoromethyl, methoxy, difluoromethoxy and phenyl. Further examples of typical optional substituents include dimethylpyrazolyl, dimethylamino, carboxy, piperidinylcarbonyl, morpholinyl, nitro, trifluoromethoxy, ethoxy, acetylamino, methoxycarbonyl, pyrazolyl, amino, aminomethyl, tetrazolyl, [(methylsulfonyl)amino]carbonyl, hydroxy, dimethylaminomethyl and oxo.

Thus, particular preferred $R^1$ groups include phenyl, cyanophenyl, bromophenyl, chlorophenyl, dichlorophenyl, fluorophenyl, difluorophenyl, trifluoromethylphenyl, bis(trifluoromethyl)phenyl, methoxyphenyl, difluoromethoxyphenyl, biphenyl, naphthyl, thienyl, phenylisoxazolyl, pyridinyl, (chloro)(methyl)benzothienyl, (methyl)(trifluoromethyl)thiazolotriazolyl and benzothienyl. Further preferred $R^1$ groups are dihydrobenzodioxinyl, benzothiazolyl, methoxyquinolinyl, quinolinyl and isoquinolinyl. Further preferred $R^1$ groups are hydroxy, quinoxalinyl, methoxynaphthyl, morpholinyl, benzyl(methyl)amino, tetrahydroisoquinolinyl, methylquinolinyl, indolyl, (dimethylpyrazolyl)phenyl, (dimethylamino)phenyl, (fluoro)(methoxy)phenyl, carboxyphenyl, dibenzo[b,d]furanyl, (piperidinylcarbonyl)phenyl, dimethylamino, methoxycarbonyl, dimethoxynaphthyl, morpholinylphenyl, nitrophenyl, trifluoromethoxyphenyl, ethoxyphenyl, acetylaminophenyl, (methoxycarbonyl)phenyl, hydrogen, bromophenyl, pyrazolylphenyl, aminophenyl, dimethoxyphenyl, (fluoro)(trifluoromethyl)phenyl, (aminomethyl)phenyl, (aminomethyl)(fluoro)phenyl, tetrazolylphenyl, {[(methylsulfonyl)amino]carbonyl}phenyl, acetyl, cyclohexyl, bromine, hydroxyphenyl, (dimethylaminomethyl)phenyl, fluoroquinolinyl, naphthyridinyl and oxodihydroquinolinyl.

Specific $R^1$ groups are phenyl, 3-cyanophenyl, 4-cyanophenyl, 4-bromophenyl, 2-chlorophenyl, 3-chlorophenyl, 4-chlorophenyl, 3,4-dichlorophenyl, 4-fluorophenyl, 3,4-difluorophenyl, 3-(trifluoromethyl)phenyl, 4-(trifluoromethyl)phenyl, 3,5-bis(trifluoromethyl)phenyl, 2-methoxyphenyl, 3-methoxyphenyl, 4-(difluoromethoxy)phenyl, biphen-4-yl, 2-naphthyl, 3-thienyl, 3-phenylisoxazol-5-yl, 2-pyridinyl, 5-chloro-3-methyl-1-benzothien-2-yl, 6-methyl-2-(trifluoromethyl) [1,3]thiazolo[3,2-b][1,2,4]triazol-5-yl and 1-benzothien-3-yl. Further specific $R^1$ groups are 3,5-dichlorophenyl, 2,3-dihydro-1,4-benzodioxin-6-yl, 2,3-dihydro-1,4-benzodioxin-5-yl, 1,3-benzothiazol-2-yl, 1-benzothien-2-yl, 4-methoxyquinolin-2-yl, quinolin-3-yl, quinolin-6-yl, quinolin-2-yl and isoquinolin-3-yl. Further specific $R^1$ groups are quinolin-8-yl, hydroxy, quinoxalin-2-yl, 3-methoxy-2-naphthyl, morpholin-4-yl, benzyl(methyl)amino, 1,2,3,4-tetrahydroisoquinolin-2-yl, 2-methylquinolin-5-yl, quinolin-5-yl, 8-methylquinolin-5-yl, 8-methoxyquinolin-5-yl, 1-benzothien-7-yl, 1H-indol-5-yl, 3-(3,5-dimethyl-1H-pyrazol-1-yl)phenyl, 4-(dimethylamino)phenyl, 2-fluoro-4-methoxyphenyl, 3-fluoro-4-methoxyphenyl, 3-carboxyphenyl, biphen-2-yl, dibenzo[b,d]furan-4-yl, 3-(piperidin-1-ylcarbonyl)phenyl, quinoxalin-6-yl, dimethylamino, methoxycarbonyl, 1,4-dimethoxy-2-naphthyl, 3,5-dimethoxy-2-naphthyl, 2-thienyl, 1-naphthyl, 2-(morpholin-4-yl)phenyl, 3-nitrophenyl, pyridin-3-yl, 3-(trifluoromethoxy)phenyl, 4-(trifluoromethoxy)phenyl, 2-(trifluoromethyl)phenyl, 2-fluorophenyl, 3-ethoxyphenyl, 4-ethoxyphenyl, 4-(acetylamino) phenyl, 2-(methoxycarbonyl)phenyl, hydrogen, 3-bromophenyl, pyridin-4-yl, 4-(1H-pyrazol-1-yl)phenyl, 2-nitrophenyl, 3-aminophenyl, 2,4-dimethoxyphenyl, 2-fluoro-5-trifluoromethylphenyl, 3-(aminomethyl)phenyl, 2-(aminomethyl)-4-fluorophenyl, biphen-3-yl, 3-(1H-tetrazol-5-yl)phenyl, 3-{[(methylsulfonyl)amino]carbonyl}phenyl, acetyl, cyclohexyl, bromine, 4-carboxyphenyl, 3-hydroxyphenyl, 4-[(dimethylamino)methyl]phenyl, 2-carboxyphenyl, 2-fluoroquinolin-3-yl, quinoxalin-6-yl, 8-methoxyquinolin-5-yl, 2-methoxyquinolin-3-yl, 1,8-naphthyridin-2-yl, 1,6-naphthyridin-2-yl, 1,6-naphthyridin-8-yl and 2-oxo-1,2-dihydroquinolin-3-yl.

In an embodiment, $R^1$ is hydroxy, halogen, $C_{1-6}$alkylcarbonyl, $N(R^h)_2$ wherein $R^h$ is independently selected from hydrogen, $C_{1-6}$alkyl, $C_{1-10}$aryl and $C_{6-10}$aryl$C_{1-6}$alkyl; $C_{3-10}$cycloalkyl, 5 or 6 membered saturated or partially saturated heterocycle containing 1, 2 or 3 heteroatoms independently selected from N, O and S, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-13 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkyl$N(R^a)_2$ and $(CO)_dR^k$ wherein d is 0 or 1 and $R^k$ is as defined above.

In another embodiment, $R^1$ is a 5 or 6 membered saturated or partially saturated heterocycle containing 1, 2 or 3 heteroatoms independently selected from N, O and S, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-13 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkyl$N(R^a)_2$ and $(CO)_dR^k$ wherein d is 0 or 1 and $R^k$ is as defined above.

In an embodiment, $R^1$ is an optionally substituted thienyl, isoxazolyl, pyridinyl, benzothienyl, thiazolotriazolyl, dihydrobenzodioxinyl, benzothiazolyl, quinolinyl, isoquinolinyl, quinoxalinyl, morpholinyl, tetrahydroisoquinolinyl, indolyl, dibenzo[b,d]furanyl, naphthyridinyl or dihydroquinolinyl.

In an embodiment, $R^1$ is thienyl, phenylisoxazolyl, pyridinyl, (chloro)(methyl)benzothienyl, (methyl)(trifluoromethyl)thiazolotriazolyl, benzothienyl, dihydrobenzodioxinyl, benzothiazolyl, methoxyquinolinyl, quinolinyl, isoquinolinyl, quinoxalinyl, morpholinyl, tetrahydroisoquinolinyl, methylquinolinyl, indolyl, dibenzo[b,d]furanyl, fluoroquinolinyl, naphthyridinyl or oxodihydroquinolinyl.

In an embodiment, $R^1$ is 3-thienyl, 3-phenylisoxazol-5-yl, 2-pyridinyl, 5-chloro-3-methyl-1-benzothien-2-yl, 6-methyl-2-(trifluoromethyl)[1,3]thiazolo[3,2-b][1,2,4]triazol-5-yl, 1-benzothien-3-yl, 2,3-dihydro-1,4-benzodioxin-6-yl, 2,3-dihydro-1,4-benzodioxin-5-yl, 1,3-benzothiazol-2-yl, 1-benzothien-2-yl, 4-methoxyquinolin-2-yl, quinolin-3-yl, quinolin-6-yl, quinolin-2-yl, isoquinolin-3-yl, quinolin-8-yl, quinoxalin-2-yl, morpholin-4-yl, 1,2,3,4-tetrahydroisoquinolin-2-yl, 2-methylquinolin-5-yl, quinolin-5-yl, 8-methylquinolin-5-yl, 8-methoxyquinolin-5-yl, 1-benzothien-7-yl, 1H-indol-5-yl, dibenzo[b,d]furan-4-yl, quinoxalin-6-yl, 2-thienyl, pyridin-3-yl, pyridin-4-yl, 2-fluoroquinolin-3-yl, quinoxalin-6-yl, 8-methoxyquinolin-5-yl, 2-methoxyquinolin-3-yl, 1,8-naphthyridin-2-yl, 1,6-naphthyridin-2-yl, 1,6-naphthyridin-8-yl or 2-oxo-1,2-dihydroquinolin-3-yl.

In an embodiment, $R^1$ is 8-13 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkyl$N(R^a)_2$ and $(CO)_dR^k$ wherein d is 0 or 1 and $R^k$ is as defined above.

In an embodiment, $R^1$ is an optionally substituted 8-13 membered unsaturated or partially saturated heterocycle containing 1, 2, 3 or 4 heteroatoms independently selected from O, N and S.

In an embodiments, $R^1$ is an optionally substituted benzothienyl, thiazolotriazolyl, dihydrobenzodioxinyl, benzothiazolyl, quinolinyl, isoquinolinyl, quinoxalinyl, tetrahydroisoquinolinyl, indonyl, dibenzo[b,d]furanyl, naphthyridinyl or dihydroquinolinyl.

In an embodiment $R^1$ is an optionally substituted quinolinyl, isoquinolinyl, quinoxalinyl, tetrahydroisoquinolinyl, naphthyridinyl or dihydroquinolinyl.

In an embodiment, $R^1$ is (chloro)(methyl)benzothienyl, (methyl)(trifluoromethyl)thiazolotriazolyl, benzothienyl, dihydrobenzodioxinyl, benzothiazolyl, methoxyquinolinyl, quinolinyl, isoquinolinyl, quinoxalinyl, tetrahydroisoquinolinyl, methylquinolinyl, indolyl, dibenzo[b,d]furanyl, fluoroquinolinyl, naphthyridinyl or oxodihydroquinolinyl.

In an embodiment, $R^1$ is 5-chloro-3-methyl-1-benzothien-2-yl, 6-methyl-2-(trifluoromethyl)[1,3]thiazolo[3,2-b][1,2,4]triazol-5-yl, 1-benzothien-3-yl, 2,3-dihydro-1,4-benzodioxin-6-yl, 2,3-dihydro-1,4-benzodioxin-5-yl, 1,3-benzothiazol-2-yl, 1-benzothien-2-yl, 4-methoxyquinolin-2-yl, quinolin-3-yl, quinolin-6-yl, quinolin-2-yl, isoquinolin-3-yl, quinolin-8-yl, quinoxalin-2-yl, 1,2,3,4-tetrahydroisoquinolin-2-yl, 2-methylquinolin-5-yl, quinolin-5-yl, 8-methylquinolin-5-yl, 8-methoxyquinolin-5-yl, 1-benzothien-7-yl, 1H-indol-5-yl, dibenzo[b,d]furan-4-yl, quinoxalin-6-yl, 2-fluoroquinolin-3-yl, quinoxalin-6-yl, 8-methoxyquinolin-5-yl, 2-methoxyquinolin-3-yl, 1,8-naphthyridin-2-yl, 1,6-naphthyridin-2-yl, 1,6-naphthyridin-8-yl or 2-oxo-1,2-dihydroquinolin-3-yl.

In an embodiment, $R^1$ is 4-methoxyquinolin-2-yl, quinolin-3-yl, quinolin-6-yl, quinolin-2-yl, isoquinolin-3-yl, quinolin-8-yl, quinoxalin-2-yl, 1,2,3,4-tetrahydroisoquinolin-2-yl, 2-methylquinolin-5-yl, quinolin-5-yl, 8-methylquinolin-5-yl, 8-methoxyquinolin-5-yl, quinoxalin-6-yl, 2-fluoroquinolin-3-yl, quinoxalin-6-yl, 8-methoxyquinolin-5-yl, 2-methoxyquinolin-3-yl, 1,8-naphthyridin-2-yl, 1,6-naphthyridin-2-yl, 1,6-naphthyridin-8-yl or 2-oxo-1,2-dihydroquinolin-3-yl.

In embodiments, $R^1$ is quinolinyl, optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkylN$(R^a)_2$ and $(CO)_dR^k$ wherein d is 0 or 1 and $R^k$ is as defined above.

In an embodiment $R^1$ is quinolinyl optionally substituted by $C_{1-6}$alkoxy, preferably methoxy.

In an embodiment $R^1$ is 2-methoxyquinolin-3-yl. $R^2$ is preferably hydrogen, hydroxy, $C_{1-6}$alkyl, $C_{1-6}$alkoxy, $C_{3-7}$cycloalkyl, halo$C_{1-6}$alkyl, hydroxy$C_{1-6}$alkyl, $N(R^b)_2$, —(C=O)N$(R^c)_2$, $C_{1-6}$alkylS$(O)_wR^g$ or an optionally substituted ring selected from thienyl, furyl and pyridinyl.

When $R^2$ is a ring, it is preferably unsubstituted or substituted by one, two or three groups. In one embodiment the $R^2$ ring is unsubstituted.

$R^2$ is preferably hydrogen, hydroxy, $C_{1-6}$alkyl, halo$C_{1-6}$alkyl, hydroxy$C_{1-6}$alkyl, $N(R^b)_2$ or —C(=O)—N$(R^c)_2$.

$R^2$ is preferably hydrogen, hydroxy, $C_{1-6}$alkyl, halo$C_{1-6}$alkyl, hydroxy$C_{1-6}$alkyl, $N(R^b)_2$ wherein $R^b$ is independently selected from hydrogen, $C_{1-6}$alkyl, hydroxy and phenyl optionally substituted by amino, hydroxy, nitro, cyano, halogen or $C_{1-6}$alkyl, —(C=O)—N$(R^c)_2$ wherein $R^c$ is independently selected from hydrogen and $C_{1-6}$alkyl or oxazole.

More particularly, $R^2$ is hydrogen, hydroxy, $C_{1-6}$alkyl or $N(R^b)_2$. A further particular $R^2$ group is halo$C_{1-6}$alkyl. Further particular $R^2$ groups are hydroxy$C_{1-6}$alkyl, $C_{1-6}$alkoxy, $C_{3-5}$cycloalkyl, $C_{1-6}$alkylS$(O)_mR^g$ and an optionally substituted ring selected from thienyl, furyl and pyridinyl.

Favourably, $R^2$ is $C_{1-4}$alkyl, hydroxy or $N(R^b)_2$. A further favoured $R^2$ group is halo$C_{1-4}$alkyl.

Preferably, when $R^b$ is a ring it is unsubstituted or substituted by one, two or three independently selected groups. More particularly, the $R^b$ ring is unsubstituted or monosubstituted.

$R^b$ is preferably hydrogen, $C_{1-4}$alkyl, hydroxy or phenyl optionally substituted by amino. Further preferred $R^b$ groups include $C_{1-4}$alkoxy, $SO_2R^g$ or a benzyl, thiazolyl or thiadiazolyl, the ring being optionally substituted by amino. A further preferred $R^b$ group is $C_{1-6}$alkylS$(O)_wR^g$.

Preferably, $R^b$ is methyl, ethyl or trifluoromethyl. A further $R^b$ group is amino. Particular $R^b$ groups include hydrogen, methyl, hydroxy and aminophenyl. Further particular $R^b$ groups include ethyl, isopropyl, methoxy, methylsulfonyl, ethylsulfonyl, trifluoromethylsulfonyl, phenyl, benzyl, thiazolyl and thiadiazolyl. Further particular $R^b$ groups include ethoxy and methylthioethyl.

Specific $R^b$ groups include hydrogen, methyl, hydroxy and 2-aminophenyl. Further specific $R^b$ groups include ethyl, isopropyl, methoxy, methylsulfonyl, ethylsulfonyl, trifluoromethylsulfonyl, phenyl, benzyl, 1,3-thiazol-2-yl and 1,3,4-thiadiazol-2-yl. Further specific $R^b$ groups include ethoxy and 2-(methylthio)ethyl.

Thus, particular $R^2$ groups are methyl, ethyl, hydroxy, methylamino, hydroxyamino, aminophenylamino, trifluoromethyl, amino, dimethylamino, isopropylamino, phenylamino, benzylamino, methylsulfonylamino, methoxymethylamino, trifluoromethylsulfonylamino, ethylsulfonylamino, ethylamino, thiazolylamino and thiadiazolylamino. Further particular $R^2$ groups include butyl, propyl, (methylthio)ethylamino, methoxyamino, ethoxyamino, (methyl)propyl, hydroxymethyl, methoxy, cyclopropyl, methylsulfinylmethyl, thienyl, methylsulfonylmethyl, pyridinyl, furyl and aminosulfonylmethyl.

More particular $R^2$ groups include methyl, ethyl, hydroxy, methylamino, hydroxyamino and 2-aminophenylamino. Further particular $R^2$ groups are trifluoromethyl, amino, dimethylamino, isopropylamino, phenylamino, benzylamino, methylsulfonylamino, methylmethoxyamino, trifluoromethylsulfonylamino, ethylamino, 1,3-thiazol-2-ylamino and 1,3,4-thiadiazol-2-ylamino. Further particular $R^2$ groups include butyl, propyl, 2-(methylthio)ethylamino, methoxyamino, ethoxyamino, isopropyl, 2-methylpropyl, hydroxymethyl, methoxy, cyclopropyl, methylsulfinylmethyl, 2-thienyl, methylsulfonylmethyl, pyridin-2-yl, 2-furyl and aminosulfonylmethyl.

In an embodiment $R^2$ is $C_{1-6}$alkyl, especially methyl or ethyl. In another embodiment $R^2$ is ethyl.

In an embodiment $R^3$ is hydroxy, $C_{1-6}$alkyl, halo$C_{1-6}$alkyl, $C_{1-6}$alkoxy, $C_{3-10}$cycloalkyl, amino, $C_{1-6}$alkylamino, di($C_{1-6}$alkyl)amino, $C_{6-10}$aryl, $C_{6-10}$aryl$C_{1-6}$alkoxy, a 9-10 membered partially saturated hydrocarbon ring; a 4, 5 or 6 membered saturated or partially saturated heterocycle containing 1, 2 or 3 heteroatoms independently selected from N, O and S, optionally bridged by a $C_{1-4}$alkyl group; a 5 membered unsaturated heterocycle containing 1, 2, 3 or 4 heteroatoms independently selected from N, O and S, but not more than one of which is O or S; a 6 membered unsaturated heterocycle containing 1, 2 or 3 nitrogen atoms; or a 8, 9, 10, 11, 12, 13 or 14 membered saturated, partially saturated or unsaturated heterocycle containing 1, 2, 3 or 4 heteroatoms independently selected from N, O and S; any of which rings being optionally substituted by one or more groups independently chosen from $(CH_2)_m(CO)_nR^d$.

$R^3$ is preferably hydroxy, $C_{1-6}$alkyl, halo$C_{1-6}$alkyl, $C_{1-6}$alkoxy, $C_{3-10}$cycloalkyl, amino, $C_{1-6}$alkylamino, di($C_{1-6}$alkyl)amino, $C_{6-10}$aryl, $C_{6-10}$aryl$C_{1-6}$alkoxy; a 5 or 6 membered saturated or partially saturated heterocycle containing 1, 2 or 3 heteroatoms independently selected from N, O and S, optionally bridged by a $C_{1-4}$alkyl group; a 6 membered unsaturated heterocycle containing 1, 2 or 3 nitrogen atoms; or a 8-13 membered saturated, partially saturated or unsaturated heterocycle containing 1, 2, 3 or 4 heteroatoms independently selected from N, O and S; any of which rings being optionally substituted by one or more groups independently chosen from $R^d$.

In one embodiment, $R^3$ is amino, $C_{1-6}$alkylamino, di($C_{1-6}$alkyl)amino, $C_{6-10}$aryl; 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or 8-10 membered saturated, partially saturated or unsaturated heterocycle containing 1, 2, 3 or 4 heteroatoms independently selected from N, O or S; any of which rings being optionally substituted by one or more groups independently chosen from $R^d$.

Particular $R^3$ groups include dimethylamino, phenyl, naphthyl, pyrrolidinyl, piperidyl, azoniabicyclo[2.2.1]heptanyl, azoniabicyclo[2.2.2]octanyl, piperazinyl, morpholinyl, thienyl, thiazolyl, imidazolyl, pyrazolyl, isoxazolyl, thiadiazolyl, pyridinyl, indolyl, benzothienyl, benzothiadiazolyl, benzoxadiazolyl, dihydrobenzofuryl, dihydrothiazolopyrimidinyl, isoquinolyl, dihydrobenzodioxinyl and dihydrobenzoxazinyl; any of which rings being optionally substituted by one or more groups independently chosen from $R^d$. Further particular $R^3$ groups are tert-butoxy, cyclopentyl, methyl, trifluoromethyl, methoxy, methylamino, amino, diethylamino, hydroxy, benzimidazolyl, benzofuranyl, triazolopyrimidinyl, dihydrobenzoxazolyl, dihydroindolyl, dihydroquinazolinyl, dihydrophthalazinyl, indazolyl, quinolinyl, benzisoxazolyl, benzotriazolyl, tetrahydrobetacarbolinyl, dihydroisoindolyl, tetrahydronaphthyridinyl, tetrazolyl, benzyloxy, thiomorpholinyl and azetidinyl; any of which rings being optionally substituted by one or more groups independently chosen from $R^d$. Further particular $R^3$ groups are dihydroisochromenyl, dihydrochromenyl, dihydroindenyl, tetrahydroquinolinyl, indenyl, benzothiazolyl, dihydrobenzothiazolyl, tetrahydronaphthyl, imidazothiazolyl, naphthyridinyl, tetrahydroindazolyl, tetrahydrobenzothienyl, hexahydronaphthyridinyl, tetrahydropyridonaphthyridinyl, tetrahydroisoquinolinyl, tetrahydroimidazolyl, tetrahydroimidazopyrazinyl and pyrrolopyridinyl; any of which rings being optionally substituted by one or more groups independently chosen from $(CH_2)_m(CO)_nR^d$.

In an embodiment, $R^3$ is unsubstituted or substituted by one, two, three or four groups independently selected from $(CH_2)_m(CO)_nR^d$.

Preferably m is 0, 1 or 2. In one embodiment m is 0.
Preferably n is 0 or 1. In one embodiment n is 0.
Preferably $R^3$ is unsubstituted or substituted by one, two or three groups selected from $R^d$.

Favoured $R^d$ groups include halogen, cyano, $C_{1-6}$alkyl, $C_{1-6}$alkoxy, halo$C_{1-6}$alkoxy, carboxy, $C_{1-6}$alkoxycarbonyl, nitro, aminosulfonyl, ($C_{1-6}$alkylcarbonyl)amino, morpholinyl, piperazinyl, thiazolyl, pyrazolyl, isoxazolyl and pyridinyl; any of which rings being optionally substituted by one or more groups independently chosen from $C_{1-6}$alkyl and halo$C_{1-6}$alkyl. Further favoured $R^d$ groups are oxo, halo$C_{1-6}$alkyl, phenyl or pyrrolidinyl, any of which rings being optionally substituted by one or more groups independently chosen from $C_{1-6}$alkyl and halo$C_{1-6}$alkyl. Further favoured $R^d$ groups are hydroxy, piperidinespiro, $C_{6-10}$aryl$C_{1-6}$alkoxy, di($C_{1-6}$alkyl)amino, $C_{1-6}$alkylcarbonyl and di($C_{1-6}$alkylamino$C_{1-6}$alkyl.

Particular $R^d$ groups include chlorine, fluorine, cyano, methyl, isopropyl, methoxy, difluoromethoxy, carboxy, nitro, aminosulfonyl, acetylamino, methylpiperazinyl, pyridinyl, methylthiazolyl, (methyl)(trifluoromethyl)pyrazolyl, isoxazolyl, methoxycarbonyl and morpholinyl. Further particular $R^d$ groups are bromine, phenyl, oxo, ethyl, trifluoromethyl and pyrrolidinyl. Further particular $R^d$ groups are hydroxy, piperidinespiro, tert-butyl, ethoxy, benzyloxy, dimethylamino, acetyl, tert-butoxycarbonyl and dimethylaminomethyl.

Specific $R^d$ groups include chlorine, fluorine, cyano, methyl, isopropyl, methoxy, difluoromethoxy, carboxy, nitro, aminosulfonyl, acetylamino, 1-methylpiperazin-4-yl, pyridin-2-yl, 2-methyl-1,3-thiazol-4-yl, 1-methyl-3-trifluoromethyl-1H-pyrazol-5-yl, isoxazol-3-yl, methoxycarbonyl and morpholin-4-yl. Further specific $R^d$ groups include bromine, phenyl, oxo, ethyl, trifluoromethyl and pyrrolidin-1-yl. Further specific $R^d$ groups are hydroxy, 4'-piperidinespiro, tert-butyl, ethoxy, benzyloxy, dimethylamino, acetyl, tert-butoxycarbonyl, pyridin-3-yl, pyrrolidin-1-yl, morpholin-4-yl, 1-methylpiperazin-4-yl and dimethylaminomethyl.

Thus, particular preferred $R^3$ groups include dimethylamino, phenyl, chlorophenyl, fluorophenyl, difluorophenyl, cyanophenyl, (chloro)(cyano)phenyl, (cyano)(fluoro)phenyl, methoxyphenyl, dimethoxyphenyl, difluoromethoxyphenyl, carboxyphenyl, nitrophenyl, (fluoro)(nitro)phenyl, acetylaminophenyl, (methylpiperazinyl)phenyl, naphthyl, methylpyrrolidinyl, piperidyl, methylpiperidyl, methylpiperazinyl, azoniabicyclo[2.2.1]heptanyl, pyridinylpiperidyl, thienyl, (methylthiazolyl)thienyl, [(methyl)(trifluoromethyl)pyrazolyl]thienyl, isoxazolylthienyl, chlorothienyl, methoxycarbonylthienyl, thiazolyl, dimethylthiazolyl, (acetylamino)(methyl)thiazolyl, dimethylimidazolyl, trimethylpyrazolyl, dimethylisoxazolyl, methylthiadiazolyl, pyridinyl, morpholinylpyridinyl, (methoxy)(methyl)indolyl, benzothienyl, benzothiadiazolyl, benzoxadiazolyl, dihydrobenzofuranyl, dihydrothiazolopyrimidinyl, isoquinolyl, dihydrobenzodioxinyl, (methyl)dihydrobenzoxazinyl, aminosulfonylphenyl, cyanopyridinyl, isopropylpiperidinyl, methylmorpholinyl, azoniabicyclo[2.2.2]octanyl and morpholinyl. Further particularly preferred $R^3$ groups include indolyl, methylindolyl, methoxyindolyl, bromoindolyl, fluoroindolyl, benzimidazolyl, methoxybenzofuranyl, triazolopyrimidinyl, phenylthiazolyl, chlorobenzothienyl, chloroindolyl, oxodihydrobenzoxazolyl, methoxyoxodihydroindolyl, ethylbenzimidazolyl, oxodihydroquinazolinyl, methyloxodihydrophthalazinyl, dichlorophenyl, fluoro(trifluoromethyl)phenyl, methylbenzimidazolyl, (trifluoromethyl)benzimidazolyl, indazolyl, quinolinyl, benzisoxazolyl, benzotriazolyl, cyanoindolyl, tetrahydrobetacarbolinyl, tert-butoxy, dihydroisoindolyl, tetrahydronaphthyridinyl, pyrrolidinyltetrazolyl, cyclopentyl, benzyloxy, methyl, dimethylpyrrolidinyl, dioxothiomorpholinyl, trifluoromethyl, methylazetidinyl, ethylpiperidinyl, methoxy, methylamino, amino, diethylamino and hydroxy. Further particular preferred $R^3$ groups include hydroxyindolyl, (piperidinespiro)dihydroisochromenyl, (piperidinspiro)dihydrochromenyl, chlorobenzimidazolyl, (oxo)dihydrobenzoxazolyl, (piperidinespiro)dihydroindenyl, (oxo)tetrahydroquinolinyl, chloroindazolyl, (ethyl)(methyl)indolyl, (methyl(nitro)indolyl, (methoxy)(methyl)indenyl, (hydroxy)(methyl)indolyl, methoxybenzimidazolyl, dimethylindolyl, methylbenzothiazolyl, (methoxy)(oxo)dihydrobenzoxazolyl, benzothiazolyl, (fluoro)(methyl)indolyl, (tert-butyl)(methyl)indolyl, (ethoxy)(methyl)indolyl, (benzyloxy)(methyl)indolyl, (oxo)dihydrobenzothiazolyl, fluorobenzimidazolyl, tetrahydronaphthyl, (methyl)tetrahydronaphthyridinyl, imidazothiazolyl, benzofuranyl, naphthyridinyl, tetrahydroindazolyl, tetrahydrobenzothienyl, (oxo)dihydroisoindolyl, [(dimethylamino)ethyl](oxo)dihydroisoindolyl, (benzyl)(oxo)hexahydronaphthyridinyl, tetrahydropyridonaphthyridinyl, (acetyl)tetrahydroisoquinolinyl, (methyl)tetrahydroisoquinolinyl, tetrahydroisoquinolinyl, [(tert-butoxy)(oxo)ethyl](methoxy)(methyl)indolyl, (methoxy)(methyl)(pyridinylmethyl)indolyl, (methoxy)dimethylindolyl, (methoxy)(methyl)(pyrrolidinylethyl)indolyl, (methoxy)(methyl)(morpholinylethyl)indolyl, methylbenzisoxazolyl, (dimethylamino)(methyl)indolyl, isoquinolinyl, (methyl)tetrahydroimidazopyridinyl, methylbenzothienyl, (carboxymethyl)(methoxy)(methyl)indolyl, (methoxy)(methyl)[(methylpiperazinyl)(oxo)ethyl]indolyl, (methyl)tetrahydroimidazopyrazinyl, [(dimethylamino)methyl](methyl)indolyl, tetrafluoroindolyl, (fluoro)(methyl)indolyl, pyrrolopyridinyl, (methoxy)pyrrolopyridinyl, imidazolyl, acetylpiperazinyl, (dimethylglycyl)azetidinyl, (methoxyethyl)azetidinyl and methoxyazetidinyl.

Specific R³ groups are dimethylamino, phenyl, 4-chlorophenyl, 2-fluorophenyl, 3-fluorophenyl, 4-fluorophenyl, 3,4-difluorophenyl, 2-cyanophenyl, 3-cyanophenyl, 4-cyanophenyl, 2-chloro-4-cyanophenyl, 3-cyano-4-fluorophenyl, 3-methoxyphenyl, 4-methoxyphenyl, 2,5-dimethoxyphenyl, 3,4-dimethoxyphenyl, 3-difluoromethoxyphenyl, 4-difluoromethoxyphenyl, 4-carboxyphenyl, 2-nitrophenyl, 3-nitrophenyl, 4-nitrophenyl, 3-fluoro-4-nitrophenyl, 4-acetylaminophenyl, 4-(1-methylpiperazin-4-yl)phenyl, 2-naphthyl, 1-methylpyrrolidin-3-yl, piperidin-1-yl, 1-methylpiperidin-2-yl, 1-methylpiperidin-3-yl, 1-methylpiperidin-4-yl, 1-methylpiperazin-4-yl, azoniabicyclo[2.2.1]heptan-2-yl, 1-pyridin-2-ylpiperidin-3-yl, 2-thienyl, 5-(2-methyl-1,3-thiazol-4-yl)-2-thienyl, 5-[1-methyl-3-(trifluoromethyl)-1H-pyrazol-5-yl]-2-thienyl, 5-isoxazol-3-yl-2-thienyl, 5-chloro-2-thienyl, 2-(methoxycarbonyl)-3-thienyl, 1,3-thiazol-5-yl, 2,4-dimethyl-1,3-thiazol-5-yl, 2-(acetylamino)-4-methyl-1,3-thiazol-5-yl, 1,2-dimethyl-1H-imidazol-4-yl, 1,3,5-trimethyl-1H-pyrazol-4-yl, 3,5-dimethylisoxazol-4-yl, 4-methyl-1,2,3-thiadiazol-5-yl, pyridin-3-yl, 2-morpholin-4-ylpyridin-5-yl, 5-methoxy-2-methyl-1H-indol-3-yl, benzothien-3-yl, 2,1,3-benzothiadiazol-5-yl, 2,1,3-benzoxadiazol-4-yl, 2,3-dihydro-1-benzofuran-5-yl, 6,7-dihydro-5H-[1,3]thiazolo[3,2-a]pyrimidin-3-yl, isoquinol-5-yl, 2,3-dihydro-1,4-benzodioxin-6-yl, 4-methyl-3,4-dihydro-2H-1,4-benzoxazin-7-yl, pyridin-4-yl, 4-aminosulfonylphenyl, 2-cyanopyridin-5-yl, 1-isopropylpiperidin-3-yl, 4-methylmorpholin-2-yl, azoniabicyclo[2.2.2]octan-4-yl and morpholin-4-yl. Further specific R³ groups are 1H-indol-3-yl, 2-methyl-1H-indol-3-yl, 5-methoxy-1H-indol-3-yl, 5-bromo-1H-indol-3-yl, 5-fluoro-1H-indol-3-yl, 1H-benzimidazol-1-yl, 7-methoxy-1-benzofuran-2-yl, 5-methoxy-1H-indol-2-yl, 5-fluoro-1H-indol-2-yl, [1,2,4]triazolo[1,5-a]pyrimidin-6-yl, 4-phenyl-1,3-thiazol-2-yl, 5-chloro-1-benzothien-3-yl, 4-chloro-1H-indol-3-yl, 2-oxo-1,3-benzoxazol-3(2H)-yl, 5-methoxy-2-oxo-2,3-dihydro-1H-indol-3-yl, 6-methoxy-2-oxo-2,3-dihydro-1H-indol-3-yl, 2-ethyl-1H-benzimidazol-1-yl, 1-naphthyl, 2-oxoquinazolin-1-(2H)-yl, 4-methyl-1-oxophthalazin-2(1H)-yl, 2,4-dichlorophenyl, 2-fluoro-6-(trifluoromethyl)phenyl, 2,6-dichlorophenyl, 2-fluoro-3-(trifluoromethyl)phenyl, 2-methyl-1H-benzimidazol-1-yl, 2-(trifluoromethyl)-1H-benzimidazol-1-yl, 1H-indazol-1-yl, quinolin-3-yl, 1,2-benzisoxazol-3-yl, 2-methyl-1H-indol-1-yl, 1H-1,2,3-benzotriazol-1-yl, 5-cyano-1H-indol-1-yl, 2,3,4,9-tetrahydro-1H-beta-carbolin-4-yl, tert-butoxy, 2,3-dihydro-1H-isoindol-2-yl, 1,2,3,4-tetrahydro-1,8-naphthyridin-5-yl, 5-pyrrolidin-1-yl-2H-tetrazol-2-yl, cyclopentyl, benzyloxy, methyl, 1,3-dimethylpyrrolidin-3-yl, 1,1-dioxothiomorpholin-4-yl, trifluoromethyl, 1-methylazetidin-3-yl, 1-ethylpiperidin-3-yl, methoxy, methylamino, amino, diethylamino, 5-cyano-1H-indol-3-yl and hydroxy. Further specific R³ groups are 1-methyl-1H-indol-3-yl, 6-fluoro-1H-indol-3-yl, 5-chloro-1H-indol-3-yl, 1H-indol-2-yl, 5-hydroxy-1H-indol-3-yl, 1,4'-piperidinespiro-3,4-dihydroisochromen-3-yl, 2,4-piperidinespiro-3,4-dihydrochromen-4-yl, 5-chloro-1H-benzimidazol-2-yl, 2-oxo-1,3-benzoxazol-3(2H)-yl, 2H-indazol-2-yl, 1,4'-piperidinespiro-2,3-dihydroinden-3-yl, 2-oxo-1,2,3,4-tetrahydroquinolin-4-yl, 5-chloro-1H-indazol-3-yl, 2-ethyl-5-methyl-1H-indol-3-yl, 2-ethyl-6-methyl-1H-indol-3-yl, 2-methyl-5-nitro-1H-indol-3-yl, 5-methoxy-2-methyl-1H-inden-3-yl, 5-hydroxy-2-methyl-1H-indol-3-yl, 5-methoxy-1H-benzimidazol-2-yl, 2,5-dimethyl-1H-indol-3-yl, 1H-benzimidazol-2-yl, 6-methoxy-1H-indol-3-yl, 1H-indol-6-yl, 2-methyl-1,3-benzothiazol-5-yl, 5-methoxy-2-oxo-1,3-benzoxazol-3(2H)-yl, 7-methoxy-1H-indol-3-yl, 1,3-benzothiazol-2-yl, 7-fluoro-2-methyl-1H-indol-3-yl, 5-ethyl-2-methyl-1H-indol-3-yl, 5-tert-butyl-2-methyl-1H-indol-3-yl, 5-ethoxy-2-methyl-1H-indol-3-yl, 5-(benzyloxy)-2-methyl-1H-indol-3-yl, 1H-indol-1-yl, 2-oxo-1,3-benzothiazol-3(2H)-yl, quinolin-5-yl, 6-fluoro-1H-benzimidazol-2-yl, 5,6,7,8-tetrahydronaphthalen-1-yl, 3-methyl-5,6,7,8-tetrahydro-1,8-naphthyridin-2-yl, imidazo[2,1-b][1,3]thiazol-6-yl, 1-benzofuran-5-yl, 1-benzothien-2-yl, 1,8-naphthyridin-2-yl, 1,2,3,4-tetrahydro-1,8-naphthyridin-7-yl, 4,5,6,7-tetrahydro-1H-indazol-3-yl, 4,5,6,7-tetrahydro-1-benzothien-3-yl, 1-oxo-1,3-dihydro-2H-isoindol-2-yl, 2-[2-(dimethylamino)ethyl]-3-oxo-2,3-dihydro-1H-isoindol-4-yl, 6-benzyl-2-oxo-1,2,5,6,7,8-hexahydro-1,6-naphthyridin-3-yl, 6,7,8,9-tetrahydropyrido[2,3-b]-1,6-naphthyridin-7-yl, 2-acetyl-1,2,3,4-tetrahydroisoquinolin-1-yl, 2-methyl-1,2,3,4-tetrahydroisoquinolin-3-yl, 1,2,3,4-tetrahydroisoquinolin-2-yl, 1-(2-tert-butoxy-2-oxoethyl)-5-methoxy-2-methyl-1H-indol-3-yl, 5-methoxy-2-methyl-1-(pyridin-3-ylmethyl)-1H-indol-3-yl, 5-methoxy-1,2-dimethyl-1H-indol-3-yl, 5-methoxy-2-methyl-1-(2-pyrrolidin-1-ylethyl)-1H-indol-3-yl, 5-methoxy-2-methyl-1-(2-morpholin-4-ylethyl)-1H-indol-3-yl, 5-methyl-1,2-benzisoxazol-3-yl, 5-(dimethylamino)-2-methyl-1H-indol-3-yl, 6-methoxy-1-benzofuran-3-yl, quinolin-6-yl, isoquinolin-6-yl, 5-methyl-4,5,6,7-tetrahydro-3H-imidazo[4,5-c]pyridin-6-yl, 5-methyl-1-benzothien-3-yl, 1-(carboxymethyl)-5-methoxy-2-methyl-1H-indol-3-yl, 5-methoxy-2-methyl-1-[2-(1-methylpiperazin-4-yl)-2-oxoethyl]-1H-indol-3-yl, 7-methyl-5,6,7,8-tetrahydroimidaz[1,2-a]pyrazin-2-yl, 5-[(dimethylamino)methyl]-2-methyl-1H-indol-3-yl, 4,5,6,7-tetrafluoro-1H-indol-3-yl, 5-fluoro-2-methyl-1H-indol-3-yl, 1H-pyrrolo[2,3-b]pyridin-3-yl, 1H-pyrrolo[3,2-c]pyridin-3-yl, 5-methoxy-1H-pyrrolo[2,3-c]pyridin-3-yl, 2-methyl-1,2,3,4-tetrahydroisoquinolin-1-yl, 1H-imidazol-1-yl, 4-acetylpiperazin-1-yl, 1-(N,N-dimethylglycyl)azetidin-3-yl, 1-(2-methoxyethyl)azetidin-3-yl, 3-methoxyazetidin-1-yl and 1-azoniabicyclo[2.2.2]octan-3-yl.

In an embodiment R³ is azoniabicyclo[2.2.1]heptanyl, azoniabicyclo[2.2.2]octanyl, thiazolyl, pyrazolyl, isoxazolyl, thiadiazolyl, benzothienyl, benzothiadiazolyl, benzoxadiazolyl, dihydrobenzofuryl, dihydrothiazolopyrimidinyl, dihydrobenzodioxinyl, dihydrobenzoxazinyl, benzimidazolyl, triazolopyrimidinyl, dihydrobenzoxazolyl, dihydroindolyl, dihydroquinazolinyl, dihydrophthalazinyl, indazolyl, benzisoxazolyl, benzotriazolyl, tetrahydrobetacarbolinyl, dihydroisoindolyl, tetrahydronaphthyridinyl, tetrazolyl, thiomorpholinyl, azetidinyl, dihydroisochromenyl, dihydrochromenyl, tetrahydroquinolinyl, indenyl, dihydrobenzothiazolyl, imidazothiazolyl, naphthyridinyl, tetrahydroindazolyl, tetrahydrobenzothienyl, hexahydronaphthyridinyl, tetrahydropyridonaphthyridinyl, tetrahydroisoquinolinyl, tetrahydroimidazopyridinyl, tetrahydroimidazopyrazinyl or pyrrolopyridinyl; any of which rings being optionally substituted by one or more groups independently chosen from $(CH_2)_m(CO)_nR^d$.

Particular preferred R³ groups azoniabicyclo[2.2.1]heptanyl, thiazolyl, dimethylthiazolyl, (acetylamino)(methyl)thiazolyl, trimethylpyrazolyl, dimethylisoxazolyl, methylthiadiazolyl, benzothienyl, benzothiadiazolyl, benzoxadiazolyl, dihydrobenzofuranyl, dihydrothiazolopyrimidinyl, dihydrobenzodioxinyl, (methyl)dihydrobenzoxazinyl, azoniabicyclo[2.2.2]octanyl, benzimidazolyl, triazolopyrimidinyl, phenylthiazolyl, chlorobenzothienyl, oxodihydrobenzoxazolyl, methoxyoxodihydroindolyl, ethylbenzimidazolyl, oxodihydroquinazolinyl, methyloxodihydrophthalazinyl, methylbenzimidazolyl, (trifluoromethyl)benzimidazolyl, indazolyl, benzisoxazolyl, benzotriazolyl, tetrahydrobetacarbolinyl, dihydroisoindolyl, tetrahydronaphthyridinyl, pyrrolidinyltetrazolyl, dioxothiomorpholinyl, methylazetidinyl, (piperidinespiro)dihydroisochromenyl, (piperidinspiro)dihydrochromenyl, chlorobenzimidazolyl, (oxo)dihydrobenzoxazolyl, (oxo)tetrahydroquinolinyl, chloroindazolyl, (methoxy)(methyl)indenyl, methoxybenzimidazolyl, (methoxy)(oxo)dihydrobenzoxazolyl, (oxo)dihydrobenzothiazolyl, fluorobenzimidazolyl, (methyl)tetrahydronaphthyridinyl, imidazothiazolyl, naphthyridinyl, tetrahydroindazolyl, tetrahydrobenzothienyl, (oxo)dihydroisoindolyl, [(dimethylamino)ethyl]dihydroisoindolyl, (benzyl)(oxo)hexahydronaphthyridinyl, tetrahydropyridonaphthyridinyl, (acetyl)tetrahydroisoquinolinyl, (methyl)tetrahydroisoquinolinyl, tetrahydroisoquinolinyl, methylbenzisoxazolyl, (methyl)tetrahydroimidazopyridinyl, methylbenzothienyl, (methyl)tetrahydroimidazopyrazinyl, pyrrolopyridinyl, (methoxy)pyrrolopyridinyl, (dimethylglycyl)azetidinyl, (methoxyethyl)azetidinyl and methoxyazetidinyl.

In an embodiment, $R^3$ is azoniabicyclo[2.2.1]heptan-2-yl, 1,3-thiazol-5-yl, 2,4-dimethyl-1,3-thiazol-5-yl, 2-(acetylamino)-4-methyl-1,3-thiazol-5-yl, 1,3,5-trimethyl-1H-pyrazol-4-yl, 3,5-dimethylisoxazol-4-yl, 4-methyl-1,2,3-thiadiazol-5-yl, benzothien-3-yl, 2,1,3-benzothiadiazol-5-yl, 2,1,3-benzoxadiazol-4-yl, 2,3-dihydro-1-benzofuran-5-yl, 6,7-dihydro-5H-[1,3]thiazolo[3,2-a]pyrimidin-3-yl, 2,3-dihydro-1,4-benzodioxin-6-yl, 4-methyl-3,4-dihydro-2H-1,4-benzoxazin-7-yl, azoniabicyclo[2.2.2]octan-4-yl, 1H-benzimidazol-1-yl, [1,2,4]triazolo[1,5-a]pyrimidin-6-yl, 4-phenyl-1,3-thiazol-2-yl, 5-chloro-1-benzothien-3-yl, 2-oxo-1,3-benzoxazol-3(2H)-yl, 5-methoxy-2-oxo-2,3-dihydro-1H-indol-3-yl, 6-methoxy-2-oxo-2,3-dihydro-1H-indol-3-yl, 2-ethyl-1H-benzimidazol-1-yl, 2-oxoquinazolin-1-(2H)-yl, 4-methyl-1-oxophthalazin-2(1H)-yl, 2-methyl-1H-benzimidazol-1-yl, 2-(trifluoromethyl)-1H-benzimidazol-1-yl, 1H-indazol-1-yl, 1,2-benzisoxazol-3-yl, 1H-1,2,3-benzotriazol-1-yl, 2,3,4,9-tetrahydro-1H-beta-carbolin-4-yl, 2,3-dihydro-1H-isoindol-2-yl, 1,2,3,4-tetrahydro-1,8-naphthyridin-5-yl, 5-pyrrolidin-1-yl-2H-tetrazol-2-yl, 1,1-dioxothiomorpholin-4-yl, 1-methylazetidin-3-yl, 1,4'-piperidinespiro-3,4-dihydroisochromen-3-yl, 2,4-piperidinespiro-3,4-dihydrochromen-4-yl, 5-chloro-1H-benzimidazol-3-yl, 2-oxo-1,3-benzoxazol-3(2H)-yl, 2H-indazol-2-yl, 1,4'-piperidinespiro-2,3-dihydroinden-3-yl, 2-oxo-1,2,3,4-tetrahydroquinolin-4-yl, 5-chloro-1H-indazol-3-yl, 5-methoxy-2-methyl-1H-inden-3-yl, 5-methoxy-1H-benzimidazol-2-yl, 1H-benzimidazol-2-yl, 5-methoxy-2-oxo-1,3-benzoxazol-3(2H)-yl, 2-oxo-1,3-benzothiazol-3(2H)-yl, 6-fluoro-1H-benzimidazol-2-yl, 5,6,7,8-tetrahydronaphthalen-1-yl, 3-methyl-5,6,7,8-tetrahydro-1,8-naphthyridin-2-yl, imidazo[2,1-b][1,3]thiazol-6-yl, 1-benzothien-2-yl, 1,8-naphthyridin-2-yl, 1,2,3,4-tetrahydro-1,8-naphthyridin-7-yl, 4,5,6,7-tetrahydro-1H-indazol-3-yl, 4,5,6,7-tetrahydro-1-benzothien-3-yl, 1-oxo-1,3-dihydro-2H-isoindol-2-yl, 2-[2-(dimethylamino)ethyl]-3-oxo-2,3-dihydro-1H-isoindol-4-yl, 6-benzyl-2-oxo-1,2,5,6,7,8-hexahydro-1,6-naphthyridin-3-yl, 6,7,8,9-tetrahydropyrido[2,3-b]-1,6-naphthyridin-7-yl, 2-acetyl-1,2,3,4-tetrahydroisoquinolin-1-yl, 2-methyl-1,2,3,4-tetrahydroisoquinolin-3-yl, 1,2,3,4-tetrahydroisoquinolin-2-yl, 5-methyl-1,2-benzisoxazol-3-yl, 5-methyl-4,5,6,7-tetrahydro-3H-imidazo[4,5-c]pyridin-6-yl, 5-methyl-1-benzothien-3-yl, 7-methyl-5,6,7,8-tetrahydroimidazo[1,2-a]pyrazin-2-yl, 1H-pyrrolo[2,3-b]pyridin-3-yl, 1H-pyrrolo[3,2-c]pyridin-3-yl, 5-methoxy-1H-pyrrolo[2,3-c]pyridin-3-yl, 2-methyl-1,2,3,4-tetrahydroisoquinolin-1-yl, 1-(N,N-dimethylglycyl)azetidin-3-yl, 1-(2-methoxyethyl)azetidin-3-yl, 3-methoxyazetidin-1-yl or 1-azoniabicyclo[2.2.2]octan-3-yl.

In an embodiment, $R^3$ is azetidinyl, optionally substituted by one or more groups independently chosen from $(CH_2)_m(CO)_nR^d$. Preferably, the optional substituent is $C_{1-6}$alkyl, especially methyl.

In an embodiment, $R^3$ is 1-methylazetidin-3-yl, 1-(N,N-dimethylglycyl)azetidin-3-yl, 1-(2-methoxyethyl)azetidin-3-yl or 3-methoxyazetidin-1-yl.

In an embodiment, $R^3$ is 1-methylazetidin-3-yl.

$R^4$ is preferably hydrogen.

$R^5$ is preferably $C_{1-6}$alkyl, especially methyl. A further preferred $R^5$ group is hydrogen.

Preferably, $R^6$ and $R^8$ are independently hydrogen, $C_{1-6}$alkyl or an optionally substituted 5 or 6 membered saturated or partially saturated heterocycle containing 1, 2 or 3 heteroatoms independently selected from N, O and S; or $R^6$ and $R^8$ together form an oxo group.

More particularly, $R^6$ is hydrogen, $C_{1-4}$alkyl or morpholinyl and $R^8$ is hydrogen or $C_{1-4}$alkyl; or $R^6$ and $R^8$ together form an oxo group.

Specifically, $R^6$ is hydrogen, methyl or morpholin-4-yl and $R^8$ is hydrogen or methyl; or $R^6$ and $R^8$ together form an oxo group.

In one embodiment, $R^6$ is hydrogen, $C_{1-6}$alkyl or a 5 or 6 membered saturated or partially saturated heterocycle containing 1, 2 or 3 heteroatoms independently selected from N, O or S, optionally substituted by $C_{1-6}$alkyl.

Particular $R^6$ groups include hydrogen, methyl and morpholinyl. Most preferably $R^6$ is hydrogen, methyl or morpholin-4-yl.

In one embodiment $R^6$ is hydrogen.

$R^8$ is preferably hydrogen or $C_{1-6}$alkyl. More particularly, $R^8$ is hydrogen or methyl.

In one embodiment $R^8$ is hydrogen.

In an embodiment, $R^6$ and $R^8$ together form an oxo group.

In an embodiment $R^a$ is hydrogen, $C_{1-6}$alkyl or $C_{1-6}$alkylcarbonyl. Preferably, $R^a$ is hydrogen, methyl or acetyl.

In an embodiment $R^c$ is hydrogen or methyl.

In an embodiment $R^e$ is hydrogen, $C_{1-6}$alkyl or $C_{1-6}$alkylcarbonyl. Preferably, $R^e$ is hydrogen, methyl or acetyl.

In an embodiment $R^h$ is hydrogen, $C_{1-6}$alkyl or $C_{6-10}$aryl$C_{1-6}$alkyl. Preferably, $R^h$ is methyl or benzyl.

In an embodiment $R^k$ is $NHSO_2R^g$, pyrazolyl, piperidinyl, morpholinyl or tetrazolyl, any of which rings being optionally substituted by $C_{1-6}$alkyl, especially methyl. Preferably, $R^k$ is dimethylpyrazolyl, piperidinyl, morpholinyl, pyrazolyl, tetrazolyl or (methylsulfonyl)amino.

Preferably, the α1 carbon asymmetric center of the compounds of the present invention has the stereochemical configuration of S. In one embodiment the α1 carbon asymmetric center has the stereochemical configuration of R.

The present invention also provides compounds of formula II:

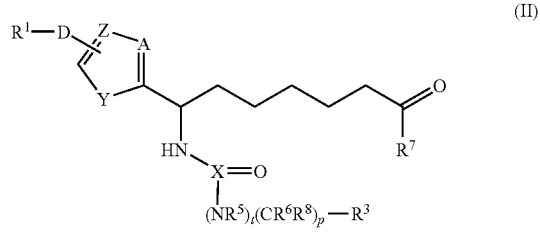

(II)

wherein:

$R^1$, $R^3$, $R^5$, $R^6$, $R^8$, X, p and t are as defined for formula I;

D is absent, $CH_2$, $CH_2CH_2$ or $CH=CH$;

A represents CH or N;

Y represents $NR^e$, O or S;

Z represents N or CRC;

$R^7$ represents $C_{1-6}$alkyl, halo$C_{1-6}$alkyl, hydroxy, $N(R^b)_2$, hydroxy$C_{1-6}$alkyl, $C_{1-6}$alkoxy, $C_{3-7}$cycloalkyl, $C_{1-6}$alkylS$(O)_mR^g$, thienyl, furyl or pyridinyl;

$R^b$ represents hydrogen, $C_{1-4}$alkyl, hydroxy, $C_{1-4}$alkoxy, $C_{1-6}$alkylS$(O)_wR^g$, $SO_2R^g$, phenyl, benzyl, thiazolyl or thiadiazolyl, any of which rings being optionally substituted by amino;

$R^e$ represents hydrogen or $C_{1-6}$alkyl;

$R^f$ represents hydrogen, $C_{1-6}$alkyl or $C_{6-10}$aryl optionally substituted by up to two groups selected from halogen, cyano, $C_{1-6}$alkyl, $C_{1-6}$alkoxy, halo$C_{1-6}$alkyl or halo$C_{1-6}$alkoxy;

$R^g$ is $C_{1-6}$alkyl, halo$C_{1-6}$alkyl, amino, $C_{1-6}$alkylamino or di($C_{1-6}$alkyl)amino;

w is 0, 1 or 2;

or a pharmaceutically acceptable salt or tautomer thereof.

In one embodiment:

D is absent;

$R^7$ is $C_{1-6}$alkyl, halo$C_{1-6}$alkyl, hydroxy, or $N(R^b)_2$;

$R^b$ is hydrogen, $C_{1-4}$alkyl, hydroxy, $C_{1-4}$alkoxy, $SO_2R^g$, phenyl, benzyl, thiazolyl or thiadiazolyl, any of which rings being optionally substituted by amino;

$R^1$ is $C_{1-6}$alkyl or halo$C_{1-6}$alkyl;

or a pharmaceutically acceptable salt or tautomer thereof.

In an embodiment of the previous embodiment:

$R^7$ is $C_{1-6}$alkyl, hydroxy or $N(R^b)_2$;

$R^8$ is hydrogen; and $R^b$ is hydrogen, $C_{1-4}$alkyl, hydroxy or phenyl optionally substituted by amino.

A favoured class of compounds of the present invention have the stereochemical configuration of formula III:

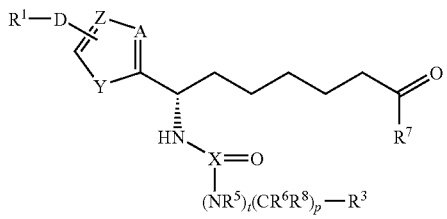

(III)

wherein $R^1$, $R^3$, $R^5$, $R^6$, $R^7$, $R^8$, A, D, X, Y, Z, p and t are as defined for formula II.

The preferred identities with reference to formula II and III are as defined previously mutatis mutandis.

In one embodiment:

D is absent;

$R^7$ is $C_{1-6}$alkyl, halo$C_{1-6}$alkyl, hydroxy, or $N(R^b)_2$;

$R^b$ is hydrogen, $C_{1-4}$alkyl, hydroxy, $C_{1-4}$alkoxy, $SO_2R^g$, phenyl, benzyl, thiazolyl or thiadiazolyl, any of which rings being optionally substituted by amino;

$R^g$ is $C_{1-6}$alkyl or halo$C_{1-6}$alkyl;

or a pharmaceutically acceptable salt or tautomer thereof.

In an embodiment of the previous embodiment:

$R^7$ is $C_{1-6}$alkyl, hydroxy or $N(R^b)_2$;

$R^8$ is hydrogen; and $R^b$ is hydrogen, $C_{1-4}$alkyl, hydroxy or phenyl optionally substituted by amino.

For the avoidance of doubt, $R^1$ may be attached to any substitutable position of the ring.

In one embodiment D is absent.

In one embodiment A is N, Y is $NR^e$ or O and Z is N or $CR^f$.

In another embodiment A is N, Y is $NR^e$ and Z is $CR^f$.

In yet another embodiment A is CH, Y is S and Z is $CR^f$.

In another embodiment A and Z are both N and Y is $NR^e$.

In yet another embodiment Y is O.

$R^1$ is preferably phenyl, naphthyl, thienyl, isoxazolyl, pyridinyl, benzothienyl or thiazolotriazolyl, optionally substituted by one or two groups independently selected from cyano, bromine, chlorine, fluorine, methyl, trifluoromethyl, methoxy, difluoromethoxy or phenyl. Further preferred $R^1$ groups are hydrogen and optionally substituted dihydrobenzodioxinyl, benzothiazolyl, quinolinyl or isoquinolinyl. Further preferred $R^1$ groups include hydroxy, (benzyl)(methyl)amino, dimethylamino, methoxycarbonyl, acetyl, cyclohexyl, bromine and optionally substituted quinoxalinyl, morpholinyl, tetrahydroisoquinolinyl, indolyl, dibenzo[b,d]furanyl, naphthyridinyl or dihydroquinolinyl.

$R^3$ is preferably dimethylamino, phenyl, napthyl, pyrrolidinyl, piperidyl, azoniabicyclo[2.2.1]heptanyl, azoniabicyclo[2.2.2]octanyl, piperazinyl, morpholinyl, thienyl, thiazolyl, imidazolyl, pyrazolyl, isoxazolyl, thiadiazolyl, pyridinyl, indolyl, benzothienyl, benzothiadiazolyl, benzoxadiazolyl, dihydrobenzofuryl, dihydrothiazolopyrimidinyl, isoquinolyl, dihydrobenzodioxinyl and dihydrobenzoxazinyl, any of which rings being optionally substituted by one, two or three groups independently selected from chlorine, fluorine, methyl, isopropyl, cyano, methoxy, difluoromethoxy, carboxy, nitro, aminosulfonyl, acetylamino, methylpiperazinyl, pyridinyl, methylthiazolyl, (methyl)(trifluoromethyl)pyrazolyl, isoxazolyl, methoxycarbonyl and morpholinyl. Further optional substituents on the rings include bromo, phenyl, oxo, ethyl, trifluoromethyl and pyrrolidinyl. Further optional substituents on the rings include hydroxy, piperidinespiro, tert-butyl, ethoxy, benzyloxy, dimethylaminoethyl, benzyl, acetyl (tert-butoxycarbonyl)methyl, pyridinylmethyl, pyrrolidinylethyl, morpholinylethyl, dimethylamino, carboxymethyl, [(methylpiperazinyl)carbonyl]methyl, dimethylaminomethyl, (dimethylaminomethyl)carbonyl and methoxyethyl. Further preferred $R^3$ groups are tert-butoxy, cyclopentyl, methyl, trifluoromethyl, methoxy, methylamino, amino, diethylamino, hydroxy or an optionally substituted ring selected from benzimidazolyl, benzofuranyl, triazolopyrimidinyl, dihydrobenzoxazolyl, dihydroindolyl, dihydroquinazolinyl, dihydrophthalazinyl, indazolyl, quinolinyl, benzisoxazolyl, benzotriazolyl, tetrahydrobetacarbolinyl, dihydroisoindolyl, tetrahydronaphthyridinyl, tetrazolyl, benzyloxy, thiomorpholinyl and azetidinyl, the optional substituents defined above. Further preferred $R^3$ groups are optionally substituted rings selected from dihydroisochromenyl, dihydrochromenyl, dihydroindenyl, tetrahydroquinolinyl, indenyl, benzothiazolyl, dihydrobenzothiazolyl, tetrahydronaphthyl, imidazothiazolyl, naphthyridinyl, tetrahydroindazolyl, tetrahydrobenzothienyl, hexahydronaphthyridinyl, tetrahydropyridonaphthyridinyl, tetrahydroisoquinolinyl, tetrahydroimidazopyridinyl, tetrahydroimidazopyrazinyl and pyrrolopyridinyl, the optional substituents defined above.

$R^5$ is preferably methyl. A further preferred $R^5$ group is hydrogen.

$R^6$ is preferably hydrogen, methyl or morpholinyl.

$R^7$ is preferably methyl, ethyl, hydroxy or $N(R^b)_2$. A further preferred $R^7$ group is trifluoromethyl. Further preferred $R^7$ groups are butyl, propyl, isopropyl, (methyl)propyl, hydroxymethyl, methoxy, cyclopropyl, methylsulfinylmethyl, thienyl, methylsulfonylmethyl, pyridinyl, furyl and aminosulfonylmethyl.

In an embodiment $R^7$ is $C_{1-6}$alkyl.

In another embodiment $R^7$ is methyl or ethyl.

$R^b$ is preferably hydrogen, methyl, hydroxy or aminophenyl. Further preferred $R^b$ groups include ethyl, isopropyl, methoxy, methylsulfonyl, ethylsulfonyl, trifluoromethylsulfonyl, phenyl, benzyl, thiazolyl and thiadiazolyl. Further preferred $R^b$ groups are methylthioethyl and ethoxy.

Thus, particular preferred $R^7$ groups include methyl, ethyl, hydroxy, methylamino, hydroxyamino and (aminophenyl) amino. Further particular $R^7$ groups include trifluoromethyl, amino, dimethylamino, isopropylamino, phenylamino, benzylamino, methylsulfonylamino, methoxymethylamino, trifluoromethylsulfonylamino, ethylsulfonylamino, ethylamino, thiazolylamino and thiadiazolylamino. Further particular $R^7$ groups include butyl, propyl, (methylthio)ethylamino, methoxyamino, ethoxyamino, propyl, (methyl)propyl, hydroxymethyl, methoxy, cyclopropyl, methylsulfinylmethyl, thienyl, methylsulfonylmethyl, pyridinyl, furyl and aminosulfonylmethyl.

$R^e$ is preferably hydrogen or methyl.

$R^f$ is preferably hydrogen, $C_{1-6}$alkyl or $C_{6-10}$aryl. More particularly $R^f$ is hydrogen, methyl or phenyl. A further particular $R^f$ group is naphthyl, especially 2-naphthyl.

$R^g$ is preferably methyl, ethyl or trifluoromethyl. A further $R^g$ group is amino.

Preferably w is 1 or 2

The present invention also provides intermediates of compounds of formula I represented by formula IA:

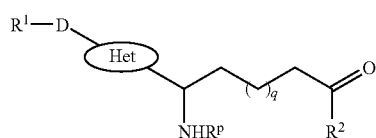

(IA)

wherein $R^p$ is $R^4$ or an appropriate protecting group such as Boc;

$R^1$, $R^2$, $R^4$, Het and q are as defined above;

or a pharmaceutically acceptable salt or tautomer thereof.

In one embodiment D is absent.

In one embodiment $R^p$ is hydrogen or Boc.

The preferred identities with reference to formula IA are as defined previously mutatis mutandis.

The present invention also provides compounds of formula IB:

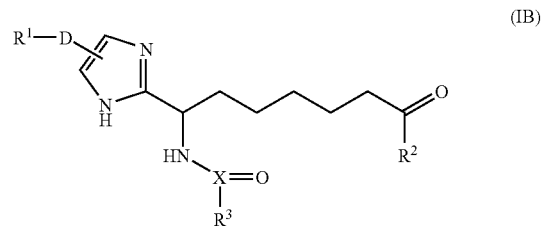

(IB)

wherein D, $R^2$ and X are as defined above for formula I;

$R^1$ is a 8-13 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkylN$(R^a)_2$ and $(CO)_d R^k$ wherein d is 0 or 1;

$R^k$ is $C_{1-6}$alkoxy, $NHSO_2 R^g$, 5 or 6 membered saturated or partially saturated heterocycle containing 1, 2 or 3 heteroatoms independently selected from N, O and S or a 5 membered unsaturated heterocycle containing 1, 2, 3 or 4 heteroatoms independently selected from N, O and S, but not more than one of which is O or S; any of which rings being optionally substituted by one or more groups independently selected from halogen and $C_{1-6}$alkyl;

$R^g$ is $C_{1-6}$alkyl, halo$C_{1-6}$alkyl, amino, $C_{1-6}$alkylamino or di($C_{1-6}$alkyl)amino;

$R^3$ is azoniabicyclo[2.2.1]heptanyl, azoniabicyclo[2.2.2] octanyl, thiazolyl, pyrazolyl, isoxazolyl, thiadiazolyl, benzothienyl, benzothiadiazolyl, benzoxadiazolyl, dihydrobenzofuryl, dihydrothiazolopyrimidinyl, dihydrobenzodioxinyl, dihydrobenzoxazinyl, benzimidazolyl, triazolopyrimidinyl, dihydrobenzoxazolyl, dihydroindolyl, dihydroquinazolinyl, dihydrophthalazinyl, indazolyl, benzisoxazolyl, benzotriazolyl, tetrahydrobetacarbolinyl, dihydroisoindolyl, tetrahydronaphthyridinyl, tetrazolyl, thiomorpholinyl, azetidinyl, dihydroisochromenyl, dihydrochromenyl, tetrahydroquinolinyl, dihydrobenzothiazolyl, imidazothiazolyl, naphthyridinyl, tetrahydroindazolyl, tetrahydrobenzothienyl, hexahydronaphthyridinyl, tetrahydropyridonaphthyridinyl, tetrahydroisoquinolinyl, tetrahydroimidazopyridinyl, tetrahydroimidazopyrazinyl or pyrrolopyridinyl; any of which rings being optionally substituted by one or more groups independently chosen from $(CH_2)_m(CO)_n R^d$;

m is 0, 1, 2 or 3;

n is 0, 1 or 2; and $R^d$ is halogen, cyano, $C_{1-6}$alkyl, $C_{1-6}$alkoxy, halo$C_{1-6}$ alkoxy, carboxy, $C_{1-6}$alkoxycarbonyl, nitro, aminosulfonyl, ($C_{1-6}$alkylcarbonyl)amino, morpholinyl, piperazinyl, thiazolyl, pyrazolyl, isoxazolyl, pyridinyl, oxo, halo$C_{1-6}$alkyl, phenyl or pyrrolidinyl, hydroxy, piperidinespiro, $C_{6-10}$aryl$C_{1-6}$alkoxy, di($C_{1-6}$alkyl)amino, $C_{1-6}$alkylcarbonyl or di($C_{1-6}$alkylamino$C_{1-6}$alkyl; any of which rings being optionally substituted by one or more groups independently chosen from $C_{1-6}$alkyl and halo$C_{1-6}$alkyl;

or a pharmaceutically acceptable salt or tautomer thereof.

The preferred identities with reference to formula IIB are the previously defined embodiments for formulae I, II and III, which fall within the scope of formula IB.

In an embodiment, $R^1$ is an optionally substituted 8-13 membered unsaturated or partially saturated heterocycle containing 1, 2, 3 or 4 heteroatoms independently selected from O, N and S.

In an embodiment:

$R^1$ is an optionally substituted benzothienyl, thiazolotriazolyl, dihydrobenzodioxinyl, benzothiazolyl, quinolinyl, isoquinolinyl, quinoxalinyl, tetrahydroisoquinolinyl, indonyl, dibenzo[b,d]furanyl, naphthyridinyl or dihydroquinolinyl; and $R^3$ is an optionally substituted azetidinyl.

In an embodiment:

$R^1$ is an optionally substituted quinolinyl, isoquinolinyl, quinoxalinyl, tetrahydroisoquinolinyl, naphthyridinyl or dihydroquinolinyl; and $R^3$ is an optionally substituted azetidinyl In an embodiment:

$R^1$ is 2-methoxyquinolin-3-yl; and $R^3$ is 1-methylazetidin-3-yl.

Preferably $R^2$ is $C_{1-6}$alkyl, especially methyl or ethyl.

Preferably D is a direct bond.

Preferably X is C.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

The compounds may exist in different isomeric forms, all of which are encompassed by the present invention.

When any variable (e.g. $R^1$ and $R^2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched and straight-chain saturated aliphatic hydrocarbon groups having the specified number of carbon atoms. For example, "$C_1$-$C_6$ alkyl" is defined to include groups having 1, 2, 3, 4, 5 or 6 carbons in a linear or branched arrangement. For example, "$C_1$-$C_6$ alkyl" specifically includes methyl, ethyl, n-propyl, i-propyl, n-butyl, t-butyl, i-butyl, pentyl, hexyl, and so on. The preferred alkyl group is methyl. The term "cycloalkyl" means a monocyclic, bicyclic or polycyclic saturated aliphatic hydrocarbon group having the specified number of carbon atoms. For example, "$C_{7-10}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

"Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy and t-butoxy. The preferred alkoxy group is methoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

The term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. The straight or branched portion of the alkenyl group may contain double bonds and may be substituted if a substituted alkenyl group is indicated. Preferred alkenyl groups include ethenyl and propenyl.

The term "$C_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. The straight or branched portion of the alkynyl group may contain triple bonds and may be substituted if a substituted alkynyl group is indicated. Preferred alkynyl groups include ethynyl and propynyl.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl, tetrahydrobenzo[7]annulene, indenyl and tetrahydroindenyl. The preferred aryl group is phenyl or naphthyl, especially phenyl.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furanyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydroisochromenyl, dihydroimidazolonyl, dihydrotriazolonyl, dihydrobenzodioxinyl, dihydrothiazolopyrimidinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, quinazolinyl, pteridinyl and N-oxides thereof. Further particular heterocycles include dihydroquinazolinyl, dihydrophthalazinyl, dihydroisoindolyl, tetrahydronaphthyridinyl, tetrahydrobetacarbolinyl and N-oxides thereof. Further particular heterocycles include dibenzofuranyl, naphthyridinyl, dihydrochromenyl, dihydrobenzothiazolyl, imidazothiazolyl, tetrahydroindazolyl, tetrahydrobenzothienyl, hexahydronaphthyridinyl, tetrahydropyridonaphthyridinyl, tetrahydroimidazopyridinyl, tetrahydroimidazopyrazinyl, pyrrolopyridinyl and N-oxides thereof. Attachment of a heterocyclyl substituent can occur via a carbon atom or via a heteroatom.

A preferred 4 membered saturated heterocycle is azetidinyl.

Preferred 5 or 6 membered saturated or partially saturated heterocycles are pyrrolidinyl, piperidyl, piperazinyl, morpholinyl, azoniabicyclo[2.2.1]heptanyl and azoniabicyclo[2.2.2]octanyl. A further preferred heterocycle is thiomorpholinyl.

Preferred 5 membered unsaturated heterocycles are thienyl, thiazolyl, pyrazolyl, isoxazolyl, imidazolyl, thiadiazolyl, oxazolyl and triazolyl. Further preferred heterocycles are tetrazolyl, furyl and oxadiazolyl.

A preferred 6 membered unsaturated heterocycle is pyridinyl.

Preferred 8-10 membered saturated, partially saturated or unsaturated heterocycles are benzothienyl, isoquinolyl, indolyl, benzothiadiazolyl, benzoxadiazolyl, thiazolotriazolyl, dihydrobenzodioxinyl, dihydrothiazolopyrimidinyl, dihydrobenzoxazinyl and dihydrobenzofuranyl. Further preferred heterocycles are benzothiazolyl, quinolinyl, isoquinolinyl, benzimidazolyl, benzofuranyl, dihydrobenzoxazolyl, dihydroindolyl, dihydroquinazolinyl, dihydrophthalazinyl, indazolyl, benzisoxazolyl, benzotriazolyl, dihydroisoindolyl, tetrahydronaphthyridinyl and triazolopyrimidinyl. Further preferred heterocycles are quinoxalinyl, tetrahydroisoquinolinyl, dibenzo[b,d]furanyl, naphthyridinyl, dihydroquinolinyl, dihydroisochromenyl, dihydrochromenyl, tetrahydroquinolinyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl and pyrrolopyridinyl.

A preferred 13 membered partially saturated heterocycle is tetrahydrobetacarbolinyl.

A preferred 14 membered partially saturated heterocycle is tetrahydropyridonaphthyridinyl.

Preferred 6-13 membered partially saturated hydrocarbon groups are tetrahydronaphthyl and dihydroindenyl.

As used herein, the term 'halogen' refers to fluorine, chlorine, bromine and iodine, of which fluorine, chlorine and bromine are preferred.

Particular compounds within the scope of the present invention include:

1-methyl-3-({[(1S)-7-oxo-1-(5-phenyl-1H-imidazol-1-ium-2-yl)octyl]amino}carbonyl)piperidinium bis(trifluoroacetate);

2-((1S)-1-{[(4-methoxyphenyl)sulfonyl]amino}-7-oxooctyl)-5-phenyl-1H-imidazol-1-ium trifluoroacetate;

2-[(1S)-1-({[[2-(dimethylammonio)ethyl](methyl)amino]sulfonyl}amino)-7-oxooctyl]-5-phenyl-1H-imidazol-1-ium bis(trifluoroacetate);

2-((1S)-1-{[(5-methoxy-2-methyl-1H-indol-3-yl)acetyl]amino}-7-oxooctyl)-5-phenyl-1H-imidazol-1-ium trifluoroacetate;

1-methyl-4-(2-oxo-2-{[(1S)-7-oxo-1-(5-phenyl-1H-imidazol-1-ium-2-yl)octyl]amino}ethyl)piperazinedium tris(trifluoroacetate);

1-methyl-2-({[(1S)-7-oxo-1-(5-phenyl-1H-imidazol-1-ium-2-yl)octyl]amino}carbonyl)piperidinium bis(trifluoroacetate);

1-(3-oxo-3-{[(1S)-7-oxo-1-(5-phenyl-1H-imidazol-1-ium-2-yl)octyl]amino}propyl)piperidinium bis(trifluoroacetate);

2-((1S)-1-{[(1-methylpyrrolidinium-3-yl)carbonyl]amino}-7-oxooctyl)-5-phenyl-1H-imidazol-1-ium bis(trifluoroacetate);

1-methyl-4-({[(1S)-7-oxo-1-(5-phenyl-1H-imidazol-1-ium-2-yl)octyl]amino}carbonyl)piperidinium bis(trifluoroacetate);

2-{(1S)-7-oxo-1-[(2-thienylcarbonyl)amino]octyl}-5-phenyl-1H-imidazol-1-ium trifluoroacetate;

2-{(1S)-7-oxo-1-[(1,3-thiazol-5-ylcarbonyl)amino]octyl}-5-phenyl-1H-imidazol-1-ium trifluoroacetate;

2-((1S)-1-{[(4-methyl-1,2,3-thiadiazol-5-yl)carbonyl]amino}-7-oxooctyl)-5-phenyl-1H-imidazol-1-ium trifluoroacetate;

2-{(1S)-1-[(2,3-dihydro-1,4-benzodioxin-6-ylsulfonyl)amino]-7-oxooctyl}-5-phenyl-1H-imidazol-1-ium trifluoroacetate;

2-(1-{[(5-methoxy-2-methyl-1H-indol-3-yl)acetyl]amino}-7-oxooctyl)-5-phenyl-1H-imidazol-1-ium trifluoroacetate;

2-((1S)-1-{[(4-cyanophenyl)sulfonyl]amino}-7-oxooctyl)-5-phenyl-1H-imidazol-1-ium trifluoroacetate;

2-{(1S)-1-[(2-naphthylsulfonyl)amino]-7-oxooctyl}-5-phenyl-1H-imidazol-1-ium trifluoroacetate;

2-((1S)-1-{[(2,4-dimethyl-1,3-thiazol-5-yl)sulfonyl]amino}-7-oxooctyl)-5-phenyl-1H-imidazol-1-ium trifluoroacetate;

2-{(1S)-1-[(1-benzothien-3-ylsulfonyl)amino]-7-oxooctyl}-5-phenyl-1H-imidazol-1-ium trifluoroacetate;

2-((1S)-1-{[(4-chlorophenyl)sulfonyl]amino}-7-oxooctyl)-5-phenyl-1H-imidazol-1-ium trifluoroacetate;

2-((1S)-1-{[(3-methoxyphenyl)sulfonyl]amino}-7-oxooctyl)-5-phenyl-1H-imidazol-1-ium trifluoroacetate;

1,2-dimethyl-4-({[(1S)-7-oxo-1-(5-phenyl-1H-imidazol-1-ium-2-yl)octyl]amino}sulfonyl)-1H-imidazol-1-ium bis(trifluoroacetate);

2-((1S)-1-{[(3,5-dimethylisoxazol-4-yl)sulfonyl]amino}-7-oxooctyl)-5-phenyl-1H-imidazol-1-ium trifluoroacetate;

4-[({1-[5-(2-methoxyphenyl)-1H-imidazol-1-ium-2-yl]-7-oxooctyl}amino)carbonyl]-1-methylpiperidinium bis(trifluoroacetate);

4-[({1-[5-(3-methoxyphenyl)-1H-imidazol-1-ium-2-yl]-7-oxooctyl}amino)carbonyl]-1-methylpiperidinium bis(trifluoroacetate);

4-[({1-[5-(4-fluorophenyl)-1H-imidazol-1-ium-2-yl]-7-oxooctyl}amino)carbonyl]-1-methylpiperidinium bis(trifluoroacetate);

4-[({1-[5-(4-chlorophenyl)-1H-imidazol-1-ium-2-yl]-7-oxooctyl}amino)carbonyl]-1-methylpiperidinium bis(trifluoroacetate);

4-[({1-[5-(4-bromophenyl)-1H-imidazol-1-ium-2-yl]-7-oxooctyl}amino)carbonyl]-1-methylpiperidinium bis(trifluoroacetate);

4-[({1-[5-(2-chlorophenyl)-1H-imidazol-1-ium-2-yl]-7-oxooctyl}amino)carbonyl]-1-methylpiperidinium bis(trifluoroacetate);

4-[({1-[5-(3,4-dichlorophenyl)-1H-imidazol-1-ium-2-yl]-7-oxooctyl}amino)carbonyl]-1-methylpiperidinium bis(trifluoroacetate);

4-[({1-[5-(4-cyanophenyl)-1H-imidazol-1-ium-2-yl]-7-oxooctyl}amino)carbonyl]-1-methylpiperidinium bis(trifluoroacetate);

4-[({1-[5-(3-cyanophenyl)-1H-imidazol-1-ium-2-yl]-7-oxooctyl}amino)carbonyl]-1-methylpiperidinium bis(trifluoroacetate);

4-({[1-(4,5-diphenyl-1H-imidazol-1-ium-2-yl)-7-oxooctyl]amino}carbonyl)-1-methylpiperidinium bis(trifluoroacetate);

4-({[1-(4,5-diphenyl-1,3-oxazol-2-yl)-7-oxooctyl]amino}carbonyl)-1-methylpiperidinium trifluoroacetate;

2-((1S)-1-{[(5-methoxy-2-methyl-1H-indol-3-yl)acetyl]amino}-7-oxooctyl)-5-phenyl-1H-imidazol-1-ium chloride;

1-methyl-4-({[(1S)-7-oxo-1-(5-phenyl-1H-imidazol-1-ium-2-yl)octyl]amino}carbonyl)piperidinium dichloride;

1-methyl-4-[4-({[(1S)-7-oxo-1-(5-phenyl-1H-imidazol-1-ium-2-yl)octyl]amino}carbonyl)phenyl]piperazinedium tris(trifluoroacetate);

3-({[(1S)-7-oxo-1-(5-phenyl-1H-imidazol-1-ium-2-yl)octyl]amino}carbonyl)-1-pyridin-2-ylpiperidinium bis(trifluoroacetate);

3-(2-oxo-2-{[(1S)-7-oxo-1-(5-phenyl-1H-imidazol-1-ium-2-yl)octyl]amino}ethyl)-6,7-dihydro-5H-[1,3]thiazolo[3,2-a]pyrimidin-4-ium bis(trifluoroacetate);

2-(3-oxo-3-{[(1S)-7-oxo-1-(5-phenyl-1H-imidazol-1-ium-2-yl)octyl]amino}propyl)-2-azoniabicyclo[2.2.1]heptane bis(trifluoroacetate);

4-(2-oxo-2-{[(1S)-7-oxo-1-(5-phenyl-1H-imidazol-1-ium-2-yl)octyl]amino}-1-pyridinium-3-ylethyl)morpholin-4-ium tris(trifluoroacetate);

1-methyl-4-({[(1S)-1-(4-methyl-5-phenyl-1H-imidazol-1-ium-2-yl)-7-oxooctyl]amino}carbonyl)piperidinium bis(trifluoroacetate);

4-({[(1S)-1-(5-biphenyl-4-yl-1H-imidazol-1-ium-2-yl)-7-oxooctyl]amino}carbonyl)-1-methylpiperidinium bis(trifluoroacetate);

1-methyl-4-[({(1S)-1-[5-(2-naphthyl)-1H-imidazol-1-ium-2-yl]-7-oxooctyl}amino)carbonyl]piperidinium bis(trifluoroacetate);

4-[({(1S)-1-[5-(3-chlorophenyl)-1H-imidazol-1-ium-2-yl]-7-oxooctyl}amino)carbonyl]-1-methylpiperidinium bis(trifluoroacetate);

4-{[((1S)-1-{5-[3,5-bis(trifluoromethyl)phenyl]-1H-imidazol-1-ium-2-yl}-7-oxooctyl)amino]carbonyl}-1-methylpiperidinium bis(trifluoroacetate);

1-methyl-4-{[((1S)-7-oxo-1-{5-[3-(trifluoromethyl)phenyl]-1H-imidazol-1-ium-2-yl}octyl)amino]carbonyl}piperidinium bis(trifluoroacetate);

2-((1S)-1-{[(3-cyanophenyl)sulfonyl]amino}-7-oxooctyl)-5-phenyl-1H-imidazol-1-ium trifluoroacetate;

2-{(1S)-7-oxo-1-[(phenylsulfonyl)amino]octyl}-5-phenyl-1H-imidazol-1-ium trifluoroacetate;

4-methyl-7-({[(1S)-7-oxo-1-(5-phenyl-1H-imidazol-1-ium-2-yl)octyl]amino}sulfonyl)-3,4-dihydro-2H-1,4-benzoxazin-4-ium bis(trifluoroacetate);

2-[(1S)-1-({[2-(acetylamino)-4-methyl-1,3-thiazol-5-yl]sulfonyl}amino)-7-oxooctyl]-5-phenyl-1H-imidazol-1-ium trifluoroacetate;

2-((1S)-1-{[(5-chloro-2-thienyl)sulfonyl]amino}-7-oxooctyl)-5-phenyl-1H-imidazol-1-ium trifluoroacetate;

1,3,5-trimethyl-4-({[(1S)-7-oxo-1-(5-phenyl-1H-imidazol-1-ium-2-yl)octyl]amino}sulfonyl)-1H-pyrazol-1-ium bis(trifluoroacetate);

2-[(1S)-1-({[5-(2-methyl-1,3-thiazol-4-yl)-2-thienyl]sulfonyl}amino)-7-oxooctyl]-5-phenyl-1H-imidazol-1-ium trifluoroacetate;

2-{(1S)-1-[({5-[1-methyl-3-(trifluoromethyl)-1H-pyrazol-5-yl]-2-thienyl}sulfonyl)amino]-7-oxooctyl}-5-phenyl-1H-imidazol-1-ium trifluoroacetate;

2-((1S)-1-{[(5-isoxazol-3-yl-2-thienyl)sulfonyl]amino}-7-oxooctyl)-5-phenyl-1H-imidazol-1-ium trifluoroacetate;

1-methyl-4-{[((1S)-7-oxo-1-{5-[4-(trifluoromethyl)phenyl]-1H-imidazol-1-ium-2-yl}octyl)amino]carbonyl}piperidinium bis(trifluoroacetate);

4-{[((1S)-1-{5-[4-(difluoromethoxy)phenyl]-1H-imidazol-1-ium-2-yl}-7-oxooctyl)amino]carbonyl}-1-methylpiperidinium bis(trifluoroacetate);

4-[({(1S)-1-[5-(3,4-difluorophenyl)-1H-imidazol-1-ium-2-yl]-7-oxooctyl}amino)carbonyl]-1-methylpiperidinium bis(trifluoroacetate);

2-((1S)-1-{[(2-nitrophenyl)sulfonyl]amino}-7-oxooctyl)-5-phenyl-1H-imidazol-3-ium trifluoroacetate;

2-((1S)-1-{[(3-nitrophenyl)sulfonyl]amino}-7-oxooctyl)-5-phenyl-1H-imidazol-3-ium trifluoroacetate;

2-[(1S)-1-({[4-(acetylamino)phenyl]sulfonyl}amino)-7-oxooctyl]-5-phenyl-1H-imidazol-3-ium trifluoroacetate;

2-((1S)-1-{[(2-cyanophenyl)sulfonyl]amino}-7-oxooctyl)-5-phenyl-1H-imidazol-3-ium trifluoroacetate;

2-((1S)-1-{[(2-chloro-4-cyanophenyl)sulfonyl]amino}-7-oxooctyl)-5-phenyl-1H-imidazol-3-ium trifluoroacetate;

2-((1S)-1-{[(3-fluoro-4-nitrophenyl)sulfonyl]amino}-7-oxooctyl)-5-phenyl-1H-imidazol-3-ium trifluoroacetate;

2-[(1S)-1-({[2-(methoxycarbonyl)-3-thienyl]sulfonyl}amino)-7-oxooctyl]-5-phenyl-1H-imidazol-3-ium trifluoroacetate;

2-((1S)-1-{[(2,5-dimethoxyphenyl)sulfonyl]amino}-7-oxooctyl)-5-phenyl-1H-imidazol-1-ium trifluoroacetate;

2-((1S)-1-{[(3-fluorophenyl)sulfonyl]amino}-7-oxooctyl)-5-phenyl-1H-imidazol-1-ium trifluoroacetate;

2-((1S)-1-{[(3-cyano-4-fluorophenyl)sulfonyl]amino}-7-oxooctyl)-5-phenyl-1H-imidazol-1-ium trifluoroacetate;

2-[(1S)-1-({[4-(difluoromethoxy)phenyl]sulfonyl}amino)-7-oxooctyl]-5-phenyl-1H-imidazol-1-ium trifluoroacetate;

2-[(1S)-1-({[3-(difluoromethoxy)phenyl]sulfonyl}amino)-7-oxooctyl]-5-phenyl-1H-imidazol-1-ium trifluoroacetate;

2-{(1S)-1-[(2,1,3-benzothiadiazol-5-ylsulfonyl)amino]-7-oxooctyl}-5-phenyl-1H-imidazol-1-ium trifluoroacetate;

2-{(1S)-1-[(2,3-dihydro-1-benzofuran-5-ylsulfonyl)amino]-7-oxooctyl}-5-phenyl-1H-imidazol-1-ium trifluoroacetate;

2-morpholin-4-yl-5-({[(1S)-7-oxo-1-(5-phenyl-1H-imidazol-1-ium-2-yl)octyl]amino}sulfonyl)pyridinium bis(trifluoroacetate);

2-{(1S)-1-[(2,1,3-benzoxadiazol-4-ylsulfonyl)amino]-7-oxooctyl}-5-phenyl-1H-imidazol-1-ium trifluoroacetate;

2-((1S)-1-{[(4-fluorophenyl)sulfonyl]amino}-7-oxooctyl)-5-phenyl-1H-imidazol-1-ium trifluoroacetate;

2-((1S)-1-{[(4-nitrophenyl)sulfonyl]amino}-7-oxooctyl)-5-phenyl-1H-imidazol-1-ium trifluoroacetate;

2-((1S)-1-{[(2-fluorophenyl)sulfonyl]amino}-7-oxooctyl)-5-phenyl-1H-imidazol-1-ium trifluoroacetate;

2-((1S)-1-{[(3,4-dimethoxyphenyl)sulfonyl]amino}-7-oxooctyl)-5-phenyl-1H-imidazol-1-ium trifluoroacetate;

2-((1S)-1-{[(3,4-difluorophenyl)sulfonyl]amino}-7-oxooctyl)-5-phenyl-1H-imidazol-1-ium trifluoroacetate;

5-({[(1S)-7-oxo-1-(5-phenyl-1H-imidazol-1-ium-2-yl)octyl]amino}sulfonyl)isoquinolinium bis(trifluoroacetate);

2-((1S)-1-{[(4-carboxyphenyl)sulfonyl]amino}-7-oxooctyl)-5-phenyl-1H-imidazol-1-ium trifluoroacetate;

1-methyl-4-[({(1S)-7-oxo-1-[5-(3-thienyl)-1H-imidazol-3-ium-2-yl]octyl}amino)carbonyl]piperidinium bis(trifluoroacetate);

2-[2-((1S)-1-{[(1-methylpiperidinium-4-yl)carbonyl]amino}-7-oxooctyl)-1H-imidazol-3-ium-5-yl]pyridinium tris(trifluoroacetate);

4-[({(1S)-1-[5-(5-chloro-3-methyl-1-benzothien-2-yl)-1H-imidazol-3-ium-2-yl]-7-oxooctyl}amino)carbonyl]-1-methylpiperidinium bis(trifluoroacetate);

1-methyl-4-[({(1S)-7-oxo-1-[5-(3-phenylisoxazol-5-yl)-1H-imidazol-3-ium-2-yl]octyl}amino)carbonyl]piperidinium bis(trifluoroacetate);

1-methyl-4-{[((1S)-1-{5-[6-methyl-2-(trifluoromethyl)[1,3]thiazolo[3,2-b][1,2,4]triazol-5-yl]-1H-imidazol-3-ium-2-yl}-7-oxooctyl)amino]carbonyl}piperidinium bis(trifluoroacetate);

1-methyl-4-[({(1S)-1-[1-methyl-4-(2-naphthyl)-1H-imidazol-3-ium-2-yl]-7-oxooctyl}amino)carbonyl]piperidinium bis(trifluoroacetate);

2-(5-methoxy-2-methyl-1H-indol-3-yl)-N-{(1S)-1-[5-(2-naphthyl)-4H-1,2,4-triazol-3-yl]-7-oxononyl}acetamide;

2-(5-methoxy-2-methyl-1H-indol-3-yl)-N-[7-oxo-1-(4-phenyl-2-thienyl)nonyl]acetamide;

4-[({(1S)-1-[5-(1-benzothien-3-yl)-1H-imidazol-1-ium-2-yl]-7-oxooctyl}amino)carbonyl]-1-methylpiperidinium bis(trifluoroacetate);

2-{(1S)-1-[(3,4-difluorobenzoyl)amino]-7-oxooctyl}-5-phenyl-1H-imidazol-1-ium trifluoroacetate;

2-((1S)-1-{[4-(acetylamino)benzoyl]amino}-7-oxooctyl)-5-phenyl-1H-imidazol-1-ium trifluoroacetate;

2-((1S)-1-{[4-(aminosulfonyl)benzoyl]amino}-7-oxooctyl)-5-phenyl-1H-imidazol-1-ium trifluoroacetate;

4-({[(1S)-7-oxo-1-(5-phenyl-1H-imidazol-1-ium-2-yl)octyl]amino}carbonyl)pyridinium bis(trifluoroacetate);

3-({[(1S)-7-oxo-1-(5-phenyl-1H-imidazol-1-ium-2-yl)octyl]amino}carbonyl)pyridinium bis(trifluoroacetate);

2-((1S)-1-{[(3,5-dimethylisoxazol-4-yl)carbonyl]amino}-7-oxooctyl)-5-phenyl-1H-imidazol-1-ium trifluoroacetate;

2-{(1S)-1-[(2,3-dihydro-1,4-benzodioxin-6-ylcarbonyl)amino]-7-oxooctyl}-5-phenyl-1H-imidazol-1-ium trifluoroacetate;

2-{(1S)-1-[(3-nitrobenzoyl)amino]-7-oxooctyl}-5-phenyl-1H-imidazol-1-ium trifluoroacetate;

2-{(1S)-1-[(3-cyanobenzoyl)amino]-7-oxooctyl}-5-phenyl-1H-imidazol-1-ium trifluoroacetate;

2-{(1S)-1-[(4-cyanobenzoyl)amino]-7-oxooctyl}-5-phenyl-1H-imidazol-1-ium trifluoroacetate;

1-methyl-4-({[7-oxo-1-(4-phenyl-2-thienyl)nonyl]amino}carbonyl)piperidinium trifluoroacetate;

4-[({(1S)-6-carboxy-1-[5-(2-naphthyl)-1H-imidazol-1-ium-2-yl]hexyl}amino)carbonyl]-1-methylpiperidinium bis(trifluoroacetate);

2-((1S)-6-carboxy-1-{[(3-nitrophenyl)sulfonyl]amino}hexyl)-5-(2-naphthyl)-1H-imidazol-1-ium trifluoroacetate;

4-[({(1S)-6-carboxy-1-[5-(3-methoxyphenyl)-1H-imidazol-1-ium-2-yl]hexyl}amino)carbonyl]-1-methylpiperidinium bis(trifluoroacetate);

2-((1S)-6-carboxy-1-{[(5-methoxy-2-methyl-1H-indol-3-yl)acetyl]amino}hexyl)-5-(3-methoxyphenyl)-1H-imidazol-1-ium trifluoroacetate;

2-((1S)-6-carboxy-1-{[(3-nitrophenyl)sulfonyl]amino}hexyl)-5-(3-methoxyphenyl)-1H-imidazol-1-ium trifluoroacetate;

2-((1S)-6-carboxy-1-{[(5-methoxy-2-methyl-1H-indol-3-yl)acetyl]amino}hexyl)-5-(2-naphthyl)-1H-imidazol-1-ium trifluoroacetate;

2-((1S)-7-(Hydroxyamino)-1-{[(5-methoxy-2-methyl-1H-indol-3-yl)acetyl]amino}-7-oxoheptyl)-5-(2-naphthyl)-1H-imidazol-1-ium trifluoroacetate;

2-{((1S)-1-[(3-fluoro-4-nitrobenzoyl)amino]-7-oxooctyl}-5-phenyl-1H-imidazol-1-ium trifluoroacetate;

2-cyano-5-({[(1S)-7-oxo-1-(5-phenyl-1H-imidazol-1-ium-2-yl)octyl]amino}carbonyl)pyridinium bis(trifluoroacetate);

2-((1S)-1-{[(4-cyanophenyl)sulfonyl]amino}-7-oxooctyl)-5-(2-naphthyl)-1H-imidazol-1-ium trifluoroacetate;
5-(2-naphthyl)-2-((1S)-1-{[(3-nitrophenyl)sulfonyl]amino}-7-oxooctyl)-1H-imidazol-1-ium trifluoroacetate;
2-[(1S)-1-({[[2-(dimethylammonio)ethyl](methyl)amino]sulfonyl}amino)-7-oxooctyl]-5-(2-naphthyl)-1H-imidazol-1-ium bis(trifluoroacetate);
5-(2-naphthyl)-2-{(1S)-7-oxo-1-[(1,3-thiazol-5-ylcarbonyl)amino]octyl}-1H-imidazol-1-ium trifluoroacetate;
5-(3-chlorophenyl)-2-((1S)-1-{[(4-cyanophenyl)sulfonyl]amino}-7-oxooctyl)-1H-imidazol-1-ium trifluoroacetate;
5-(3-chlorophenyl)-2-((S)-1-{[(3-nitrophenyl)sulfonyl]amino}-7-oxooctyl)-1H-imidazol-1-ium trifluoroacetate;
2-((1S)-1-{[(4-cyanophenyl)sulfonyl]amino}-7-oxooctyl)-5-(3-methoxyphenyl)-1H-imidazol-1-ium trifluoroacetate;
5-(3-methoxyphenyl)-2-((1S)-1-{[(3-nitrophenyl)sulfonyl]amino}-7-oxooctyl)-1H-imidazol-1-ium trifluoroacetate;
5-(3-methoxyphenyl)-2-{(1S)-7-oxo-1-[(1,3-thiazol-5-ylcarbonyl)amino]octyl}-1H-imidazol-1-ium trifluoroacetate;
2-((1S)-7-[(2-aminophenyl)amino]-1-{[(5-methoxy-2-methyl-1H-indol-3-yl)acetyl]amino}-7-oxoheptyl)-5-(2-naphthyl)-1H-imidazol-1-ium trifluoroacetate;
5-(3-methoxyphenyl)-2-[(1S)-1-({[(3S)-1-methylpyrrolidinium-3-yl]carbonyl}amino)-7-oxooctyl]-1H-imidazol-1-ium bis(trifluoroacetate);
(3S)-3-[({(1S)-1-[5-(3-methoxyphenyl)-1H-imidazol-1-ium-2-yl]-7-oxooctyl}amino)carbonyl]-1-methylpiperidinium bis(trifluoroacetate);
(3S)-1-isopropyl-3-[({(1S)-1-[5-(3-methoxyphenyl)-1H-imidazol-1-ium-2-yl]-7-oxooctyl}amino)carbonyl]piperidinium bis(trifluoroacetate);
5-(3-chlorophenyl)-2-[(1S)-1-({[(3R)-1-methylpyrrolidinium-3-yl]carbonyl}amino)-7-oxooctyl]-1H-imidazol-1-ium bis(trifluoroacetate);
2-[(1S)-1-({[(3R)-1-methylpyrrolidinium-3-yl]carbonyl}amino)-7-oxooctyl]-5-(2-naphthyl)-1H-imidazol-1-ium bis(trifluoroacetate);
4-methyl-2-[({(1S)-1-[5-(2-naphthyl)-1H-imidazol-1-ium-2-yl]-7-oxooctyl}amino)carbonyl]morpholin-4-ium bis(trifluoroacetate);
4-[({(1S)-1-[5-(2-naphthyl)-1H-imidazol-1-ium-2-yl]-7-oxooctyl}amino)carbonyl]-1-azoniabicyclo[2.2.2]octane bis(trifluoroacetate);
4-[2-({(1S)-1-[5-(3-chlorophenyl)-1H-imidazol-1-ium-2-yl]-7-oxooctyl}amino)-1-methyl-2-oxoethyl]morpholin-4-ium bis(trifluoroacetate);
2-[(1S)-1-{[(5-methoxy-2-methyl-1H-indol-3-yl)acetyl]amino}-7-(methylamino)-7-oxoheptyl]-5-(2-naphthyl)-1H-imidazol-1-ium trifluoroacetate;
5-(3-methoxyphenyl)-2-[(1S)-1-({[(3R)-1-methylpyrrolidinium-3-yl]carbonyl}amino)-7-oxooctyl]-1H-imidazol-1-ium bis(trifluoroacetate);
(3R)-3-[({(1S)-1-[5-(3-methoxyphenyl)-1H-imidazol-1-ium-2-yl]-7-oxooctyl}amino)carbonyl]-1-methylpiperidinium bis(trifluoroacetate);
5-(3-chlorophenyl)-2-[(1S)-1-({[(3S)-1-methylpyrrolidinium-3-yl]carbonyl}amino)-7-oxooctyl]-1H-imidazol-1-ium bis(trifluoroacetate);
2-[(1S)-1-({[(3S)-1-methylpyrrolidinium-3-yl]carbonyl}amino)-7-oxooctyl]-5-(2-naphthyl)-1H-imidazol-1-ium bis(trifluoroacetate);
2-((1S)-1-{[(5-methoxy-2-methyl-1H-indol-3-yl)acetyl]amino}-7-oxononyl)-5-phenyl-1H-imidazol-1-ium trifluoroacetate;
1-methyl-4-({[(1S)-7-oxo-1-(5-phenyl-1H-imidazol-1-ium-2-yl)nonyl]amino}carbonyl)piperidinium bis(trifluoroacetate);

and the pharmaceutically acceptable free bases, salts, alternative salts and stereoisomers thereof.

Further particular compounds within the scope of the present invention are:
2-(5-methoxy-2-methyl-1H-indol-3-yl)-N-{(1S)-1-[5-(2-naphthyl)-1,3,4-oxadiazol-2-yl]-7-oxononyl}acetamide;
2-(5-methoxy-2-methyl-1H-indol-3-yl)-N-{(1S)-1-[5-(2-naphthyl)-1,3-oxazol-2-yl]-7-oxononyl}acetamide;
5-(1-{[(5-methoxy-2-methyl-1H-indol-3-yl)acetyl]amino}-7-oxononyl)-2-(2-naphthyl)-1H-imidazol-1-ium trifluoroacetate;
2-(5-methoxy-2-methyl-1H-indol-3-yl)-N-[7-oxo-1-(2-phenyl-1,3-thiazol-5-yl)nonyl]acetamide;
2-((1S)-1-{[(1-methylpiperidinium-4-yl)carbonyl]amino}-7-oxononyl)-4-phenylpyridinium bis(trifluoroacetate);
(7S)-7-{[(5-methoxy-2-methyl-1H-indol-3-yl)acetyl]amino}-7-[5-(2-naphthyl)-1,3,4-oxadiazol-2-yl]heptanoic acid;
(7S)-7-{[(5-methoxy-2-methyl-1H-indol-3-yl)acetyl]amino}-7-[5-(2-naphthyl)-1,3,4-oxadiazol-2-yl]heptanamide;
(7S)-7-{[(5-methoxy-2-methyl-1H-indol-3-yl)acetyl]amino}-7-[5-(2-naphthyl)-4H-1,2,4-triazol-3-yl]heptanoic acid;
(7S)-7-{[(5-methoxy-2-methyl-1H-indol-3-yl)acetyl]amino}-7-[5-(2-naphthyl)-4H-1,2,4-triazol-3-yl]heptanamide;
2-(5-methoxy-2-methyl-1H-indol-3-yl)-N-{(1S)-1-[5-(2-naphthyl)-1,2,4-oxadiazol-3-yl]-7-oxononyl}acetamide;
2-(5-methoxy-2-methyl-1H-indol-3-yl)-N-{(1S)-1-[3-(2-naphthyl)-1,2,4-oxadiazol-5-yl]-7-oxononyl}acetamide;
2-{(1S)-1-[(methoxycarbonyl)amino]-7-oxononyl}-5-(2-naphthyl)-1H-imidazol-1-ium trifluoroacetate;
2-((1S)-1-{[(dimethylamino)carbonyl]amino}-7-oxononyl)-5-(2-naphthyl)-1H-imidazol-1-ium trifluoroacetate;
3-nitro-N-[7-oxo-1-(4-phenyl-2-furyl)octyl]benzenesulfonamide;
2-((1S)-7-[(ethylsulfonyl)amino]-1-{[(5-methoxy-2-methyl-1H-indol-3-yl)acetyl]amino}-7-oxoheptyl)-5-(2-naphthyl)-1H-imidazol-1-ium trifluoroacetate;
5-(2-naphthyl)-2-((1S)-8,8,8-trifluoro-1-{[(5-methoxy-2-methyl-1H-indol-3-yl)acetyl]amino}-7-oxooctyl)-1H-imidazol-1-ium trifluoroacetate;
3-nitro-N-[7-oxo-1-(4-phenyl-1,3-thiazol-2-yl)octyl]benzenesulfonamide;
2-((1S)-7-amino-1-{[(5-methoxy-2-methyl-1H-indol-3-yl)acetyl]amino}-7-oxoheptyl)-5-(2-naphthyl)-1H-imidazol-1-ium trifluoroacetate;
2-((1S)-7-(dimethylamino)-1-{[(5-methoxy-2-methyl-1H-indol-3-yl)acetyl]amino}-7-oxoheptyl)-5-(2-naphthyl)-1H-imidazol-1-ium trifluoroacetate;
2-((1S)-7-(isopropylamino)-1-{[(5-methoxy-2-methyl-1H-indol-3-yl)acetyl]amino}-7-oxoheptyl)-5-(2-naphthyl)-1H-imidazol-1-ium trifluoroacetate;
2-((1S)-7-anilino-1-{[(5-methoxy-2-methyl-1H-indol-3-yl)acetyl]amino}-7-oxoheptyl)-5-(2-naphthyl)-1H-imidazol-1-ium trifluoroacetate;
2-((1S)-7-(benzylamino)-1-{[(5-methoxy-2-methyl-1H-indol-3-yl)acetyl]amino}-7-oxoheptyl)-5-(2-naphthyl)-1H-imidazol-1-ium trifluoroacetate;
2-{(1S)-1-{[(5-methoxy-2-methyl-1H-indol-3-yl)acetyl]amino}-7-[(methylsulfonyl)amino]-7-oxoheptyl}-5-(2-naphthyl)-1H-imidazol-1-ium trifluoroacetate;

1-methyl-4-[({(1S)-1-[5-(2-naphthyl)-4h-1,2,4-triazol-3-yl]-7-oxononyl}amino)carbonyl]piperidinium trifluoroacetate;

(3S)-1-methyl-3-[({(1S)-1-[5-(2-naphthyl)-4H-1,2,4-triazol-3-yl]-7-oxononyl}amino)carbonyl]pyrrolidinium trifluoroacetate;

(3S)-1-methyl-3-[({(1S)-1-[5-(2-naphthyl)-4H-1,2,4-triazol-3-yl]-7-oxononyl}amino)carbonyl]piperidinium trifluoroacetate;

N-{(1S)-1-[5-(2-naphthyl)-4H-1,2,4-triazol-3-yl]-7-oxononyl}-1,3-thiazole-5-carboxamide;

4-cyano-N-{(1S)-1-[3-(2-naphthyl)-1H-1,2,4-triazol-5-yl]-7-oxononyl}benzenesulfonamide;

2-((1S)-7-[methoxy(methyl)amino]-1-{[(5-methoxy-2-methyl-1H-indol-3-yl)acetyl]amino}-7-oxoheptyl)-5-(2-naphthyl)-1H-imidazol-1-ium trifluoroacetate;

1-methyl-4-[({(1S)-7-(methylamino)-1-[5-(2-naphthyl)-1H-imidazol-1-ium-2-yl]-7-oxoheptyl}amino)carbonyl]piperidinium bis(trifluoroacetate);

4-[({(1S)-7-(hydroxyamino)-1-[5-(2-naphthyl)-1H-imidazol-1-ium-2-yl]-7-oxoheptyl}amino)carbonyl]-1-methylpiperidinium bis(trifluoroacetate);

2-{(1S)-6-carboxy-1-[(1,3-thiazol-5-ylcarbonyl)amino]hexyl}-5-(2-naphthyl)-1H-imidazol-1-ium trifluoroacetate;

4-[({(1S)-7-[(2-aminophenyl)amino]-1-[5-(2-naphthyl)-1H-imidazol-1-ium-2-yl]-7-oxoheptyl}amino)carbonyl]-1-methylpiperidinium bis(trifluoroacetate);

2-[(1S)-6-carboxy-1-({[(3R)-1-methylpyrrolidinium-3-yl]carbonyl}amino)hexyl]-5-(2-naphthyl)-1H-imidazol-1-ium bis(trifluoroacetate);

2-[(1S)-6-carboxy-1-({[(3S)-1-methylpyrrolidinium-3-yl]carbonyl}amino)hexyl]-5-(2-naphthyl)-1H-imidazol-1-ium bis(trifluoroacetate);

2-((1S)-6-carboxy-1-{[(dimethylamino)sulfonyl]amino}hexyl)-5-(2-naphthyl)-1H-imidazol-1-ium trifluoroacetate;

4-[({(1S)-7-[methoxy(methyl)amino]-1-[5-(2-naphthyl)-1H-imidazol-1-ium-2-yl]-7-oxoheptyl}amino)carbonyl]-1-methylpiperidinium bis(trifluoroacetate);

2-((1S)-1-{[(5-methoxy-2-methyl-1H-indol-3-yl)acetyl]amino}-7-oxo-7-{[(trifluoromethyl)sulfonyl]amino}heptyl)-5-(2-naphthyl)-1H-imidazol-1-ium trifluoroacetate;

2-((1S)-7-(ethylamino)-1-{[(5-methoxy-2-methyl-1H-indol-3-yl)acetyl]amino}-7-oxoheptyl)-5-(2-naphthyl)-1H-imidazol-1-ium trifluoroacetate;

(3S)-3-[({(1S)-1-[3-(3,5-dichlorophenyl)-1H-1,2,4-triazol-5-yl]-7-oxononyl}amino)carbonyl]-1-methylpyrrolidinium trifluoroacetate;

4-[({((1S)-1-[3-(3,5-dichlorophenyl)-1H-1,2,4-triazol-5-yl]-7-oxononyl}amino)carbonyl]-1-azoniabicyclo[2.2.2]octane trifluoroacetate;

N-{(1S)-1-[3-(3,5-dichlorophenyl)-1H-1,2,4-triazol-5-yl]-7-oxononyl}-2-(5-methoxy-2-methyl-1H-indol-3-yl)acetamide;

2-(5-methoxy-2-methyl-1H-indol-3-yl)-N-{(1S)-1-[3-(3-methoxyphenyl)-1H-1,2,4-triazol-5-yl]-7-oxononyl}acetamide;

2-(5-methoxy-2-methyl-1H-indol-3-yl)-N-[7-oxo-1-(4-phenyl-1,3-thiazol-2-yl)octyl]acetamide;

2-((1S)-1-{[(5-methoxy-2-methyl-1H-indol-3-yl)acetyl]amino}-7-oxononyl)-5-(2-naphthyl)-1H-imidazol-3-ium trifluoroacetate;

2-{(1S)-1-[(1H-indol-3-ylacetyl)amino]-7-oxononyl}-5-(2-naphthyl)-1H-imidazol-3-ium trifluoroacetate;

2-((1S)-1-{[(2-methyl-1H-indol-3-yl)acetyl]amino}-7-oxononyl)-5-(2-naphthyl)-1H-imidazol-3-ium trifluoroacetate;

2-((1S)-1-{[(5-methoxy-1H-indol-3-yl)acetyl]amino}-7-oxononyl)-5-(2-naphthyl)-1H-imidazol-3-ium trifluoroacetate;

2-((1S)-1-{[(5-bromo-1H-indol-3-yl)acetyl]amino}-7-oxononyl)-5-(2-naphthyl)-1H-imidazol-3-ium trifluoroacetate;

2-((1S)-1-{[(5-fluoro-1H-indol-3-yl)acetyl]amino}-7-oxononyl)-5-(2-naphthyl)-1H-imidazol-3-ium trifluoroacetate;

1-[2-({(1S)-1-[5-(2-naphthyl)-1H-imidazol-3-ium-2-yl]-7-oxononyl}amino)-2-oxoethyl]-1H-benzimidazol-3-ium bis(trifluoroacetate);

2-((1S)-1-{[(7-methoxy-1-benzofuran-2-yl)carbonyl]amino}-7-oxononyl)-5-(2-naphthyl)-1H-imidazol-3-ium trifluoroacetate;

2-((1S)-{[(5-methoxy-1H-indol-2-yl)carbonyl]amino}-7-oxononyl)-5-(2-naphthyl)-1H-imidazol-3-ium trifluoroacetate;

2-((1S)-1-{[(5-fluoro-1H-indol-2-yl)carbonyl]amino}-7-oxononyl)-5-(2-naphthyl)-1H-imidazol-3-ium trifluoroacetate;

6-[2-({(1S)-1-[5-(2-naphthyl)-1H-imidazol-3-ium-2-yl]-7-oxononyl}amino)-2-oxoethyl][1,2,4]triazolo[1,5-a]pyrimidin-4-ium bis(trifluoroacetate);

5-(2-naphthyl)-2-((1S)-7-oxo-1-{[(4-phenyl-1,3-thiazol-2-yl)acetyl]amino}nonyl)-1H-imidazol-3-ium trifluoroacetate;

2-((1S)-1-{[(5-chloro-1-benzothien-3-yl)acetyl]amino}-7-oxononyl)-5-(2-naphthyl)-1H-imidazol-3-ium trifluoroacetate;

2-((1S)-1-{[(4-chloro-1H-indol-3-yl)acetyl]amino}-7-oxononyl)-5-(2-naphthyl)-1H-imidazol-3-ium trifluoroacetate;

5-(2-naphthyl)-2-((1S)-7-oxo-1-{[(2-oxo-1,3-benzoxazol-3(2H)-yl)acetyl]amino}nonyl)-1H-imidazol-3-ium trifluoroacetate;

2-((1S)-1-{[(5-methoxy-2-oxo-2,3-dihydro-1H-indol-3-yl)acetyl]amino}-7-oxononyl)-5-(2-naphthyl)-1H-imidazol-3-ium trifluoroacetate;

2-((1S)-1-{[(6-methoxy-2-oxo-2,3-dihydro-1H-indol-3-yl)acetyl]amino}-7-oxononyl)-5-(2-naphthyl)-1H-imidazol-3-ium trifluoroacetate;

2-ethyl-1-[3-({(1S)-1-[5-(2-naphthyl)-1H-imidazol-3-ium-2-yl]-7-oxononyl}amino)-3-oxopropyl]-1H-benzimidazol-3-ium bis(trifluoroacetate);

5-(2-naphthyl)-2-{(1S)-1-[(1-naphthylacetyl)amino]-7-oxononyl}-1H-imidazol-3-ium trifluoroacetate;

5-(2-naphthyl)-2-{(1S)-1-[(2-naphthylacetyl)amino]-7-oxononyl}-1H-imidazol-3-ium trifluoroacetate;

5-(2-naphthyl)-2-((1S)-7-oxo-1-{[(2-oxoquinazolin-1(2H)-yl)acetyl]amino}nonyl)-1H-imidazol-3-ium trifluoroacetate;

2-((1S)-1-{[(4-methyl-1-oxophthalazin-2(1H)-yl)acetyl]amino}-7-oxononyl)-5-(2-naphthyl)-1H-imidazol-3-ium trifluoroacetate;

5-(2-naphthyl)-2-{(1S)-7-oxo-1-[(phenylacetyl)amino]nonyl}-1H-imidazol-3-ium trifluoroacetate;

2-((1S)-1-{[(2,6-dichlorophenyl)acetyl]amino}-7-oxononyl)-5-(2-naphthyl)-1H-imidazol-3-ium trifluoroacetate;

2-((1S)-1-{[(2,4-dichlorophenyl)acetyl]amino}-7-oxononyl)-5-(2-naphthyl)-1H-imidazol-3-ium trifluoroacetate;

2-[(1S)-1-({[2-fluoro-6-(trifluoromethyl)phenyl]
acetyl}amino)-7-oxononyl]-5-(2-naphthyl)-1H-imidazol-
3-ium trifluoroacetate;

2-[(1S)-1-({[2-fluoro-3-(trifluoromethyl)phenyl]
acetyl}amino)-7-oxononyl]-5-(2-naphthyl)-1H-imidazol-
3-ium trifluoroacetate;

2-[(1S)-1-{[(5-methoxy-2-methyl-1H-indol-3-yl)acetyl]
amino}-7-oxo-7-(1,3-thiazol-2-ylamino)heptyl]-5-(2-
naphthyl)-1H-imidazol-3-ium trifluoroacetate;

2-[(1S)-1-{[(5-methoxy-2-methyl-1H-indol-3-yl)acetyl]
amino}-7-oxo-7-(1,3,4-thiadiazol-2-ylamino)heptyl]-5-
(2-naphthyl)-1H-imidazol-3-ium trifluoroacetate;

2-methyl-1-[2-({(1S)-1-[5-(2-naphthyl)-1H-imidazol-1-
ium-2-yl]-7-oxononyl}amino)-2-oxoethyl]-1H-benzimi-
dazol-3-ium bis(trifluoroacetate);

1-[2-({(1S)-1-[5-(2-naphthyl)-1H-imidazol-1-ium-2-yl]-7-
oxononyl}amino)-2-oxoethyl]-2-(trifluoromethyl)-1H-
benzimidazol-3-ium bis(trifluoroacetate);

2-{(1S)-1-[(1H-indazol-1-ylacetyl)amino]-7-oxononyl}-5-
(2-naphthyl)-1H-imidazol-1-ium trifluoroacetate;

3-[2-({(1S)-1-[5-(2-naphthyl)-1H-imidazol-1-ium-2-yl]-7-
oxononyl}amino)-2-oxoethyl]quinolinium bis(trifluoro-
acetate);

2-((1S)-1-{[(dimethylamino)(oxo)acetyl]amino}-7-ox-
ononyl)-5-(2-naphthyl)-1H-imidazol-1-ium trifluoroac-
etate;

2-{(1S)-1-[(1,2-benzisoxazol-3-ylacetyl)amino]-7-ox-
ononyl}-5-(2-naphthyl)-1H-imidazol-1-ium trifluoroac-
etate;

2-((1S)-1-{[(2-methyl-1H-indol-1-yl)acetyl]amino}-7-ox-
ononyl)-5-(2-naphthyl)-1H-imidazol-1-ium trifluoroac-
etate;

2-{(1S)-1-[(1H-1,2,3-benzotriazol-1-ylacetyl)amino]-7-ox-
ononyl}-5-(2-naphthyl)-1H-imidazol-1-ium trifluoroac-
etate;

2-((1S)-1-{[(5-cyano-1H-indol-1-yl)acetyl]amino}-7-ox-
ononyl)-5-(2-naphthyl)-1H-imidazol-1-ium trifluoroac-
etate;

2-((1S)-1-{[(dimethylammonio)acetyl]amino}-7-ox-
ononyl)-5-(2-naphthyl)-1H-imidazol-1-ium bis(trifluoro-
acetate);

1-methyl-4-[({(1S)-1-[5-(2-naphthyl)-1H-imidazol-1-ium-
2-yl]-7-oxononyl}amino)carbonyl]piperidinium bis(trif-
luoroacetate);

4-[({(1S)-1-[5-(2-naphthyl)-1H-imidazol-1-ium-2-yl]-7-
oxononyl}amino)carbonyl]-1-azoniabicyclo[2.2.2]octane
bis(trifluoroacetate);

(7S)-7-{[(5-methoxy-2-methyl-1H-indol-3-yl)acetyl]
amino}-N-methyl-7-[5-(2-naphthyl)-4H-1,2,4-triazol-3-
yl]heptanamide;

4-[({(1S)-1-[5-(2-naphthyl)-1,3,4-oxadiazol-2-yl]-7-
oxononyl}amino)carbonyl]-1-azoniabicyclo[2.2.2]octane
trifluoroacetate;

2-ethyl-1-[3-({(1S)-1-[5-(2-naphthyl)-1,3,4-oxadiazol-2-
yl]-7-oxononyl}amino)-3-oxopropyl]-1H-benzimidazol-
3-ium trifluoroacetate;

6-[2-({(1S)-1-[5-(2-naphthyl)-1,3,4-oxadiazol-2-yl]-7-
oxononyl}amino)-2-oxoethyl][1,2,4]triazolo[1,5-a]pyri-
midin-3-ium trifluoroacetate;

1-methyl-4-[({(1S)-1-[5-(2-naphthyl)-1,3,4-oxadiazol-2-
yl]-7-oxononyl}amino)carbonyl]piperidinium trifluoro-
acetate;

(3R)-1-methyl-3-[({(1S)-1-[5-(2-naphthyl)-1,3,4-oxadia-
zol-2-yl]-7-oxononyl}amino)carbonyl]pyrrolidinium trif-
luoroacetate;

(4R)-4-[({(1S)-1-[5-(2-naphthyl)-1H-imidazol-3-ium-2-yl]-
7-oxononyl}amino)carbonyl]-2,3,4,9-tetrahydro-1H-
beta-carbolin-2-ium bis(trifluoroacetate);

(7S)-7-{[(5-methoxy-2-methyl-1H-indol-3-yl)acetyl]
amino}-N-methyl-7-[5-(2-naphthyl)-1,3,4-oxadiazol-2-
yl]heptanamide;

4-[({(1S)-6-carboxy-1-[5-(2-naphthyl)-1,3,4-oxadiazol-2-
yl]hexyl}amino)carbonyl]-1-methylpiperidinium trifluo-
roacetate;

(7S)-7-[5-(2-naphthyl)-1,3,4-oxadiazol-2-yl]-7-[(1,3-thia-
zol-4-ylcarbonyl)amino]heptanoic acid;

4-[({(1S)-1-[5-(2,3-dihydro-1,4-benzodioxin-6-yl)-1H-imi-
dazol-3-ium-2-yl]-7-oxononyl}amino)carbonyl]-1-meth-
ylpiperidinium bis(trifluoroacetate);

2-(5-methoxy-2-methyl-1H-indol-3-yl)-N-{(1S)-1-[4-(2-
naphthyl)-1,3-oxazol-2-yl]-7-oxononyl}acetamide;

2-((1S)-7-(methylamino)-7-oxo-1-{[(1-pyridin-2-ylpiperi-
din-3-yl)carbonyl]amino}heptyl)-5-(2-naphthyl)-1H-imi-
dazol-1-ium trifluoroacetate;

2-[2-({(1S)-7-(methylamino)-1-[5-(2-naphthyl)-1H-imida-
zol-1-ium-2-yl]-7-oxoheptyl}amino)-2-oxoethyl]-2,3-di-
hydro-1H-isoindolium bis(trifluoroacetate);

2-{(1S)-7-(methylamino)-7-oxo-1-[(piperidin-1-ylacetyl)
amino]heptyl}-5-(2-naphthyl)-1H-imidazol-1-ium trif-
luoroacetate;

4-[({(1S)-7-(methylamino)-1-[5-(2-naphthyl)-1H-imidazol-
1-ium-2-yl]-7-oxoheptyl}amino)carbonyl]-1-azoniabicy-
clo[2.2.2]octane bis(trifluoroacetate);

5-[({(1S)-7-(methylamino)-1-[5-(2-naphthyl)-1H-imidazol-
1-ium-2-yl]-7-oxoheptyl}amino)carbonyl]-1,2,3,4-tet-
rahydro-1,8-naphthyridin-1-ium bis(trifluoroacetate);

2-((1S)-7-(methylamino)-7-oxo-1-{[(5-pyrrolidin-1-yl-2H-
tetrazol-2-yl)acetyl]amino}heptyl)-5-(2-naphthyl)-1H-
imidazol-1-ium trifluoroacetate;

2-{(1S)-7-(methylamino)-7-oxo-1-[(1,3-thiazol-5-ylcarbo-
nyl)amino]heptyl}-5-(2-naphthyl)-1H-imidazol-1-ium
trifluoroacetate;

2-((1S)-7-(methylamino)-1-{[(4-methyl-1,2,3-thiadiazol-5-
yl)carbonyl]amino}-7-oxoheptyl)-5-(2-naphthyl)-1H-
imidazol-1-ium trifluoroacetate;

2-{(1S)-7-(methylamino)-7-oxo-1-[(pyridin-3-ylcarbonyl)
amino]heptyl}-5-(2-naphthyl)-1H-imidazol-1-ium trif-
luoroacetate;

2-{(1S)-7-(methylamino)-7-oxo-1-[(phenylacetyl)amino]
heptyl}-5-(2-naphthyl)-1H-imidazol-1-ium trifluoroac-
etate;

(7S)-7-({[(3S)-1-methylpyrrolidin-3-yl]carbonyl}amino)-7-
[5-(2-naphthyl)-1,3,4-oxadiazol-2-yl]heptanoic acid;

(3S)-3-[({(1S)-6-carboxy-1-[5-(2-naphthyl)-4H-1,2,4-tria-
zol-3-yl]hexyl}amino)carbonyl]-1-methylpyrrolidinium
trifluoroacetate;

(3S)-3-[({(1S)-7-amino-1-[5-(2-naphthyl)-4H-1,2,4-triazol-
3-yl]-7-oxoheptyl}amino)carbonyl]-1-methylpyrroli-
dinium trifluoroacetate;

4-[({(1S)-1-[5-(2,3-dihydro-1,4-benzodioxin-5-yl)-1H-imi-
dazol-3-ium-2-yl]-7-oxononyl}amino)carbonyl]-1-meth-
ylpiperidinium bis(trifluoroacetate);

4-[({(1S)-1-[5-(1,3-benzothiazol-2-yl)-1H-imidazol-3-ium-
2-yl]-7-oxononyl}amino)carbonyl]-1-methylpiperi-
dinium bis(trifluoroacetate);

4-[({(1S)-1-[5-(1-benzothien-2-yl)-1H-imidazol-3-ium-2-
yl]-7-oxononyl}amino)carbonyl]-1-methylpiperidinium
bis(trifluoroacetate);

2-[(1S)-1-{[(benzylamino)carbonyl]amino}-7-(methy-
lamino)-7-oxoheptyl]-5-(2-naphthyl)-1H-imidazol-1-ium
trifluoroacetate;

2-[(1S)-1-({[(4-methoxyphenyl)amino]carbonyl}amino)-7-(methylamino)-7-oxoheptyl]-5-(2-naphthyl)-1H-imidazol-1-ium trifluoroacetate;

2-[(1S)-1-{[(cyclopentylamino)carbonyl]amino}-7-(methylamino)-7-oxoheptyl]-5-(2-naphthyl)-1H-imidazol-1-ium trifluoroacetate;

2-((1S)-7-(methylamino)-1-{[(3-nitrophenyl)sulfonyl]amino}-7-oxoheptyl)-5-(2-naphthyl)-1H-imidazol-1-ium trifluoroacetate;

2-[(1S)-1-{[(4-cyanophenyl)sulfonyl]amino}-7-(methylamino)-7-oxoheptyl]-5-(2-naphthyl)-1H-imidazol-1-ium trifluoroacetate;

2-[(1S)-7-(methylamino)-1-({[(3S)-1-methylpyrrolidinium-3-yl]carbonyl}amino)-7-oxoheptyl]-5-(2-naphthyl)-1H-imidazol-1-ium bis(trifluoroacetate);

2-[(1S)-7-(methylamino)-1-({[(3R)-1-methylpyrrolidinium-3-yl]carbonyl}amino)-7-oxoheptyl]-5-(2-naphthyl)-1H-imidazol-1-ium bis(trifluoroacetate);

2-[(1S)-1-{[(benzyloxy)carbonyl]amino}-7-(methylamino)-7-oxoheptyl]-5-(2-naphthyl)-1H-imidazol-1-ium trifluoroacetate;

1-methyl-4-[({(1R)-1-[5-(2-naphthyl)-1H-imidazol-1-ium-2-yl]-7-oxononyl}amino)carbonyl]piperidinium bis(trifluoroacetate);

(3R)-3-[({(1S)-6-carboxy-1-[5-(2-naphthyl)-1,3,4-oxadiazol-2-yl]hexyl}amino)carbonyl]-1-methylpyrrolidinium trifluoroacetate;

5-methoxy-N-{(1S)-7-(methylamino)-1-[5-(2-naphthyl)-1,3,4-oxadiazol-2-yl]-7-oxoheptyl}-1H-indole-2-carboxamide;

(7S)-7-{[(benzylamino)carbonyl]amino}-N-methyl-7-[5-(2-naphthyl)-1,3,4-oxadiazol-2-yl]heptanamide;

2-((1R)-1-{[(5-methoxy-2-methyl-1H-indol-3-yl)acetyl]amino}-7-oxononyl)-5-(2-naphthyl)-1H-imidazol-1-ium trifluoroacetate;

4-[({((S)-1-[5-(4-methoxyquinolin-2-yl)-1H-imidazol-3-ium-2-yl]-7-oxononyl}amino)carbonyl]-1-methylpiperidinium bis(trifluoroacetate);

3-[2-((1S)-1-{[(1-methylpiperidinium-4-yl)carbonyl]amino}-7-oxononyl)-1H-imidazol-1-ium-5-yl]quinolinium tris(trifluoroacetate);

6-[2-((1S)-1-{[(1-methylpiperidinium-4-yl)carbonyl]amino}-7-oxononyl)-1H-imidazol-1-ium-5-yl]quinolinium tris(trifluoroacetate);

1-methyl-4-({[(1S)-7-oxo-1-(5-quinolin-2-yl-1H-imidazol-1-ium-2-yl)nonyl]amino}carbonyl)piperidinium bis(trifluoroacetate);

4-({[(1S)-1-(5-isoquinolin-3-yl-1H-imidazol-1-ium-2-yl)-7-oxononyl]amino}carbonyl)-1-methylpiperidinium bis(trifluoroacetate);

1-methyl-N-{1-[2-(2-naphthyl)-1H-imidazol-5-yl]-7-oxononyl}piperidine-4-carboxamide;

1-methyl-N-[7-oxo-1-(3-phenyl-1H-pyrazol-5-yl)nonyl]piperidine-4-carboxamide;

2-[(1S)-1-(acetylamino)-7-oxononyl]-5-(2-naphthyl)-1H-imidazol-1-ium trifluoroacetate;

2-((1S)-1-{[(1,3-dimethylpyrrolidinium-3-yl)carbonyl]amino}-7-oxononyl)-5-(2-naphthyl)-1H-imidazol-1-ium bis(trifluoroacetate);

4-[3-({(1S)-1-[5-(2-naphthyl)-1H-imidazol-1-ium-2-yl]-7-oxononyl}amino)-3-oxopropyl]thiomorpholin-4-ium 1,1-dioxide bis(trifluoroacetate);

5-(2-naphthyl)-2-{(1S)-7-oxo-1-[(trifluoroacetyl)amino]nonyl}-1H-imidazol-1-ium trifluoroacetate;

2-((1S)-1-{[2-(dimethylammonio)-2-methylpropanoyl]amino}-7-oxononyl)-5-(2-naphthyl)-1H-imidazol-1-ium bis(trifluoroacetate);

2-((1S)-1-{[(1-methylazetidinium-3-yl)carbonyl]amino}-7-oxononyl)-5-(2-naphthyl)-1H-imidazol-1-ium bis(trifluoroacetate);

2-[(1S)-1-{[3-(2-ethyl-1H-benzimidazol-1-yl)propanoyl]amino}-7-(methylamino)-7-oxoheptyl]-5-(2-naphthyl)-1H-imidazol-1-ium trifluoroacetate;

6-[2-({(1S)-7-(methylamino)-1-[5-(2-naphthyl)-1H-imidazol-1-ium-2-yl]-7-oxoheptyl}amino)-2-oxoethyl][1,2,4]triazolo[1,5-a]pyrimidin-3-ium bis(trifluoroacetate);

2-((1S)-7-(methylamino)-7-oxo-1-{[(2-oxoquinazolin-1(2H)-yl)acetyl]amino}heptyl)-5-(2-naphthyl)-1H-imidazol-1-ium trifluoroacetate;

2-((1S)-7-(methylamino)-7-oxo-1-{[(2-oxo-1,3-benzoxazol-3(2H)-yl)acetyl]amino}heptyl)-5-(2-naphthyl)-1H-imidazol-1-ium trifluoroacetate;

1-ethyl-3-[({(1S)-7-(methylamino)-1-[5-(2-naphthyl)-1H-imidazol-1-ium-2-yl]-7-oxoheptyl}amino)carbonyl]piperidinium bis(trifluoroacetate);

2-((1S)-1-{[methoxy(oxo)acetyl]amino}-7-oxononyl)-5-(2-naphthyl)-1H-imidazol-1-ium trifluoroacetate;

2-((1S)-1-{[2-methyl-2-(methylammonio)propanoyl]amino}-7-oxononyl)-5-(2-naphthyl)-1H-imidazol-1-ium bis(trifluoroacetate);

2-(5-methoxy-2-methyl-1H-indol-3-yl)-N-[7-oxo-1-(3-phenyl-1H-pyrazol-5-yl)nonyl]acetamide;

1-methyl-4-({[(1S)-7-oxo-1-(5-quinolin-2-yl-1H-imidazol-1-ium-2-yl)nonyl]amino}carbonyl)piperidinium dichloride;

1-methyl-4-[({(1S)-1-[5-(2-naphthyl)-1H-imidazol-1-ium-2-yl]-7-oxononyl}amino)(oxo)acetyl]piperazin-1-ium bis(trifluoroacetate);

2-((1S)-1-{[morpholin-4-yl(oxo)acetyl]amino}-7-oxononyl)-5-(2-naphthyl)-1H-imidazol-1-ium trifluoroacetate;

2-((1S)-1-{[amino(oxo)acetyl]amino}-7-oxononyl)-5-(2-naphthyl)-1H-imidazol-1-ium trifluoroacetate;

2-((1S)-1-{[3-(diethylammonio)propanoyl]amino}-7-oxononyl)-5-(2-naphthyl)-1H-imidazol-1-ium bis(trifluoroacetate);

2-((1S)-1-{[3-(dimethylammonio)propanoyl]amino}-7-oxononyl)-5-(2-naphthyl)-1H-imidazol-1-ium bis(trifluoroacetate);

2-((1S)-1-{[(5-cyano-1H-indol-3-yl)acetyl]amino}-7-oxooctyl)-5-phenyl-1H-imidazol-1-ium trifluoroacetate;

2-{(1S)-1-[(carboxycarbonyl)amino]-7-oxononyl}-5-(2-naphthyl)-1H-imidazol-1-ium trifluoroacetate;

2-{(1S)-1-[(methylsulfonyl)amino]-7-oxononyl}-5-(2-naphthyl)-1H-imidazol-1-ium trifluoroacetate;

2-((1S)-1-{[(dimethylamino)sulfonyl]amino}-7-oxononyl)-5-(2-naphthyl)-1H-imidazol-1-ium trifluoroacetate;

5-methoxy-2-methyl-3-(2-oxo-2-{[(1S)-7-oxo-1-(4-phenylpyridinium-2-yl)nonyl]amino}ethyl)-1H-indolium bis(trifluoroacetate);

2-ethyl-1-(3-oxo-3-{[(1S)-7-oxo-1-(4-phenylpyridinium-2-yl)nonyl]amino}propyl)-1H-3,1-benzimidazol-1-ium bis(trifluoroacetate);

1-methyl-N-{(1S)-1-[5-(2-naphthyl)-1,3,4-oxadiazol-2-yl]-7-oxononyl}piperidine-4-carboxamide;

6-[2-((1S)-1-{[(1-methylpiperidinium-4-yl)carbonyl]amino}-7-oxononyl)-1H-imidazol-1-ium-5-yl]quinolinium trichloride;

N-{(1S)-1-[5-(2-naphthyl)-1,3,4-oxadiazol-2-yl]-7-oxononyl}quinuclidine-4-carboxamide;

4-methoxy-2-[2-((1S)-1-{[(1-methylpiperidinium-4-yl)carbonyl]amino}-7-oxononyl)-1H-imidazol-3-ium-5-yl]quinolinium trichloride;

and the pharmaceutically acceptable free bases, salts, alternative salts and stereoisomers thereof.

Particular intermediates within the scope of the present invention include:

2-[(1S)-1-Ammonio-6-carboxyhexyl]-5-(2-naphthyl)-1H-imidazol-1-ium bis(trifluoroacetate);

(1S)-1-[3-(2-Naphthyl)-1H-1,2,4-triazol-5-yl]-7-oxononan-1-aminium trifluoroacetate;

tert-Butyl {(1S)-1-[5-(2-naphthyl)-1H-imidazol-2-yl]-7-oxononyl}carbamate;

(1S)-7-oxo-1-(4-phenylpyridin-2-yl)nonan-1-aminium trifluoroacetate;

2-[(1S)-1-Ammonio-7-oxooctyl]-5-(2-naphthyl)-1H-imidazol-3-ium bis(trifluoroacetate);

2-[(1S)-1-Ammonio-7-oxooctyl]-5-phenyl-1H-imidazol-3-ium bis(trifluoroacetate);

and the pharmaceutically acceptable bases, salts, alternative salts and stereoisomers thereof.

Further particular compounds within the scope of the present inventions are:

2-{(1S)-1-[(carboxycarbonyl)amino]-7-oxononyl}-5-(2-naphthyl)-1H-imidazol-1-ium trifluoroacetate;

2-((1S)-1-{[morpholin-4-yl(oxo)acetyl]amino}-7-oxononyl)-5-(2-naphthyl)-1H-imidazol-1-ium trifluoroacetate;

5-(2-naphthyl)-2-{(1S)-7-oxo-1-[(trifluoroacetyl)amino]nonyl}-1H-imidazol-1-ium trifluoroacetate;

2-((1S)-1-{[(1-methylazetidinium-3-yl)carbonyl]amino}-7-oxononyl)-5-(2-naphthyl)-1H-imidazol-3-ium dichloride;

2-((1S)-1-{[(5-methoxy-2-methyl-1H-indol-3-yl)acetyl]amino}-7-oxononyl)-5-[4-(1H-pyrazol-1-yl)phenyl]-1H-imidazol-3-ium trifluoroacetate;

5-(2-methoxyquinolin-3-yl)-2-((1S)-1-{[(1-methylazetidinium-3-yl)carbonyl]amino}-7-oxononyl)-1H-imidazol-3-ium bis(trifluoroacetate);

2-((1S)-1-{[3-(dimethylammonio)propanoyl]amino}-7-oxononyl)-5-(2-naphthyl)-1H-imidazol-3-ium dichloride;

4-methoxy-2-[2-((1S)-1-{[(1-methylazetidinium-3-yl)carbonyl]amino}-7-oxononyl)-1H-imidazol-1-ium-5-yl]quinolinium trichloride;

N-{(1S)-1-[5-(2-naphthyl)-1,3,4-oxadiazol-2-yl]-5-oxoheptyl}quinuclidine-4-carboxamide;

N-{(1S)-1-[5-(4-methoxyquinolin-2-yl)-1,3,4-oxadiazol-2-yl]-7-oxononyl}-1-methylazetidine-3-carboxamide;

5-(hydroxymethyl)-2-(1-{[(5-methoxy-2-methyl-1H-indol-3-yl)acetyl]amino}-7-oxononyl)-1H-imidazol-1-ium trifluoroacetate;

4-{[2-(1-{[(5-methoxy-2-methyl-1H-indol-3-yl)acetyl]amino}-7-oxononyl)-1H-imidazol-1-ium-5-yl]methyl}morpholin-4-ium bis(trifluoroacetate);

2-(1-{[(5-methoxy-2-methyl-1H-indol-3-yl)acetyl]amino}-7-oxononyl)-5-[(1E)-3-methoxy-3-oxoprop-1-en-1-yl]-1H-imidazol-1-ium trifluoroacetate;

5-(2-carboxyethyl)-2-(1-{[(5-methoxy-2-methyl-1H-indol-3-yl)acetyl]amino}-7-oxononyl)-1H-imidazol-1-ium trifluoroacetate;

5-acetyl-2-((1S)-1-{[(5-methoxy-2-methyl-1H-indol-3-yl)acetyl]amino}-7-oxononyl)-1H-imidazol-1-ium trifluoroacetate;

5-cyclohexyl-2-((1S)-1-{[(5-methoxy-2-methyl-1H-indol-3-yl)acetyl]amino}-7-oxononyl)-1H-imidazol-1-ium trifluoroacetate;

2-((1S)-1-{[(5-methoxy-2-methyl-1H-indol-3-yl)acetyl]amino}-7-oxoundecyl)-5-phenyl-1H-imidazol-1-ium trifluoroacetate;

2-((1S)-7-cyclopropyl-1-{[(5-methoxy-2-methyl-1H-indol-3-yl)acetyl]amino}-7-oxoheptyl)-5-phenyl-1H-imidazol-1-ium trifluoroacetate;

2-((1S)-1-{[(5-methoxy-2-methyl-1H-indol-3-yl)acetyl]amino}-9-methyl-7-oxodecyl)-5-phenyl-1H-imidazol-1-ium trifluoroacetate;

2-((1S)-8-hydroxy-1-{[(5-methoxy-2-methyl-1H-indol-3-yl)acetyl]amino}-7-oxooctyl)-5-phenyl-1H-imidazol-1-ium trifluoroacetate;

2-((1S)-7-(2-furyl)-1-{[(5-methoxy-2-methyl-1H-indol-3-yl)acetyl]amino}-7-oxoheptyl)-5-(2-naphthyl)-1H-imidazol-1-ium trifluoroacetate;

2-[(1S)-1-{[(5-methoxy-2-methyl-1H-indol-3-yl)acetyl]amino}-8-(methylsulfinyl)-7-oxooctyl]-5-(2-naphthyl)-1H-imidazol-1-ium trifluoroacetate;

2-[(1S)-1-{[(5-methoxy-2-methyl-1H-indol-3-yl)acetyl]amino}-8-(methylsulfonyl)-7-oxooctyl]-5-(2-naphthyl)-1H-imidazol-1-ium trifluoroacetate;

2-((1S)-8-(aminosulfonyl)-1-{[(5-methoxy-2-methyl-1H-indol-3-yl)acetyl]amino}-7-oxooctyl)-5-(2-naphthyl)-1H-imidazol-1-ium trifluoroacetate;

1-methyl-4-({[(1S)-7-oxo-1-(4-phenyl-1H-imidazol-3-ium-2-yl)-7-pyridin-2-ylheptyl]amino}carbonyl)piperidinium bis(trifluoroacetate);

2-((1S)-7-amino-1-{[(5-methoxy-2-methyl-1H-indol-3-yl)acetyl]amino}-7-oxoheptyl)-5-(2-naphthyl)-1H-imidazol-3-ium trifluoroacetate;

2-((1S)-6-carboxy-1-{[(dimethylamino)sulfonyl]amino}hexyl)-5-(2-naphthyl)-1H-imidazol-3-ium trifluoroacetate;

2-((1S)-7-(methylamino)-7-oxo-1-{[(1-pyridin-2-ylpiperidin-3-yl)carbonyl]amino}heptyl)-5-(2-naphthyl)-1H-imidazol-3-ium trifluoroacetate;

2-[(1S)-1-{[(benzylamino)carbonyl]amino}-7-(methylamino)-7-oxoheptyl]-5-(2-naphthyl)-1H-imidazol-3-ium trifluoroacetate;

5-(2-methoxyquinolin-3-yl)-2-((1S)-1-{[(1-methylazetidinium-3-yl)carbonyl]amino}-7-oxononyl)-1H-imidazol-3-ium-L-tartrate;

2-((1S)-1-{[(1-methyl-1H-indol-3-yl)carbonyl]amino}-7-oxooctyl)-5-phenyl-1H-imidazol-3-ium trifluoroacetate;

2-((1S)-1-{[(5-methoxy-1H-indol-2-yl)carbonyl]amino}-7-oxooctyl)-5-phenyl-1H-imidazol-3-ium trifluoroacetate;

2-((1S)-1-{[(6-fluoro-1H-indol-3-yl)acetyl]amino}-7-oxooctyl)-5-phenyl-1H-imidazol-3-ium trifluoroacetate;

2-((1S)-1-{[(2-methyl-1H-indol-3-yl)acetyl]amino}-7-oxooctyl)-5-phenyl-1H-imidazol-3-ium trifluoroacetate;

2-{(1S)-1-[(1H-indol-3-ylacetyl)amino]-7-oxooctyl}-5-phenyl-1H-imidazol-3-ium trifluoroacetate;

2-{(1S)-1-[(1H-indol-3-ylcarbonyl)amino]-7-oxooctyl}-5-phenyl-1H-imidazol-3-ium trifluoroacetate;

2-((1S)-1-{[(5-bromo-1H-indol-3-yl)acetyl]amino}-7-oxooctyl)-5-phenyl-1H-imidazol-3-ium trifluoroacetate;

2-((1S)-1-{[(7-methoxy-6,7-dihydro-1-benzofuran-2-yl)carbonyl]amino}-7-oxooctyl)-5-phenyl-1H-imidazol-3-ium trifluoroacetate;

2-{(1S)-1-[(1-naphthylacetyl)amino]-7-oxooctyl}-5-phenyl-1H-imidazol-3-ium trifluoroacetate;

2-((1S)-1-{[(5-fluoro-1H-indol-3-yl)acetyl]amino}-7-oxooctyl)-5-phenyl-1H-imidazol-3-ium trifluoroacetate;

2-((1S)-1-{[(5-chloro-1H-indol-3-yl)acetyl]amino}-7-oxooctyl)-5-phenyl-1H-imidazol-3-ium trifluoroacetate;

2-{(1S)-1-[(1H-indol-2-ylcarbonyl)amino]-7-oxooctyl}-5-phenyl-1H-imidazol-3-ium trifluoroacetate;

2-((1S)-1-{[(5-fluoro-1H-indol-2-yl)carbonyl]amino}-7-oxooctyl)-5-phenyl-1H-imidazol-3-ium trifluoroacetate;

2-((1S)-1-{[(5-methoxy-1H-indol-3-yl)acetyl]amino}-7-oxooctyl)-5-phenyl-1H-imidazol-3-ium trifluoroacetate;

2-((1S)-1-{[(5-hydroxy-1H-indol-3-yl)acetyl]amino}-7-oxooctyl)-5-phenyl-1H-imidazol-3-ium trifluoroacetate;

2-((1S)-1-{[(6-methoxy-2-oxo-2,3-dihydro-1H-indol-3-yl)acetyl]amino}-7-oxooctyl)-5-phenyl-1H-imidazol-3-ium trifluoroacetate;

2-((1S)-1-{[(5-methoxy-2-oxo-2,3-dihydro-1H-indol-3-yl)acetyl]amino}-7-oxooctyl)-5-phenyl-1H-imidazol-3-ium trifluoroacetate;

6-(2-oxo-2-{[(1S)-7-oxo-1-(5-phenyl-1H-imidazol-3-ium-2-yl)octyl]amino}ethyl)[1,2,4]triazolo[1,5-a]pyrimidin-3-ium bis(trifluoroacetate);

3-({[(1S)-7-oxo-1-(5-phenyl-1H-imidazol-3-ium-2-yl)octyl]amino}carbonyl)-3,4-dihydrospiro[isochromene-1,4'-piperidinium]bis(trifluoroacetate);

4-({[(1S)-7-oxo-1-(5-phenyl-1H-imidazol-3-ium-2-yl)octyl]amino}carbonyl)-3,4-dihydrospiro[chromene-2,4'-piperidinium]bis(trifluoroacetate);

5-chloro-2-(2-oxo-2-{[(1S)-7-oxo-1-(5-phenyl-1H-imidazol-3-ium-2-yl)octyl]amino}ethyl)-1H-3,1-benzimidazol-3-ium bis(trifluoroacetate);

2-((1S)-7-oxo-1-{[(2-oxoquinazolin-1(2H)-yl)acetyl]amino}octyl)-5-phenyl-1H-imidazol-3-ium trifluoroacetate;

2-((1S)-7-oxo-1-{[(2-oxo-1,3-benzoxazol-3(2H)-yl)acetyl]amino}octyl)-5-phenyl-1H-imidazol-3-ium trifluoroacetate;

2-{(1S)-1-[(2H-indazol-2-ylacetyl)amino]-7-oxooctyl}-5-phenyl-1H-imidazol-3-ium trifluoroacetate;

3-({[(1S)-7-oxo-1-(5-phenyl-1H-imidazol-3-ium-2-yl)octyl]amino}carbonyl)-2,3-dihydrospiro[indene-1,4'-piperidinium]bis(trifluoroacetate);

2-((1S)-7-oxo-1-{[(2-oxo-1,2,3,4-tetrahydroquinolin-4-yl)carbonyl]amino}octyl)-5-phenyl-1H-imidazol-3-ium trifluoroacetate;

2-((1S)-1-{[(5-cyano-1H-indol-1-yl)acetyl]amino}-7-oxooctyl)-5-phenyl-1H-imidazol-3-ium trifluoroacetate;

2-{(1S)-1-[(2-naphthylacetyl)amino]-7-oxooctyl}-5-phenyl-1H-imidazol-3-ium trifluoroacetate;

2-((1S)-1-{[(5-chloro-1-benzothien-3-yl)acetyl]amino}-7-oxooctyl)-5-phenyl-1H-imidazol-3-ium trifluoroacetate;

2-((1S)-1-{[(5-chloro-1H-indazol-3-yl)acetyl]amino}-7-oxooctyl)-5-phenyl-1H-imidazol-3-ium trifluoroacetate;

2-(2-{(1S)-1-[(1-azoniabicyclo[2.2.2]oct-4-ylcarbonyl)amino]-7-oxononyl}-1H-imidazol-1-ium-5-yl)-4-methoxyquinolinium tris(trifluoroacetate);

4-methoxy-2-[2-((1S)-1-{[(5-methoxy-2-methyl-1H-indol-3-yl)acetyl]amino}-7-oxononyl)-1H-imidazol-1-ium-5-yl]quinolinium bis(trifluoroacetate);

5-methoxy-N-{(1S)-1-[5-(2-naphthyl)-1,3-oxazol-2-yl]-7-oxononyl}-1H-indole-2-carboxamide;

1-methyl-4-[({(1S)-1-[5-(2-naphthyl)-1,3-oxazol-2-yl]-7-oxononyl}amino)carbonyl]piperidinium trifluoroacetate;

4-[({(1S)-1-[5-(2-naphthyl)-1,3-oxazol-2-yl]-7-oxononyl}amino)carbonyl]-1-azoniabicyclo[2.2.2]octane trifluoroacetate;

N,N,2-trimethyl-1-({(1S)-1-[5-(2-naphthyl)-1,3-oxazol-2-yl]-7-oxononyl}amino)-1-oxopropan-2-aminium trifluoroacetate;

1-methyl-3-[({(1S)-1-[5-(2-naphthyl)-1,3-oxazol-2-yl]-7-oxononyl}amino)carbonyl]azetidinium trifluoroacetate;

N-{(1S)-1-[5-(2-naphthyl)-1,3-oxazol-2-yl]-7-oxononyl}acetamide;

N,N-dimethyl-N'-{(1S)-1-[5-(2-naphthyl)-1,3-oxazol-2-yl]-7-oxononyl}ethanediamide;

8-[2-(1-{[(1-methylpiperidinium-4-yl)carbonyl]amino}-7-oxononyl)-1H-imidazol-1-ium-5-yl]quinolinium tris(trifluoroacetate);

2-((1S)-1-{[(1-methylpiperidinium-4-yl)carbonyl]amino}-7-oxononyl)-6-phenylpyridinium bis(trifluoroacetate);

N-{(1S)-1-[5-(2-naphthyl)-1,3-oxazol-2-yl]-7-oxononyl}-2-(2-oxoquinazolin-1(2H)-yl)acetamide;

3-(2-ethyl-1H-benzimidazol-1-yl)-N-{(1S)-1-[5-(2-naphthyl)-1,3-oxazol-2-yl]-7-oxononyl}propanamide;

N,N-dimethyl-2-({(1S)-1-[5-(2-naphthyl)-1,3-oxazol-2-yl]-7-oxononyl}amino)-2-oxoethanaminium trifluoroacetate;

2-ethyl-1-(3-oxo-3-{[(1S)-7-oxo-1-(6-phenylpyridinium-2-yl)nonyl]amino}propyl)-1H-3,1-benzimidazol-1-ium bis(trifluoroacetate);

4-({[(1S)-7-oxo-1-(6-phenylpyridinium-2-yl)nonyl]amino}carbonyl)-1-azoniabicyclo[2.2.2]octane bis(trifluoroacetate);

2-((1S)-1-{[(benzylamino)carbonyl]amino}-7-oxononyl)-6-phenylpyridinium trifluoroacetate;

2-((1S)-7-[methoxy(methyl)amino]-1-{[(5-methoxy-2-methyl-1H-indol-3-yl)acetyl]amino}-7-oxoheptyl)-5-phenyl-1H-imidazol-1-ium trifluoroacetate;

2-((1S)-1-{[(5-methoxy-2-methyl-1H-indol-3-yl)acetyl]amino}-7-oxononyl)-5-quinoxalin-2-yl-1H-imidazol-1-ium trifluoroacetate;

2-((1S)-1-{[(5-methoxy-2-methyl-1H-indol-3-yl)acetyl]amino}-7-oxononyl)-5-(3-methoxy-2-naphthyl)-1H-imidazol-1-ium trifluoroacetate;

5-{[benzyl(methyl)ammonio]methyl}-2-(1-{[(5-methoxy-2-methyl-1H-indol-3-yl)acetyl]amino}-7-oxononyl)-1H-imidazol-1-ium bis(trifluoroacetate);

2-{[2-(1-{[(5-methoxy-2-methyl-1H-indol-3-yl)acetyl]amino}-7-oxononyl)-1H-imidazol-1-ium-5-yl]methyl}-1,2,3,4-tetrahydroisoquinolinium bis(trifluoroacetate);

2-((1S)-1-{[(5-methoxy-2-methyl-1H-indol-3-yl)acetyl]amino}-7-oxodecyl)-5-phenyl-1H-imidazol-1-ium trifluoroacetate;

2-(1-{[(5-methoxy-2-methyl-1H-indol-3-yl)acetyl]amino}-7-oxononyl)-5-(2-methoxyphenyl)-1H-imidazol-3-ium trifluoroacetate;

2-(1-{[(5-methoxy-2-methyl-1H-indol-3-yl)acetyl]amino}-7-oxononyl)-5-(3-methoxyphenyl)-1H-imidazol-3-ium trifluoroacetate;

6-[2-(1-{[(5-methoxy-2-methyl-1H-indol-3-yl)acetyl]amino}-7-oxononyl)-1H-imidazol-3-ium-5-yl]quinolinium bis(trifluoroacetate);

5-[2-(1-{[(5-methoxy-2-methyl-1H-indol-3-yl)acetyl]amino}-7-oxononyl)-1H-imidazol-3-ium-5-yl]-2-methylquinolinium bis(trifluoroacetate);

5-[2-(1-{[(5-methoxy-2-methyl-1H-indol-3-yl)acetyl]amino}-7-oxononyl)-1H-imidazol-3-ium-5-yl]quinolinium bis(trifluoroacetate);

5-[2-(1-{[(5-methoxy-2-methyl-1H-indol-3-yl)acetyl]amino}-7-oxononyl)-1H-imidazol-3-ium-5-yl]-8-methylquinolinium bis(trifluoroacetate);

8-methoxy-5-[2-(1-{[(5-methoxy-2-methyl-1H-indol-3-yl)acetyl]amino}-7-oxononyl)-1H-imidazol-3-ium-5-yl]quinolinium bis(trifluoroacetate);

5-(1-benzothien-7-yl)-2-(1-{[(5-methoxy-2-methyl-1H-indol-3-yl)acetyl]amino}-7-oxononyl)-1H-imidazol-3-ium trifluoroacetate;

5-(1H-indol-5-yl)-2-(1-{[(5-methoxy-2-methyl-1H-indol-3-yl)acetyl]amino}-7-oxononyl)-1H-imidazol-3-ium trifluoroacetate;

5-[3-(3,5-dimethyl-1H-pyrazol-1-yl)phenyl]-2-(1-{[(5-methoxy-2-methyl-1H-indol-3-yl)acetyl]amino}-7-oxononyl)-1H-imidazol-3-ium trifluoroacetate;

5-(3-methoxy-2-naphthyl)-2-((1S)-1-{[(1-methylazetidinium-3-yl)carbonyl]amino}-7-oxononyl)-1H-imidazol-1-ium bis(trifluoroacetate);

2-((1S)-1-{[(2-ethyl-5-methyl-1H-indol-3-yl)acetyl]amino}-7-oxononyl)-5-phenyl-1H-imidazol-1-ium trifluoroacetate;

2-((1S)-1-{[(1-methylazetidinium-3-yl)carbonyl]amino}-7-oxononyl)-5-quinoxalin-2-yl-1H-imidazol-1-ium bis(trifluoroacetate);

2-((1S)-1-{[(2-ethyl-6-methyl-1H-indol-3-yl)acetyl]amino}-7-oxononyl)-5-phenyl-1H-imidazol-1-ium trifluoroacetate;

5-[4-(dimethylammonio)phenyl]-2-1-{[(5-methoxy-2-methyl-1H-indol-3-yl)acetyl]amino}-7-oxononyl)-1H-imidazol-1-ium bis(trifluoroacetate);

5-(2-fluoro-4-methoxyphenyl)-2-(1-{[(5-methoxy-2-methyl-1H-indol-3-yl)acetyl]amino}-7-oxononyl)-1H-imidazol-1-ium trifluoroacetate;

5-(3-fluoro-4-methoxyphenyl)-2-(1-{[(5-methoxy-2-methyl-1H-indol-3-yl)acetyl]amino}-7-oxononyl)-1H-imidazol-1-ium trifluoroacetate;

5-(3-carboxyphenyl)-2-(1-{[(5-methoxy-2-methyl-1H-indol-3-yl)acetyl]amino}-7-oxononyl)-1H-imidazol-1-ium trifluoroacetate;

5-biphenyl-2-yl-2-(1-{[(5-methoxy-2-methyl-1H-indol-3-yl)acetyl]amino}-7-oxononyl)-1H-imidazol-1-ium trifluoroacetate;

5-dibenzo[b,d]furan-4-yl-2-(1-{[(5-methoxy-2-methyl-1H-indol-3-yl)acetyl]amino}-7-oxononyl)-1H-imidazol-1-ium trifluoroacetate;

2-(1-{[(5-methoxy-2-methyl-1H-indol-3-yl)acetyl]amino}-7-oxononyl)-5-[3-(piperidin-1-ylcarbonyl)phenyl]-1H-imidazol-1-ium trifluoroacetate;

2-(1-{[(5-methoxy-2-methyl-1H-indol-3-yl)acetyl]amino}-7-oxononyl)-5-quinoxalin-6-yl-1H-imidazol-1-ium trifluoroacetate;

5-[(dimethylammonio)methyl]-2-(1-{[(5-methoxy-2-methyl-1H-indol-3-yl)acetyl]amino}-7-oxononyl)-1H-imidazol-1-ium bis(trifluoroacetate);

5-(1,4-dimethoxy-2-naphthyl)-2-((1S)-1-{[(5-methoxy-2-methyl-1H-indol-3-yl)acetyl]amino}-7-oxononyl)-1H-imidazol-1-ium trifluoroacetate;

2-((1S)-1-{[(5-methoxy-2-methyl-1H-indol-3-yl)acetyl]amino}-7-{[2-(methylthio)ethyl]amino}-7-oxoheptyl)-5-(2-naphthyl)-1H-imidazol-1-ium trifluoroacetate;

2-((1S)-7-(methoxyamino)-1-{[(5-methoxy-2-methyl-1H-indol-3-yl)acetyl]amino}-7-oxoheptyl)-5-(2-naphthyl)-1H-imidazol-1-ium trifluoroacetate;

2-((1S)-7-(ethoxyamino)-1-{[(5-methoxy-2-methyl-1H-indol-3-yl)acetyl]amino}-7-oxoheptyl)-5-(2-naphthyl)-1H-imidazol-1-ium trifluoroacetate;

2-((1S)-1-{[(2-methyl-5-nitro-1H-indol-3-yl)acetyl]amino}-7-oxononyl)-5-phenyl-1H-imidazol-1-ium trifluoroacetate;

2-((1S)-1-{[(5-methoxy-2-methyl-1H-inden-3-yl)acetyl]amino}-7-oxononyl)-5-phenyl-1H-imidazol-1-ium trifluoroacetate;

2-((1S)-1-{[(5-hydroxy-2-methyl-1H-indol-3-yl)acetyl]amino}-7-oxononyl)-5-phenyl-1H-imidazol-1-ium trifluoroacetate;

2-((1S)-1-{[3-(5-methoxy-1H-benzimidazol-2-yl)propanoyl]amino}-7-oxononyl)-5-phenyl-1H-imidazol-1-ium trifluoroacetate;

2-{(1S)-1-[(1-benzothien-3-ylacetyl)amino]-7-oxononyl}-5-phenyl-1H-imidazol-1-ium trifluoroacetate;

2-((1S)-1-{[(2,5-dimethyl-1H-indol-3-yl)acetyl]amino}-7-oxononyl)-5-phenyl-1H-imidazol-1-ium trifluoroacetate;

2-((1S)-1-{[3-(1H-benzimidazol-2-yl)propanoyl]amino}-7-oxononyl)-5-phenyl-1H-imidazol-1-ium trifluoroacetate;

2-((1S)-1-{[(6-methoxy-1H-indol-3-yl)acetyl]amino}-7-oxononyl)-5-phenyl-1H-imidazol-1-ium trifluoroacetate;

2-{(1S)-1-[(1H-indol-6-ylacetyl)amino]-7-oxononyl}-5-phenyl-1H-imidazol-1-ium trifluoroacetate;

2-((1S)-1-{[(2-methyl-1,3-benzothiazol-5-yl)acetyl]amino}-7-oxononyl)-5-phenyl-1H-imidazol-1-ium trifluoroacetate;

2-((1S)-1-{[3-(5-methoxy-2-oxo-1,3-benzoxazol-3(2H)-yl)propanoyl]amino}-7-oxononyl)-5-phenyl-1H-imidazol-1-ium trifluoroacetate;

2-((1S)-1-{[3-(7-methoxy-1H-indol-3-yl)propanoyl]amino}-7-oxononyl)-5-phenyl-1H-imidazol-1-ium trifluoroacetate;

2-((1S)-1-{[3-(1,3-benzothiazol-2-yl)propanoyl]amino}-7-oxononyl)-5-phenyl-1H-imidazol-1-ium trifluoroacetate;

2-((1S)-1-{[(5-methoxy-2-oxo-2,3-dihydro-1H-indol-3-yl)acetyl]amino}-7-oxononyl)-5-phenyl-1H-imidazol-1-ium trifluoroacetate;

2-((1S)-1-{[(6-methoxy-2-oxo-2,3-dihydro-1H-indol-3-yl)acetyl]amino}-7-oxononyl)-5-phenyl-1H-imidazol-1-ium trifluoroacetate;

2-((1S)-1-{[(benzylamino)carbonyl]amino}-7-oxononyl)-4-phenylpyridinium trifluoroacetate;

4-({[(1S)-7-oxo-1-(4-phenylpyridinium-2-yl)nonyl]amino}carbonyl)-1-azoniabicyclo[2.2.2]octane bis(trifluoroacetate);

2-((1S)-1-{[2-(dimethylammonio)-2-methylpropanoyl]amino}-7-oxononyl)-4-phenylpyridinium bis(trifluoroacetate);

5-(3,5-dimethoxy-2-naphthyl)-2-((1S)-1-{[(5-methoxy-2-methyl-1H-indol-3-yl)acetyl]amino}-7-oxononyl)-1H-imidazol-1-ium trifluoroacetate;

2-((1S)-1-{[(benzyloxy)carbonyl]amino}-7-oxononyl)-4-phenylpyridinium trifluoroacetate;

2-((1S)-1-{([(1-methyl-1H-indol-3-yl)acetyl]amino}-7-oxononyl)-5-phenyl-1H-imidazol-1-ium trifluoroacetate;

2-((1S)-1-{[(7-fluoro-2-methyl-1H-indol-3-yl)acetyl]amino}-7-oxononyl)-5-phenyl-1H-imidazol-1-ium trifluoroacetate;

2-((1S)-1-{[(5-ethyl-2-methyl-1H-indol-3-yl)acetyl]amino}-7-oxononyl)-5-phenyl-1H-imidazol-1-ium trifluoroacetate;

2-(5-tert-butyl-2-methyl-1H-indol-3-yl)-N-[(1S)-7-oxo-1-(5-phenyl-1H-imidazol-2-yl)nonyl]acetamide;

2-((1S)-1-{[(5-ethoxy-2-methyl-1H-indol-3-yl)acetyl]amino}-7-oxononyl)-5-phenyl-1H-imidazol-1-ium trifluoroacetate;

2-[5-(benzyloxy)-2-methyl-1H-indol-3-yl]-N-[(1S)-7-oxo-1-(5-phenyl-1H-imidazol-2-yl)nonyl]acetamide;

3-(1H-indol-1-yl)-N-[(1S)-7-oxo-1-(5-phenyl-1H-imidazol-2-yl)nonyl]propanamide;

2-((1S)-1-{[(5-methoxy-1H-indol-3-yl)acetyl]amino}-7-oxononyl)-5-phenyl-1H-imidazol-1-ium trifluoroacetate;

2-((1S)-7-oxo-1-{[3-(2-oxo-1,3-benzothiazol-3(2H)-yl)propanoyl]amino}nonyl)-5-phenyl-1H-imidazol-1-ium trifluoroacetate;

2-{(1S)-7-oxo-1-[(quinolin-3-ylacetyl)amino]nonyl}-5-phenyl-1H-imidazol-1-ium trifluoroacetate;

2-{(1S)-7-oxo-1-[(quinolin-5-ylacetyl)amino]nonyl}-5-phenyl-1H-imidazol-1-ium trifluoroacetate;

2-((1S)-1-{[3-(6-chloro-1H-benzimidazol-2-yl)propanoyl]amino}-7-oxononyl)-5-phenyl-1H-imidazol-1-ium trifluoroacetate;

2-((1S)-1-{[3-(6-fluoro-1H-benzimidazol-2-yl)propanoyl] amino}-7-oxononyl)-5-phenyl-1H-imidazol-1-ium trifluoroacetate;

N-[(1S)-7-oxo-1-(5-phenyl-1H-imidazol-2-yl)nonyl]-2-(5, 6,7,8-tetrahydronaphthalen-1-yl)acetamide;

2-((1S)-1-{[(5-methoxy-2-methyl-1H-indol-3-yl)acetyl] amino}-8-methyl-7-oxononyl)-5-phenyl-1H-imidazol-1-ium trifluoroacetate;

2-((1S)-6-carboxy-1-{[(5-methoxy-2-methyl-1H-indol-3-yl)acetyl]amino}hexyl)-5-phenyl-1H-imidazol-1-ium trifluoroacetate;

2-((1S)-1-{[(5-methoxy-2-methyl-1H-indol-3-yl)acetyl] amino}-7-oxononyl)-5-(2-thienyl)-1H-imidazol-3-ium trifluoroacetate;

2-((1S)-1-{[(5-methoxy-2-methyl-1H-indol-3-yl)acetyl] amino}-7-oxononyl)-5-(1-naphthyl)-1H-imidazol-3-ium trifluoroacetate;

2-((1S)-1-{[(5-methoxy-2-methyl-1H-indol-3-yl)acetyl] amino}-7-oxononyl)-5-quinolin-8-yl-1H-imidazol-3-ium trifluoroacetate;

2-((1S)-1-{[(5-methoxy-2-methyl-1H-indol-3-yl)acetyl] amino}-7-oxononyl)-5-(2-morpholin-4-ylphenyl)-1H-imidazol-3-ium trifluoroacetate;

2-((1S)-1-{[(5-methoxy-2-methyl-1H-indol-3-yl)acetyl] amino}-7-oxononyl)-5-(3-nitrophenyl)-1H-imidazol-3-ium trifluoroacetate;

3-[2-((1S)-1-{[(5-methoxy-2-methyl-1H-indol-3-yl)acetyl] amino}-7-oxononyl)-1H-imidazol-3-ium-5-yl]pyridinium bis(trifluoroacetate);

5-(3-cyanophenyl)-2-((1S)-1-{[(5-methoxy-2-methyl-1H-indol-3-yl)acetyl]amino}-7-oxononyl)-1H-imidazol-3-ium trifluoroacetate;

2-((1S)-1-{[(5-methoxy-2-methyl-1H-indol-3-yl)acetyl] amino}-7-oxononyl)-5-[3-(trifluoromethoxy)phenyl]-1H-imidazol-3-ium trifluoroacetate;

2-((1S)-1-{[(5-methoxy-2-methyl-1H-indol-3-yl)acetyl] amino}-7-oxononyl)-5-[4-(trifluoromethoxy)phenyl]-1H-imidazol-3-ium trifluoroacetate;

2-((1S)-1-{[(5-methoxy-2-methyl-1H-indol-3-yl)acetyl] amino}-7-oxononyl)-5-[4-(trifluoromethyl)phenyl]-1H-imidazol-3-ium trifluoroacetate;

2-((1S)-1-{[(5-methoxy-2-methyl-1H-indol-3-yl)acetyl] amino}-7-oxononyl)-5-[3-(trifluoromethyl)phenyl]-1H-imidazol-3-ium trifluoroacetate;

2-((1S)-1-{[(5-methoxy-2-methyl-1H-indol-3-yl)acetyl] amino}-7-oxononyl)-5-[2-(trifluoromethyl)phenyl]-1H-imidazol-3-ium trifluoroacetate;

2-((1S)-1-{[(5-methoxy-2-methyl-1H-indol-3-yl)acetyl] amino}-7-oxononyl)-5-[2-fluoro-phenyl]-1H-imidazol-3-ium trifluoroacetate;

2-((1S)-1-{[(5-methoxy-2-methyl-1H-indol-3-yl)acetyl] amino}-7-oxononyl)-5-[3-(ethoxy)phenyl]-1H-imidazol-3-ium trifluoroacetate;

2-((1S)-1-{[(5-methoxy-2-methyl-1H-indol-3-yl)acetyl] amino}-7-oxononyl)-5-[4-(ethoxy)phenyl]-1H-imidazol-3-ium trifluoroacetate;

5-[4-(acetylamino)phenyl]-2-((1S)-1-{[(5-methoxy-2-methyl-1H-indol-3-yl)acetyl]amino}-7-oxononyl)-1H-imidazol-3-ium trifluoroacetate;

5-[2-(methoxycarbonyl)phenyl]-2-((1S)-1-{[(5-methoxy-2-methyl-1H-indol-3-yl)acetyl]amino}-7-oxononyl)-1H-imidazol-3-ium trifluoroacetate;

2-((1S)-1-{[(5-methoxy-2-methyl-1H-indol-3-yl)acetyl] amino}-7-oxononyl)-5-[4-cyano-phenyl]-1H-imidazol-3-ium trifluoroacetate;

2-((1S)-1-{[5-(3-methyl-5,6,7,8-tetrahydro-1,8-naphthyridin-2-yl)pentanoyl]amino}-7-oxononyl)-5-phenyl-1H-imidazol-1-ium trifluoroacetate;

6-(2-oxo-2-{[(1S)-7-oxo-1-(5-phenyl-1H-imidazol-1-ium-2-yl)nonyl]amino}ethyl)imidazo[2,1-b][1,3]thiazol-4-ium bis(trifluoroacetate);

2-{(1S)-1-[(1-benzofuran-5-ylacetyl)amino]-7-oxononyl}-5-phenyl-1H-imidazol-1-ium trifluoroacetate;

2-{(1S)-1-[(1-benzothien-2-ylacetyl)amino]-7-oxononyl}-5-phenyl-1H-imidazol-1-ium trifluoroacetate;

2-((1S)-1-{[(2-ethyl-1H-benzimidazol-1-yl)acetyl]amino}-7-oxononyl)-5-phenyl-1H-imidazol-1-ium trifluoroacetate;

2-(1-{[(5-methoxy-2-methyl-1H-indol-3-yl)acetyl]amino}-7-oxononyl)-1H-imidazol-1-ium trifluoroacetate;

2-[2-((1S)-1-{[3-(dimethylammonio)propanoyl]amino}-7-oxononyl)-1H-imidazol-1-ium-5-yl]-4-methoxyquinolinium tris(trifluoroacetate);

5-(4-chlorophenyl)-2-((1S)-1-{[(5-methoxy-2-methyl-1H-indol-3-yl)acetyl]amino}-7-oxononyl)-1H-imidazol-1-ium trifluoroacetate;

5-(3,4-dichlorophenyl)-2-((1S)-1-{[(5-methoxy-2-methyl-1H-indol-3-yl)acetyl]amino}-7-oxononyl)-1H-imidazol-1-ium trifluoroacetate;

5-(3-bromophenyl)-2-((1S)-1-{[(5-methoxy-2-methyl-1H-indol-3-yl)acetyl]amino}-7-oxononyl)-1H-imidazol-1-ium trifluoroacetate;

2-((1S)-7-methoxy-1-{[(5-methoxy-2-methyl-1H-indol-3-yl)acetyl]amino}-7-oxoheptyl)-5-phenyl-1H-imidazol-1-ium trifluoroacetate;

2-(1-{[(5-methoxy-2-methyl-1H-indol-3-yl)acetyl]amino}-7-oxononyl)-5-(2-phenylethyl)-1H-imidazol-1-ium trifluoroacetate;

7-(3-oxo-3-{[(1S)-7-oxo-1-(5-phenyl-1H-imidazol-1-ium-2-yl)nonyl]amino}propyl)-1,8-naphthyridin-1-ium bis(trifluoroacetate);

7-(3-oxo-3-{[(1S)-7-oxo-1-(5-phenyl-1H-imidazol-1-ium-2-yl)nonyl]amino}propyl)-1,2,3,4-tetrahydro-1,8-naphthyridin-1-ium bis(trifluoroacetate);

$N^3,N^3$-dimethyl-N-[{(1S)-1-[5-(2-naphthyl)-1,3,4-oxadiazol-2-yl]-7-oxononyl}-α-alaninamide;

2-{(1S)-7-oxo-1-[(4,5,6,7-tetrahydro-1H-indazol-3-ylcarbonyl)amino]nonyl}-5-phenyl-1H-imidazol-1-ium trifluoroacetate;

2-{(1S)-7-oxo-1-[(4,5,6,7-tetrahydro-1-benzothien-3-ylcarbonyl)amino]nonyl}-5-phenyl-1H-imidazol-1-ium trifluoroacetate;

2-((1S)-7-oxo-1-{[3-(1-oxo-1,3-dihydro-2H-isoindol-2-yl) propanoyl]amino}nonyl)-5-phenyl-1H-imidazol-1-ium trifluoroacetate;

2-{(1S)-1-[({2-[2-(dimethylammonio)ethyl]-3-oxo-2,3-dihydro-1H-isoindol-4-yl}carbonyl)amino]-7-oxononyl}-5-phenyl-1H-imidazol-1-ium bis(trifluoroacetate);

6-benzyl-2-oxo-3-({[(1S)-7-oxo-1-(5-phenyl-1H-imidazol-1-ium-2-yl)nonyl]amino}carbonyl)-1,2,5,6,7,8-hexahydro-1,6-naphthyridin-6-ium bis(trifluoroacetate);

7-(4-oxo-4-{[(1S)-7-oxo-1-(5-phenyl-1H-imidazol-1-ium-2-yl)nonyl]amino}butanoyl)-6,7,8,9-tetrahydropyrido[2,3-b]-1,6-naphthyridin-1-ium bis(trifluoroacetate);

2-((1S)-1-{[(2-acetyl-1,2,3,4-tetrahydroisoquinolin-1-yl) acetyl]amino}-7-oxononyl)-5-phenyl-1H-imidazol-1-ium trifluoroacetate;

2-methyl-3-({[(1S)-7-oxo-1-(5-phenyl-1H-imidazol-1-ium-2-yl)nonyl]amino}carbonyl)-1,2,3,4-tetrahydroisoquinolinium bis(trifluoroacetate);

2-(2-oxo-2-{[(1S)-7-oxo-1-(5-phenyl-1H-imidazol-1-ium-2-yl)nonyl]amino}ethyl)-1,2,3,4-tetrahydroisoquinolinium bis(trifluoroacetate);

4-[2-((1S)-1-{[(5-methoxy-2-methyl-1H-indol-3-yl)acetyl]amino}-7-oxononyl)-1H-imidazol-3-ium-5-yl]pyridinium bis(trifluoroacetate);

2-((1S)-1-{[(5-methoxy-2-methyl-1H-indol-3-yl)acetyl]amino}-7-oxononyl)-5-(2-nitrophenyl)-1H-imidazol-3-ium trifluoroacetate;

5-(3-ammoniophenyl)-2-((1S)-1-{[(5-methoxy-2-methyl-1H-indol-3-yl)acetyl]amino}-7-oxononyl)-1H-imidazol-3-ium bis(trifluoroacetate);

5-(2,3-dihydro-1,4-benzodioxin-6-yl)-2-((1S)-1-{[(5-methoxy-2-methyl-1H-indol-3-yl)acetyl]amino}-7-oxononyl)-1H-imidazol-3-ium trifluoroacetate;

5-(2,4-dimethoxyphenyl)-2-((1S)-1-{[(5-methoxy-2-methyl-1H-indol-3-yl)acetyl]amino}-7-oxononyl)-1H-imidazol-3-ium trifluoroacetate;

5-[2-fluoro-5-(trifluoromethyl)phenyl]-2-((1S)-1-{[(5-methoxy-2-methyl-1H-indol-3-yl)acetyl]amino}-7-oxononyl)-1H-imidazol-3-ium trifluoroacetate;

5-[3-(ammoniomethyl)phenyl]-2-((1S)-1-{[(5-methoxy-2-methyl-1H-indol-3-yl)acetyl]amino}-7-oxononyl)-1H-imidazol-3-ium bis(trifluoroacetate);

5-[2-(ammoniomethyl)-4-fluorophenyl]-2-((1S)-1-{[(5-methoxy-2-methyl-1H-indol-3-yl)acetyl]amino}-7-oxononyl)-1H-imidazol-3-ium bis(trifluoroacetate);

5-biphenyl-3-yl-2-((1S)-1-{[(5-methoxy-2-methyl-1H-indol-3-yl)acetyl]amino}-7-oxononyl)-1H-imidazol-3-ium trifluoroacetate;

3-[2-((1S)-1-{[(5-methoxy-2-methyl-1H-indol-3-yl)acetyl]amino}-7-oxononyl)-1H-imidazol-3-ium-5-yl]quinolinium bis(trifluoroacetate);

5-(3-carboxyphenyl)-2-((1S)-1-{[(5-methoxy-2-methyl-1H-indol-3-yl)acetyl]amino}-7-oxononyl)-1H-imidazol-3-ium trifluoroacetate;

2-((1S)-1-{[(5-methoxy-2-methyl-1H-indol-3-yl)acetyl]amino}-7-oxononyl)-5-[3-(1H-tetrazol-5-yl)phenyl]-1H-imidazol-3-ium trifluoroacetate;

2-((1S)-1-{[(5-methoxy-2-methyl-1H-indol-3-yl)acetyl]amino}-7-oxononyl)-5-(3-{[(methylsulfonyl)amino]carbonyl}phenyl)-1H-imidazol-3-ium trifluoroacetate;

2-((1R)-1-{[(1-methylazetidinium-3-yl)carbonyl]amino}-7-oxononyl)-5-(2-naphthyl)-1H-imidazol-1-ium bis(trifluoroacetate);

2-[(1S)-1-({[1-(2-tert-butoxy-2-oxoethyl)-5-methoxy-2-methyl-1H-indol-3-yl]acetyl}amino)-7-oxononyl]-5-phenyl-1H-imidazol-1-ium trifluoroacetate;

2-[(1S)-1-({[5-methoxy-2-methyl-1-(pyridin-3-ylmethyl)-1H-indol-3-yl]acetyl}amino)-7-oxononyl]-5-phenyl-1H-imidazol-1-ium trifluoroacetate;

2-((1S)-1-{[(5-methoxy-1,2-dimethyl-1H-indol-3-yl)acetyl]amino}-7-oxononyl)-5-phenyl-1H-imidazol-1-ium trifluoroacetate;

2-[(1S)-1-({[5-methoxy-2-methyl-1-(2-pyrrolidinium-1-ylethyl)-1H-indol-3-yl]acetyl}amino)-7-oxononyl]-5-phenyl-1H-imidazol-1-ium bis(trifluoroacetate);

4-{2-[5-methoxy-2-methyl-3-(2-oxo-2-{[(1S)-7-oxo-1-(5-phenyl-1H-imidazol-1-ium-2-yl)nonyl]amino}ethyl)-1H-indol-1-yl]ethyl}morpholin-4-ium bis(trifluoroacetate);

2-((1S)-1-{[(5-methyl-1,2-benzisoxazol-3-yl)acetyl]amino}-7-oxononyl)-5-phenyl-1H-imidazol-1-ium trifluoroacetate;

2-[(1S)-1-({[5-(dimethylammonio)-2-methyl-1H-indol-3-yl]acetyl}amino)-7-oxononyl]-5-phenyl-1H-imidazol-1-ium bis(trifluoroacetate);

1-methyl-4-[({(1S)-1-[5-(2-naphthyl)-1H-imidazol-1-ium-2-yl]-7-oxoundecyl}amino)carbonyl]piperidinium bis(trifluoroacetate);

1-methyl-4-[({(1S)-1-[5-(2-naphthyl)-1H-imidazol-1-ium-2-yl]-7-oxodecyl}amino)carbonyl]piperidinium bis(trifluoroacetate);

N-[1-(5-acetyl-1H-imidazol-2-yl)-7-oxononyl]-2-(5-methoxy-2-methyl-1H-indol-3-yl)acetamide;

2-[2-((1S)-1-{[3-(dimethylammonio)propanoyl]amino}-7-oxononyl)-1H-imidazol-1-ium-5-yl]-4-methoxyquinolinium trichloride;

2-((1S)-1-{[(6-methoxy-1-benzofuran-3-yl)acetyl]amino}-7-oxononyl)-5-phenyl-1H-imidazol-1-ium trifluoroacetate;

6-({[(1S)-7-oxo-1-(5-phenyl-1H-imidazol-1-ium-2-yl)nonyl]amino}carbonyl)quinolinium bis(trifluoroacetate);

6-({[(1S)-7-oxo-1-(5-phenyl-1H-imidazol-1-ium-2-yl)nonyl]amino}carbonyl)isoquinolinium bis(trifluoroacetate);

5-methyl-6-({[(1S)-7-oxo-1-(5-phenyl-1H-imidazol-1-ium-2-yl)nonyl]amino}carbonyl)-4,5,6,7-tetrahydro-3H-imidazo[4,5-c]pyridine-3,5-diium tris(trifluoroacetate);

2-(5-methyl-1-benzothien-3-yl)-N-[(1S)-7-oxo-1-(5-phenyl-1H-imidazol-2-yl)nonyl]acetamide;

2-[(1S)-1-({[1-(carboxymethyl)-5-methoxy-2-methyl-1H-indol-3-yl]acetyl}amino)-7-oxononyl]-5-phenyl-1H-imidazol-1-ium trifluoroacetate;

4-{[5-methoxy-2-methyl-3-(2-oxo-2-{[(1S)-7-oxo-1-(5-phenyl-1H-imidazol-1-ium-2-yl)nonyl]amino}ethyl)-1H-indol-1-yl]acetyl}-1-methylpiperazin-1-ium bis(trifluoroacetate);

7-methyl-2-({[(1S)-7-oxo-1-(5-phenyl-1H-imidazol-1-ium-2-yl)nonyl]amino}carbonyl)-5,6,7,8-tetrahydroimidazo[1,2-a]pyrazine-4,7-diium tris(trifluoroacetate);

2-{(1S)-1-[({5-[(dimethylammonio)methyl]-2-methyl-1H-indol-3-yl}acetyl)amino]-7-oxononyl}-5-phenyl-1H-imidazol-1-ium bis(trifluoroacetate);

5-bromo-2-((1S)-1-{[(5-methoxy-2-methyl-1H-indol-3-yl)acetyl]amino}-7-oxononyl)-1H-imidazol-3-ium trifluoroacetate;

5-(4-carboxyphenyl)-2-((1S)-1-{[(5-methoxy-2-methyl-1H-indol-3-yl)acetyl]amino}-7-oxononyl)-1H-imidazol-3-ium trifluoroacetate;

5-(3-hydroxyphenyl)-2-((1S)-1-{[(5-methoxy-2-methyl-1H-indol-3-yl)acetyl]amino}-7-oxononyl)-1H-imidazol-1-ium trifluoroacetate;

5-[2-((1S)-1-{[(5-methoxy-2-methyl-1H-indol-3-yl)acetyl]amino}-7-oxononyl)-1H-imidazol-1-ium-5-yl]isoquinolinium bis(trifluoroacetate);

5-{4-[(dimethylammonio)methyl]phenyl}-2-((1S)-1-{[(5-methoxy-2-methyl-1H-indol-3-yl)acetyl]amino}-7-oxononyl)-1H-imidazol-1-ium bis(trifluoroacetate);

4-methoxy-2-[2-((1S)-1-{[(1-methylazetidinium-3-yl)carbonyl]amino}-7-oxononyl)-1H-imidazol-1-ium-5-yl]quinolinium tris(trifluoroacetate);

5-(2-carboxyphenyl)-2-((1S)-1-{[(5-methoxy-2-methyl-1H-indol-3-yl)acetyl]amino}-7-oxononyl)-1H-imidazol-1-ium trifluoroacetate;

5-[4-(dimethylammonio)phenyl]-2-((1S)-1-{[(5-methoxy-2-methyl-1H-indol-3-yl)acetyl]amino}-7-oxononyl)-1H-imidazol-1-ium bis(trifluoroacetate);

2-((1S)-7-oxo-1-{[(4,5,6,7-tetrafluoro-1H-indol-3-yl)acetyl]amino}nonyl)-5-phenyl-1H-imidazol-1-ium trifluoroacetate;

2-((1S)-1-{[(5-fluoro-2-methyl-1H-indol-3-yl)acetyl]amino}-7-oxononyl)-5-phenyl-1H-imidazol-1-ium trifluoroacetate;

1-methyl-N-{(1S)-1-[5-(2-naphthyl)-1,3,4-oxadiazol-2-yl]-7-oxononyl}azetidine-3-carboxamide;

2-{(1S)-7-oxo-1-[(1H-pyrrolo[2,3-b]pyridin-3-ylacetyl)amino]nonyl}-5-phenyl-1H-imidazol-1-ium trifluoroacetate;

4-({[(1S)-6-carboxy-1-(5-phenyl-1H-imidazol-1-ium-2-yl)hexyl]amino}carbonyl)-1-azoniabicyclo[2.2.2]octane bis(trifluoroacetate);

4-({[(1S)-7-(methoxyamino)-7-oxo-1-(5-phenyl-1H-imidazol-1-ium-2-yl)heptyl]amino}carbonyl)-1-azoniabicyclo[2.2.2]octane bis(trifluoroacetate);

1-methyl-4-({[(1S)-7-oxo-1-(4-phenyl-1H-imidazol-3-ium-2-yl)-7-(2-thienyl)heptyl]amino}carbonyl)piperidinium bis(trifluoroacetate);

2-{(1S)-7-oxo-1-[(1H-pyrrolo[3,2-c]pyridin-3-ylacetyl)amino]nonyl}-5-phenyl-1H-imidazol-1-ium trifluoroacetate;

2-((1S)-1-{[(5-methoxy-1H-pyrrolo[2,3-c]pyridin-3-yl)acetyl]amino}-7-oxononyl)-5-phenyl-1H-imidazol-1-ium trifluoroacetate;

5-(2-fluoroquinolin-3-yl)-2-((1S)-1-{[(1-methylazetidinium-3-yl)carbonyl]amino}-7-oxononyl)-1H-imidazol-3-ium bis(trifluoroacetate);

2-((1S)-1-{[(1-methylazetidinium-3-yl)carbonyl]amino}-7-oxononyl)-5-quinoxalin-6-yl-1H-imidazol-3-ium bis(trifluoroacetate);

8-methoxy-5-[2-((1S)-1-{[(1-methylazetidinium-3-yl)carbonyl]amino}-7-oxononyl)-1H-imidazol-3-ium-5-yl]quinolinium tris(trifluoroacetate);

5-[4-(dimethylamino)phenyl]-2-((1S)-1-{[(1-methylazetidinium-3-yl)carbonyl]amino}-7-oxononyl)-1H-imidazol-3-ium bis(trifluoroacetate);

2-methyl-1-({[(1S)-7-oxo-1-(5-phenyl-1H-imidazol-1-ium-2-yl)nonyl]amino}carbonyl)-1,2,3,4-tetrahydroisoquinolinium bis(trifluoroacetate);

5-(3-carboxyphenyl)-2-{(1S)-7-oxo-1-[(2-thienylcarbonyl)amino]nonyl}-1H-imidazol-3-ium trifluoroacetate;

4-methoxy-2-(2-{(1S)-1-[(3-morpholin-4-ium-4-ylpropanoyl)amino]-7-oxononyl}-1H-imidazol-1-ium-5-yl)quinolinium trichloride;

2-[2-((1S)-1-{[3-(1H-imidazol-1-ium-1-yl)propanoyl]amino}-7-oxononyl)-1H-imidazol-1-ium-5-yl]-4-methoxyquinolinium trichloride;

2-[2-((1S)-1-{[(4-acetylpiperazin-1-ium-1-yl)acetyl]amino}-7-oxononyl)-1H-imidazol-1-ium-5-yl]-4-methoxyquinolinium trichloride;

2-[2-((1S)-1-{[(dimethylammonio)acetyl]amino}-7-oxononyl)-1H-imidazol-1-ium-5-yl]-4-methoxyquinolinium trichloride;

4-methoxy-2-(2-{(1S)-7-oxo-1-[(piperidinium-1-ylacetyl)amino]nonyl}-1H-imidazol-1-ium-5-yl)quinolinium trichloride;

4-methoxy-2-[2-((1S)-1-{[(4-methylpiperazin-4-ium-1-yl)acetyl]amino}-7-oxononyl)-1H-imidazol-1-ium-5-yl]quinolinium trichloride;

4-methoxy-2-[2-((1S)-1-{[(4-methylmorpholin-4-ium-2-yl)carbonyl]amino}-7-oxononyl)-1H-imidazol-1-ium-5-yl]quinolinium tris(trifluoroacetate);

4-methoxy-2-[2-((S)-1-{[3-(4-methylpiperazin-4-ium-1-yl)propanoyl]amino}-7-oxononyl)-1H-imidazol-1-ium-5-yl]quinolinium tris(trifluoroacetate);

4-methoxy-2-[2-((1S)-1-{[(4-methylpiperazin-4-ium-1-yl)(oxo)acetyl]amino}-7-oxononyl)-1H-imidazol-1-ium-5-yl]quinolinium tris(trifluoroacetate);

2-[(1S)-1-({[1-(N,N-dimethylglycyl)azetidin-3-yl]carbonyl}amino)-7-oxononyl]-5-(4-methoxyquinolin-2-yl)-1H-imidazol-1-ium trifluoroacetate;

2-[(1S)-1-({[1-(2-methoxyethyl)azetidinium-3-yl]carbonyl}amino)-7-oxononyl]-5-(4-methoxyquinolin-2-yl)-1H-imidazol-1-ium bis(trifluoroacetate);

1-methyl-3-[({(1S)-1-[5-(1,8-naphthyridin-2-yl)-1,3,4-oxadiazol-2-yl]-7-oxononyl}amino)carbonyl]azetidinium formate;

1-methyl-3-[({(1S)-1-[5-(1,6-naphthyridin-2-yl)-1,3,4-oxadiazol-2-yl]-7-oxononyl}amino)carbonyl]azetidinium formate;

1-methyl-3-[({(1S)-1-[5-(1,6-naphthyridin-8-yl)-1,3,4-oxadiazol-2-yl]-7-oxononyl}amino)carbonyl]azetidinium formate;

3-({(1S)-1-[5-(4-methoxyquinolin-2-yl)-1,3,4-oxadiazol-2-yl]-7-oxononyl}amino)-N,N-dimethyl-3-oxopropan-1-aminium formate;

4-[({(1S)-1-[5-(4-methoxyquinolin-2-yl)-1,3,4-oxadiazol-2-yl]-7-oxononyl}amino)carbonyl]-1-azoniabicyclo[2.2.2]octane formate;

2-((1S)-1-{[(1-methylazetidinium-3-yl)carbonyl]amino}-7-oxononyl)-5-(2-oxo-1,2-dihydroquinolin-3-yl)-1H-imidazol-3-ium bis(trifluoroacetate);

N-{(S)-1-[5-(4-methoxyquinolin-2-yl)-1,3,4-oxadiazol-2-yl]-7-oxononyl}-2-(1H-pyrrolo[3,2-c]pyridin-3-yl)acetamide;

5-(4-methoxyquinolin-2-yl)-2-{(1S)-7-oxo-1-[(1H-pyrrolo[3,2-c]pyridin-3-ylacetyl)amino]nonyl}-1H-imidazol-1-ium trifluoroacetate;

5-(3-carboxyphenyl)-2-((1S)-1-{[(1-methylpiperidin-4-yl)carbonyl]amino}-7-oxononyl)-1H-imidazol-3-ium trifluoroacetate;

5-(3-carboxyphenyl)-2-{(1S)-1-[(morpholin-4-ylacetyl)amino]-7-oxononyl}-1H-imidazol-3-ium trifluoroacetate;

5-(3-carboxyphenyl)-2-{(1S)-1-[(N,N-dimethylglycyl)amino]-7-oxononyl}-1H-imidazol-3-ium trifluoroacetate;

2-((1S)-1-{[(1-methylpiperidin-4-yl)carbonyl]amino}-7-oxononyl)-5-(3-{[(methylsulfonyl)amino]carbonyl}phenyl)-1H-imidazol-3-ium trifluoroacetate;

2-((1S)-1-{[3-(3-methoxyazetidinium-1-yl)propanoyl]amino}-7-oxononyl)-5-quinoxalin-6-yl-1H-imidazol-1-ium bis(trifluoroacetate);

3-({[(1S)-7-oxo-1-(5-quinoxalin-6-yl-1H-imidazol-3-ium-2-yl)nonyl]amino}carbonyl)-1-azoniabicyclo[2.2.2]octane bis(trifluoroacetate);

4-({[(1S)-7-Oxo-1-(5-quinoxalin-6-yl-1H-imidazol-1-ium-2-yl)nonyl]amino}carbonyl)-1-azoniabicyclo[2.2.2]octane bis(trifluoroacetate);

5-(2-methoxyquinolin-3-yl)-2-((1S)-1-{[(1-methylazetidinium-3-yl)carbonyl]amino}-7-oxononyl)-1H-imidazol-3-ium dichloride;

2-((1S)-1-{[(dimethylammonio)acetyl]amino}-7-oxononyl)-5-(4-methoxyquinolin-2-yl)-1H-imidazol-1-ium dichloride;

3-[({(1S)-1-[5-(2-methoxyquinolin-3-yl)-1H-imidazol-2-yl]-7-oxononyl}amino)carbonyl]-1-methylazetidinium chloride;

N-{(1S)-1-[5-(2-methoxyquinolin-3-yl)-1H-imidazol-2-yl]-7-oxononyl}-1-methylazetidine-3-carboxamide;

N-{(1S)-7-[methoxy(methyl)amino]-1-[5-(2-methoxyquinolin-3-yl)-1H-imidazol-2-yl]-7-oxoheptyl}-1-methylazetidine-3-carboxamide;

and the pharmaceutically acceptable free bases, salts, alternative salts and stereoisomers thereof.

Included in the instant invention is the free base of compounds of Formula I, as well as the pharmaceutically acceptable salts and stereoisomers thereof. Some of the specific compounds exemplified herein are the protonated salts of amine compounds. Compounds of Formula I with a heterocycle ring containing 2 or more N atoms may be protonated on any one, some or all of the N atoms. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts, especially the trifluoroacetate salts. Preferably, pharmaceutically acceptable salts of this invention are the tartrate salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention can be used in a method of treatment of the human or animal body by therapy.

The compounds of the invention find use in a variety of applications for human and animal health. The compounds of the invention are histone deacetylase (HDAC) inhibitors useful in the treatment of cancer among other diseases. HDACs catalyse the removal of acetyl groups from lysine residues on proteins, including histones and HDAC inhibitors show diverse biological functions including affecting gene expression, cell differentiation, cell cycle progression, growth arrest, and/or apoptosis. See *J. Med. Chem.* 2003, 46:5097 and *Curr. Med. Chem.* 2003, 10:2343.

The compounds of the invention are used to treat cellular proliferation diseases. Disease states which can be treated by the methods and compositions provided herein include, but are not limited to, cancer (further discussed below), neurodegenerative diseases, schizophrenia and stroke The compounds, compositions and methods provided herein are particularly deemed useful for the treatment of cancer including solid tumors such as skin, breast, brain, cervical carcinomas, testicular carcinomas, etc. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Thus, the present invention provides a compound of formula I for use in the manufacture of a medicament for treating cellular proliferation diseases.

The present invention also provides a method for the treatment of cellular proliferation diseases, which method comprises administration to a patient in need thereof of an effective amount of a compound of formula I or a composition comprising a compound of formula I.

The compounds of the instant invention may also be useful in the treatment or prevention of neurodegenerative diseases, including, but not limited to, polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS). See WO 02/090534 and WO 03/083067.

Thus, the present invention provides a compound of formula I for use in the manufacture of a medicament for treating or preventing neurodegenerative diseases.

The present invention also provides a method for treating or preventing neurodegenerative diseases, which method comprises administration to a patient in need thereof of an effective amount of a compound of formula I or a composition comprising a compound of formula I.

The compounds of the invention may also be useful in the treatment or prevention of mental retardation, in particular "X chromosome-linked mental retardation" and "Rubinstein-Taybi syndrome".

Thus, the present invention provides a compound of formula I for the manufacture of a medicament for treating or preventing mental retardation.

The present invention also provides a method for treating or preventing mental retardation, which method comprises administration to a patient in need thereof of an effective amount of a compound of formula I or a composition comprising a compound of formula I.

The compounds of the invention may also be useful in the treatment or prevention of schizophrenia, see WO 02/090534.

Thus, the present invention provides a compound of formula I for the manufacture of a medicament for treating or preventing schizophrenia.

The present invention also provides a method for treating or preventing schizophrenia, which method comprises administration to a patient in need thereof of an effective amount of a compound of formula I or a composition comprising a compound of formula I.

The compounds of the invention may also be useful in the treatment or prevention of inflammatory diseases, including, but not limited to stroke, rheumatoid arthritis, lupus erythematosus, ulcerative colitis and traumatic brain injuries. See Leoni et al., PNAS, 99(5):2995-3000 (2002), Suuronen et al., J. Neurochem. 87:407-416 (2003) and Drug Discovery Today, 10: 197-204 (2005).

Thus, the present invention provides a compound of formula I for the manufacture of a medicament for treating or preventing inflammatory diseases.

The present invention also provides a method for treating or preventing inflammatory diseases, which method comprises administration to a patient in need thereof of an effective amount of a compound of formula I or a composition comprising a compound of formula I.

The compounds of the present invention are also useful in the inhibition of smooth muscle cell proliferation and/or migration and are thus useful in the prevention and/or treatment of restenosis, for example after angioplasty and/or stent implantation.

Thus, the present invention provides a compound of formula I for the manufacture of a medicament for treating or preventing restenosis.

The present invention also provides a method for treating or prevention restenosis, which method comprises administration to a patient in need thereof of an effective amount of a compound of formula I or a composition comprising a compound of formula I.

In one embodiment, smooth muscle cell proliferation and/or migration is inhibited and restenosis is prevented and/or treated by providing a stent device having one or more of the compounds of the instant invention in or on the stent device, e.g. coated onto the stent device. The stent device is designed to controllably release the compounds of the invention, thereby inhibiting smooth miscle cell proliferation and/or migration and preventing and/or treating restenosis.

Stenosis and restenosis are conditions associated with a narrowing of blood vessels. Stenosis of blood vessels generally occurs gradually over time. Restenosis, in contrast, relates to a narrowing of blood vessels following an endovascular procedure, such as balloon angioplasty and/or stent implantation, or a vascular injury.

Balloon angioplasty is typically performed to open a stenotic blood vessel; stenting is usually performed to maintain the patency of a blood vessel after, or in combination with, balloon angioplasty. A stenotic blood vessel is opened with balloon angioplasty by navigating a balloon-tipped catheter to the site of stenosis, and expanding the balloon tip effectively to dilate the occluded blood vessel. In an effort to maintain the patency of the dilated blood vessel, a stent may be implanted in the blood vessel to provide intravascular support to the opened section of the blood vessel, thereby limiting the extent to which the blood vessel will return to its occluded state after release of the balloon catheter. Restenosis is typically caused by trauma inflicted during angioplasty, effected by, for example, ballon dilation, atherectomy or laser ablation treatment of the artery. For these procedures, restenosis occurs at a rate of about 30% to about 60% depending on the vessel location, lesion length and a number of other variables. This reduces the overall success of the relatively non-invasive balloon angioplasty and stenting procedures Restenosis is attributed to many factors, including proliferation of smooth muscle cells (SMC). SMC proliferation is triggered by the initial mechanical injury to the intima that is sustained at the time of balloon angioplasty and stent implantation. The process is characterized by early platelet activation and thrombus formation, followed by SMC recruitment and migration, and, finally, cellular proliferation and extracellular matrix accumulation. Damaged endothelial cells, SMCs, platelets, and macrophages secrete cytokines and growth factors which promote restenosis. SMC proliferation represents the final common pathway leading to neointimal hyperplasia. Therefore, anti-proliferative therapies aimed at inhibiting specific regulatory events in the cell cycle may constitute the most reasonable approach to restenosis after angioplasty.

The compounds of the invention may also be used as immunosuppressants or immunomodulators and can accordingly be used in the treatment or prevention of immune response or immune-mediated responses and diseases such as systemic lupus erythematosus (SLE) and acute or chronic transplant rejection in a recipient of an organ, tissue or cell transplant, (see WO 05/013958).

Examples of autoimmune diseases for which the compounds of the invention may be employed include autoimmune hematological disorders (including hemolytic anaemia, aplastic anaemia, pure red cell anaemia and idiopathic thrombocytopenia), systemic lupus erythematosus, thyroiditis, Hashimoto's thyroiditis, polychondritis, sclerodoma, Wegener granulamatosis, dermatomyositis, chronic active hepatitis, myasthenia gravis, psoriasis, atopic dermatitis, vasculitis, Steven-Johnson syndrome, idiopathic sprue, autoimmune inflammatory bowel disease (including ulcerative colitis and Crohn's disease) endocrine opthalmopathy, Graves disease, sarcoidosis, multiple sclerosis, primary billiary cirrhosis, juvenile diabetes (diabetes mellitus type I), diabetes type II and the disorders associated therewith, uveitis (anterior and posterior), keratoconjunctivitis sicca and vernal keratoconjunctivitis, interstitial lung fibrosis, psoriatic arthritis, glomerulonephritis (with and without nephrotic syndrome, including idiopathic nephrotic syndrome or minimal change nephropathy), juvenile dermatomyositisinfectious, auto-antibody mediated diseases, aplastic anemia, Evan's syndrome, autoimmune hemolytic anemia, infectious diseases causing aberrant immune response and/or activation, such as traumatic or pathogen induced immune disregulation, including for example, that which are caused by hepatitis B and C infections, *staphylococcus aureus* infection, viral encephalitis, sepsis, parasitic diseases wherein damage is induced by inflammatory response (e.g. leprosy); and circulatory diseases, such as arteriosclerosis, atherosclerosis, polyarteritis nodosa and myocarditis.

Thus, the present invention provides a compound of formula I for the manufacture of a medicament for the treatment or prevention of immune disorders.

The present invention also provides a method for treating or preventing immune disorders, which method comprises administration to a patent in need thereof of an effective amount of a compound of formula I or a composition comprising a compound of formula I.

The compounds of the invention may also be useful in the treatment or prevention of other diseases such as diabetes, cardiovascular disorders and asthma.

The compounds of the invention may also be useful in the treatment or prevention of cardiac hypertrophy and heart failure, as described in *Cell,* 110:479-488 (2002).

In an embodiment the compounds of this invention may be useful for the treatment or prevention of neurodegenerative diseases, schizophrenia, stroke, mental retardation, immune disorders or asthma.

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration generally occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. Thus, this invention provides combinations of compounds of formula (I) and known therapeutic agents and/or anti-cancer agents for simultaneous, separate or sequential administration. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: other HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: other HDAC inhibitors, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Examples of "other HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diaridinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin, bortezomib, epoxomicin and peptide aldehydes such as MG 132, MG 115 and PSI.

In an embodiment, the compounds of the present invention may be used in combination with other HDAC inhibitors such as SAHA and proteasome inhibitors.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5, 6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-bexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 02/056880, WO 03/050,064, WO 03/050,122, WO 03/049,527, WO 03/049,679, WO 03/049,678, WO 03/039460, WO 03/079973, WO 03/099211, WO 2004/039774, WO 03/105855, WO 03/106417, WO 2004/087050, WO 2004/058700, WO 2004/058148 and WO 2004/037171 and US applications US 2004/132830 and US 2004/132719. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RP14610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$ $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with antiviral agents (such as nucleoside analogs including ganciclovir for the treatment of cancer. See WO 98/04290.

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine*, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with a second compound selected from: other HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: other HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: other HDAC inhibitors, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of cell proliferation and survival signaling, an agent that interfers with a cell cycle checkpoint, an apoptosis inducing agent and a bisphosphonate.

These and other aspects of the invention will be apparent from the teachings contained herein.

All patents, publications and pending patent applications identified are hereby incorporated by reference.

Abbreviations used in the description of the chemistry and in the Examples that follow are:

AcOH (acetic acid); BuLi (n-butyl lithium); BSA (bovine serum albumin); DBU (1,8-diazabicyclo[5.4.0]undec-7-ene), DCE (1,2-dichloroethane); DIPEA (diisopropylethylamine); DCM (dichloromethane); DME (ethylene glycol dimethyl ether); DMEM (Dulbecco's Modified Eagle Medium); DMF (dimethylformamide); DMSO (dimethyl sulfoxide); DPPA (diphenylphosphorazide); DTT (dithiothreitol); EDC and EDCI (N-(3-dimethylaminopropyl)-N'-ethylcarbodiimide); EDC.HCl (1-Ethyl-3-(3-dimethyllaminopropyl)carbodiimide hydrochloride); EDTA (ethylenediaminetetraacetic acid); EGTA (Ethyleneglycotetraacetic acid); em (emission); Eq. (equivalent); ES (electrospray); EtOAc (ethyl acetate); EtOH (ethanol); ex (exitation); FACS (fluorescence activated cell sorting); FITC (Fluorescein isothiocyanate); Hepes ((N-(2-Hydroxyethyl)piperazine)-N'-(2-ethanesulfonic acid)); HOBt (1-hydroxybenzotriazole); HPLC (high performance liquid chromatography); IPTG (Isopropyl-beta-D-thiogalactopyranoside); LEP (Lysyl End Peptidase); Lys C (Lysyl C endoprotease); MeCN (acetonitrile); MeOH (methanol); MS (mass spectrometry); NMR (nuclear magnetic resonance); NP40 (Nonidet P40); PBS (Phosphate buffered saline); PMSF (phenylmethylsulphonyl fluoride); $^i$PrOH (iso-propanol), PTSA (p-Toluenesulphonic acid); PyBop (1H-1,2,3-benzotriazol-1-yloxy)(tripyrrolidin-1-yl)phosphonium hexafluorophosphate); RP (reverse phase); RT (room temperature); SCX (Varian or Isolute cation exchange resin); SiO$_2$ (silica gel); TEA (triethyl amine); THF (tetrahydrofuran); TFA (trifluoroacteic acid); Tris-HCl (Tris Hydroxymethylaminoethane); and TSA (Trichostatin A).

Further abbreviations include:

App (Apparent); PS-BEMP (2-tert-butylimino-2-diethylamino-1,3-dimethyl-perhydro-1,3,2-diazaphosphorine); Py (pyridine); sat. aq (saturated aqueous); SEM-Ci ([2-(chloromethoxy)ethyl](trimethyl)silane); TBAF (Tetrabutylammonium fluoride); TBTU (2-(1H-Benzotriazole-1-yl)-1,1,3,3-tetramethyluronium tetrafluoroborate); TFAA (Trifluoroacetic anhydride); and TsCl (para toluene sulfonyl chloride). A further abbreviation is BOM (benzyloxymethyl).

Compounds of formula I may be prepared by reacting a compound of formula IV with a compound of formula V:

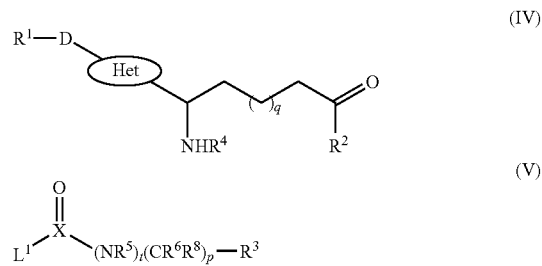

wherein D, $R^1$, $R^2$, $R^3$, $R^4$, $R^5$, $R^6$, $R^8$, X, Het, p, q and t are as defined for formula I and L' is a leaving group such as hydroxy or chlorine. When $L^1$ is a leaving group such as chlorine, the reaction is generally carried out in the presence of a base such as Et$_3$N and a solvent such as DMF or DCM at about room temperature. When $L^1$ is a leaving group such as hydroxy, a coupling agent such as EDC.HCl and a base such as Et$_3$N may also be added. Further additives such as HOBt and DIPEA may also be present.

Protecting groups such as SEM on the Het ring and dioxane at the carbonyl position of the compounds of formula IV may be present during the reaction. The compounds can subsequently be deprotected using standard methods, such as adding TBAF in a solvent such as THF at reflux, or adding DCM and TFA or HCl(aq) in a solvent such as THF at about room temperature.

Compounds of formula IV wherein Het is imidazole may be prepared by reacting a compound of formula VI:

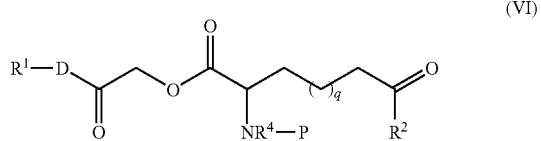

(VI)

wherein D, $R^1$, $R^2$, $R^4$ and q are as defined above and P is a protecting group such as Boc with a cyclisation agent such as ammonium acetate, generally in a solvent such as xylene at about 150° C.

Compounds of formula VI can be prepared by reacting a compound of formula VII with a compound of formula VIII:

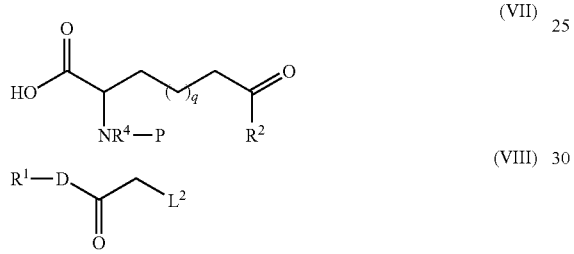

(VII)

(VIII)

wherein D, $R^1$, $R^2$, $R^4$, q and P are as defined above and $L^2$ is a leaving group such as halogen, particularly bromine, generally in the presence of a base such as cesium carbonate in a solvent such as DMF at room temperature.

Compounds of formula IV in which $R^4$ is hydrogen may alternatively be prepared by reacting a compound of formula IX:

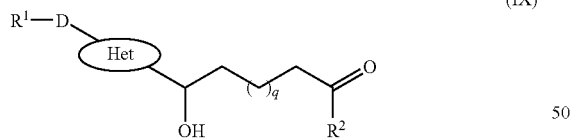

(IX)

wherein D, $R^1$, $R^2$, Het and q are as defined above with an azide reagent such as diphenylphosphorazide, generally in the presence of a base such as DBU and in a solvent such as toluene. The resulting azide may then be hydrogenated to produce the compound of formula IV wherein $R^4$ is hydrogen. For example, the reaction can be carried out firstly under hydrogen and then nitrogen atmosphere, in a solvent such as EtOAc and in the presence of a catalyst such as Pd on carbon. Alternatively, the resulting azide may be reacted with organophosphine such as $PPh_3$ and in solvents such as THF and water at about room temperature. Protecting groups such as SEM on the Het ring and dioxane at the carbonyl position of the compounds of formula IX may be present during the reaction.

Compounds of formula IX may be prepared by reacting a compound of formula X with a compound of formula XI:

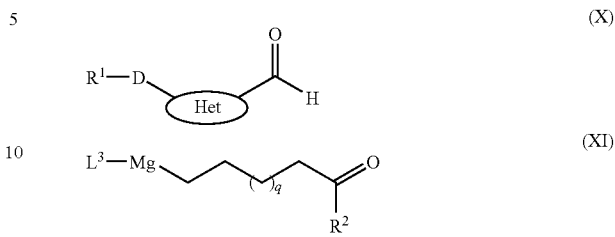

(X)

(XI)

wherein D, $R^1$, $R^2$, Het and q are as defined above and $L^3$ is a halogen atom such as bromine, generally in a solvent such as THF.

Compounds of formula IV may alternatively be prepared by reacting a compound of formula XII:

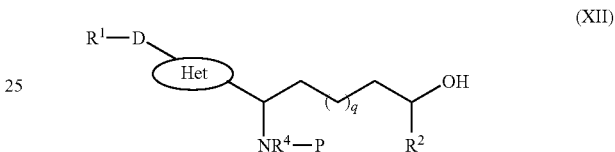

(XII)

wherein D, $R^1$, $R^2$, $R^4$, Het, q and P are as defined above with an oxidising agent such as Dess-Martin periodinane, generally in a solvent such as DCM at about room temperature.

Compounds of formula XII in which Het is a triazole ring may be prepared by reacting a compound of formula XIII with a compound of formula XIV:

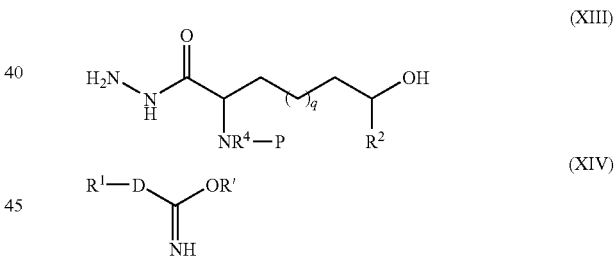

(XIII)

(XIV)

wherein D, $R^1$, $R^2$, $R^4$, q and P are as defined above and R' is $C_{1-6}$alkyl, such as methyl, generally in a solvent such as toluene at about room temperature.

Compounds of formula XIII can be prepared by reacting a compound of formula XV:

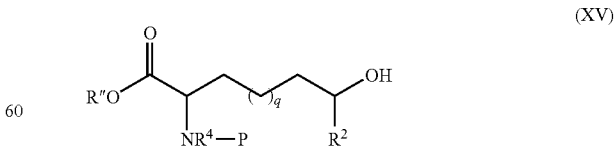

(XV)

wherein $R^2$, $R^4$, q and P are as defined above and R" is $C_{1-6}$alkyl, such as methyl, with hydrazine hydrate, generally in the presence of an alcoholic solvent such as isopropanol at about 80° C.

Compounds of formula XV can be prepared by reacting a compound of formula VII with a reducing agent such as BH$_3$Me$_2$S, generally in a solvent such as THF at about 0° C.

Compounds of formula IV wherein Het is 1,3,4-oxadiazole can be prepared by reacting a compound of formula XVI:

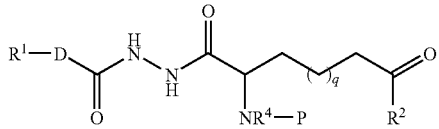
(XVI)

wherein D, R$^1$, R$^2$, R$^4$, q and P are as defined above with cyclisation agents such as PS-BEMP and TsCl, generally in a solvent such as THF at about 65° C.

Compounds of formula XVI can be prepared by reacting a compound of formula XVII:

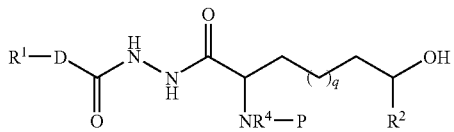
(XVII)

wherein D, R$^1$, R$^2$, R$^4$, q and P are as defined above with an oxidising agent such as Dess-Martin periodinane, generally in a solvent such as DCM at about room temperature.

Compounds of formula XVII can be prepared by reacting a compound of formula XIII with a formula of XVIII:

R$^1$-D-CO$_2$H    (XVIII)

wherein D and R$^1$ are as defined above, generally in the presence of coupling agents such as HOBt and EDC.HCl in a solvent such as DCM at about room temperature.

Compounds of formula IV wherein Het is oxazole can be prepared by reacting a compound of formula XIX:

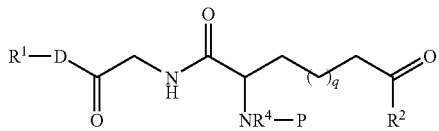
(XIX)

wherein D, R$^1$, R$^2$, R$^4$, q and P are as defined above with cyclisation agents such as hexachloroethane (C$_2$Cl$_6$) and triphenylphosphine (PPh$_3$), generally in the presence of a base such as Et$_3$N and in a solvent such as DCM at about room temperature.

Compounds of formula XIX can be prepared by reacting a compound of formula VII with a compound of formula XX:

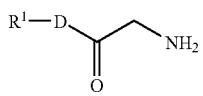
(XX)

wherein D and R$^1$ are as defined above. The reaction is generally carried out in the presence of coupling agents such as HOBt and EDC.HCl, in a base such as DIPEA and a solvent such as DMF.

Compounds of formula XX can be prepared by hydrogenation of the corresponding azido of formula XXI:

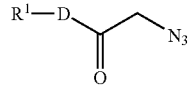
(XXI)

wherein D and R$^1$ are as defined above. The reaction is generally carried out in an acid such as HCl, in the presence of a catalyst such as Pd on carbon and in a solvent such as methanol at about room temperature.

Compounds of formula XXI can be prepared by reacting a compound of formula VIII with an azide source such as NaN$_3$, generally in a solvent such as acetone at about room temperature.

Compounds of formula IX can alternatively be prepared by reacting a compound of formula XXII with an organometallic reagent such as BuLi to facilitate a halogen-lithium exchange, followed by quenching with a compound of formula XXIII:

(XXII)

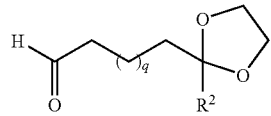
(XXIII)

wherein D, R$^1$, R$^2$, q and Het are as defined above and L$^2$ is a leaving group such as halogen, particularly bromine. The reaction is generally carried out in a solvent such as THF at about −78° C. A protecting group such as SEM may be present as described previously.

Compounds of formula XXII can be prepared by reacting a compound of formula XXIV with a compound of formula XXV;

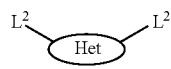
(XXIV)

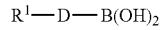
(XXV)

wherein D, R$^1$ and L$^2$ are independently as defined above. The reaction is generally carried out in a solvent such as toluene and in the presence of a catalyst such as Pd(PPh$_3$)$_4$ at reflux.

Compounds of formula XXIII can be prepared by reacting a compound of formula XXVI:

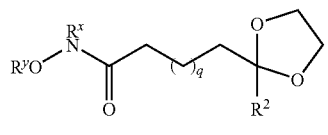

(XXVI)

wherein $R^2$ and q are as defined above and $R^x$ and $R^y$ are independently $C_{1-6}$alkyl groups such as methyl, with a reducing agent such as $LiAlH_4$, generally in a solvent such as THF at about −78° C.

Compounds of formula IX can alternatively be formed by reacting a compound of formula XXVII with an organometallic reagent derived from treating a compound of formula XXVIII with a reagent such as tert-BuLi:

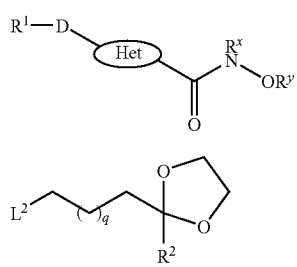

(XXVII)

(XXVIII)

wherein D, $R^1$, $R^2$, q, Het, $R^x$, $R^y$ and $L^2$ are as defined above. The reaction is generally carried out in a solvent such as THF and pentane at about −78° C. The ketone can subsequently be converted to the required alcohol in the presence of a reducing agent such as $NaBH_4$ and in a solvent such as ethanol at about room temperature.

Compounds of formula IV wherein $R^4$ is hydrogen can alternatively be prepared by reacting an organometallic reagent derived from a compound of formula XXII with a compound of formula XXIX:

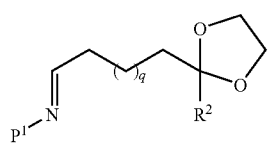

(XXIX)

wherein $R^2$ and q are as defined above and $P^1$ is a chiral auxiliary such as tert-butanesulfine. The reaction is generally carried out in a solvent such as THF, at about −78° C. The $P^1$ group such as tert-butanesulfine can subsequently be removed under acidic conditions, such as HCl in a solvent such as methanol at about room temperature.

Compounds of formula XXIX can be prepared by reacting a compound of formula XXIII with a compound of formula XXX:

$P^1$—$NH_2$ (XXX)

wherein $P^1$ is as defined above, generally in the presence of a catalyst such as copper sulfate ($CuSO_4$), in a solvent such as DCM at about room temperature.

Compounds of formula XVI can alternatively be prepared by reacting a compound of formula VII with a compound of formula XXXI:

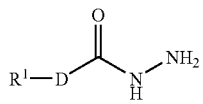

(XXXI)

wherein D and $R^1$ are as defined above. The reaction is generally carried out in the presence of coupling agents such as EDC.HCl and HOBt, in a solvent such as DMF at room temperature.

Compounds of formula XII wherein Het is oxadiazole can alternatively be prepared by reacting a compound of formula XVIII with a compound of formula XXXII:

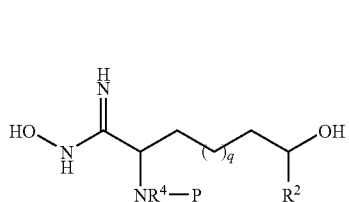

(XXXII)

wherein $R^2$, $R^4$, P and q are as defined above. The reaction is generally carried out in the presence of coupling agents such as TBTU and HOBt, in a base such as DIPEA and in a solvent such as DMF at about room temperature and then heated at about 110° C.

Compounds of formula XXXII can be prepared by reacting a compound of formula XXXIII:

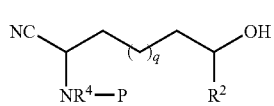

(XXXIII)

wherein $R^2$, $R^4$, P and q are as defined above, with a hydroxyamino reagent such as $NH_2OH.HCl$, generally in a solvent such as methanol and in the presence of a base such as KOH at reflux.

Compounds of formula XXXIII can be prepared by reacting a compound of formula XXXIV:

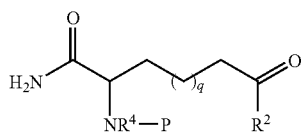

(XXXIV)

wherein $R^2$, $R^4$, P and q are as defined above with a dehydrating agent such as TFAA, generally in the presence of a base such as $Et_3N$ and in a solvent such as DCM at about 0° C. A further reducing agent such as $NaBH_4$ in a solvent such as methanol can subsequently be added to reduce the carbonyl group at the $R^2$ position.

Compounds of formula XXXIV can be prepared by reacting a compound of formula VII with an amino source such as ammonium bicarbonate, generally in the presence of pyridine and Boc$_2$O, in a solvent such as dioxane at about room temperature.

Compounds of formula IV wherein Het is a 1,2,4-oxadiazol-5-yl can be prepared by reacting a compound of formula VII with a compound of formula XXXV:

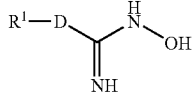
(XXXV)

wherein D and R$^1$ are as defined above, generally in the presence of coupling reagents such as TBTU and HOBt, in a base such as DIPEA and in a solvent such as DMF at about room temperature and then at a temperature of about 110° C.

Alternatively, compounds of formula I wherein R$^2$ is methyl can be prepared by reacting a compound of formula XXXVI:

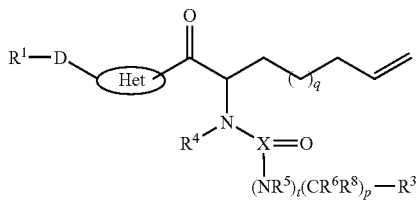
(XXXVI)

wherein D, R$^1$, R$^3$, R$^4$, R$^5$, R$^6$, R$^8$, X, p, q, t and Het are as defined above with an oxidising agent, such as oxygen gas and CuCl, in the presence of a catalyst such as PdCl$_2$ and in a solvent such as DMF.

Compounds of formula XXXVI can be prepared by reacting a compound of formula V with a compound of formula XXXVII:

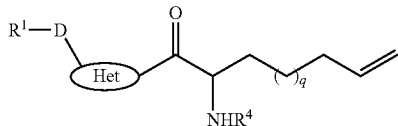
(XXXVII)

wherein D, R$^1$, R$^4$, Het and q are as defined above, generally under coupling conditions as described previously.

Compounds of formula XXXVII wherein R$^4$ is hydrogen can be prepared by reacting a compound of formula XXXVIII:

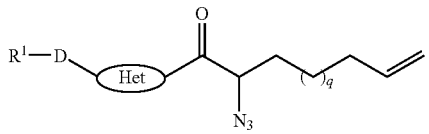
(XXXVIII)

wherein D, R$^1$, Het and q are as defined above with an organophosphine such as PPh$_3$ and solvents such as THF and water at about room temperature.

Compounds of formula XXXVIII can be prepared by reacting a compound of formula XXXIX:

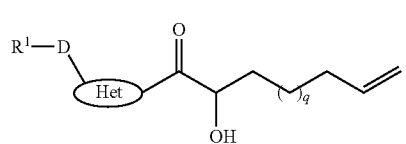
(XXXIX)

wherein D, R$^1$, Het and q are as defined above with an azide reagent such as diphenylphosphorazide, generally in the presence of a base such as DBU and in a solvent such as toluene at about 50° C.

Compounds of formula XXXIX can be prepared by reacting a compound of formula X with a compound of formula XL:

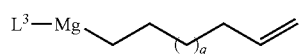
(XL)

wherein L$^3$ and q are as defined above, generally in a solvent such as THF at about 0° C. and under an argon atmosphere.

Compounds of formula I may alternatively be prepared by reacting a compound of formula XXV with a compound of formula XLI:

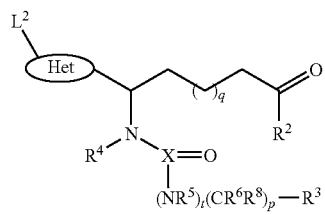
(XLI)

wherein R$^2$, R$^3$, R$^4$, R$^5$, R$^6$, R$^8$, X, Het, p, q, t and L$^2$ are as defined above. The reaction is generally carried out in a solvent such as n-BuOH and in the presence of catalysts such as Pd(OAc)$_2$, K$_3$PO$_4$ and dicyclohexly-(2',6'-dimethoxybiphenyl-2-yl)phospene, at about 90° C.

Protecting groups such as SEM on the Het ring may be present during the reaction, which can subsequently be removed under standard conditions described above.

Compounds of formula XXXI can be prepared by reacting a compound of formula XLII with hydrazine monohydrate:

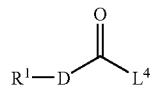
(XLII)

wherein D and R$^1$ are as defined above and L$^4$ is an appropriate leaving group such as methoxy. The reaction is generally carried out in a solvent such a i-PrOH at about 80° C.

Compounds of formula IX may alternatively be prepared by reacting a compound of formula X with an organometallic reagent derived from reacting a compound of formula XXVIII with a reagent such as tert-BuLi. The reaction is generally carried out in a solvent such as Et$_2$O at about room temperature.

The Het group may be protected as described previously.

Alternatively, compounds of formula I when X is C, t is 1 and R$^5$ is hydrogen can be prepared by reacting a compound of formula IV with a compound of formula XLIII:

wherein R$^3$, R$^6$, R$^8$ and p are as defined above. The reaction is generally carried out in the presence of a base such as DIPEA, in a solvent such as DCM at about room temperature.

Where the synthesis of intermediates and starting materials is not described, these compounds are commercially available or can be made from commercially available compounds by standard methods or by extension of the Examples herein.

Compounds of formula I may be converted to other compounds of formula I by known methods or by methods described in the Examples.

Thus, compounds of formula I wherein R$^2$ is hydroxy can be converted to compounds of formula I wherein R$^2$ is N(R$^b$)$_2$ by reacting with HN(R$^b$)$_2$, generally in the presence of a coupling agent such as EDCI and DMAP and in a solvent such as DCM at about room temperature. HATU may also be used, generally in a solvent such as 1,4-dioxane. Coupling agents such as ED.HCl and HOBt, a base such as DIPEA and a solvent such as DMF at about room temperature may also be used.

Compounds of formula I wherein R$^2$ is hydroxy can be converted into compounds of formula I wherein R$^2$ is perfluoroalkyl by reacting with a perfluoroalkylacetic anhydride such as TFAA, generally in the presence of a base such as pyridine and a solvent such as DCM at about 0° C.

Compounds of formula I wherein R$^2$ is N(R$^b$)$_2$ may be converted to compounds wherein R$^2$ is C$_{1-6}$alkylS(O)$_w$R$^g$ by reacting with an organometallic reagent derived from treating a compound of formula H—C$_{1-6}$alkylS(O)$_w$R$^g$ with a reagent such as n-BuLi, generally in a solvent such as THF at a temperature from about −78° C. to room temperature.

Compounds of formula I wherein R$^2$ is N(R$^b$)$_2$ can be converted to compounds wherein other groups are present at R$^2$ by reacting with an appropriate organometallic reagent such as an organolithium or grignard reagent derived from the required R$^2$ group. The reaction is generally carried out in a solvent such as THF and at a temperature from about −78° C. to room temperature Compounds of formula IV wherein R$^2$ is hydrogen can be converted to compounds wherein R$^2$ is other than hydrogen by reacting with an organometallic reagent derived from treating a compound of formula XLIV with a reagent such as n-BuLi:

wherein R$^2$ and L$^3$ are as defined above. The reaction is generally carried out in the presence of a solvent such as THF at about 0° C. to room temperature. The resulting alcohol there formed can then be oxidized to compounds of formula IV using reagents such as Dess-Martin reagent. If appropriate, functionality elsewhere in the molecule can be protecting with the appropriate protecting groups as described previously.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis,* 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the BoC protecting group is present, it may be removed by the addition of solvents such as TFA and DCM. The compound may also be hydrogenated using standard methods, such as treating with a catalyst such ad Pd/C, in a solvent such as methanol in a hydrogen atmosphere.

As described previously the Het group may be protected by protecting groups such as SEM during the synthesis of the compounds of formula I, which can subsequently be removed under standard conditions as described above.

Further examples of protecting groups on the Het ring include tert-butyl(dimethyl)silylmethyl and BOM. The BOM group may subsequently be removed using standard methods, for example by the addition of a reagent such as BBr$_3$ and a solvent such as toluene at about room temperature.

Compounds of this invention can be prepared as described in Scheme 1 from a suitably elaborated alkyl chain functionalised in the α-position with an amino derivative. These derivatives can be prepared by those skilled in the art and methods to synthesise such heterocycles are described in Alan Katritzky, *Comprehensive Heterocyclic Chemistry*, (Pergamon Press, New York, 1984) and *Comprehensive Heterocylic Chemistry II*, (Pergamon Press, New York, 1996) amongst other texts. The free amino group can be coupled with an acid derivative to from amides, methods for coupling carboxylic acids (and acid derivatives) with amines to form carboxamides are well known in the art. Suitable methods are described, for example, in Jerry March, *Advanced Organic Chemistry,* 3rd edition, John Wiley & Sons, 1985, pp. 370-376. Likewise reaction with a sulfonyl chloride in the presence of base gives the corresponding sulfonamide, see Jerry March, *Advanced Organic Chemistry,* 4th edition, John Wiley & Sons, 1992, pp. 496-499. In a similar manner, reaction of the amine with a sulfamoyl chloride gives the corresponding sulfamide.

Scheme 1

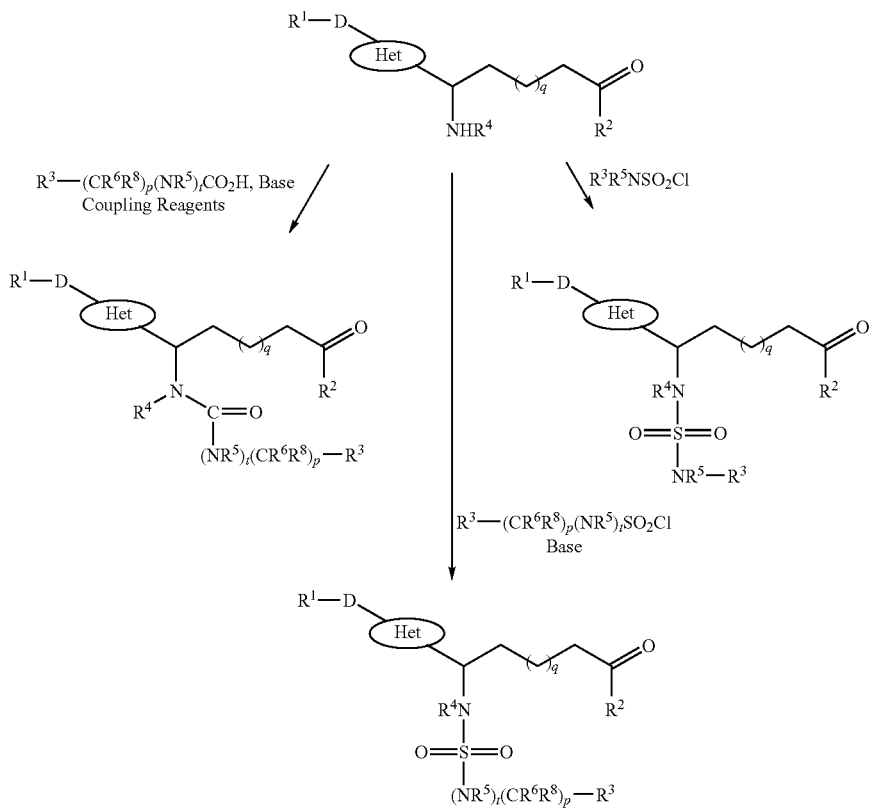

A route to pendant imidazoles is shown in Scheme 2 from the key protected amino ester (these amino acid derivatives can be prepared by those skilled in the art using standard chemistry, such as described in Williams, R. M. *Synthesis of Optically Active α-Amino Acids*, Pergamon Press, 1989). These acids can be alkylated with a halomethyl ketone in the presence of base, for example $Cs_2CO_3$, and the resulting ester is treated with an excess of ammonium acetate and heated at 150° C. to yield the desired imidazole, such conditions are described in *Bioorg. Med. Chem. Lett.* 1996, 6, 1601, Tetrahedron 1996, 52, 10131 and *J. Am. Chem. Soc.* 1981, 103, 3446. Removal of the protecting group enables further functionalisation. Examples include: amide formation by reaction of an acid in the presence of coupling reagent; sulfonylation by reaction of a sulfonyl chloride in the presence of base; and sulfamoylation by reaction with a sulfamoyl chloride and base.

Scheme 2

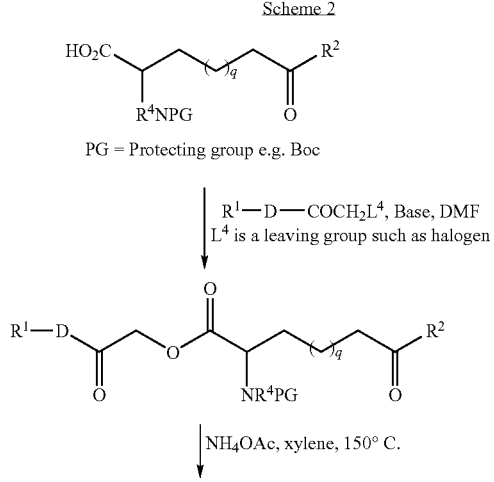

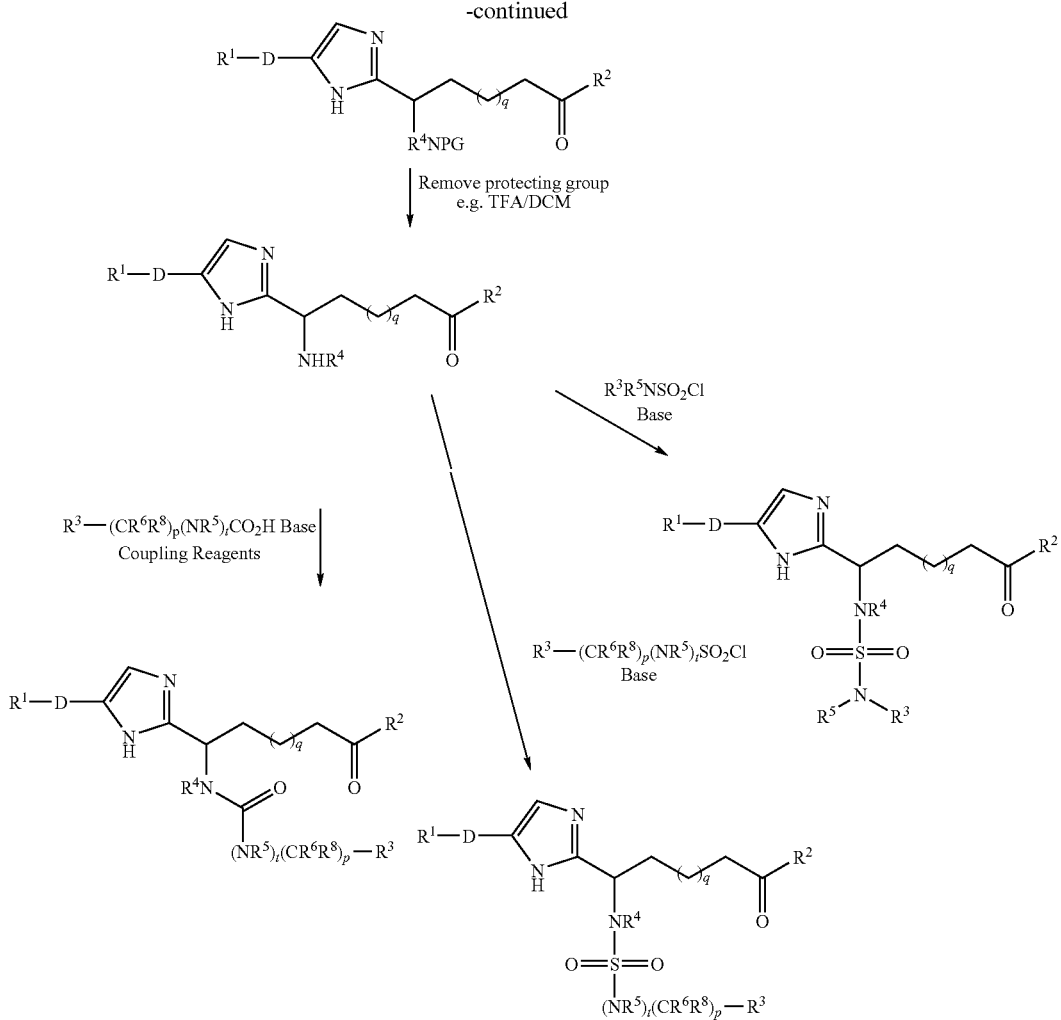

Compounds of this invention can be prepared as described in Scheme 3 from a suitable heterocyclic aldehyde (commercially available or readily synthesised by oxidation of the corresponding alcohol) by reacting with a Grignard reagent, itself prepared under standard conditions from the corresponding alkyl bromide with magnesium turnings in refluxing THF. The resulting secondary alcohol thereby obtained can be reacted with diphenylphosphorazide and DBU using the conditions of Thompson et al. (*J. Org. Chem.* 1993, 58, 5886-8) to yield the azide. Hydrogenation at atmospheric pressure using palladium on carbon as catalyst gives racemic amine which can then be coupled with carboxylic acids, sulfonyl chlorides and sulfamyl chloride. Final deprotection with mineral acid liberates the corresponding ketone.

Scheme 3

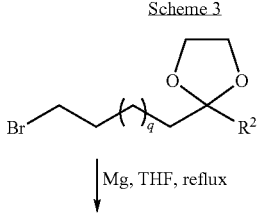

Mg, THF, reflux

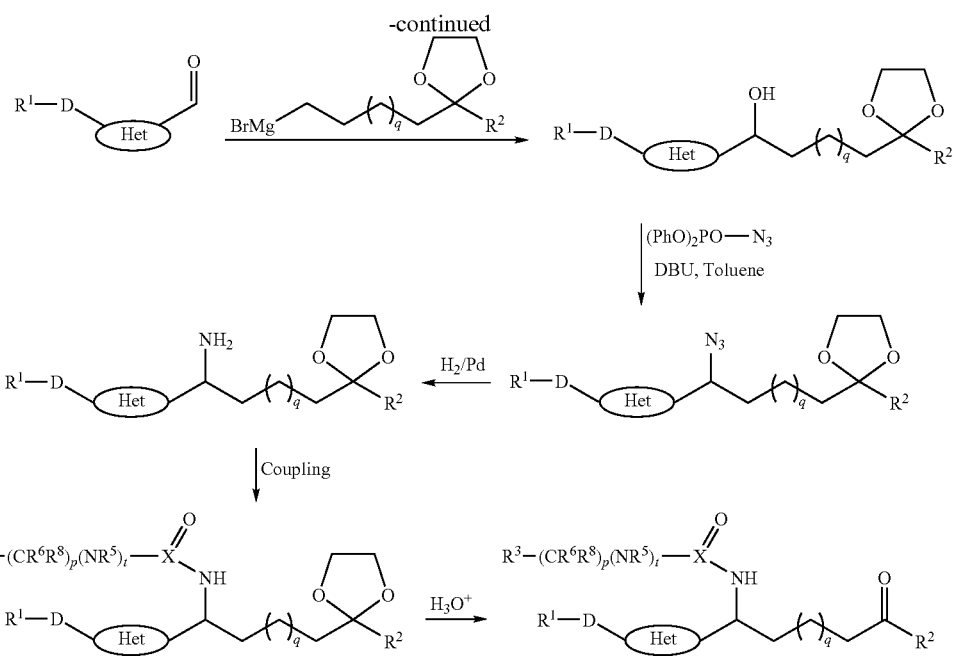

A modification of the route to the pendant imidazoles is shown in Scheme 4 whereby the alkylated acid is treated with a mixture of ammonium acetate and an alkyl ammonium acetate at 150° C. in xylene to give a mixture of products including the desired alkylated imidazole. The compounds then can be manipulated as described previously to give the desired inhibitors then reacted with an imino ether, first at RT and then at 110° C. to yield the desired heterocycle. Finally oxidation of the alcohol back to the corresponding ketone yields an intermediate which can be converted into the required inhibitors as described previously.

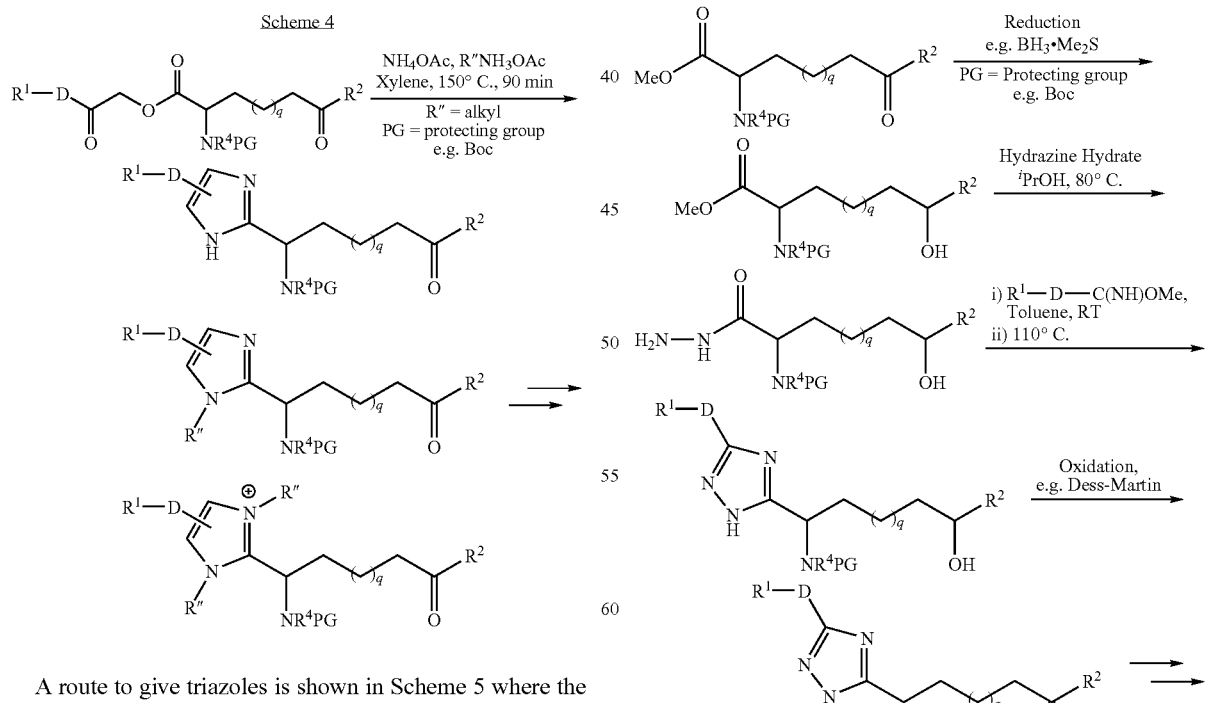

A route to give triazoles is shown in Scheme 5 where the amino acid bearing a ketone is first reduced, for instance with $BH_3.Me_2S$ complex, to the alcohol and then the ester group converted into the hydrazide by heating in the presence of hydrazine hydrate in an alcoholic solvent. This hydrazine is A method to prepare further analogues is illustrated in Scheme 6 whereby alkylation of a lithiated Schollkopf derivative with a suitably functionalised alkyl iodide gives after mild acid hydrolysis a chiral α-amino ester (see U. Schollkopf et al. *Synthesis* 1982, 866). Saponification yields to the chiral α-amino acid. This acid can be transformed into the requisite imidazole as already outlined, firstly by alkylation with an α-bromoketone and then by treatment with ammonium acetate in xylene at 150° C. Deprotection, for instance with a mixture of TFA in DCM liberates the ammonium salt, which can be coupled to give the desired inhibitors Scheme 6

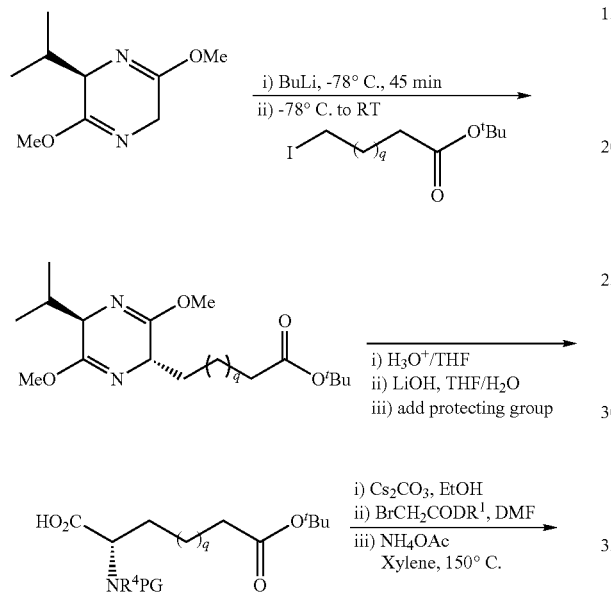

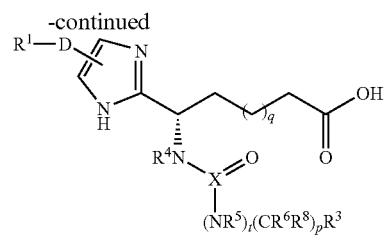

The carboxylic acid can be further functionalised by coupling to a variety of $N(R^b)_2$ groups to yield amides and hydroxamic acids as desired inhibitors, for instance, using EDC as coupling reagent, as illustrated in Scheme 7.

Scheme 7

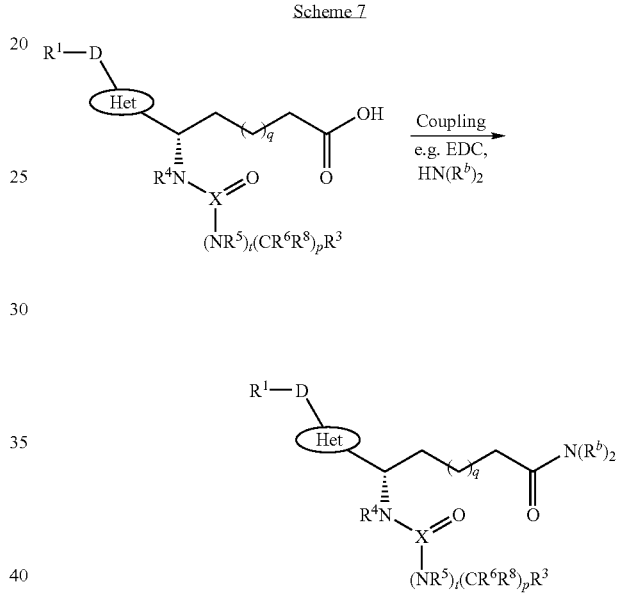

A synthetic route to the preparation of 1,3,4-oxadiazoles is shown in scheme 8 where a hydrazide is readily coupled with a second carboxylic acids and then cyclised under dehydrative conditions to form the desired heterocyclic ring. Suitable conditions include the use of tosyl chloride and polymer supported BEMP as described by Brain et al. *Synlett* 2001, 3, 382-384. Subsequently, the protecting group can be removed from the nitrogen atom and the required inhibitors can be synthesised as previously described.

Scheme 8

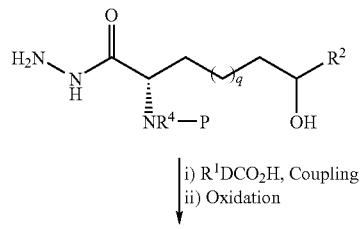

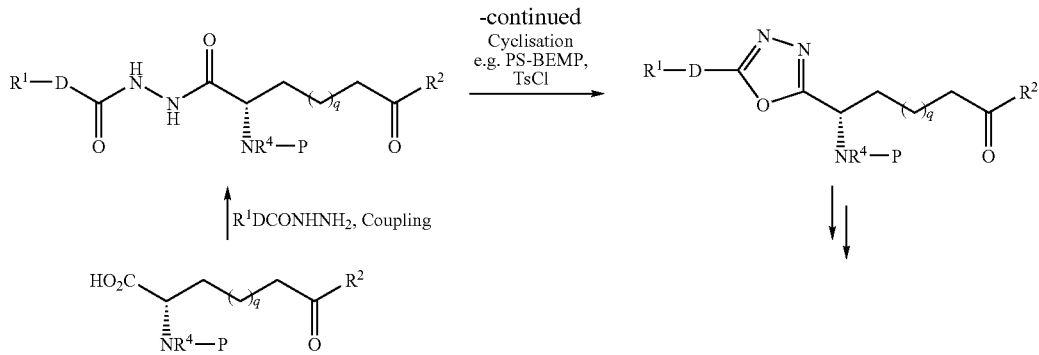

Isomeric 1,2,4-oxadiazoles can be prepared as described in scheme 9. The amino acid can be coupled to make the primary amide, which in turn can be dehydrated to the nitrile using reagents such as trifluoroacetic anhydride and a base. In certain cases, a reductive step is required to ensure functional group compatibility with an oxidative step later in the synthetic sequence. Formation of the aldoxime can be achieved with hydroxylamine.HCl in the presence of potassium hydroxide. The cyclisation to the oxadiazole can be accomplished by coupling with a carboxylic acid using TBTU as coupling reagent and then heating the reaction at 111° C. to accomplish the cyclisation as described by Poulin et al. *Tetrahedron Letters* 2001, 42, 1495-8. Alternatively, to synthesise the isomeric heterocycle, the coupling partners can be inverted, and the reaction of the α-amino acid with the aldoxime derived from the heterocycle inverts the substitution pattern.

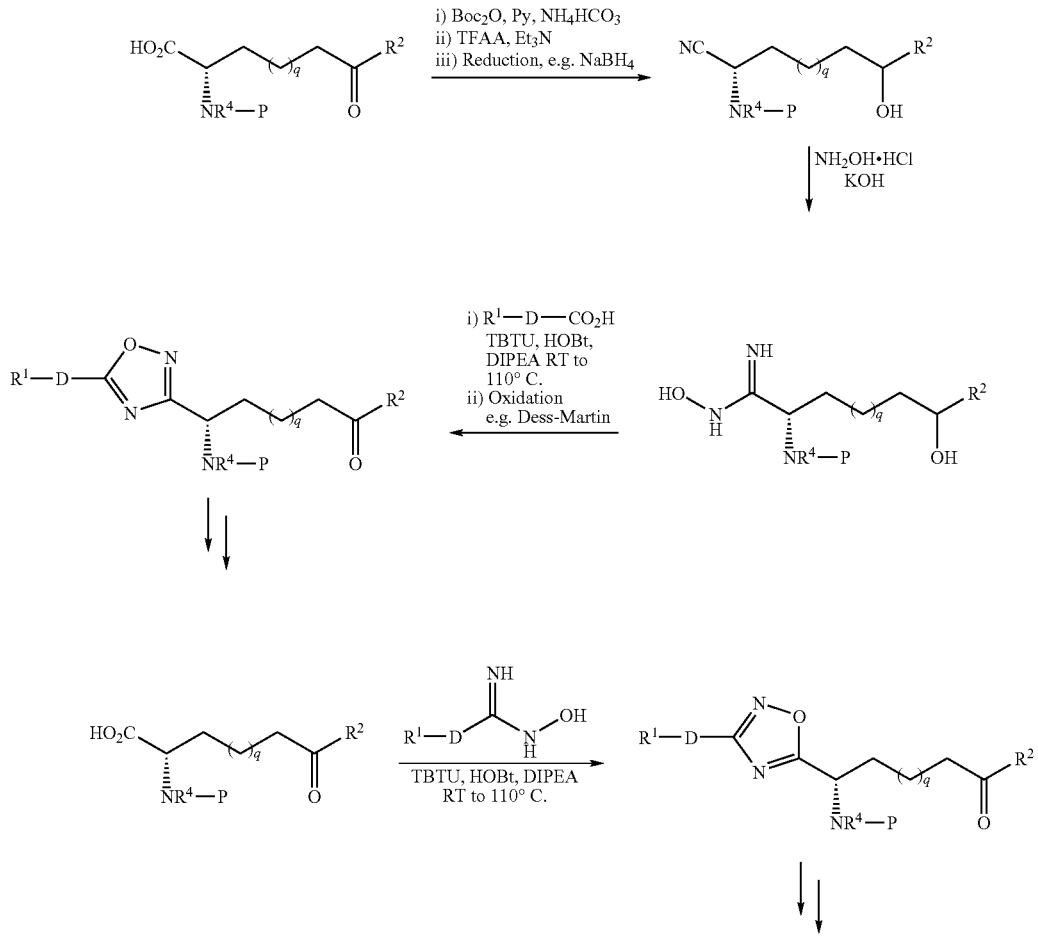

An alternative procedure, in this case for the preparation of oxazoles, is shown in scheme 10 where an α-aminoketone is coupled with a carboxylic acid, the resulting amide there formed can then be cyclised again under dehydrative conditions to yield the desired heterocycle. One method for performing the cyclisation is to use hexachloroethane and triphenylphosphine as described by Nicolaou et al. *J. Am. Chem. Soc.* 2004, 126, 10162-10173.

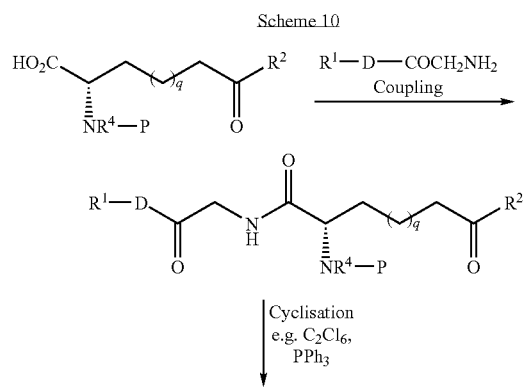

An alternative procedure to that shown in scheme 3 to introduce other heterocycles is outlined in scheme 11. For instance, a suitable elaborated Weinreb amide could be reacted with an organometallic species to yield the corresponding ketone. Suitable organometallic reagents include organolithium species, which are readily available from halogen-lithium exchange or alternatively from deprotonating heterocycles with strong base, for instance see: L. Brandsma and H. Verkruijsse, *Preparative Polar Organometallic Chemistry* 1, Springer-Verlag. The key ketone can also be prepared by the addition of a alkyl-lithium, available from halogen-lithium exchange of the alkyl iodide/bromide with tert-BuLi (as described in *J. Am. Chem. Soc.* 1990, 55, 5404 and 5406), to an heterocyclic Weinreb amide. These ketones can readily be converted to the required alcohols using reducing agents such as sodium borohydride.

The alcohols can also be made directly by the above methods but using an aldehyde in place of the Weinreb amide and thereby eliminating the reduction step.

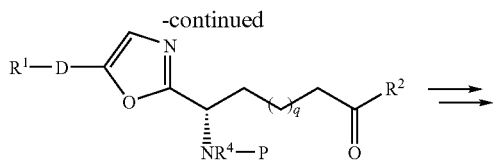

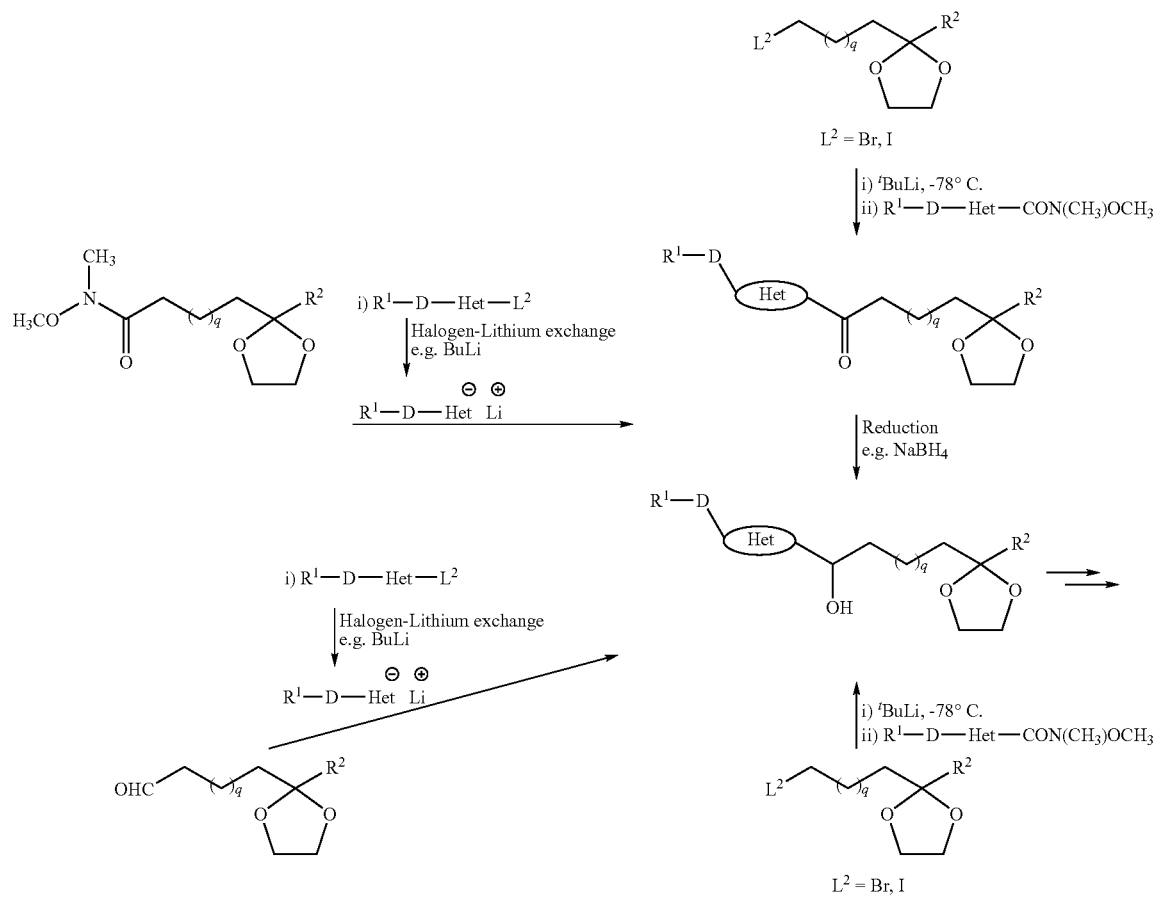

An alternative to this strategy involves the use of a terminal alkene as a masked methyl ketone group, the latter can readily be unmasked by Wacker oxidation as show in scheme 12. The alkene is readily introduced into the inhibitors through generation of the Grignard reagent from ω-haloalk-1-enes and their addition to aldehydes. Conversion of the benzylic alcohols to the corresponding amines is accomplished as described above using DPPA and DBU to form the azide and a Staudiger reaction to reduce the azide to the requisite amine. After functionalisation of the amine, the alkene can readily be converted to the ketone using oxygen and CuCl and catalytic $PdCl_2$ as described in *Synthesis* 1984, 369-384.

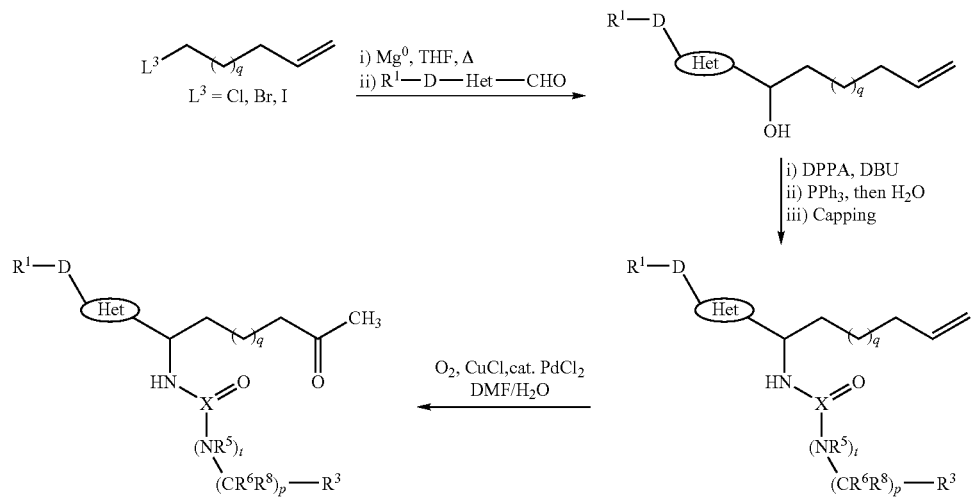

Scheme 12

A variant of the above procedure is to adopt Ellman chemistry to enable the key amine to be produced in a stereospecific way as shown in scheme 13. Condensation of an aldehyde with (R)-tert-butylsulfinamide results in the formation of the N—(R)-tert-butylsulfinimine. Addition of an organometallic reagent to this imine can be achieved in a highly stereospecific manner as described in: *Tetrahedron* 1999, 55, 8883-8904; *J. Org. Chem.* 1999, 64, 1278-84 and *J. Comb. Chem.* 2003, 5, 590-6, and the diastereomers can be separated as necessary. Hydrolysis of the chiral auxiliary with acidic methanol yields the key chiral amine suitable for further functionalisation.

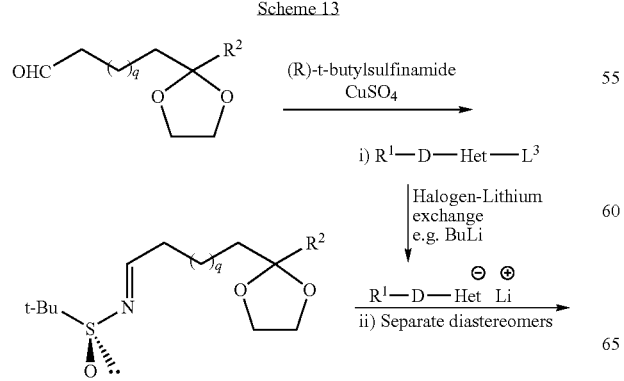

Scheme 13

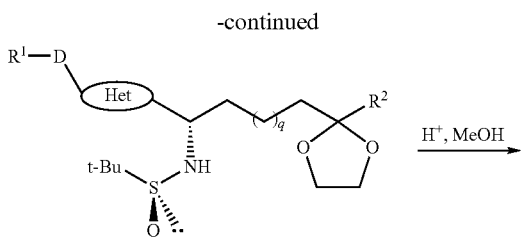

-continued

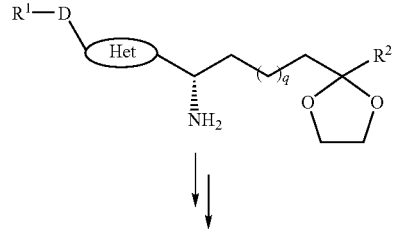

Perfluoroalkyl ketones can be prepared as described in scheme 14 whereby the corresponding carboxylic acid is deprotonated and then the corresponding anion is reacted with perfluoroalkylacetic anhydride, such as TFAA, in the presences of a base such as pyridine to yield the fluoroalkyl ketone as described in *Tetrahedron Letters*, 1992, 33, 1285-8.

Scheme 14

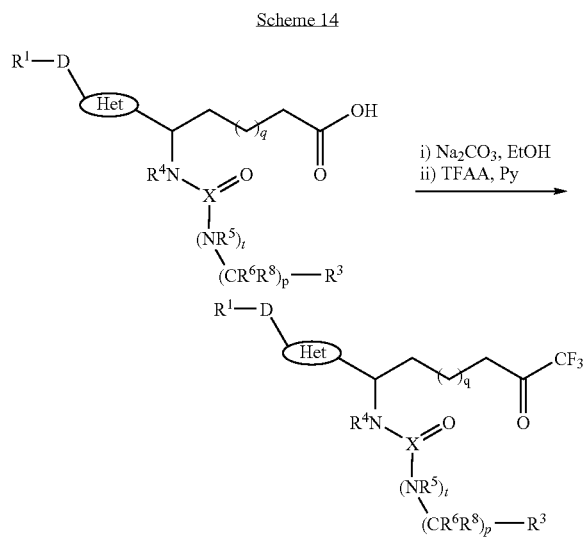

In some circumstances the desired inhibitors can be converted into other analogues by simple functional group manipulations known to those skilled in the art. For instance, carboxylic acids contained in the various $R^x$ groups can be cleaved and coupled to introduce amide groups. Likewise protected amines in the $R^x$ groups can be deprotected and functionalised with reactions such as coupling to carboxylic acid derivatives or by reductive amination reactions as shown in Scheme 15.

Scheme 15

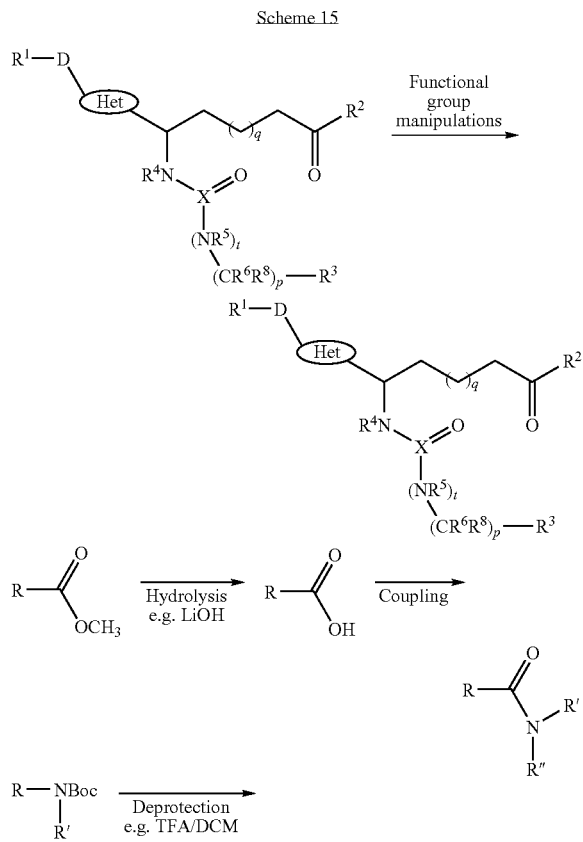

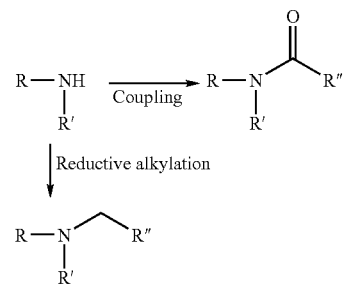

A modification of Scheme 13 is shown in Scheme 16 whereby 2,5-dibromoimidazole is protected and then lithiated, by bromine-lithium exchange with BuLi, and added to the tert-butylsulfinimine of the alkyl chain to give a mixture of diastereomers which can be separated readily by chromatography. Hydrolysis of the chiral auxiliary is readily achieved in acidic media and coupling introduces one of the capping groups. Cross-coupling reaction, for instance Suzuki reaction with a boronic acid under palladium catalysis, introduces the $R^1$-D-group and final deprotection readily liberates the desired inhibitors.

Scheme 16

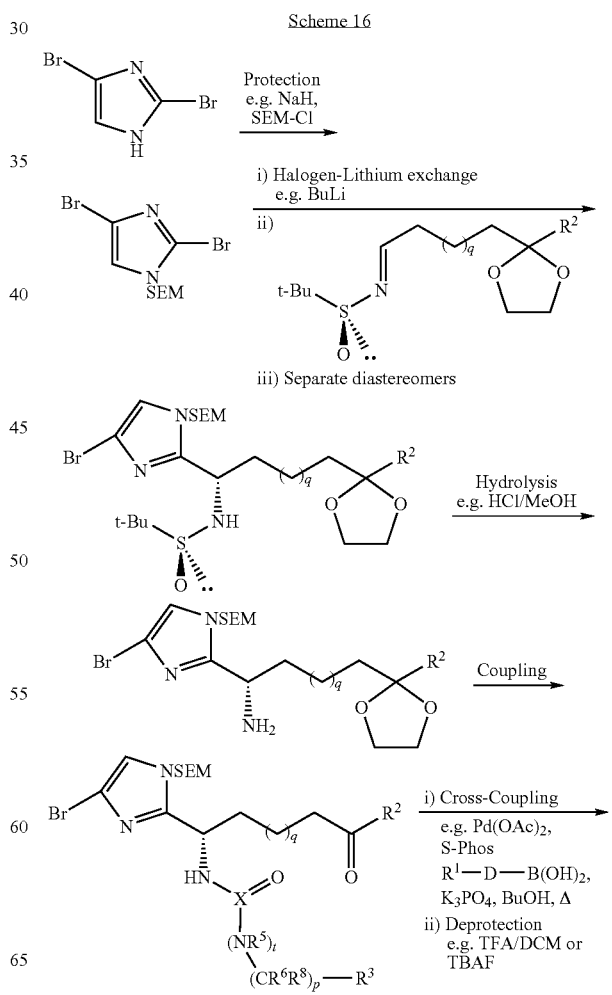

-continued

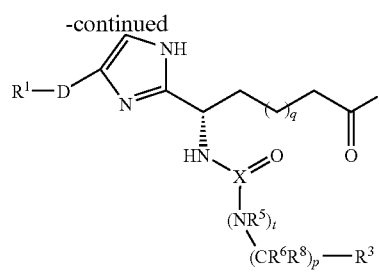

A further modification is shown in Scheme 17 whereby the bromide can be cross coupled in a Stille reaction with an 1-(1-alkoxyalkenyl)stannane in the presence of palladium(0) catalysis and then hydrolysed to yield compounds with a ketone moiety present in the $R^1$-D-group. Alternatively, if the bromide is cross-coupled in a Suzuki reaction with an alkenyl boronic acid the resulting product with a double bond present in the inhibitor can be subjected to a hydrogenation reaction to yield derivatives with alkyl groups at D.

group through the synthetic sequence as shown in Scheme 18. Lithiation on the 2-position of the imidazole and quenching on DMF introduces a aldehyde group on the imidazole, and this in turn can be reacted with a functionalised organolithium reagent, comprising of the side chain of the inhibitors, to build up the core of the desired molecules. Conversion of the resulting secondary alcohol into the corresponding azide and hydrolysis with $PPh_3$ in a Staudinger reaction liberates an amine which can be coupled to introduce one of the capping groups. This key building block can then be elaborated into a number of different classes of inhibitors as shown above. For instance: deprotection affords a hydroxylmethyl $R^1$-D-group; whereas removal of the silicon protecting groups and oxidation gives a key aldehyde which in turn can be functionalised by reductive aminations to introduce amines on the $R^1$-D-sidechain, alternatively the aldehyde can easily be homologated by reactions such as Wittig olefinations to form unsat- Scheme 17

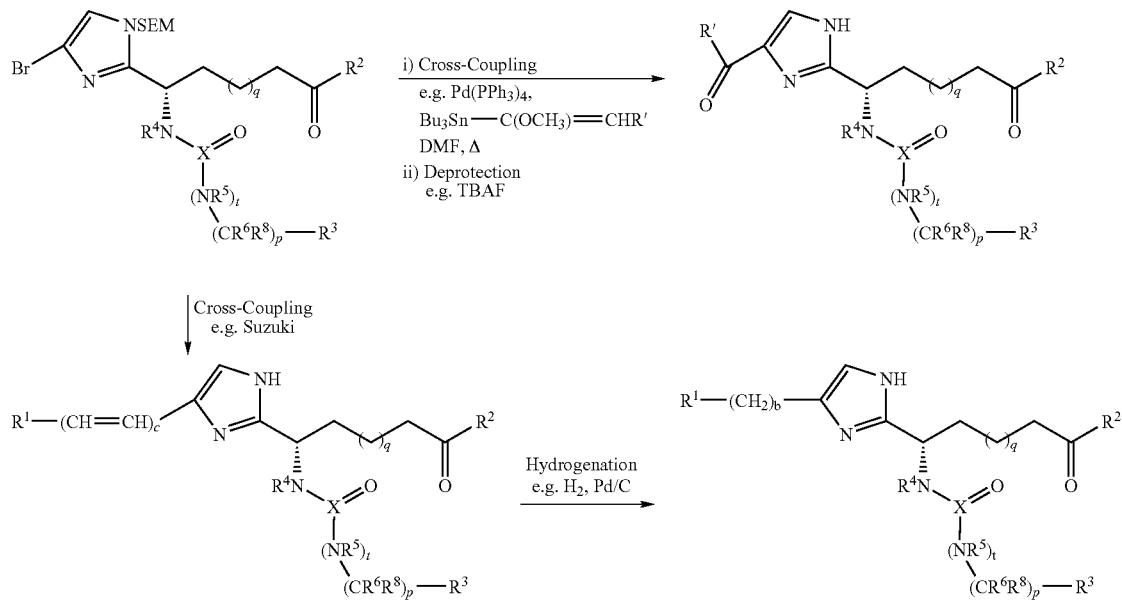

Further modification in the nature of the $R^1$-D-substitutent can be made by carrying through a protected hydroxylmethyl urated compounds which can be hydrogenated to their saturated counterparts.

Scheme 18

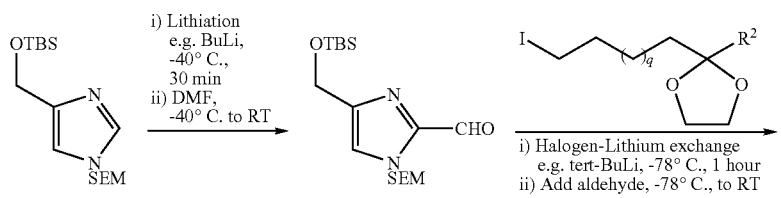

-continued
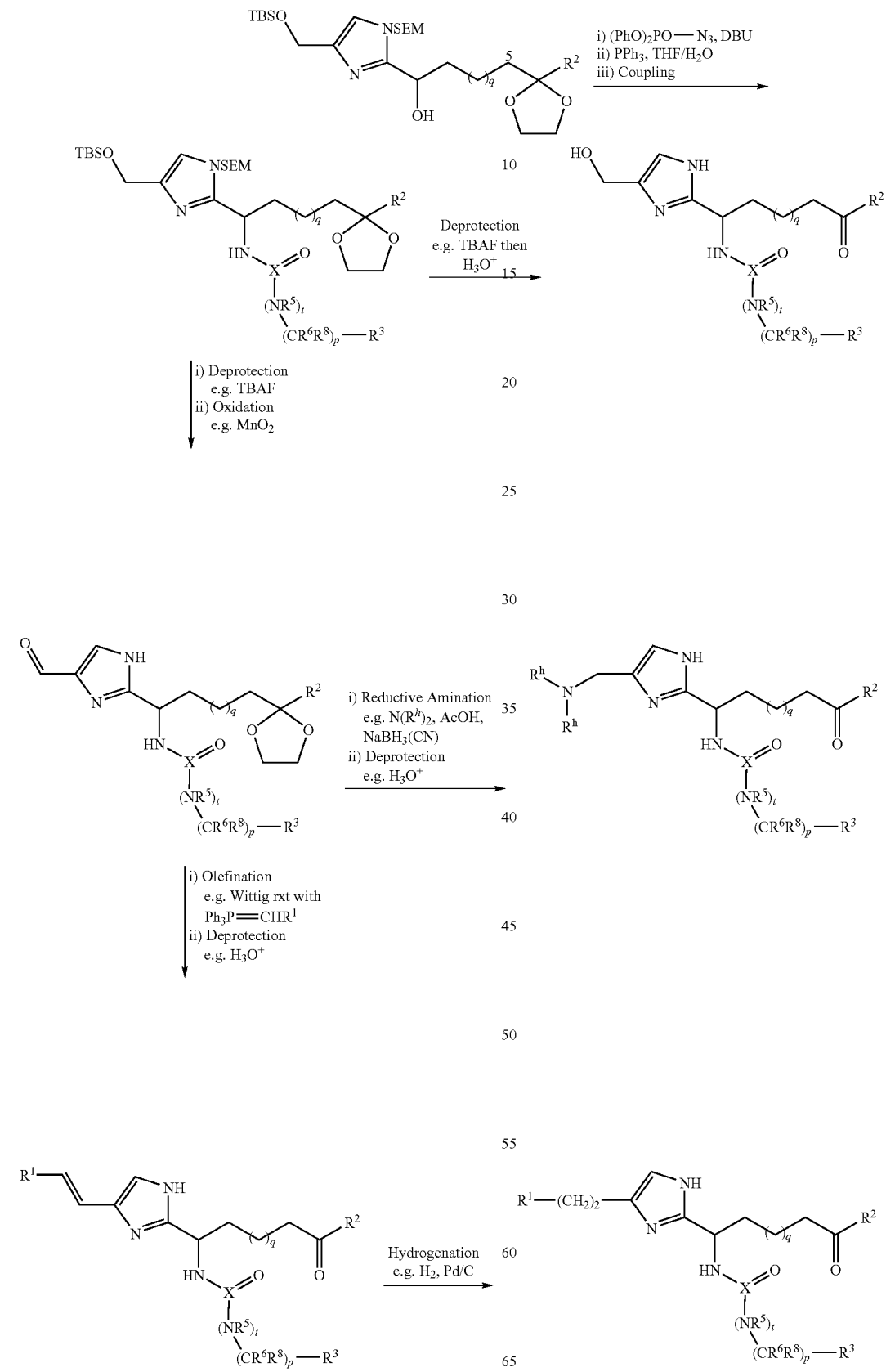

An alternative procedure to scheme 8 is shown above in scheme 19, where a hydrazide bearing the desired R¹-D-group is coupled with an activated amino-acid derivative. Suitable pre-activation strategies include treatment of the amino acid component with EDCI and HOBt for 10 minutes prior to the addition of the hydrazide. The resulting compound can then be readily cyclised under dehydrative conditions, such as the use of tosyl chloride and polymer supported BEMP. Functional group manipulations yield the desired inhibitors.

Scheme 19

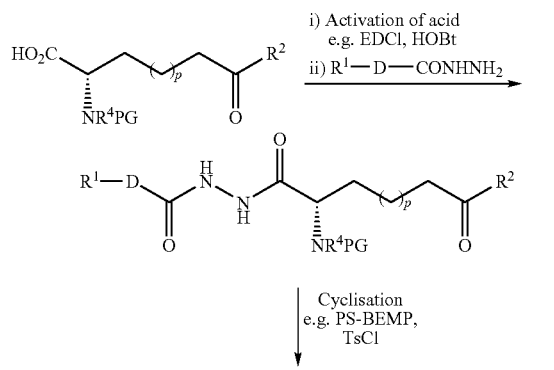

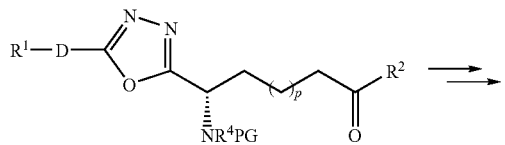

A procedure to modify the nature of the R²-group is shown in Scheme 20 whereby a Weinreb amide is treated with an organometallic reagent, typically an organolithium reagent or a Grignard reagent, to give rise to a series of alkyl ketones and functionalised alkyl ketones. A particular example is when the organolithium is generated from chloroiodomethane. In this case, the intermediate thereby formed can be treated with potassium acetate to yield the acetoxymethylketone which upon basic cleavage yields the hydroxymethyl ketone.

A variant of these procedures (not shown) is to use an aldehyde in place of the Weinreb amide. In this case after the addition of the organometallic reagent an oxidation step is required to give the corresponding ketone, this can be achieved with Dess-Martin reagent.

Scheme 20

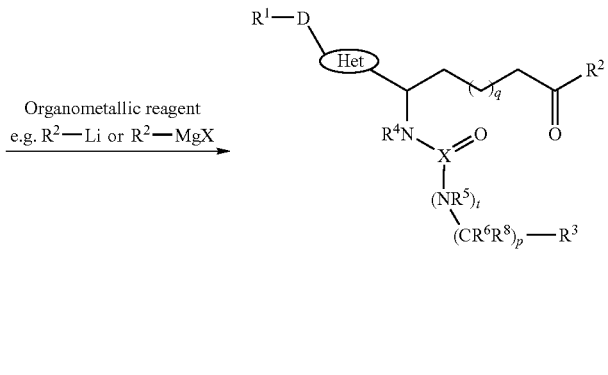

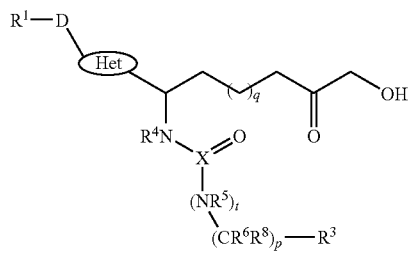

A modification of Scheme 6 is shown above in Scheme 21 whereby through careful choice of the protecting groups, such as the use of a Cbz-group as the amino protecting group, the tert-butyl ester can be cleaved without touching the amino protecting group. This allows the nature of the $R^2$-group to be varied and then at a final stage the amino protecting group can be removed and a variety of the capping groups introduced.

Scheme 21

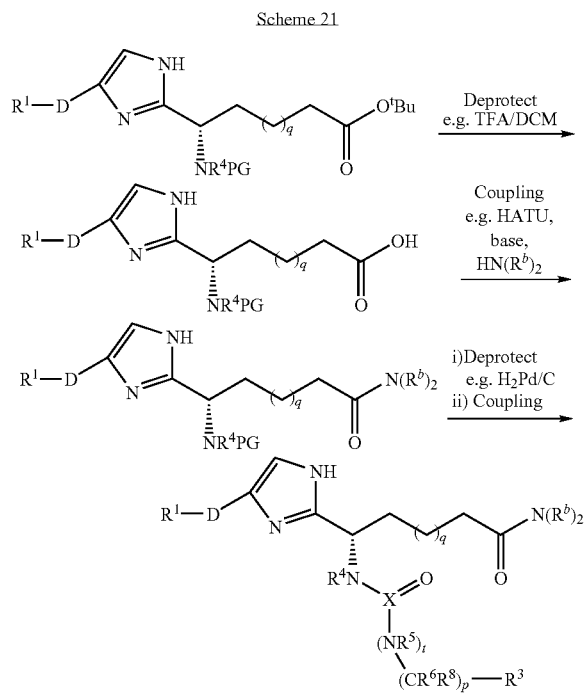

The exemplified compounds described herein were tested by the assays described below and were found to have an $IC_{50}$ value of less than 10 µM.

HDAC1 and NE Assays

Assay Description:

The HDAC_NE and HDAC1 assays are used to quantify the histone deacetylase (HDAC) activity. The assay is performed in 96 well microtiter plates by pre-incubating serial dilutions of compounds with a fixed concentration of HeLa nuclear extract or purified HDAC1 and then adding an acetylated lysine-containing substrate/developer that fluoresces upon deacetylation. The deacetylase reaction is performed at 37° C. for 60 min, terminated by addition of the developer solution, and then fluorescence (ex 360 nM, em 460 nM) is measured using a plate reader.

HDAC Substrate Buffer System

Reagents of the HDAC Fluorescent Activity Assay are purchased from BioMol Research Laboratories (Plymouth Meeting, Pa.) and feature the Fluor-de-Lys™ Substrate/Developer System. The reagents include the proprietary fluorescent substrate as a 50 mM stock solution (KI-104), and the Developer Concentrate (KI-105). Deacetylation of the lysine residue of the Fluor-de-Lys substrate is quantified by measuring the fluorescence (ex 360 nM, em 460 nM) after addition of the proprietary Developer.

Working Reagents:

TSA Stock: TSA is provided as a 10 mM stock solution in 100% dimethylsulfoxide (DMSO).

Assay Buffer: 25 mM Tris/HCl pH8, 137 mM NaCl, 2.7 mM KCl, 1 mM MgCl2, 0.1 mg/ml BSA Diluted Substrate Solution: The commercial 50 mM Fluor-de-Lys substrate (KI-104) is diluted to 150 uM with HDAC Assay Buffer prior to each use. The final concentration in the assay is 30 uM.

Diluted Developer Solution: The commercial 20X Developer Concentrate (KI-105) is diluted 1:167 into HDAC Assay Buffer. 2 uM [final] TSA to this solution increases its ability to stop the reaction.

HDAC_NE Working Solution: The HeLa nuclear extract is diluted in assay buffer prior to each use from a fresh aliquot. The final concentration in the assay is 20 ug/ml.

HDAC1 Working Solution: The HDAC1 enzyme is diluted in assay buffer prior to each use from a fresh aliquot of enzyme. The final concentration in the assay is 1-2 nM.

Compounds: Test compounds should be prepared as a 10×5% DMSO solution in assay buffer. The final DMSO concentration in the reaction is 0.5%.

Experimental Design:

The reaction is performed in 96-well microplate in a final volume of 50 ul/well, as following:
   Add 5 ul of DMSO/compound solution
   Add 35 ul of HeLa NE or HDAC1 in assay buffer (or 35 ul assay buffer in the negative controls)
   Incubate 10' at room temperature
   Start the reaction by adding 10 ul of the 150 uM Substrate Solution
   Incubate 1 h at 37° C.
   Stop by adding 50 ul of Developer/4 uM TSA solution
   Incubate 10 min at room temperature
   Measure the fluorescence at Ex.360 nM and Em.460 nM Protocol for Nuclei Extraction from HeLa Cells (Adherent or in Suspension)

For a protocol on Nuclei extraction from HeLa S3 cells (adherent or in suspension) refer to Nare et al. 1999 *Anal. Biochem.*, 267: 390-396.

Nuclei preparation for adherent HeLa S3 cells (0.5-1×109 cells) is as follows: wash cells twice with 1×PBS, scrape cells into 1×PBS, wash plates with 1×PBS, pool and spin cells at 800×g 10 minutes at 4° C., wash cell pellets with 1×PBS (count cells), spin cells at 800×g 10 minutes at 4° C., freeze cell pellets in liquid nitrogen and store −80° C.

Nuclei preparation for HeLa S3 cells in suspension (0.5-1×109 cells) is as follows: collect cells by centrifugation at 800×g 10 minutes at 4° C., wash cell pellets with 1×PBS, spin cells at 800×g 10 minutes at 4° C., repeat wash step twice (count cells), freeze cell pellet in liquid nitrogen and store at −80° C.

Resuspend cell pellets in lysis buffer (5 ml/1×108 cells; buffer contains: 0.25M sucrose, 0.45% NP40, 10 mM Tris-HCl (7.5), 10 mM NaCl, 5 mM $MgCl_2$, 0.1 mM EGTA, 0.5 mM PMSF, COMPLETE protease inhibitor mix), vortex 10 sec and leave on ice for 15 minutes, spin through cushion (25 ml of lysate/5 ml cushion; cushion contains: 30% sucrose, 10 mM Tris-HCl (7.5), 10 mM NaCl, 3 mM $MgCl_2$), spin through cushion at 1,300×g 10 minutes at 4° C., remove super/cushion, resuspend in lysis buffer as above and re-spin through cushion as above, remove super/cushion.

For nuclear extraction, resuspend nuclear pellets in nuclei extraction buffer (13.5 ml/5 ml nuclear pellet; nuclei extraction buffer contains: 50 mM Hepes pH 7.4, sonicate into suspension on ice (1 min, output control between 4 and 5), leave on ice 30 min., centrifuge 100,000×g for 1 hr at 4° C., keep super on ice, repeat sonication/ice/centrifuge steps two more times, pool three supernatants and dialyze in 50 mM Hepes pH 7.4/10% glycerol and Snap-freeze suitable aliquots in liquid nitrogen and store −80° C.

Extraction and Purification Protocol for Flag-Tagged HDAC1 Expressed in HeLa Cells HeLa cells transiently transfected with pCDNA3-HDAC1-FLAG are grown to 80% confluence on 10 cm culture dishes in DMEM, 10% Fetal bovine serum supplemented with antibiotics and glutamine. Cells are washed with 10 ml cold PBS and scraped into 2 ml of PBS. Cells are centrifuged for 5 minutes at 800×g at 4° C., washed with 30 ml PBS and resuspended in 10 ml PBS, counted, re-centrifuged and frozen at −80° C.

The frozen cell pellet is re-suspended in 1 ml of hypotonic lysis buffer (LB: 20 mM Hepes pH7.9, 0.25 mM EDTA, 10% glycerol) containing COMPLETE protease inhibitor and incubated on ice for 15 minutes, followed by homogenization on a 2-ml DounceB homogenizer (25 strokes). 150 mM KCl and 0.5% NP-40 are added to the homogenate and the solution is sonicated twice for 30 seconds (output5/6, duty cycle 90) and incubated for 1 hour at 4° C. After a 30 minutes centrifugation at 12000 rpm and 4° C. the supernatant (soluble extract) is collected and protein concentration is determined using the BIORAD assay.

Anti-FLAG M2 affinity resin (Sigma) is washed three times with TBS and twice with LB. 10 µl of the LB-washed resin/mg of protein (2-3 ug of Flagged-HDAC1) are added to the soluble extract (1 mL) and incubated overnight at 4° C. with gentle mixing. The resin is then collected by centrifugation, washed once with LB, twice with LB+0.1% NP40 and twice with elution buffer (50 mM Hepes pH 7.4, 5% glycerol, 100 mM KCl, 0.01% Triton X-100).

The affinity-purified HDAC is eluted from the resin by addition of a 10-fold excess (with respect to the resin) of elution buffer containing 100 µg/ml 3×FLAG peptide (SIGMA). The concentration of purified HDAC is determined by Western blot analysis.

Other assays are known in the literature and can be readily performed by those skilled in the art.

The following Examples illustrate the present invention.

Example 1

1-Methyl-3-({[(1S)-7-oxo-1-(5-phenyl-1H-imidazol-1-ium-2-yl)octyl]amino}carbonyl)piperidinium bis(trifluoroacetate) (A4)

Step 1: (2S)-2-[(tert-Butoxycarbonyl)amino]-8-oxononanoic acid (A1)

(2S)-2-[(tert-Butoxycarbonyl)amino]-8-oxononanoic acid methyl ester (1 eq.) was dissolved in a 1:1 mixture of THF and water at RT and LiOH hydrate (1.2 eq.) was added and the mixture was stirred for 30 min. The mixture was partitioned between 0.1M HCl and DCM, separated and the organic phase was washed with water, dried ($Na_2SO_4$) and concentrated under reduced pressure. The colourless oil A1 obtained was used in the next step without purification. MS (ES) $C_{14}H_{25}NO_5$ requires: 287, found: 288 $(M+H)^+$.

Step 2: tert-Butyl[(1S)-7-oxo-1-(5-phenyl-1H-imidazol-2-yl)octyl]carbamate (A2)

A solution of A1 (1 eq.) and $Cs_2CO_3$ (0.5 eq) in EtOH was stirred for 30 min at RT and then concentrated under reduced pressure. 2-Bromoacetophenone (1 eq.) was added to the resulting salt in DMF and the mixture was stirred for 1 h at RT under $N_2$. The DMF was removed by azeotroping with xylene. EtOAc was added, the mixture was filtered and the residue was washed with EtOAc. The combined filtrates were concentrated under reduced pressure. A solution of the resulting oil and ammonium acetate (20 eq.) in xylene was heated at reflux (150° C. bath temperature) for 3 h. The mixture was cooled to RT, diluted with EtOAc and washed with water (×2), sat. aq. $NaHCO_3$ solution and brine. The solution was dried ($Na_2SO_4$), concentrated under reduced pressure and the resulting brown oil was purified by chromatography on silica gel eluting with EtOAc/petrol ether (1.5:1) to obtain the imidazole A2 as a colourless oil. $^1H$ NMR (300 MHz, $CDCl_3$) δ: 10.50-9.60 (1H, m), 7.82-7.40 (2H, m), 7.38-7.29 (2H, m), 7.22-7.15 (2H, m), 5.13 (1H, br. s), 4.68-4.55 (1H, m), 2.39 (2H, t, J=7.2 Hz), 2.22-2.06 (4H, m), 1.99-1.80 (1H, m), 1.60-1.50 (2H, m), 1.43 (9H, s), 1.40-1.27 (4H, m). MS (ES) $C_{22}H_{31}N_3O_3$ requires: 385, found: 386 $(M+H)^+$.

Step 3: 2-[(1S)-1-Ammonio-7-oxooctyl]-5-phenyl-1H-imidazol-1-ium bis(trifluoroacetate) (A3)

A2 (1 eq.) was dissolved in TFA/DCM (1:1) at 0° C. The cooling bath was removed and the mixture was stirred for 60 min at RT. The solvents were removed under reduced pressure and the residue was left under high vacuum for a further 3 h. The crude amine salt A3 was used without further purification. MS (ES) $C_{17}H_{23}N_3O$ requires: 285, found: 286 $(M+H)^+$.

Step 4: 1-Methyl-3-({[(1S)-7-oxo-1-(5-phenyl-1H-imidazol-1-ium-2-yl)octyl]amino}carbonyl)piperidinium bis(trifluoroacetate) (A4)

To a solution of A3 (1 eq.) and $Et_3N$ (2.2 eq.) in DMF was added a solution of EDC.HCl (1.2 eq), HOBt (1.2 eq) and 1-methylpiperidine-3-carboxylic acid (1.2 eq) in DMF. The mixture was shaken at RT for 16 h and the desired material was isolated by preparative RP-HPLC, using $H_2O$ (+0.1% TFA) and MeCN (+0.1% TFA) as eluents (C18 column). The desired fractions were lyophilized to afford the imidazole A4 as a colourless oil which solidified upon standing. $^1H$ NMR (300 MHz, DMSO-d6) δ: 8.96-8.91 (1H, m), 7.98 (1H, s), 7.78 (2H, d, J=7.5 Hz), 7.50 (2H, t, J=7.5 Hz), 7.45-7.32 (1H, m), 5.06-4.90 (1H, m), 3.16-2.67 (8H, m), 2.40 (2H, t, J=7.2 Hz), 2.05 (3H, s), 2.03-1.16 (12H, m). MS (ES) $C_{24}H_{34}N_4O_2$ requires: 410, found: 411 $(M+H)^+$.

Example 2

2-((1S)-1-{[(4-Methoxyphenyl)sulfonyl]amino}-7-oxooctyl)-5-phenyl-1H-imidazol-1-ium trifluoroacetate (B1)

To a solution of Example 1, A3 and $Et_3N$ (1.1 eq.) in DCM was added 4-methoxybenzene sulfonyl chloride (1.1 eq.). The reaction mixture was stirred at RT for 3 hr and the mixture was washed with sat. aq. $NaHCO_3$. The organic phase was concentrated under reduced pressure and the crude residue was purified by preparative RP-HPLC, using $H_2O$ (0.1% TFA) and MeCN (+0.1% TFA) as eluents (column: C18). The desired fractions were lyophilized to afford the titled compound B1 as a colourless oil. $^1$H NMR (300 MHz, CD$_3$CN) δ: 8.87 (1H, d, J=9.3 Hz), 7.60-7.52 (4H, m), 7.51-7.40 (3H, m), 7.31 (1H, s), 6.79-6.63 (2H, m), 4.78-4.65 (1H, m), 3.51 (1H, s), 2.37 (2H, t, J=7.3 Hz), 2.04 (3H, s), 1.89-1.78 (2H, m), 1.51-1.32 (3H, m), 1.31-1.14 (3H, m). MS (ES) C$_{24}$H$_{29}$N$_3$O$_4$S requires: 455, found: 456 (M+H)$^+$.

Example 3

2-[(1S)-1-({[[2-(Dimethylammonio)ethyl](methyl)amino]-sulfonyl}amino)-7-oxooctyl]-5-phenyl-1H-imidazol-1-ium bis(trifluoroacetate) (C2)

Step 1: 2-[(Chlorosulfonyl)(methyl)amino]-N,N-dimethylethanaminium chloride (C1)

To a solution of sulfuryl chloride (1.0 eq.) in CHCl$_3$ at 0° C. was added dropwise trimethylethylenediamine (1.0 eq.) over 15 mins. After the addition, the cooling bath was removed and the mixture was stirred overnight at RT. The solvent was removed under reduced pressure and the residue was left under high vacuum for 4 h. The crude product was obtained as a pale yellow solid and was used without further purification. $^1$H NMR (300 MHz, DMSO-d6) δ: 3.46-3.29 (4H, m), 2.83 (6H, s), 2.60 (3H, s).

Step 2: 2-[(1S)-1-({[[2-(Dimethylammonio)ethyl](methyl)amino]-sulfonyl}amino)-7-oxooctyl]-5-phenyl-1H-imidazol-1-ium bis(trifluoroacetate) (C2)

To a solution Example 1, A3 and Et$_3$N (4 eq.) in DCM was added crude C1 (1.2 eq). The mixture was stirred at RT for 16 hr. The mixture was purified by preparative RP-HPLC, using H$_2$O (0.1% TFA) and MeCN (+0.1% TFA) as eluents (column: C18). The desired fractions were lyophilized to afford the titled compound C2 as a colourless oil. $^1$H NMR (300 MHz, DMSO-d$_6$) δ: 8.18 (1H, br. s), 7.87 (1H, br. s), 7.83-7.71 (2H, m), 7.58-7.28 (3H, m), 4.64-4.45 (1H, m), 3.41-3.16 (4H, m), 2.79 (6H, s), 2.63 (3H, s), 2.39 (2H, t, J=6.8 Hz), 2.05 (3H, s), 1.98-1.78 (2H, m), 1.53-1.19 (6H, m). MS (ES) C$_{22}$H$_{35}$N$_5$O$_3$S requires: 449, found: 450 (M+H)$^+$.

Example 4

2-((1S)-1-{[(5-Methoxy-2-methyl-1H-indol-3-yl)acetyl]amino}-7-oxooctyl)-5-phenyl-1H-imidazol-1-ium trifluoroacetate (D1)

To a solution of Example 1, A3 and Et$_3$N (1 eq.) in DCM was added a solution of EDC hydrochloride (1.2 eq.), HOBt (1.2 eq.) and (5-methoxy-2-methyl-1H-indol-3-yl)acetic acid (1.2 eq.) in DCM. The mixture was shaken at RT for 1.5 hr and then the reaction mixture was diluted with DCM, washed with saturated aqueous NaHCO$_3$, dried (Na$_2$SO$_4$), filtered and concentrated under reduced pressure. The crude residue was purified by preparative RP-HPLC, using H$_2$O (0.1% TFA) and MeCN (+0.1% TFA) as eluents (column: C18). The desired fractions were lyophilized to afford the titled compound D1 as a white fluffy powder.

$^1$H NMR (400 MHz, DMSO-d6+TFA) δ: 14.43 (2H, bs), 10.61 (1H, s), 8.59 (1H, d, J=6.6 Hz), 8.05 (1H, s), 7.79-7.73 (2H, m), 7.56-7.48 (2H, m), 7.47-7.41 (1H, m), 7.10 (1H, d, J=8.6 Hz), 6.96 (1H, d, J=2.4 Hz), 6.60 (1H, dd, J=8.6, 2.4 Hz), 5.06-4.97 (1H, m), 3.68 (3H, s), 3.57 (1H, d, J=15.3 Hz), 3.48 (1H, d, J=15.3 Hz), 2.36-2.27 (5H, m), 2.03 (3H, s), 1.97-1.83 (2H, m), 1.43-1.13 (6H, m). MS (ES) C$_{29}$H$_{34}$N$_4$O$_3$ requires: 486, found: 487 (M+H)$^+$.

Examples 5-31 were made according to the reaction schemes and the processes given in Examples 1-4.

| Example | Name | (M + H)$^+$ | Procedure from Example Number |
|---|---|---|---|
| 5 | 1-Methyl-4-(2-oxo-2-{[(1S)-7-oxo-1-(5-phenyl-1H-imidazol-1-ium-2-yl)octyl]amino}ethyl)piperazinediium tris(trifluoroacetate) | 426 | 1 |
| 6 | 1-Methyl-2-({[(1S)-7-oxo-1-(5-phenyl-1H-imidazol-1-ium-2-yl)octyl]amino}carbonyl)piperidinium bis(trifluoroacetate) | 411 | 1 |
| 7 | 1-(3-Oxo-3-{[(1S)-7-oxo-1-(5-phenyl-1H-imidazol-1-ium-2-yl)octyl]amino}propyl)piperidinium bis(trifluoroacetate) | 425 | 1 |
| 8 | 2-((1S)-1-{[(1-Methylpyrrolidinium-3-yl)carbonyl]amino}-7-oxooctyl)-5-phenyl-1H-imidazol-1-ium bis(trifluoroacetate) | 397 | 1 |
| 9 | 1-Methyl-4-({[(1S)-7-oxo-1-(5-phenyl-1H-imidazol-1-ium-2-yl)octyl]amino}carbonyl)piperidinium bis(trifluoroacetate) | 411 | 1 |
| 10 | 2-{(1S)-7-Oxo-1-[(2-thienylcarbonyl)amino]octyl}-5-phenyl-1H-imidazol-1-ium trifluoroacetate | 396 | 1 |
| 11 | 2-{(1S)-7-Oxo-1-[(1,3-thiazol-5-ylcarbonyl)amino]octyl}-5-phenyl-1H-imidazol-1-ium trifluoroacetate | 397 | 1 |
| 12 | 2-((1S)-1-{[(4-Methyl-1,2,3-thiadiazol-5-yl)carbonyl]amino}-7-oxooctyl)-5-phenyl-1H-imidazol-1-ium trifluoroacetate | 412 | 1 |
| 13 | 2-{(1S)-1-[(2,3-Dihydro-1,4-benzodioxin-6-ylsulfonyl)amino]-7-oxooctyl}-5-phenyl-1H-imidazol-1-ium trifluoroacetate | 484 | 2 |

-continued

| Example | Name | (M + H)+ | Procedure from Example Number |
|---|---|---|---|
| 14 | 2-(1-{[(5-Methoxy-2-methyl-1H-indol-3-yl)acetyl]amino}-7-oxooctyl)-5-phenyl-1H-imidazol-1-ium trifluoroacetate | 487 | 4 |
| 15 | 2-((1S)-1-{[(4-Cyanophenyl)sulfonyl]amino}-7-oxooctyl)-5-phenyl-1H-imidazol-1-ium trifluoroacetate | 451 | 2 |
| 16 | 2-{(1S)-1-[(2-Naphthylsulfonyl)amino]-7-oxooctyl}-5-phenyl-1H-imidazol-1-ium trifluoroacetate | 476 | 2 |
| 17 | 2-((1S)-1-{[(2,4-Dimethyl-1,3-thiazol-5-yl)sulfonyl]amino}-7-oxooctyl)-5-phenyl-1H-imidazol-1-ium trifluoroacetate | 461 | 2 |
| 18 | 2-{(1S)-1-[(1-Benzothien-3-ylsulfonyl)amino]-7-oxooctyl}-5-phenyl-1H-imidazol-1-ium trifluoroacetate | 482 | 2 |
| 19 | 2-((1S)-1-{[(4-Chlorophenyl)sulfonyl]amino}-7-oxooctyl)-5-phenyl-1H-imidazol-1-ium trifluoroacetate | 460 | 2 |
| 20 | 2-((1S)-1-{[(3-Methoxyphenyl)sulfonyl]amino}-7-oxooctyl)-5-phenyl-1H-imidazol-1-ium trifluoroacetate | 456 | 2 |
| 21 | 1,2-Dimethyl-4-({[[(1S)-7-oxo-1-(5-phenyl-1-imidazol-1-ium-2-yl)octyl]amino}sulfonyl)-1H-imidazol-1-ium bis(trifluoroacetate) | 444 | 2 |
| 22 | 2-((1S)-1-{[(3,5-Dimethylisoxazol-4-yl)sulfonyl]amino}-7-oxooctyl)-5-phenyl-1H-imidazol-1-ium trifluoroacetate | 445 | 2 |
| 23 | 4-[({1-[5-(2-Methoxyphenyl)-1H-imidazol-1-ium-2-yl]-7-oxooctyl}amino)carbonyl]-1-methylpiperidinium bis(trifluoroacetate) | 441 | 1 |
| 24 | 4-[({1-[5-(3-Methoxyphenyl)-1H-imidazol-1-ium-2-yl]-7-oxooctyl}amino)carbonyl]-1-methylpiperidinium bis(trifluoroacetate) | 441 | 1 |
| 25 | 4-[({1-[5-(4-Fluorophenyl)-1H-imidazol-1-ium-2-yl]-7-oxooctyl}amino)carbonyl]-1-methylpiperidinium bis(trifluoroacetate) | 429 | 1 |
| 26 | 4-[({1-[5-(4-Chlorophenyl)-1H-imidazol-1-ium-2-yl]-7-oxooctyl}amino)carbonyl]-1-methylpiperidinium bis(trifluoroacetate) | 445 | 1 |
| 27 | 4-[({1-[5-(4-Bromophenyl)-1H-imidazol-1-ium-2-yl]-7-oxooctyl}amino)carbonyl]-1-methylpiperidinium bis(trifluoroacetate) | 489 | 1 |
| 28 | 4-[({1-[5-(2-Chlorophenyl)-1H-imidazol-1-ium-2-yl]-7-oxooctyl}amino)carbonyl]-1-methylpiperidinium bis(trifluoroacetate) | 445 | 1 |
| 29 | 4-[({1-[5-(3,4-Dichlorophenyl)-1H-imidazol-1-ium-2-yl]-7-oxooctyl}amino)carbonyl]-1-methylpiperidinium bis(trifluoroacetate) | 479 | 1 |
| 30 | 4-[({1-[5-(4-Cyanophenyl)-1H-imidazol-1-ium-2-yl]-7-oxooctyl}amino)carbonyl]-1-methylpiperidinium bis(trifluoroacetate) | 436 | 1 |
| 31 | 4-[({1-[5-(3-Cyanophenyl)-1H-imidazol-1-ium-2-yl]-7-oxooctyl}amino)carbonyl]-1-methylpiperidinium bis(trifluoroacetate) | 436 | 1 |

ExampleS 32 and 33

4-({[(1S)-1-(4,5-Diphenyl-1,3-oxazol-2-yl)-7-oxooctyl]amino}carbonyl)-1-methylpiperidinium trifluoroacetate (E2a) and 4-({[(1S)-1-(4,5-Diphenyl-1H-imidazol-1-ium-2-yl)-7-oxooctyl]amino}carbonyl)-1-methylpiperidinium bis(trifluoroacetate) (E2b)

Step 1: tert-Butyl [(1S)-1-(4,5-diphenyl-1,3-oxazol-2-yl)-7-oxooctyl]carbamate (E1a) and tert-butyl [(1S)-1-(4,5-diphenyl-1,3-imidazol-2-yl)-7-oxooctyl]carbamate (E1b)

A solution of Example 1, Al and $Cs_2CO_3$ (0.5 eq) in EtOH was stirred at RT for 30 min and was then concentrated to dryness under reduced pressure. To the resulting salt dissolved in DMF was added 2-bromo-1,2-diphenylethanone (1 eq.). The resulting mixture was stirred for 1 hr at RT and then the DMF was removed under reduced pressure. EtOAc was added and the mixture was filtered and the filter was washed with further EtOAc. The combined filtrates were concentrated under reduced pressure. A solution of the resulting oil and $NH_4OAc$ (20 eq.) in xylene was heated at reflux (150° C. bath temperature) for 90 min and was then cooled to RT and diluted with EtOAc. The solution was washed with $H_2O$ (2×), sat. aq. $NaHCO_3$, and brine, then dried ($Na_2SO_4$) and concentrated under reduced pressure. The resulting brown oil was used in the next step without further purification.

tert-Butyl [(1S)-1-(4,5-diphenyl-1,3-oxazol-2-yl)-7-oxooctyl]carbamate: MS (ES) $C_{28}H_{34}N_2O_4$ requires: 462, found: 463 (M+H)+.

tert-Butyl [(1S)-1-(4,5-diphenyl-1,3-imidazol-2-yl)-7-oxooctyl]carbamates: MS (ES) $C_{28}H_{35}N_3O_3$ requires: 461, found: 462 (M+H)$^+$.

Step 2: 4-({[(1S)-1-(4,5-Diphenyl-1,3-oxazol-2-yl)-7-oxooctyl]amino}-carbonyl)-1-methylpiperidinium trifluoroacetate (E2a) and 4-({[(1S)-1-(4,5-Diphenyl-1H-imidazol-1-ium-2-yl)-7-oxooctyl]amino}carbonyl)-1-methylpiperidinium bis(trifluoroacetate) (E2b)

The mixture of carbamates from the previous step (E1a and E1b) was dissolved in TFA/DCM (1:1) and the mixture was stirred for 60 min at RT. The solvents were removed under vacuum and the residue was partitioned between sat. aq. NaHCO$_3$ and DCM. The organic phase was dried (Na$_2$SO$_4$) and concentrated under reduced pressure. To the obtained residue was added a solution of EDC.HCl (1.2 eq), HOBt (1.2 eq) and 4-carboxy-1-methylpiperidinium chloride (1.2 eq) in DMF, followed by Et$_3$N (1.2 eq). The mixture was stirred at RT for 4 hr. The products were isolated by preparative RP-HPLC, using H$_2$O (0.1% TFA) and MeCN (+0.1% TFA) as eluents (column: C18), to yield first the imidazole E2a and then the oxazole E2b. The desired fractions were lyophilized to afford the titled compounds as colourless oils.

Eluted first: (4-({[(1S)-1-(4,5-Diphenyl-1H-imidazol-1-ium-2-yl)-7-oxooctyl]amino}carbonyl)-1-methyl piperidinium bis(trifluoroacetate): MS (ES) $C_{30}H_{38}N_4O_2$ requires: 486, found: 487 (M+H)$^+$.

Eluted second: 4-({[(1S)-1-(4,5-diphenyl-1,3-oxazol-2-yl)-7-oxooctyl]amino}-carbonyl)-1-methylpiperidinium trifluoroacetate: $^1$H NMR (300 MHz, DMSO-d6) δ: 9.50-9.13 (1H, m), 8.63 (1H, d, J=8.2 Hz), 7.65-7.30 (10H, m), 5.01 (1H, m), 3.51-3.24 (2H, m), 3.22-2.84 (2H, m), 2.82-2.70 (3H, m), 2.55-2-45 (1H, m), 2.41 (2H, t, J=3.6 Hz), 2.05 (3H, s), 2.02-1.64 (6H, m), 1.54-1.19 (6H, m). MS (ES) $C_{30}H_{37}N_3O_3$ requires: 487, found: 488 (M+H)$^+$.

Examples 34-86 were made according to the reaction schemes and the processes given in Examples 14, 32 and 33.

| Example | Name | (M + H)$^+$ | Procedure from Example Number |
|---|---|---|---|
| 34 | 2-((1S)-1-{[(5-Methoxy-2-methyl-1H-indol-3-yl)acetyl]amino}-7-oxooctyl)-5-phenyl-1H-imidazol-1-ium chloride | 487 | 1 |
| 35 | 1-Methyl-4-({[(1S)-7-oxo-1-(5-phenyl-1H-imidazol-1-ium-2-yl)octyl]amino}carbonyl)piperidinium dichloride | 411 | 1 |
| 36 | 1-Methyl-4-[4-({[(1S)-7-oxo-1-(5-phenyl-1H-imidazol-1-ium-2-yl)octyl]amino}-carbonyl)phenyl]piperazinediium tris(trifluoroacetate) | 488 | 1 |
| 37 | 3-({[(1S)-7-Oxo-1-(5-phenyl-1H-imidazol-1-ium-2-yl)octyl]amino}carbonyl)-1-pyridin-2-ylpiperidinium bis(trifluoroacetate) | 474 | 1 |
| 38 | 3-(2-Oxo-2-{[(1S)-7-oxo-1-(5-phenyl-1H-imidazol-1-ium-2-yl)octyl]amino}ethyl)-6,7-dihydro-5H-[1,3]thiazolo[3,2-a]pyrimidin-4-ium bis(trifluoroacetate) | 466 | 1 |
| 39 | 2-(3-Oxo-3-{[(1S)-7-oxo-1-(5-phenyl-1H-imidazol-1-ium-2-yl)octyl]amino}propyl)-2-azoniabicyclo[2.2.1]heptane bis(trifluoroacetate) | 437 | 1 |
| 40 | 4-(2-Oxo-2-{[(1S)-7-oxo-1-(5-phenyl-1H-imidazol-1-ium-2-yl)octyl]amino}-1-pyridinium-3-ylethyl)morpholin-4-ium tris(trifluoroacetate) | 490 | 1 |
| 41 | 1-Methyl-4-({[(1S)-1-(4-methyl-5-phenyl-1H-imidazol-1-ium-2-yl)-7-oxooctyl]amino}carbonyl)piperidinium bis(trifluoroacetate) | 425 | 32 |
| 42 | 4-({[(1S)-1-(5-Biphenyl-4-yl-1H-imidazol-1-ium-2-yl)-7-oxooctyl]amino}carbonyl)-1-methylpiperidinium bis(trifluoroacetate) | 487 | 1 |
| 43 | 1-Methyl-4-[({(1S)-1-[5-(2-naphthyl)-1H-imidazol-1-ium-2-yl]-7-oxooctyl}amino)carbonyl]piperidinium bis(trifluoroacetate) | 461 | 1 |
| 44 | 4-[({(1S)-1-[5-(3-Chlorophenyl)-1H-imidazol-1-ium-2-yl]-7-oxooctyl}amino)carbonyl]-1-methylpiperidinium bis(trifluoroacetate) | 445 | 1 |
| 45 | 4-{[((1S)-1-{5-[3,5-bis(Trifluoromethyl)phenyl]-1H-imidazol-1-ium-2-yl}-7-oxooctyl)amino]carbonyl}-1-methylpiperidinium bis(trifluoroacetate) | 547 | 1 |
| 46 | 1-Methyl-4-{[((1S)-7-oxo-1-{5-[3-(trifluoromethyl)phenyl]-1H-imidazol-1-ium-2-yl}octyl)amino]carbonyl}piperidinium bis(trifluoroacetate) | 479 | 1 |
| 47 | 2-((1S)-1-{[(3-Cyanophenyl)sulfonyl]amino}-7-oxooctyl)-5-phenyl-1H-imidazol-1-ium trifluoroacetate | 451 | 2 |
| 48 | 2-{(1S)-7-Oxo-1-[(phenylsulfonyl)amino]octyl}-5-phenyl-1H-imidazol-1-ium trifluoroacetate | 426 | 2 |

-continued

| Example | Name | (M + H)⁺ | Procedure from Example Number |
|---|---|---|---|
| 49 | 4-Methyl-7-({[(1S)-7-oxo-1-(5-phenyl-1H-imidazol-1-ium-2-yl)octyl]amino}sulfonyl)-3,4-dihydro-2H-1,4-benzoxazin-4-ium bis(trifluoroacetate) | 497 | 2 |
| 50 | 2-[(1S)-1-({[2-(Acetylamino)-4-methyl-1,3-thiazol-5-yl]sulfonyl}amino)-7-oxooctyl]-5-phenyl-1H-imidazol-1-ium trifluoroacetate | 504 | 2 |
| 51 | 2-((1S)-1-{[(5-Chloro-2-thienyl)sulfonyl]amino}-7-oxooctyl)-5-phenyl-1H-imidazol-1-ium trifluoroacetate | 466 | 2 |
| 52 | 1,3,5-Trimethyl-4-({[(1S)-7-oxo-1-(5-phenyl-1H-imidazol-1-ium-2-yl)octyl]amino}sulfonyl)-1H-pyrazol-1-ium bis(trifluoroacetate) | 458 | 2 |
| 53 | 2-[(1S)-1-({[5-(2-Methyl-1,3-thiazol-4-yl)-2-thienyl]sulfonyl}amino)-7-oxooctyl]-5-phenyl-1H-imidazol-1-ium trifluoroacetate | 529 | 2 |
| 54 | 2-{(1S)-1-[({5-[1-Methyl-3-(trifluoromethyl)-1H-pyrazol-5-yl]-2-thienyl}sulfonyl)amino]-7-oxooctyl}-5-phenyl-1H-imidazol-1-ium trifluoroacetate | 580 | 2 |
| 55 | 2-((1S)-1-{[(5-Isoxazol-3-yl-2-thienyl)sulfonyl]amino}-7-oxooctyl)-5-phenyl-1H-imidazol-1-ium trifluoroacetate | 499 | 2 |
| 56 | 1-Methyl-4-{[((1S)-7-oxo-1-{5-[4-(trifluoromethyl)phenyl]-1H-imidazol-1-ium-2-yl}octyl)amino]carbonyl}piperidinium bis(trifluoroacetate) | 479 | 1 |
| 57 | 4-{[((1S)-1-{5-[4-(Difluoromethoxy)phenyl]-1H-imidazol-1-ium-2-yl}-7-oxooctyl)amino]carbonyl}-1-methylpiperidinium bis(trifluoroacetate) | 477 | 1 |
| 58 | 4-[({(1S)-1-[5-(3,4-Difluorophenyl)-1H-imidazol-1-ium-2-yl]-7-oxooctyl}amino)carbonyl]-1-methylpiperidinium bis(trifluoroacetate) | 447 | 1 |
| 59 | 2-((1S)-1-{[(2-Nitrophenyl)sulfonyl]amino}-7-oxooctyl)-5-phenyl-1H-imidazol-3-ium trifluoroacetate | 471 | 2 |
| 60 | 2-((1S)-1-{[(3-Nitrophenyl)sulfonyl]amino}-7-oxooctyl)-5-phenyl-1H-imidazol-3-ium trifluoroacetate | 471 | 2 |
| 61 | 2-[(1S)-1-({[4-(Acetylamino)phenyl]sulfonyl}amino)-7-oxooctyl]-5-phenyl-1H-imidazol-3-ium trifluoroacetate | 483 | 2 |
| 62 | 2-((1S)-1-{[(2-Cyanophenyl)sulfonyl]amino}-7-oxooctyl)-5-phenyl-1H-imidazol-3-ium trifluoroacetate | 451 | 2 |
| 63 | 2-((1S)-1-{[(2-Chloro-4-cyanophenyl)sulfonyl]amino}-7-oxooctyl)-5-phenyl-1H-imidazol-3-ium trifluoroacetate | 485 | 2 |
| 64 | 2-((1S)-1-{[(3-Fluoro-4-nitrophenyl)sulfonyl]amino}-7-oxooctyl)-5-phenyl-1H-imidazol-3-ium trifluoroacetate | 489 | 2 |
| 65 | 2-[(1S)-1-({[2-(Methoxycarbonyl)-3-thienyl]sulfonyl}amino)-7-oxooctyl]-5-phenyl-1H-imidazol-3-ium trifluoroacetate | 490 | 2 |
| 66 | 2-((1S)-1-{[(2,5-Dimethoxyphenyl)sulfonyl]amino}-7-oxooctyl)-5-phenyl-1H-imidazol-1-ium trifluoroacetate | 486 | 2 |
| 67 | 2-((1S)-1-{[(3-Fluorophenyl)sulfonyl]amino}-7-oxooctyl)-5-phenyl-1H-imidazol-1-ium trifluoroacetate | 444 | 2 |
| 68 | 2-((1S)-1-{[(3-Cyano-4-fluorophenyl)sulfonyl]amino}-7-oxooctyl)-5-phenyl-1H-imidazol-1-ium trifluoroacetate | 469 | 2 |
| 69 | 2-[(1S)-1-({[4-(Difluoromethoxy)phenyl]sulfonyl}amino)-7-oxooctyl]-5-phenyl-1H-imidazol-1-ium trifluoroacetate | 492 | 2 |
| 70 | 2-[(1S)-1-({[3-(Difluoromethoxy)phenyl]sulfonyl}amino)-7-oxooctyl]-5-phenyl-1H-imidazol-1-ium trifluoroacetate | 492 | 2 |
| 71 | 2-{(1S)-1-[(2,1,3-Benzothiadiazol-5-ylsulfonyl)amino]-7-oxooctyl}-5-phenyl-1H-imidazol-1-ium trifluoroacetate | 484 | 2 |

| Example | Name | (M + H)⁺ | Procedure from Example Number |
|---|---|---|---|
| 72 | 2-{(1S)-1-[(2,3-Dihydro-1-benzofuran-5-ylsulfonyl)amino]-7-oxooctyl}-5-phenyl-1H-imidazol-1-ium trifluoroacetate | 468 | 2 |
| 73 | 2-Morpholin-4-yl-5-({[(1S)-7-oxo-1-(5-phenyl-1H-imidazol-1-ium-2-yl)octyl]amino}sulfonyl)pyridinium bis(trifluoroacetate) | 512 | 2 |
| 74 | 2-{(1S)-1-[(2,1,3-Benzoxadiazol-4-ylsulfonyl)amino]-7-oxooctyl}-5-phenyl-1H-imidazol-1-ium trifluoroacetate | 468 | 2 |
| 75 | 2-((1S)-1-{[(4-Fluorophenyl)sulfonyl]amino}-7-oxooctyl)-5-phenyl-1H-imidazol-1-ium trifluoroacetate | 444 | 2 |
| 76 | 2-((1S)-1-{[(4-Nitrophenyl)sulfonyl]amino}-7-oxooctyl)-5-phenyl-1H-imidazol-1-ium trifluoroacetate | 471 | 2 |
| 77 | 2-((1S)-1-{[(2-Fluorophenyl)sulfonyl]amino}-7-oxooctyl)-5-phenyl-1H-imidazol-1-ium trifluoroacetate | 444 | 2 |
| 78 | 2-((1S)-1-{[(3,4-Dimethoxyphenyl)sulfonyl]amino}-7-oxooctyl)-5-phenyl-1H-imidazol-1-ium trifluoroacetate | 486 | 2 |
| 79 | 2-((1S)-1-{[(3,4-Difluorophenyl)sulfonyl]amino}-7-oxooctyl)-5-phenyl-1H-imidazol-1-ium trifluoroacetate | 462 | 2 |
| 80 | 5-({[(1S)-7-Oxo-1-(5-phenyl-1H-imidazol-1-ium-2-yl)octyl]amino}sulfonyl)isoquinolinium bis(trifluoroacetate) | 477 | 2 |
| 81 | 2-((1S)-1-{[(4-Carboxyphenyl)sulfonyl]amino}-7-oxooctyl)-5-phenyl-1H-imidazol-1-ium trifluoroacetate | 470 | 2 |
| 82 | 1-Methyl-4-[({(1S)-7-oxo-1-[5-(3-thienyl)-1H-imidazol-3-ium-2-yl]octyl}amino)carbonyl]piperidinium bis(trifluoroacetate) | 417 | 1 |
| 83 | 2-[2-((1S)-1-{[(1-Methylpiperidinium-4-yl)carbonyl]amino}-7-oxooctyl)-1H-imidazol-3-ium-5-yl]pyridinium tris(trifluoroacetate) | 412 | 1 |
| 84 | 4-[({(1S)-1-[5-(5-Chloro-3-methyl-1-benzothien-2-yl)-1H-imidazol-3-ium-2-yl]-7-oxooctyl}amino)carbonyl]-1-methylpiperidinium bis(trifluoroacetate) | 515 | 1 |
| 85 | 1-Methyl-4-[({(1S)-7-oxo-1-[5-(3-phenylisoxazol-5-yl)-1H-imidazol-3-ium-2-yl]octyl}amino)carbonyl]piperidinium bis(trifluoroacetate) | 478 | 1 |
| 86 | 1-Methyl-4-{[(((1S)-1-{5-[6-methyl-2-(trifluoromethyl)[1,3]thiazolo[3,2-b][1,2,4]triazol-5-yl]-1H-imidazol-3-ium-2-yl}-7-oxooctyl)amino]carbonyl}piperidinium bis(trifluoroacetate) | 540 | 1 |

Example 87

1-Methyl-4-[({(1S)-1-[1-methyl-4-(2-naphthyl)-1H-imidazol-3-ium-2-yl]-7-oxooctyl}amino)carbonyl]piperidinium bis(trifluoroacetate) (F3)

Step 1: 2-(2-Naphthyl)-2-oxoethyl (2S)-2-[(tert-butoxycarbonyl)amino]-8-oxo nonanoate (F1)

A solution of Example 1, Al and Cs$_2$CO$_3$ (0.5 eq) in EtOH was stirred for 30 min at RT and was then concentrated to dryness under reduced pressure. To the resulting salt in DMF was added 2-bromo-1-(2-naphthyl)ethanone (1 eq.). The mixture was stirred for 1 hr at RT and the DMF was removed under reduced pressure. EtOAc was added, the mixture was filtered and the filter was washed with EtOAc. The combined filtrates were concentrated under reduced pressure. The colourless oil obtained was used in the next step without purification. MS (ES) C$_{26}$H$_{33}$NO$_6$ requires: 455, found: 456 (M+H)⁺.

Step 2: 2-{(1S)-1-[(tert-Butoxycarbonyl)amino]-7-oxooctyl}-1-methyl-4-(2-naphthyl)-1H-imidazol-1-ium trifluoroacetate (F2)

To a solution of F1 in xylene was added NH$_4$OAc (10 eq.) and MeNH$_3$OAc (10 eq.). The mixture was heated at reflux (150° C. bath temperature) for 90 min. After cooling to RT, the mixture was diluted with EtOAc and washed with H$_2$O and sat. aq. NaHCO$_3$. The organic phase was concentrated under reduced pressure and the desired product was isolated by preparative RP-HPLC, using water (0.1% TFA) and MeCN (0.1% TFA) as eluents (column: C18). The desired fractions were lyophilized to afford the product as colourless oil. MS (ES) C$_{27}$H$_{35}$N$_3$O$_3$ requires: 449, found: 450 (M+H)+

Step 3: 1-Methyl-4-[({(1S)-1-[1-methyl-4-(2-naphthyl)-1H-imidazol-1-ium-2-yl]-7-oxooctyl}amino)carbonyl]piperidinium bis(trifluoroacetate) (F3)

F2 was dissolved in TFA/DCM (1:1) and the mixture was stirred for 60 min at RT. The solvents were removed under reduced pressure and the residue was partitioned between sat. aq. NaHCO$_3$ and DCM. The organic phase was separated, dried (Na$_2$SO$_4$) and concentrated under reduced pressure.

To the resulting residue was added a solution of EDC.HCl (1.2 eq), HOBt (1.2 eq) and 4-carboxy-1-methylpiperidinium chloride (1.2 eq) in DMF, followed by DIPEA (1.2 eq.). The mixture was stirred at RT for 2 hr and then the product F3 was isolated by preparative RP-HPLC, using water (0.1% TFA) and MeCN (0.1% TFA) as eluents (column: C18). The desired fractions were lyophilized to afford the final product as a colourless oil. $^1$H NMR (300 MHz, DMSO-d6) δ: 9.62-9.20 (1H, m), 8.69 (1H, s), 8.29 (1H, s), 8.01-7.81 (5H, m), 7.59-7.44 (2H, m), 5.05 (1H, m), 3.77 (3H, s), 3.50-3.22 (2H, m), 3.20-2.82 (2H, m), 2.81-2.70 (3H, m), 2.55-2.45 (1H, m), 2.41 (2H, t, J=3.6 Hz), 2.06 (3H, s), 2.02-1.64 (6H, m), 1.54-1.19 (6H, m). MS (ES) C$_{29}$H$_{38}$N$_4$O$_2$ requires: 474, found: 475 (M+H)$^+$.

Example 88

2-(5-Methoxy-2-methyl-1H-indol-3-yl)-N-{(1S)-1-[5-(2-naphthyl)-4H-1,2,4-triazol-3-yl]-7-oxononyl}acetamide (G5)

Step 1: Methyl (2S)-2-[(tert-butoxycarbonyl)amino]-8-hydroxydecanoate (G1)

To a solution of (2S)-2-[(tert-butoxycarbonyl)amino]-8-oxodecanoic acid in anhydrous THF at 0° C. under a nitrogen atmosphere was added slowly a solution of BH$_3$.Me$_2$S in THF (2 M, 2 eq.). The mixture was stirred for 5 min at 0° C. and 3 hr at 55° C. The reaction was quenched with MeOH and partitioned between EtOAc and sat. aq. NaHCO$_3$. The organic phase was dried (Na$_2$SO$_4$) and concentrated under reduced pressure. The obtained product was used in the next step without purification. MS (ES) C$_{16}$H$_{31}$NO$_5$ requires: 317, found: 318 (M+H)$^+$.

Step 2: (2S)-2-[(tert-Butoxycarbonyl)amino]-8-hydroxydecanohydrazide (G2)

G1 was dissolved in $^i$PrOH and NH$_2$NH$_2$.H$_2$O (3 eq.) was added, the mixture was then heated at 80° C. for 16 hr. The mixture was cooled to RT and partitioned between DCM and H$_2$O. The organics were washed with brine, dried (Na$_2$SO$_4$) and concentrated under reduced pressure. The crude product was used in the next step without purification. MS (ES) C$_{15}$H$_{31}$N$_3$O$_4$ requires: 317, found: 318 (M+H)$^+$.

Step 3: tert-Butyl {(1S)-7-Hydroxy-1-[3-(2-naphthyl)-1H-1,2,4-triazol-5-yl]nonyl}carbamate (G3)

To a solution of the 2-naphthonitrile in anhydrous MeOH was added dropwise a solution of NaOMe in MeOH (31%, 1 eq.). The mixture was warmed to 40° C. for 5 min and then left to stir at RT for 1 hr. The mixture was left standing at 5° C. overnight and then neutralized with AcOH and added to G2. The resulting mixture was stirred for 3 hr at RT. The solvent was removed under reduced pressure and the residue was suspended in anhydrous toluene and was heated to 110° C. for 2.5 hr. After cooling to RT, the mixture was partitioned between EtOAc and water. The organic phase was washed with brine, dried (Na$_2$SO$_4$) and concentrated under reduced pressure. The residue was purified by flash chromatography on silica using 50% EtOAc/petroleum ether as eluent to give the desired product was obtained as a colourless oil. MS (ES) C$_{26}$H$_{36}$N$_4$O$_3$ requires: 452, found: 453 (M+H)$^+$.

Step 4: tert-Butyl {(1S)-1-[3-(2-Naphthyl)-1H-1,2,4-triazol-5-yl]-7-oxononyl}carbamate (G4)

To a solution of G3 in anhydrous DCM was added Dess-Martin periodinane (1.5 eq.). The mixture was stirred for 2 hr at RT and then a sat. aq. NaHCO$_3$ (containing Na$_2$S$_2$O$_3$ (6 eq.)) was added and the mixture was stirred for 15 min. The phases were separated and the H$_2$O phase was washed with DCM. The combined organic phases were dried (Na$_2$SO$_4$) and concentrated under reduced pressure. The obtained product was used in the next step without further purification. MS (ES) C$_{26}$H$_{34}$N$_4$O$_3$ requires: 450, found: 451 (M+H)$^+$.

Step 5: 2-(5-Methoxy-2-methyl-1H-indol-3-yl)-N-{(1S)-1-[3-(2-naphthyl)-1H-1,2,4-triazol-5-yl]-7-oxononyl}acetamide (G5)

G4 was dissolved in a mixture of DCM and TFA (1:1) and stirred at RT. After 20 min, the solvents were removed under reduced pressure and the residue was partitioned between DCM and sat. aq. NaHCO$_3$. The organic phase was separated, dried (Na$_2$SO$_4$) and concentrated under reduced pressure.

To the residue was added a solution of (5-methoxy-2-methyl-1H-indol-3-yl)acetic acid (1.3 eq.), HOBt (1.3 eq.) and EDC.HCl (1.3 eq.) in DMF (premixed for 3 min), followed by DIPEA (1.3 eq.). The mixture was left stirring at room temperature for 3 hr. The product was isolated by preparative RP-HPLC, using water (0.1% TFA) and acetonitrile (0.1% TFA) as eluents (column: C18), the desired fractions were lyophilized to afford the final product as a colourless oil. $^1$H NMR (300 MHz, DMSO-d6) δ: 10.57 (1H, s), 8.52 (1H, s), 8.39 (1H, d, J=7.5 Hz), 8.18-7.18 (4H, m), 7.65-7.49 (2H, m), 7.16-6.98 (2H, m), 6.64-6.54 (1H, m), 5.00 (1H, m), 3.67 (3H, s), 3.60-3.40 (2H, m), 2.40-2.23 (7H, m), 1.98-1.72 (2H, m), 1.45-1.11 (6H, m), 0.89 (3H, t, J=7.3 Hz). MS (ES) C$_{33}$H$_{37}$N$_5$O$_3$ requires: 551, found: 552 (M+H)$^+$.

Example 89

2-(5-Methoxy-2-methyl-1H-indol-3-yl)-N-[7-oxo-1-(4-phenyl-2-thienyl)nonyl]acetamide (H4)

Step 1: 6-(2-Ethyl-1,3-dioxolan-2-yl)-1-(4-phenyl-2-thienyl)hexan-1-ol (H1)

To a stirred mixture of Mg (2.5 eq.) in anhydrous THF under Ar was added 12 (>5 mol %) and the mixture heated at reflux until the solution became colourless. Then 2-(5-bromopentyl)-2-ethyl-1,3-dioxolane (2.2 eq.) [Sanghee, K. et al Synthesis 2003, 14, 2194-2198] was added dropwise, upon complete addition the mixture was heated at reflux for 2.5 hr. The resulting Grignard reagent obtained was used immediately for the next step.

The resulting Grignard solution was added to a solution of 4-phenylthiophene-2-carbaldehyde (1 eq.) in THF at 0° C. under Ar and the mixture was stirred for 30 min. The reaction was quenched by slow addition of sat. NH$_4$Cl solution and the desired product was extracted with EtOAc. The organic layer was washed with brine, dried (Na$_2$SO$_4$) and concentrated under reduced pressure. The crude was purified by column chromatography eluting with 90% Petroleum ether/EtOAc to afford the desired alcohol H1. $^1$H NMR (300 MHz, CD$_3$CN) δ: 7.60-7.50 (2H, d, J=7.3 Hz), 7.42-7.32 (3H, m), 7.33-7.27 (2H, m), 5.05-4.89 (1H, t, J=7.3 Hz), 4.88-4.83 (1H, s), 3.94-3.89 (4H, s), 1.89-1.78 (2H, m), 1.65-1.55 (4H, m), 1.40-1.25 (6H, m), 0.90-0.80 (3H, m). MS (ES) C$_{21}$H$_{28}$O$_3$S requires: 360, found: 361 (M+H)$^+$.

Step 2: 2-[6-Azido-6-(4-phenyl-2-thienyl)hexyl]-2-ethyl-1,3-dioxolane (H2)

The alcohol H1 was dissolved in toluene, to give a solution of 0.5 M, together with diphenylphosphorazide (DPPA, 1.2 eq.) and then DBU (1.2 eq.) was added and the mixture was heated with stirring at 50° C. overnight. After cooling to RT, EtOAc was added and the mixture was washed with H$_2$O and then with 5% HCl solution. The organic layer was washed with brine, dried (Na$_2$SO$_4$) and concentrated under reduced pressure. The residue was purified by column chromatography eluting with 50% Petroleum ether/EtOAc to afford H2. $^1$H NMR (300 MHz, CDCl$_3$) δ: 7.62-7.55 (2H, d, J=8.1 Hz), 7.45-7.20 (5H, m), 4.65 (1H, t, J=7.3 Hz), 3.95 (4H, s), 1.89-1.78 (2H, m), 1.65-1.55 (4H, m), 1.45-1.25 (6H, m), 0.9-0.8 (3H, m). MS (ES) C$_{21}$H$_{27}$N$_3$O$_2$S requires: 385, found: 386 (M+H)$^+$.

Step 3: [6-(2-Ethyl-1,3-dioxolan-2-yl)-1-(4-phenyl-2-thienyl)hexyl]amine (H3)

The azide H2 was dissolved in MeOH and stirred in the presence of 10% Pd/C under an H2 atmosphere for 1 hr. The H2 atmosphere removed and N$_2$ introduced. The reaction mixture was filtered and the catalyst washed with MeOH and the filtrates concentrated under reduced pressure. The residue was purified by column chromatography eluting with 30% Petroleum ether/EtOAc to afford the amine H3. $^1$H NMR (300 MHz, CDCl$_3$) δ: 7.54 (2H, d, J=7.6 Hz), 7.45-7.35 (3H, m), 7.33-7.28 (2H, m), 4.67 (1H, t, J=7.0 Hz), 3.90 (4H, s), 1.89-1.78 (2H, m), 1.65-1.55 (4H, m), 1.45-1.25 (6H, m), 0.90-0.80 (3H, m). MS (ES) C$_{21}$H$_{29}$NO$_2$S requires: 359, found: 360 (M+H)$^+$.

Step 4: 2-(5-Methoxy-2-methyl-1H-indol-3-yl)-N-[7-oxo-1-(4-phenyl-2-thienyl)nonyl]acetamide (H4)

To a stirred solution of (5-methoxy-2-methyl-1H-indol-3-yl) acetic acid (1.2 eq.), HOBt (1.2 eq.) and EDCI (1.2 eq.) in DCM was added H3. The mixture was stirred at RT for 16 hr. The reaction mixture was washed successively with 0.25 M HCl solution, 0.25 M NaOH solution and brine, dried (Na$_2$SO$_4$) and concentrated under reduced pressure. The resulting N-[6-(2-ethyl-1,3-dioxolan-2-yl)-1-(4-phenyl-2-thienyl)hexyl]-2-(5-methoxy-2-methyl-1H-indol-3-yl)acetamide taken up in 1M HCl solution (4 eq.) and THF and was stirred at RT for 4 hr. The mixture neutralized with 1 M NaOH and the ketone was extracted with EtOAc. The organics were washed with brine and concentrated under reduced pressure. The mixture was purified by preparative RP-HPLC, using H$_2$O (+0.1% TFA) and MeCN (+0.1% TFA) as eluents (column: C18). The desired fractions were lyophilized to afford the titled compound H4 as a colourless oil. $^1$H NMR (300 MHz, CD$_3$CN) δ: 9.00-8.90 (1H, br. s), 7.52 (2H, d, J=7.3 Hz), 7.43-7.34 (3H, m), 7.32-7.22 (1H, m), 7.18 (1H, d, J=8.5 Hz), 7.10 (1H, s), 6.97 (1H, s), 6.69 (1H, dd, J=8.6, 2.0 Hz), 6.60 (1H, d, J=8.6 Hz), 5.17 (1H, q, J=6.0 Hz), 3.76 (3H, s), 3.56-3.50 (2H, br. s), 2.45-2.30 (7H, m), 1.90-1.20 (8H, m), 0.93 (3H, t, J=7.3 Hz). MS (ES) C$_{31}$H$_{36}$N$_2$O$_3$S requires: 516, found: 517

| Example | Name | (M + H)$^+$ | Procedure from Example Number |
|---|---|---|---|
| 90 | 4-[({(1S)-1-[5-(1-Benzothien-3-yl)-1H-imidazol-1-ium-2-yl]-7-oxooctyl}amino)carbonyl]-1-methylpiperidinium bis(trifluoroacetate) | 467 | 1 |
| 91 | 2-{(1S)-1-[(3,4-Difluorobenzoyl)amino]-7-oxooctyl}-5-phenyl-1H-imidazol-1-ium trifluoroacetate | 426 | 1 |
| 92 | 2-((1S)-1-{[4-(Acetylamino)benzoyl]amino}-7-oxooctyl)-5-phenyl-1H-imidazol-1-ium trifluoroacetate | 447 | 1 |
| 93 | 2-((1S)-1-{[4-(Aminosulfonyl)benzoyl]amino}-7-oxooctyl)-5-phenyl-1H-imidazol-1-ium trifluoroacetate | 469 | 1 |
| 94 | 4-({[(1S)-7-Oxo-1-(5-phenyl-1H-imidazol-1-ium-2-yl)octyl]amino}carbonyl)pyridinium bis(trifluoroacetate) | 391 | 1 |
| 95 | 3-({[(1S)-7-Oxo-1-(5-phenyl-1H-imidazol-1-ium-2-yl)octyl]amino}carbonyl)pyridinium bis(trifluoroacetate) | 391 | 1 |
| 96 | 2-((1S)-1-{[(3,5-Dimethylisoxazol-4-yl)carbonyl]amino}-7-oxooctyl)-5-phenyl-1H-imidazol-1-ium trifluoroacetate | 409 | 1 |
| 97 | 2-{(1S)-1-[(2,3-Dihydro-1,4-benzodioxin-6-ylcarbonyl)amino]-7-oxooctyl}-5-phenyl-1H-imidazol-1-ium trifluoroacetate | 448 | 1 |
| 98 | 2-{(1S)-1-[(3-Nitrobenzoyl)amino]-7-oxooctyl}-5-phenyl-1H-imidazol-1-ium trifluoroacetate | 435 | 1 |
| 99 | 2-{(1S)-1-[(3-Cyanobenzoyl)amino]-7-oxooctyl}-5-phenyl-1H-imidazol-1-ium trifluoroacetate | 415 | 1 |
| 100 | 2-{(1S)-1-[(4-Cyanobenzoyl)amino]-7-oxooctyl}-5-phenyl-1H-imidazol-1-ium trifluoroacetate | 415 | 1 |
| 101 | 1-Methyl-4-({[7-oxo-1-(4-phenyl-2-thienyl)nonyl]amino}carbonyl)piperidinium trifluoroacetate | 441 | 89 |

-continued

| Example | Name | (M + H)+ | Procedure from Example Number |
|---|---|---|---|
| 102 | 4-[({(1S)-6-Carboxy-1-[5-(2-naphthyl)-1H-imidazol-1-ium-2-yl]hexyl}amino)carbonyl]-1-methylpiperidinium bis(trifluoroacetate) | 463 | 107 |
| 103 | 2-((1S)-6-Carboxy-1-{[(3-nitrophenyl)sulfonyl]amino}hexyl)-5-(2-naphthyl)-1H-imidazol-1-ium trifluoroacetate | 523 | 326 |
| 104 | 4-[({(1S)-6-Carboxy-1-[5-(3-methoxyphenyl)-1H-imidazol-1-ium-2-yl]hexyl}amino)carbonyl]-1-methylpiperidinium bis(trifluoroacetate) | 443 | 107 |
| 105 | 2-((1S)-6-Carboxy-1-{[(5-methoxy-2-methyl-1H-indol-3-yl)acetyl]amino}hexyl)-5-(3-methoxyphenyl)-1H-imidazol-1-ium trifluoroacetate | 519 | 107 |
| 106 | 2-((1S)-6-Carboxy-1-{[(3-nitrophenyl)sulfonyl]amino}hexyl)-5-(3-methoxyphenyl)-1H-imidazol-1-ium trifluoroacetate | 503 | 107 |

Example 107

2-((1S)-6-Carboxy-1-{[(5-methoxy-2-methyl-1H-indol-3-yl)acetyl]amino}hexyl)-5-(2-naphthyl)-1H-imidazol-1-ium trifluoroacetate (I6)

Step 1: tert-Butyl 6-[(2S,5R)-5-isopropyl-3,6-dimethoxy-2,5-dihydropyrazin-2-yl]hexanoate (I1)

To a stirred solution of (2R)-2-isopropyl-3,6-dimethoxy-2,5-dihydropyrazine (1.0 eq.) in THF at −78° C., was added dropwise over 10 min a solution of BuLi (1.6 N in hexane, 1.0 eq.) and stirring was continued at −78° C. for 45 min. A pre-cooled solution of tert-butyl 6-iodohexanoate (1.0 eq.) in THF was then added by cannula over 5 min and the reaction stirred overnight, slowly warming to RT. The reaction was then left to stir at RT for a further hour and was quenched by the addition of aqueous NH$_4$Cl solution. The THF layer was decanted off and concentrated under reduced pressure, meanwhile and the aqueous mixture was extracted with EtOAc (3×). The EtOAc extracts were used to redissolve the oily THF residue and this solution was washed with brine, dried (Na$_2$SO$_4$) and concentrated under reduced pressure. The crude was used directly in the next step without further purification (I1).

Step 2: 8-tert-Butyl 1-methyl (2S)-2-[(tert-butoxycarbonyl)amino]octanedioate (I2)

I1 was dissolved in THF (0.12 M solution) and cooled at 0° C. with an ice-bath; 1M HCl (4 eq.) was added and the mixture was stirred 20 min at the same temperature. 1M NaOH was added (4 eq), the aqueous phase was extracted with EtOAc and the collected organic phases were treated with brine, dried (Na$_2$SO$_4$), then solvent removed under reduced pressure. The pale yellow oil obtained was dissolved in 1,4-dioxane/water (1:1, 0.09M solution) then NaHCO$_3$ (4 eq.) and Boc$_2$O (2 eq.) were added and the mixture was stirred overnight at RT. The dioxane was removed under reduced pressure and the aqueous phase was extracted with EtOAc. The collected organic phases were washed with brine and dried (Na$_2$SO$_4$) and concentrated under reduced pressure. The amber oil was purified by chromatography on silica gel eluting with EtOAc/petroleum ether (4:1) to obtain the title compound as a colorless oil. $^1$H NMR (400 MHz, CDCl$_3$) δ: 5.00 (1H, br. s), 4.30 (1H, br. s), 3.75 (3H, s), 2.21 (2H, t, J=7.4 Hz), 1.70-1.80 (1H, m), 1.70-1.50 (3H, m), 1.45 (18H, s), 1.40-1.27 (4H, m). MS (ES) C$_{18}$H$_{33}$NO$_6$ requires: 359, found: 360 (M+H)$^+$.

Step 3: (2S)-8-tert-Butoxy-2-[(tert-butoxycarbonyl)amino]-8-oxooctanoic acid (I3)

I2 was dissolved in a mixture of THF and H$_2$O (4:1, 0.35M solution) at RT and LiOH.H$_2$O (1.1 eq.) was added and the mixture was then stirred for 1.5 hr. 1M HCl was added until pH 4-5, then the THF was removed under reduced pressure. The aqueous phase was extracted with EtOAc (3×); the collected organic phases were washed with brine and then dried (Na$_2$SO$_4$). After removal of the solvent the title compound was obtained as a colorless oil which solidified upon standing, this was used in the next step without purification. $^1$H NMR (400 MHz, CDCl$_3$) δ: 5.23 (1H, br. s), 4.13 (1H, br. s), 2.21 (2H, t, J=7.4 Hz), 1.75-1.90 (1H, m), 1.70-1.50 (3H, m), 1.45 (9H, s), 1.44 (9H, s), 1.50-1.25 (4H, m) MS (ES) C$_{17}$H$_{31}$NO$_6$ requires: 345, found: 346 (M+H)$^+$.

Step 4: tert-Butyl (7S)-7-[(tert-butoxycarbonyl)amino]-7-[5-(2-naphthyl)-1H-imidazol-2-yl]heptanoate (I4)

A solution of I3 and Cs$_2$CO$_3$ (0.5 eq) in EtOH (0.47M solution) was stirred for 30 min at RT and then concentrated under reduced pressure. 2-Bromo-1-(2-naphthyl)ethanone (1 eq.) was added to the resulting salt in DMF (0.27M solution) and the mixture was stirred for 1.5 hr at RT under N$_2$. The DMF removed under reduced pressure, azeotroping with toluene. EtOAc was added, the mixture was filtered and the residue was washed with EtOAc. The combined filtrates were concentrated under reduced pressure. A solution of the resulting oil and NH$_4$OAc (20 eq.) in xylene was heated at reflux (150° C. bath temperature) for 2 hr. Excess NH$_4$OAc and H$_2$O were removed using a Dean-Stark trap. The mixture was cooled to RT, diluted with EtOAc and washed with water (×2), sat. aq. NaHCO$_3$ solution, water (×2) and brine. The solution was dried (Na$_2$SO$_4$), concentrated under reduced pressure and the resulting brown oil was purified by chromatography on silica gel eluting with EtOAc/petroleum ether (9:1 to 1:1) to obtain the title compound as a colourless oil. $^1$H NMR (300 MHz, CDCl$_3$) δ: 11.83 (1H, s), 8.24 (1H, s), 8.00-7.75 (4H, m), 7.62 (1H, s), 7.53-7.35 (2H, m), 7.08 (1H, d, J=7.5 Hz), 4.55-4.70 (1H, m), 2.16 (2H, t, J=7.0 Hz), 1.95-1.65 (2H, m), 1.60-1.15 (6H, m), 1.40 (9H, s), 1.38 (9H, s). MS (ES) C$_{29}$H$_{39}$N$_3$O$_4$ requires: 493, found: 494 (M+H)$^+$.

Step 5: 2-[(1S)-1-Ammonio-6-carboxyhexyl]-5-(2-naphthyl)-1H-imidazol-1-ium bis(trifluoroacetate) (I5)

The foregoing compound I4 was dissolved in TFA/DCM (1:1) (0.2M solution) at 0° C. The cooling bath was removed and the mixture was stirred for 60 min at RT. The solvents were removed under reduced pressure and the residue was concentrated under reduced pressure, azeotroping with toluene. The crude amino acid salt was used without further purification. MS (ES) $C_{20}H_{23}N_3O_2$ requires: 337, found: 338 (M+H)$^+$.

Step 6: 2-((1S)-6-Carboxy-1-{[(5-methoxy-2-methyl-1H-indol-3-yl)acetyl]amino}hexyl)-5-(2-naphthyl)-1H-imidazol-1-ium trifluoroacetate (I6)

A solution of EDC.HCl (1 eq.), HOBt (1 eq.) and (5-methoxy-2-methyl-1H-indol-3-yl)acetic acid (1 eq.) in DMF was premixed at RT for 1 hr, and then this was added to a solution of I5 and $^i$PrNEt$_2$ (3 eq.) in DMF. The mixture was stirred for 3 hr at RT and after this time the crude was directly purified by preparative RP-HPLC, using H$_2$O (0.1% TFA) and MeCN (+0.1% TFA) as eluents (column: C18). The desired fractions were lyophilized to afford the titled compound as a white fluffy powder.

$^1$H NMR (400 MHz, DMSO-d6) δ: 14.56 (1H, br. s), 12.00 (1H, br. s), 10.62 (1H, s), 8.65 (1H, s), 8.33 (1H, s), 8.20-7.80 (6H, m), 7.59 (2H, s), 7.10 (1H, d, J=7.68 Hz), 6.97 (1H, s), 6.60 (1H, s), 5.10-5.00 (1H, m), 3.67 (3H, s), 3.65-3.40 (2H, m), 2.31 (3H, s), 2.16 (2H, br. s), 2.05-1.95 (2H, m), 1.50-1.20 (6H, m). MS (ES) $C_{32}H_{34}N_4O_4$ requires: 538, found: 539 (M+H)$^+$.

Example 108

2-((1S)-7-(Hydroxyamino)-1-{[(5-methoxy-2-methyl-1H-indol-3-yl)acetyl]amino}-7-oxoheptyl)-5-(2-naphthyl)-1H-imidazol-1-ium trifluoroacetate (J1)

2-((1S)-6-Carboxy-1-{[(5-methoxy-2-methyl-1H-indol-3-yl)acetyl]amino}hexyl)-5-(2-naphthyl)-1H-imidazole was prepared as described in Example 107 step 6, Once the coupling was completed, to the coupling reaction solution were added EDC.HCl (1.5 eq.) and HOBt (1.5 eq.) and after 1 h at RT hydroxylamine.HCl (1.5 eq) and DIPEA (1.5 eq.) were added. The mixture was stirred for overnight, then the crude was directly purified by preparative RP-HPLC, using H$_2$O (0.1% TFA) and MeCN (+0.1% TFA) as eluents (column: C18). The desired fractions were lyophilized to afford the titled compound as a white powder. $^1$H NMR (400 MHz, DMSO-d6) δ: 14.44 (1H, br. s), 10.62 (1H, br. s), 10.31 (1H, s), 8.61 (1H, d, J=7.5 Hz), 8.33 (1H, s), 8.16 (1H, s), 8.06 (1H, d, J=8.6 Hz), 8.01-7.86 (3H, m), 7.61 (2H, m), 7.10 (1H, d, J=8.6 Hz), 6.96 (1H, d, J=2.2 Hz), 6.59 (1H, dd, J=8.5, 2.2 Hz), 5.03 (1H, m), 3.67 (3H, s), 3.65-3.40 (2H, m), 2.31 (3H, s), 2.03-1.85 (2H, m), 1.91 (2H, t, J=7.4 Hz), 1.50-1.20 (6H, m). MS (ES) $C_{32}H_{35}N_5O_4$ requires: 553, found: 554 (M+H)$^+$.

| Example | Name | (M + H)$^+$ | Procedure from Example Number |
|---|---|---|---|
| 109 | 2-{(1S)-1-[(3-Fluoro-4-nitrobenzoyl)amino]-7-oxooctyl}-5-phenyl-1H-imidazol-1-ium trifluoroacetate | 453 | 1 |
| 110 | 2-Cyano-5-({[[(1S)-7-oxo-1-(5-phenyl-1H-imidazol-1-ium-2-yl)octyl]amino}carbonyl)pyridinium bis(trifluoroacetate) | 416 | 1 |
| 111 | 2-((1S)-1-{[(4-Cyanophenyl)sulfonyl]amino}-7-oxooctyl)-5-(2-naphthyl)-1H-imidazol-1-ium trifluoroacetate | 501 | 2 |
| 112 | 5-(2-Naphthyl)-2-((1S)-1-{[(3-nitrophenyl)sulfonyl]amino}-7-oxooctyl)-1H-imidazol-1-ium trifluoroacetate | 522 | 2 |
| 113 | 2-[(1S)-1-({[[2-(Dimethylammonio)ethyl](methyl)amino]sulfonyl}amino)-7-oxooctyl]-5-(2-naphthyl)-1H-imidazol-1-ium bis(trifluoroacetate) | 500 | 3 |
| 114 | 5-(2-Naphthyl)-2-{(1S)-7-oxo-1-[(1,3-thiazol-5-ylcarbonyl)amino]octyl}-1H-imidazol-1-ium trifluoroacetate | 447 | 1 |
| 115 | 5-(3-Chlorophenyl)-2-((1S)-1-{[(4-cyanophenyl)sulfonyl]amino}-7-oxooctyl)-1H-imidazol-1-ium trifluoroacetate | 485 | 2 |
| 116 | 5-(3-Chlorophenyl)-2-((1S)-1-{[(3-nitrophenyl)sulfonyl]amino}-7-oxooctyl)-1H-imidazol-1-ium trifluoroacetate | 507 | 2 |
| 117 | 2-((1S)-1-{[(4-Cyanophenyl)sulfonyl]amino}-7-oxooctyl)-5-(3-methoxyphenyl)-1H-imidazol-1-ium trifluoroacetate | 481 | 2 |
| 118 | 5-(3-Methoxyphenyl)-2-((1S)-1-{[(3-nitrophenyl)sulfonyl]amino}-7-oxooctyl)-1H-imidazol-1-ium trifluoroacetate | 501 | 2 |
| 119 | 5-(3-Methoxyphenyl)-2-{(1S)-7-oxo-1-[(1,3-thiazol-5-ylcarbonyl)amino]octyl}-1H-imidazol-1-ium trifluoroacetate | 427 | 1 |
| 120 | 2-((1S)-7-[(2-Aminophenyl)amino]-1-{[(5-methoxy-2-methyl-1H-indol-3-yl)acetyl]amino}-7-oxoheptyl)-5-(2-naphthyl)-1H-imidazol-1-ium trifluoroacetate | 630 | 108 |

-continued

| Example | Name | (M + H)⁺ | Procedure from Example Number |
|---|---|---|---|
| 121 | 5-(3-Methoxyphenyl)-2-[(1S)-1-({[(3S)-1-methylpyrrolidinium-3-yl]carbonyl}amino)-7-oxooctyl]-1H-imidazol-1-ium bis(trifluoroacetate) | 427 | 1 |
| 122 | (3S)-3-[({(1S)-1-[5-(3-Methoxyphenyl)-1H-imidazol-1-ium-2-yl]-7-oxooctyl}amino)carbonyl]-1-methylpiperidinium bis(trifluoroacetate) | 441 | 1 |
| 123 | (3S)-1-Isopropyl-3-[({(1S)-1-[5-(3-methoxyphenyl)-1H-imidazol-1-ium-2-yl]-7-oxooctyl}amino)carbonyl]piperidinium bis(trifluoroacetate) | 469 | 1 |
| 124 | 5-(3-Chlorophenyl)-2-[(1S)-1-({[(3R)-1-methylpyrrolidinium-3-yl]carbonyl}amino)-7-oxooctyl]-1H-imidazol-1-ium bis(trifluoroacetate) | 431 | 1 |
| 125 | 2-[(1S)-1-({[(3R)-1-Methylpyrrolidinium-3-yl]carbonyl}amino)-7-oxooctyl]-5-(2-naphthyl)-1H-imidazol-1-ium bis(trifluoroacetate) | 447 | 1 |
| 126 | 4-Methyl-2-[({(1S)-1-[5-(2-naphthyl)-1H-imidazol-1-ium-2-yl]-7-oxooctyl}amino)carbonyl]morpholin-4-ium bis(trifluoroacetate) | 463 | 1 |
| 127 | 4-[({(1S)-1-[5-(2-Naphthyl)-1H-imidazol-1-ium-2-yl]-7-oxooctyl}amino)carbonyl]-1-azoniabicyclo[2.2.2]octane bis(trifluoroacetate) | 473 | 1 |
| 128 | 4-[2-({(1S)-1-[5-(3-Chlorophenyl)-1H-imidazol-1-ium-2-yl]-7-oxooctyl}amino)-1-methyl-2-oxoethyl]morpholin-4-ium bis(trifluoroacetate) | 461 | 1 |
| 129 | 2-[(1S)-1-{[(5-Methoxy-2-methyl-1H-indol-3-yl)acetyl]amino}-7-(methylamino)-7-oxoheptyl]-5-(2-naphthyl)-1H-imidazol-1-ium trifluoroacetate | 552 | 108 |
| 130 | 5-(3-Methoxyphenyl)-2-[(1S)-1-({[(3R)-1-methylpyrrolidinium-3-yl]carbonyl}amino)-7-oxooctyl]-1H-imidazol-1-ium bis(trifluoroacetate) | 427 | 1 |
| 131 | (3R)-3-[({(1S)-1-[5-(3-Methoxyphenyl)-1H-imidazol-1-ium-2-yl]-7-oxooctyl}amino)carbonyl]-1-methylpiperidinium bis(trifluoroacetate) | 441 | 1 |
| 132 | 5-(3-Chlorophenyl)-2-[(1S)-1-({[(3S)-1-methylpyrrolidinium-3-yl]carbonyl}amino)-7-oxooctyl]-1H-imidazol-1-ium bis(trifluoroacetate) | 431 | 1 |
| 133 | 2-[(1S)-1-({[(3S)-1-Methylpyrrolidinium-3-yl]carbonyl}amino)-7-oxooctyl]-5-(2-naphthyl)-1H-imidazol-1-ium bis(trifluoroacetate) | 447 | 1 |
| 134 | 2-((1S)-1-{[(5-Methoxy-2-methyl-1H-indol-3-yl)acetyl]amino}-7-oxononyl)-5-phenyl-1H-imidazol-1-ium trifluoroacetate | 501 | 1 |
| 135 | 1-Methyl-4-({[(1S)-7-oxo-1-(5-phenyl-1H-imidazol-1-ium-2-yl)nonyl]amino}carbonyl)piperidinium bis(trifluoroacetate) | 425 | 1 |

Example 136

2-(5-Methoxy-2-methyl-1H-indol-3-yl)-N-{(1S)-1-[5-(2-naphthyl)-1,3,4-oxadiazol-2-yl]-7-oxononyl}acetamide (K5)

Step 1: N'-(2S)-2-(tert-Butoxycarbonylamino]-8-hydroxydecanoyl-2-naphthohydrazide (K1)

Naphthyl-2-carboxylic acid, HOBt (1 eq.) and EDC.HCl (1 eq.) were stirred in DCM for 3 h, then (2S)-2-[(tert-butoxycarbonyl)amino]-8-hydroxydecanohydrazide (G2, Example 88, step 2) was added and the mixture was left stirring at RT for 16 h. The mixture was partitioned between DCM and 0.1 M HCl. The organic phase separated, washed with sat aq. NaHCO₃ solution, dried (Na₂SO₄) and concentrated under reduced pressure. The crude product was used without purification in the next step. MS (ES) $C_{26}H_{37}N_3O_5$ requires: 471, found: 472 (M+H)⁺.

Step 2: N'-(2S)-2-[(tert-Butoxycarbonyl)amino]-8-oxodecanoyl-2-naphthohydrazide (K2)

The crude hydrazide (K1) was dissolved in anhydrous DCM and Dess-Martin periodinane (1.5 eq.) was added and the mixture was stirred for 2 h at RT. Sat. aq. NaHCO₃ solution and 1M Na₂S₂O₃ aq. solution (6 eq.) were added and the mixture was stirred vigorously for 15 min. The phases were separated and the water phase was extracted with DCM. The combined DCM phases were dried (Na₂SO₄) and concentrated under reduced pressure. The product was purified by preparative TLC using (SiO₂, EtOAc/Petroleum ether (2:1) as eluent) to yield the product as a colourless oil. MS (ES) $C_{26}H_{35}N_3O_5$ requires: 469, found: 470 (M+H)⁺.

Step 3: tert-Butyl {(1S)-1-[5-(2-naphthyl)-1,3,4-oxadiazol-2-yl]-7-oxononyl}-carbamate (K3)

A mixture of the hydrazide (K2), 2-tert-butylimino-2-diethylamino-1,3-dimethyl-perhydro-1,3,2-diazaphosphorine bound on polystyrene (2.3 mmol/g, 5 eq.) and TsCl (1.2 eq.) was suspended in anhydrous THF. The suspension was gently stirred and heated at 65° C. for 4 h. The mixture was filtered, and the resin was washed with THF. The combined filtrates were concentrated under reduced pressure and the crude product was used in the next step without purification. MS (ES) $C_{26}H_{33}N_3O_4$ requires: 451, found: 452 $(M+H)^+$.

Step 4: (9S)-9-Amino-9-[5-(2-naphthyl)-1,3,4-oxadiazol-2-yl]nonan-3-one (K4)

To a solution of the oxadiazole (K3) in DCM at 0° C. was added the same volume TFA. The cooling bath was removed and the mixture was stirred for 30 min at RT. The solvents were removed under reduced pressure and the residue was partitioned between DCM and sat. aq. $NaHCO_3$ solution. The organic phase was dried ($Na_2SO_4$) and concentrated under reduced pressure and the crude product was used as such in the next step. MS (ES) $C_{21}H_{25}N_3O_2$ requires: 351, found: 352 $(M+H)^+$.

Step 5: 2-(5-Methoxy-2-methyl-1H-indol-3-yl)-N-{(1S)-1-[5-(2-naphthyl)-1,3,4-oxadiazol-2-yl]-7-oxononyl}acetamide (K5)

To the crude amine (K4) was added a solution of (5-methoxy-2-methyl-1H-indol-3-yl)acetic acid (1.3 eq.), HOBt (1.3 eq.) and EDC.HCl (1.3 eq.) in DMF (premixed for 3 min), followed by DIPEA (1.3 eq.). The mixture was left stirring at RT for 3 h. The product was isolated by preparative RP-HPLC, using $H_2O$ (+0.1% TFA) and MeCN (+0.1% TFA) as eluents (column: C18). The acetonitrile was removed under reduced pressure from the desired fractions and the remaining water phase was partitioned between sat aq. $NaHCO_3$ solution and DCM. The DCM phase was dried ($Na_2SO_4$) and concentrated under reduced pressure. The residue was then lyophilized from MeCN/$H_2O$ to obtained the desired product as a white solid. $^1H$ NMR (300 MHz, DMSO-d6) δ: 10.60 (1H, s), 8.71 (1H, d, J=8.2 Hz), 8.47 (1H, s), 8.12-7.85 (4H, m), 7.65-7.45 (2H, m), 7.12-6.96 (2H, m), 6.62-6.50 (1H, m), 5.22-5.07 (1H, m), 3.65 (3H, s), 3.52 (2H, s), 2.42-2.23 (7H, m), 2.05-1.75 (2H, m), 1.47-1.15 (6H, m), 0.90 (3H, t, J=7.3 Hz). MS (ES) $C_{33}H_{36}N_4O_4$ requires: 552, found: 553 $(M+H)^+$. $[α]_D$=−13°, c=0.163 (EtOH)

Example 137

2-(5-Methoxy-2-methyl-1H-indol-3-yl)-N-{(1S)-1-[5-(2-naphthyl)-1,3-oxazol-2-yl]-7-oxononyl}acetamide (L5)

Step 1: 2-Azido-1-(2-naphthyl)ethanone (L1)

To 2-bromo-1-(2-naphthyl)ethanone in acetone was added $NaN_3$ (1 eq.) and the mixture was stirred at RT for 24 h. EtOAc was added (10 vol.) and the mixture was filtered. The filtrate was concentrated under reduced pressure and the residue was purified by flash chromatography on silica eluting with 10% EtOAc/Petroleum ether to obtain the product as a white solid. $^1H$ NMR (300 MHz, $CDCl_3$) δ: 8.39 (1H, s), 8.02-7.82 (4H, m), 7.69-7.50 (2H, m), 4.68 (2H, s). MS (ES) $C_{12}H_9N_3O$ requires: 211, found: 212 $(M+H)^+$.

Step 2: 2-Amino-1-(2-naphthyl)ethanone.HCl (L2)

A solution of the azide (L1) in MeOH, was added 1 M HCl (1 eq.) and Pd on carbon (10% wt) and the mixture was stirred at RT under a H2 atmosphere for 3.5 h. The catalyst was filtered off and washed with MeOH. The combined filtrate was concentrated under reduced pressure and the crude material was used without purification in the next step. MS (ES) $C_{12}H_{11}NO$ requires: 185, found: 186 $(M+H)^+$.

Step 3: tert-Butyl [(1S)-1-({[2-oxo-(2-naphthyl)ethyl]amino}carbonyl)-7-oxononyl]-carbamate (L3)

A solution of (2S)-2-[(tert-butoxycarbonyl)amino]-8-oxodecanoic acid, EDC.HCl (1.3 eq.) and HOBt (1.3 eq.) in DMF was shaken for 5 min. To the mixture was added a solution of crude amine (L2) (1 eq.) and DIPEA (1 eq.) in DMF. The mixture was left to stir for 1 h. It was partitioned between DMF and 1 M NaOH. The DCM phase was washed sequentially with 1 M NaOH, 1 M HCl and brine, dried ($Na_2SO_4$) and concentrated under reduced pressure. The residue was purified by chromatography on silica using 50% EtOAc/Petroleum ether as eluent to yield the product was obtained as a colourless oil. MS (ES) $C_{27}H_{36}N_2O_5$ requires: 468, found: 469 $(M+H)^+$

Step 4: tert-Butyl {(1S)-1-[5-(2-naphthyl)-1,3-oxazol-2-yl]-7-oxononyl}-carbamate (L4)

$PPh_3$ and $C_2Cl_6$ (1 eq.) were dissolved in DCM at RT and $Et_3N$ (2 eq.) was added, followed after 5 min. of stirring by dropwise addition of a solution of the amide (L3) (0.5 eq.) in DCM. The mixture was stirred for 4 h at RT and was then poured into $H_2O$. The organic phase was separated, dried ($Na_2SO_4$) and concentrated under reduced pressure. The crude product was purified by flash chromatography on silica using 30% EtOAc/Petroleum ether as eluent to afford the product as a white solid. MS (ES) $C_{27}H_{34}N_2O_4$ requires: 450, found: 451 $(M+H)^+$.

Step 5: 2-(5-Methoxy-2-methyl-1H-indol-3-yl)-N-{(1S)-1-[5-(2-naphthyl)-1,3-oxazol-2-yl]-7-oxononyl}acetamide (L5)

The oxazoles (L4) (1 eq.) was dissolved in a mixture of DCM and TFA (1:1) and stirred at RT for 30 min, after which the solvents were removed under reduced pressure and the residue was partitioned between DCM and sat. aq. $NaHCO_3$ solution. The DCM phase was separated, dried ($Na_2SO_4$) and concentrated under reduced pressure. To the residue was added a solution of (5-methoxy-2-methyl-1H-indol-3-yl)acetic acid (1.3 eq.), HOBt (1.3 eq.) and EDC.HCl (1.3 eq.) in DMF (premixed for 3 min), followed by DIPEA (1.3 eq.). The mixture was stirred at RT for 2 h and then the desired product was isolated by preparative RP-HPLC, using water (+0.1% TFA) and MeCN (+0.1% TFA) as eluents (column: C18). The pooled product fractions were concentrated under reduced pressure and the product was obtained as a white solid. $^1H$ NMR (300 MHz, DMSO-d6) δ: 10.58 (1H, s), 8.58 (1H, d, J=8.2 Hz), 8.12 (1H, s), 8.05-7.85 (3H, m), 7.85-7.72 (1H, m), 7.71 (1H, s), 7.60-7.44 (2H, m), 7.13-7.01 (2H, m), 6.62-6.54 (1H, m), 5.10-4.93 (1H, m), 3.67 (3H, s), 3.51 (2H, s), 2.42-2.20 (7H, m), 2.05-1.77 (2H, m), 1.47-1.15 (6H, m), 0.89 (3H, t, J=7.3 Hz). MS (ES) $C_{34}H_{37}N_3O_4$ requires: 551, found: 552 $(M+H)^+$.

Example 138

5-(1-{[(5-Methoxy-2-methyl-1H-indol-3-yl)acetyl]amino}-7-oxononyl)-2-(2-naphthyl)-1H-imidazol-1-ium trifluoroacetate (M7)

Step 1: 2,5-Dibromo-1-{[2-(dimethylsilyl)ethoxy]methyl}-1H-imidazole (M1)

To a stirred solution of 2,5-dibromo-1H-imidazole (1 eq.) in DMF at 0° C. under Ar was added NaH (1.2 eq.) and the mixture stirred for 30 min at 0° C. Then SEM-Cl (1.1 eq.) was added dropwise, and the mixture stirred 16 h warming to RT. The reaction was quenched by slow addition of $H_2O$ and the desired product was extracted with EtOAc. The organic layer was washed with brine, dried ($Na_2SO_4$) and concentrated under reduced pressure. The crude was purified by column chromatography eluting with 10% EtOAc/Petroleum ether to afford the desired product. $^1$H NMR (300 MHz, $CD_3CN$) δ: 7.10 (1H, s), 5.21 (2H, s), 3.53 (2H, t, J=7.3 Hz), 0.90 (2H, t, J=7.3 Hz), 0.10 (9H, s). MS (ES) $C_9H_{16}Br_2N_2OSi$ requires: 354:356:358 [1:2:1], found: 355:357:359 [1:2:1] (M+H)$^+$.

Step 2: 5-Bromo-2-(2-naphthyl)-1-{[2-(trimethylsilyl)ethoxy]methyl}-1H-imidazole (M2)

To a stirred mixture of the imidazole (M1) (1 eq.) in toluene, 2 M $Na_2CO_3$ aq. solution (2 eq.) and 2-naphthylboronic acid (1 eq.) under Ar was added Pd(PPh$_3$)$_4$ (5 mol %) and the mixture heated at reflux 16 h. After cooling to RT, EtOAc was added and the mixture was washed with 2M NaOH. The organic layer was washed with brine, dried ($Na_2SO_4$) and concentrated under reduced pressure. The residue was purified by column chromatography eluting with 10% EtOAc/Petroleum ether to afford the bromoimidazole. $^1$H NMR (300 MHz, $CD_3CN$) δ: 8.28 (1H, s), 7.95-7.80 (4H, m), 7.58-7.48 (2H, m), 7.10 (1H, s), 5.20 (2H, s), 3.58-3.48 (2H, t, J=7.3 Hz), 0.95-0.85 (2H, t, J=7.3 Hz), 0.10 (9H, s). MS (ES) $C_{19}H_{23}BrN_2OSi$ requires: 402:404 [1:1], found: 403:405 [1:1] (M+H)$^+$.

Step 3: 5-(2-Ethyl-1,3-dioxolan-2-yl)hexanal (M3)

To a stirred mixture of 5-(2-ethyl-1,3-dioxolan-2-yl)-N-methoxy-N-methyl-pentanamide (1 eq.) [Prepared by coupling 7-oxononanoic acid with N, O-dimethylhydroxylamine and subsequent ketal protection] in anhydrous THF at –78° C. was added a 1 M LiAlH$_4$ solution in THF (1.6 eq.) slowly over 5 min. After 45 min the reaction was quenched by addition of Et$_2$O and then aq. Rochelle's salt solution (10% w/v). The mixture was warmed to RT with a vigourous stirring. The organic phase was separated, washed with brine, dried ($Na_2SO_4$) and concentrated under reduced pressure. The residue was purified by column chromatography eluting with 5% EtOAc/Petroleum ether to afford the desired aldehyde. $^1$H NMR (300 MHz, $CD_3CN$) δ: 9.77 (1H, s), 4.00 (4H, s), 2.44 (2H, t, J=7.0 Hz), 1.75-1.48 (6H, m), 1.46-1.25 (4H, m), 1.00-0.80 (3H, t, J=7.0 Hz).

Step 4: 6-(2-Ethyl-1,3-dioxolan-2-yl)-1-(2-(2-naphthyl)-1-{[2-(trimethylsilyl)ethoxy]methyl}-1H-imidazol-5-yl)hexan-1-ol (M4)

To a stirred mixture of the bromoimidazole (M2) (1 eq.) in THF at –78° C. under Ar was added dropwise n-BuLi (1.2 eq., 1.6M solution in pentane). After 15 min a pre-cooled solution of the aldehyde (M3) (1.6 eq.) in THF was added and the mixture was stirred at –78° C. for a further 60 min. The reaction was quenched by slow addition of sat. aq. NH$_4$Cl solution and the desired product was then extracted with EtOAc. The organic layer was washed with brine, dried ($Na_2SO_4$) and concentrated under reduced pressure. The crude material was purified by column chromatography eluting with 5% EtOAc/Petroleum ether to afford the desired alcohol. $^1$H NMR (300 MHz, $CD_3CN$) δ: 8.30 (1H, s), 7.95-7.80 (4H, m), 7.58-7.48 (2H, m), 7.10 (1H, s), 5.30 (2H, s), 4.80-4.65 (1H, m), 3.91 (4H, s), 2.52-2.35 (2H, m), 1.75-1.48 (6H, m), 1.46-1.25 (4H, m), 1.10-0.80 (5H, m), 0.20-0.00 (9H, m). MS (ES) $C_{30}H_4N_2O_4Si$ requires: 524, found: 525 (M+H)$^+$.

Step 5: 5-[1-Azido-6-(2-ethyl-1,3-dioxolan-2-yl)hexyl]-2-(2-naphthyl)-1-{[2-(trimethyl silyl)ethoxy]methyl}-1H-imidazole (M5)

The alcohol (M4) (1 eq.) was dissolved in toluene and DPPA (1.2 eq.) and then DBU (1.2 eq.) were added and the mixture was heated with stirring at 50° C. overnight. After cooling to RT, EtOAc was added and the mixture was washed with H$_2$O and then with 5% HCl solution. The organic layer was washed with brine, dried ($Na_2SO_4$) and concentrated under reduced pressure. The residue was purified by column chromatography eluting with 50% EtOAc/Petroleum ether to afford the desired azide. $^1$H NMR (300 MHz, CDCl$_3$) δ: 8.30 (1H, s), 7.95-7.80 (4H, m), 7.58-7.48 (2H, m), 7.10 (1H, s), 5.32 (2H, s), 4.70-4.58 (1H, m), 3.90 (4H, s), 3.69-3.59 (2H, m), 2.52-2.35 (2H, m), 1.75-1.48 (6H, m), 1.46-1.25 (4H, m), 1.00-0.80 (5H, m), 0.10 (9H, s). MS (ES) $C_{30}H_{43}N_5O_3Si$ requires: 549, found: 550 (M+H)$^+$.

Step 6: [6-(2-Ethyl-1,3-dioxolan-2-yl)-1-(2-(2-naphthyl)-1-{[2-(trimethylsilyl)ethoxy]methyl}-1H-imidazol-5-yl)hexyl]amine (M6)

The azide (M5) (1 eq.) was dissolved in EtOAc and stirred in the presence of 10% Pd/C under an H2 atmosphere for 1 hr. The H2 atmosphere removed and N$_2$ introduced. The reaction mixture was filtered and the catalyst washed with MeOH and the filtrates concentrated under reduced pressure. The residue was purified by column chromatography eluting with 70% EtOAc/Petroleum ether to afford the amine.
$^1$H NMR (300 MHz, CDCl$_3$) δ: δ: 8.42-8.35 (1H, s), 7.97-7.87 (2H, m), 7.85-7.70 (2H, m), 7.58-7.45 (2H, m), 7.10 (1H, s), 5.37-5.25 (2H, s), 4.70-4.58 (1H, m), 3.94-3.89 (4H, s), 3.69-3.59 (2H, m), 2.52-2.35 (2H, m), 1.75-1.48 (6H, m), 1.46-1.25 (4H, m), 1.00-0.80 (5H, m), 0.10 (9H, s). MS (ES) $C_{30}H_{45}N_3O_3Si$ requires: 523, found: 524 (M+H)$^+$.

Step 7: 5-(1-{[(5-Methoxy-2-methyl-1H-indol-3-yl)acetyl]amino}-7-oxononyl)-2-(2-naphthyl)-1H-imidazol-1-ium trifluoroacetate (M7)

To a stirred solution of (5-methoxy-2-methyl-1-indol-3-yl)acetic acid (1.2 eq.), HOBt (1.2 eq.) and EDCI (1.2 eq.) in DCM was added the amine (M6). The mixture was stirred at RT for 16 hr. The reaction mixture was washed successively with 0.25 M HCl solution, 0.25 M NaOH solution and brine, dried (Na$_2$SO$_4$) and concentrated under reduced pressure. The resulting amide was taken up in THF and a 1 M solution of TBAF (2 eq.) in THF was added and the mixture was heated at reflux for 6 h. After cooling to RT, EtOAc was added and the mixture was washed with H$_2$O and brine, dried (Na$_2$SO$_4$) and concentrated under reduced pressure. The deprotected imidazole was then taken up in THF and 1 M HCl solution (4 eq.) was added and the mixture was stirred at RT for 4 hr. The mixture neutralized with 1 M NaOH and the ketone was extracted with EtOAc. The organics were washed with brine and concentrated under reduced pressure. The mixture was purified by preparative RP-HPLC, using $H_2O$ (+0.1% TFA) and MeCN (+0.1% TFA) as eluents (column: C18). The desired fractions were lyophilized to afford the titled compound as a colourless oil. $^1H$ NMR (300 MHz, d6-DMSO) δ: 10.70-10.60 (1H, s) 8.65-8.53 (1H, s), 8.45-8.33 (1H, d, J=8 Hz), 8.25-8.12 (1H, d, J=8 Hz), 8.10-7.90 (3H, br, s), 7.75-7.65 (2H, m), 7.55 (1H, s), 7.23-7.13 (2H, d, J=8 Hz), 7.06 (1H, s), 6.65 (1H, s), 5.05-4.95 (1H, m), 3.76 (3H, s), 3.53 (2H, s), 2.45-2.30 (7H, m), 1.90-1.20 (8H, m), 0.93 (3H, t, J=7.3 Hz). MS (ES) $C_{31}H_{36}N_2O_3S$ requires: 550, found: 551.

Example 139

2-(5-Methoxy-2-methyl-1H-indol-3-yl)-N-[7-oxo-1-(2-phenyl-1,3-thiazol-5-yl)nonyl]acetamide (N4)

Step 1: 6-(2-Ethyl-1,3-dioxolan-2-yl)-1-(2-phenyl-1,3-thiazol-5-yl)hexan-1-one (N1)

To a stirred mixture of 2-(5-bromopentyl)-2-ethyl-1,3-dioxolane (1.6 eq.) in anhydrous THF at −78° C. under Ar in the was added dropwise a 1.6 M solution t-BuLi (3.2 eq.) in pentane. After 30 min a precooled solution of N-methoxy-N-methyl-2-phenyl-1,3-thiazole-5-carboxamide (1 eq., WO 2001052846) in THF was added and the mixture was stirred for 60 min. at −78° C. and was then quenched by slow addition of sat. aq. $NH_4Cl$ solution and the desired product was extracted with EtOAc. The organic layer was washed with brine, dried ($Na_2SO_4$) and concentrated under reduced pressure. The crude was purified by column chromatography eluting with 10% EtOAc/Petroleum ether to afford the desired alcohol. $^1H$ NMR (300 MHz, $CD_3CN$) δ: 8.76 (1H, s), 8.15-8.05 (2H, m), 7.70-7.52 (3H, m), 3.94-3.89 (4H, m), 3.02-2.91 (2H, t, J=8.0 Hz), 1.75-1.65 (4H, m), 1.60-1.50 (4H, m), 1.45-1.30 (2H, m), 1.00-0.80 (3H, m). MS (ES) $C_{20}H_{25}NO_3S$ requires: 359, found: 360 $(M+H)^+$.

Step 2: 6-(2-Ethyl-1,3-dioxolan-2-yl)-1-(2-phenyl-1,3-thiazol-5-yl)hexan-1-ol (N2)

To a stirred solution of the ketone (N1) in anhydrous EtOH at RT was added $NaBH_4$ (1 eq.) and the mixture stirred for 30 min. The reaction was quenched by slow addition of sat. aq. $NH_4Cl$ solution and the desired product was extracted with EtOAc. The organic layer was washed with brine, dried ($Na_2SO_4$) and concentrated under reduced pressure. The crude was purified by column chromatography eluting with 10% EtOAc/Petroleum ether to afford the desired alcohol. $^1H$ NMR (300 MHz, $CD_3CN$) δ: 7.95 (2H, d, J=7.5 Hz), 7.65-7.45 (1H, s), 7.45-7.35 (3H, m), 5.05-4.95 (1H, m), 3.94-3.89 (4H, m), 1.75-1.55 (6H, m), 1.45-1.25 (6H, m), 1.00-0.80 (3H, m). MS (ES) $C_{20}H_{27}NO_3S$ requires: 361, found: 362 $(M+H)^+$.

Step 3: [6-(2-Ethyl-1,3-dioxolan-2-yl)-1-(2-phenyl-1,3-thiazol-5-yl)hexyl]amine (N3)

5-[1-azido-6-(2-ethyl-1,3-dioxolan-2-yl)hexyl]-2-phenyl-1,3-thiazole from alcohol (N2) was prepared according to the procedure used in Example 89 Step 2. $^1H$ NMR (300 MHz, $CDCl_3$) δ: 8.00-7.90 (2H, d, J=7.5 Hz), 7.57 (1H, s), 7.45-7.35 (3H, m), 5.10 (1H, t, J=7.3 Hz), 3.95 (4H, s), 1.89-1.78 (2H, m), 1.65-1.55 (4H, m), 1.45-1.25 (6H, m), 0.90-0.80 (3H, m). MS (ES) $C_{20}H_{26}N_4O_2S$ requires: 386, found: 387 $(M+H)^+$. The azide was then reduced according to the Example 89 Step 3 to afford the desired amine (N3). $^1H$ NMR (300 MHz, $CDCl_3$) δ: 7.95 (2H, d, J=7.5 Hz), 7.57 (1H, s), 7.45-7.35 (3H, m), 4.95 (1H, t, J=7.3 Hz), 3.95 (4H, s), 1.89-1.78 (2H, m), 1.65-1.55 (4H, m), 1.45-1.25 (6H, m), 0.90-0.80 (3H, m). MS (ES) $C_{20}H_{28}N_2O_2S$ requires: 360, found: 361 $(M+H)^+$.

Step 4: 2-(5-Methoxy-2-methyl-1H-indol-3-yl)-N-[7-oxo-1-(2-phenyl-1,3-thiazol-5-yl)nonyl]acetamide (N4)

This was prepared from amine (N3) according to the Example 89 Step 4. $^1H$ NMR (300 MHz, $(CD_3)SO$) δ: 10.65 (1H, s), 8.60-8.40 (1H, d, J=5 Hz), 7.92-7.82 (2H, m) 7.66 (1H, s), 7.55-7.44 (3H, m), 7.10 (1H, d, J=8.6 Hz), 7.05 (1H, s), 6.60 (1H, d, J=8.6 Hz), 5.17 (1H, app. q, J=6.0 Hz), 3.76 (3H, s), 3.56-3.50 (2H, br. s), 2.45-2.30 (7H, m), 1.90-1.20 (8H, m), 0.93 (3H, t, J=7.3 Hz). MS (ES) $C_{30}H_{35}N_3O_3S$ requires: 517, found: 518.

Example 140

2-((1S)-1-{[(1-Methylpiperidinium-4-yl)carbonyl]amino}-7-oxononyl)-4-phenylpyridinium bis(trifluoroacetate) (O4)

Step 1: N-[(1E)-6-(2-Ethyl-1,3-dioxolan-2-yl)hexylidene]-2-methylpropane-2-sulfinamide (O1)

A solution of 6-(2-ethyl-1,3-dioxolan-2-yl)hexanal (M3) (1.1 eq.), (R)-(+)-tert-butanesulfinamide (1.0 eq.) and anhydrous copper sulfate (2.2 eq.) in DCM was stirred for 70 h at RT. The reaction mixture was filtered through Celite. The solvent was removed under reduced pressure. The crude product was purified by flash chromatography with hexane/ethyl acetate mixture as eluent to yield the desired product as an oil. $^1H$ NMR (300 MHz, $CDCl_3$) δ: 8.05 (1H, t, J=4.6 Hz), 3.91 (4H, s), 2.60-2.40 (2H, m), 1.70-1.50 (6H, m), 1.47-1.28 (4H, m), 1.18 (9H, s), 0.88 (3H, t, J=7.5 Hz). $^{13}C$ NMR (75 MHz, $CDCl_3$) δ: 169.6, 111.9, 65.0, 56.5, 36.5, 36.0, 29.8, 29.5, 25.5, 23.5, 22.3, 8.1. MS (ES) $C_{15}H_{29}NO_3S$ requires: 303, found: 304 $(M+H)^+$.

Step 2: N-[(1S)-6-(2-Ethyl-1,3-dioxolan-2-yl)-1-(4-phenylpyridin-2-yl)hexyl]-2-methylpropane-2-sulfinamide (O2)

A solution of 2-bromo-4-phenylpyridine (1 eq.) in THF was cooled to −78° C. and treated dropwise with n-BuLi (1.1 eq.). After 30 min, a solution of the imine (O1) (1.2 eq.) in THF was added. The reaction mixture was stirred for 2 h at −78° C. and than slowly warmed to RT. The reaction was quenched with $H_2O$ and the aqueous phase was extracted with EtOAc. The combined organic phase was dried ($MgSO_4$) and solvent was removed under reduced pressure. The crude amine was used without further purification; LC-MS analysis shows two diastereomers 4.3:1. MS (ES) $C_{26}H_{38}N_2O_3S$ requires: 459, found: 460 $(M+H)^+$.

Step 3: (1S)-7-Oxo-1-(4-phenylpyridin-2-yl)nonan-1-aminium trifluoroacetate (O3)

The disubstituted pyridine (O2) (1 eq.) was dissolved in 1.25 N HCl in MeOH and was stirred for 30 min at RT. The reaction was quenched with 1N NaOH solution and was extracted with EtOAc. The organic phase was dried (MgSO₄) and the solvent was removed under reduced pressure. The crude amine was used without further purification. A small portion was purified by RP-HPLC and showed: ¹H NMR (300 MHz, d6-DMSO) δ: 8.68 (1H, d, J=5.1 Hz), 8.41 (3H, br. s), 7.87-7.74 (5H, m), 7.57-7.49 (2H, m), 4.43 (1H, m), 2.39-2.31 (4H, m), 1.95-1.80 (2H, m), 1.45-1.13 (6H, m), 0.86 (3H, t, J=4.6 Hz). MS (ES) $C_{20}H_{26}N_2O$ requires: 310, found: 311 (M+H)⁺.

Step 4: 2-((1S)-1-{[(1-Methylpiperidinium-4-yl)carbonyl]amino}-7-oxononyl)-4-phenylpyridinium bis(trifluoroacetate) (O4)

To a solution of the amine (O3) (1 eq.) and DIPEA (2.2 eq.) in DMF was added a solution of EDC.HCl (1.3 eq), HOBt (1.3 eq) and 1-methylpiperidine-4-carboxylic acid (1.2 eq) in DMF. The mixture was stirred at RT for 3 h and the desired material was isolated by preparative RP-HPLC, using H₂O (+0.1% TFA) and MeCN (+0.1% TFA) as eluents (C18 column). The desired fractions were lyophilized to afford the imidazole as a colourless oil. ¹H NMR (300 MHz, CDCl₃) δ: 9.22 (1H, bs), 8.65 (1H, s), 8.05 (1H, s), 7.93-7.71 (4H, m), 7.66-7.53 (3H, m), 5.17 (1H, m), 3.60 (1H, m), 3.44-3.13 (1H, m), 2.85-2.63 (5H, m), 2.60-2.46 (1H, m), 2.43-2.33 (4H, m), 2.24-1.82 (6H, m), 1.61-1.25 (6H, m), 1.03 (3H, t, J=7.3 Hz). MS (ES) $C_{27}H_{37}N_3O_2$ requires: 436, found: 437 (M+H)⁺.

Example 141

(7S)-7-{[(5-Methoxy-2-methyl-1H-indol-3-yl)acetyl]amino}-7-[5-(2-naphthyl)-1,3,4-oxadiazol-2-yl]heptanoic acid (P4)

Step 1: N'-(2)-8-tert-Butoxy-2-[(tert-Butoxycarbonyl)amino]-8-oxooctanyl-2-naphtho hydrazide (P1)

A solution of EDC.HCl (1.5 eq.), HOBt (1.5 eq.) and (2S)-8-tert-Butoxy-2-[(tert-butoxycarbonyl)amino]-8-oxooctanoic acid (13, Example 107 Step 3) (1 eq.) in DMF (0.1 M) was premixed at RT for 1 hr, and then 2-naphthohydrazide was added. The mixture was stirred for 16 hr at RT and then concentrated to dryness under reduced pressure. The residue was dissolved in DCM, washed with 1 M HCl solution and brine. The solution was dried (Na₂SO₄), concentrated under reduced pressure and the resulting brown oil was purified by chromatography on silica gel eluting with 30% EtOAc/petroleum to obtain the hydrazide as a white solid. ¹H NMR (400 MHz, CDCl₃, 300 K) δ9.36 (1H, broad s), 9.12 (1H, broad s), 8.36 (1H, s), 7.90-7.80 (4H, m), 7.61-7.49 (2H, m), 5.15 (1H, d, J=8 Hz), 4.38-4.24 (1H, m), 2.20 (2H, t, J=7 Hz), 1.98-1.85 (1H, m), 1.76-1.64 (1H, m), 1.64-1.52 (2H, m), 1.50-1.30 (22H, m). MS (ES) $C_{28}H_{39}N_3O_6$ requires: 513, found: 514 (M+H)⁺.

Step 2: tert-Butyl (7S)-7-[(tert-butoxycarbonyl)amino]-7-[5-(2-naphthyl)-1,3,4-oxadiazol-2-yl]heptanoate (P2)

The desired compound was prepared as a yellow solid from the hydrazide (P1) as described in Example 136 step 3. ¹H NMR (500 MHz, d6-DMSO, 325 K) δ 8.57 (1H, s), 8.19-8.11 (2H, m), 8.09-8.00 (2H, m), 7.72-7.60 (2H, m), 7.58 (1H, broad s), 4.92-4.80 (1H, m), 2.18 (2H, t, J=7 Hz), 2.00-1.80 (2H, m), 1.55-1.25 (24H, m). MS (ES) $C_{28}H_{37}N_3O_5$ requires: 495, found: 496 (M+H)⁺.

Step 3: (1S)-6-Carboxy-1-[5-(2-naphthyl)-1,3,4-oxadiazol-2-yl]hexan-1-aminium trifluoroacetate (P3)

The desired compound was prepared as a yellow solid from the carbamate (P2) as described in Example 136 step 4, however without the basic work up. ¹H NMR (300 MHz, d6-DMSO, 300 K) δ12.0 (1H, broad s), 8.84 (3H, broad s), 8.65 (1H, s), 8.25-8.00 (4H, m), 7.76-7.62 (2H, m), 4.94-4.84 (1H, m), 2.21 (2H, t, J=7 Hz), 2.15-1.95 (2H, m), 1.60-1.25 (6H, m). MS (ES) $C_{19}H_{21}N_3O_3$ requires: 339, found: 340 (M+H⁺).

Step 4: (7S)-7-{[(5-methoxy-2-methyl-1H-indol-3-yl)acetyl]amino}-7-[5-(2-naphthyl)-1,3,4-oxadiazol-2-yl]heptanoic acid (P4)

The titled compound (P4) was obtained from the amine (P3) as described in Example 136 step 5 to yield a white powder. ¹H NMR (300 MHz, d6-DMSO, 300 K) δ 11.95 (1H, broad s), 10.59 (1H, broad s), 8.71 (1H, d, J=8 Hz), 8.46 (1H, s), 8.14-7.90 (4H, m), 7.72-7.62 (2H, m), 7.10 (1H, d, J=8 Hz), 7.04 (1H, d, J=2 Hz), 6.58 (1H, dd, J=8 Hz, J=2 Hz), 5.22-5.10 (1H, m), 3.64 (3H, s), 3.52 (2H, s), 2.33 (3H, s), 2.17 (2H, t, J=7 Hz), 2.05-1.85 (2H, m), 1.50-1.20 (6H, m). MS (ES) $C_{31}H_{32}N_4O_5$ requires: 540, found: 541 (M+H⁺).

Example 142

(7S)-7-{[(5-Methoxy-2-methyl-1H-indol-3-yl)acetyl]amino}-7-[5-(2-naphthyl)-1,3,4-oxadiazol-2-yl]heptanamide (O1)

(7S)-7-{[(5-Methoxy-2-methyl-1H-indol-3-yl)acetyl]amino}-7-[5-(2-naphthyl)-1,3,4-oxadiazol-2-yl]heptanoic acid was obtained as described in Example 141 step 4. Once the coupling was complete, to the reaction mixture were added HATU (1.3 eq) and after 30 min a solution of NH₃ in 1,4-dioxane (10 eq). The mixture was stirred for overnight, then the crude was directly purified by preparative RP-HPLC, using H₂O (+0.1% TFA) and MeCN (+0.1% TFA) as eluents (column: C18). The desired fractions were lyophilized to afford Q1 as a white powder. ¹H NMR (300 MHz, d6-DMSO, 300 K) δ 10.59 (1H, broad s), 8.71 (1H, d, J=8 Hz), 8.46 (1H, s), 8.15-7.90 (4H, m), 7.72-7.60 (2H, m), 7.18 (1H, broad s), 7.09 (1H, d, J=8 Hz), 7.03 (1H, d, J=2 Hz), 6.65 (1H, broad s), 6.58 (1H, dd, J=8 Hz, J=2 Hz), 5.20-5.10 (1H, m), 3.64 (3H, s), 3.52 (2H, s), 2.33 (3H, s), 2.00 (2H, t, J=7 Hz), 2.10-1.85 (2H, m), 1.50-1.20 (6H, m). MS (ES) $C_{31}H_{33}N_5O_4$ requires: 539, found: 540 (M+H⁺).

Example 143

(7S)-7-{[(5-Methoxy-2-methyl-1H-indol-3-yl)acetyl]amino}-7-[5-(2-naphthyl)-4H-1,2,4-triazol-3-yl]heptanoic acid (R4)

Step 1: (2S)-8-tert-Butoxy-2-[(tert-Butoxycarbonyl)amino]-8-oxooctanohydrazide (R1)

The hydrazide (R1) was obtained as pale yellow oil from 8-tert-butyl 1-methyl (2S)-2-[(tert-butoxycarbonyl)amino]octanedioate (12, Example 107 Step 2) as described in Example 88 step 2. MS (ES) $C_{17}H_{33}N_3O_5$ requires: 359, found: 360 (M+H)⁺.

Step 2: tert-butyl (7S)-7-[(tert-butoxycarbonyl) amino]-7-[5-(2-naphthyl)-4H-1,2,4-triazol-3-yl]heptanoate (R2)

The Desired Triazole was Prepared from the Hydrazide (R1) and 2-Naphthonitrile as Described in Example 88 step 3 to yield a pale yellow oil. $^1$H NMR (300 MHz, d6-DMSO, 340 K) δ15.5 (1H, broad s), 8.82 (1H, s), 8.82 (1H, d, J=8 Hz), 8.05-7.84 (4H, m), 7.58-7.48 (2H, m), 5.55-5.40 (1H, m), 2.50-2.32 (1H, m), 2.28 (2H, t, J=7 Hz), 2.32-2.12 (1H, m), 1.80-1.30 (24H, m). MS (ES) $C_{28}H_{38}N_4O_4$ requires: 494, found: 495 (M+H)$^+$.

Step 3: (1S)-6-Carboxy-1-[5-(2-naphthyl)-4H-1,2,4-triazol-3-yl]hexan-1-aminium trifluoroacetate (R3)

The desired compound was prepared as a brown oil from the carbamate (R2) as described in Example 136 step 4, however without the basic work up. $^1$H NMR (300 MHz, d6-DMSO, 300 K) δ14.78 (1H, broad s), 11.98 (1H, broad s), 8.58 (1H, s), 8.48 (3H, broad s), 8.18-7.95 (4H, m), 7.68-7.55 (2H, m), 4.55-4.40 (1H, m), 2.20 (2H, t, J=7 Hz), 2.06-1.86 (2H, m), 1.60-1.20 (6H, m). MS (ES) $C_{19}H_{22}N_4O_2$ requires: 338, found: 339 (M+H$^+$).

Step 4: (7S)-7-{[(5-Methoxy-2-methyl-1H-indol-3-yl)acetyl]amino}-7-[5-(2-naphthyl)-4H-1,2,4-triazol-3-yl]heptanoic acid (R4)

The titled compound (R4) was obtained from the amine (R3) as described in Example 88 step 5 to yield a white powder. $^1$H NMR (300 MHz, d6-DMSO, 300 K) δ 10.57 (1H, broad s), 8.52 (1H, s), 8.39 (1H, d, J=8 Hz), 8.15-7.90 (4H, m), 7.62-7.52 (2H, m), 7.09 (1H, d, J=9 Hz), 7.03 (1H, d, J=2 Hz), 6.59 (1H, dd, J=9 Hz, J=2 Hz), 5.07-4.95 (1H, m), 3.67 (3H, s), 3.60-3.40 (2H, m), 2.32 (3H, s), 2.14 (2H, t, J=7 Hz), 1.97-1.77 (2H, m), 1.50-1.20 (6H, m). MS (ES) $C_{31}H_{33}N_5O_4$ requires: 539, found: 540 (M+H$^+$).

Example 144

(7S)-7-{[(5-Methoxy-2-methyl-1H-indol-3-yl)acetyl]amino}-7-[5-(2-naphthyl)-4H-1,2,4-triazol-3-yl]heptanamide (S1)

The titled compound (S1) was obtained from the amine (R3) as described in Example 142 step 1 to yield a white powder. $^1$H NMR (300 MHz, d6-DMSO, 300 K) δ 10.57 (1H, broad s), 8.52 (1H, s), 8.39 (1H, d, J=8 Hz), 8.14-7.91 (4H, m), 7.61-7.53 (2H, m), 7.17 (1H, broad s), 7.09 (1H, d, J=8 Hz), 7.02 (1H, d, J=2 Hz), 6.65 (1H, broad s), 6.59 (1H, dd, J=8 Hz, J=2 Hz), 5.07-4.95 (1H, m), 3.67 (3H, s), 3.60-3.40 (2H, m), 2.32 (3H, s), 1.98 (2H, t, J=7 Hz), 1.94-1.78 (2H, m), 1.50-1.20 (6H, m). MS (ES) $C_{31}H_{34}N_6O_3$ requires: 538, found: 539 (M+H$^+$).

Example 145

2-(5-Methoxy-2-methyl-1H-indol-3-yl)-N-{(1S)-1-[5-(2-naphthyl)-1,2,4-oxadiazol-3-yl]-7-oxononyl}acetamide (T7)

Step 1: tert-Butyl [(1S)-1-(aminocarbonyl)-7-oxononyl]carbamate (T1)

To a solution of (2S)-2-[(tert-butoxycarbonyl)amino]-8-oxodecanoic acid in dioxane were added Py (1 eq.), Boc$_2$O (1.3 eq) and ammonium bicarbonate (1.26 eq.). The reaction mixture was stirred at RT for 72 hours and then the solvent was evaporated under reduced pressure. The resulting crude was diluted with EtOAc and washed with H$_2$O, 1 N HCl and brine. The organic phase was dried (Na$_2$SO$_4$) and concentrated under reduced pressure to yield a white powder which was as such in the next step. MS (ES) $C_{15}H_{28}N_2O_4$ requires: 300, found: 301 (M+H$^+$).

Step 2: tert-Butyl [(1S)-1-cyano-7-oxononyl]carbamate (T2)

To a solution of the amide (T1) (1 eq.) and Et$_3$N (2.2 eq) in DCM at 0° C., TFAA (2 eq) was added dropwise. The reaction mixture was stirred at RT for 1 h, and then washed with sat. aq. NaHCO$_3$ solution, H$_2$O, brine. The organic phase was dried (Na$_2$SO$_4$) and concentrated under reduced pressure affording a yellow oil compound used as such in the next step. MS (ES) $C_{15}H_{26}N_2O_3$ requires: 282, found: 305 (M+Na$^+$).

Step 3: tert-Butyl [(1S)-1-cyano-7-hydroxynonyl]carbamate (T3)

A solution of the nitrile (T2) (1 eq.) in MeOH was cooled to 0° C. and NaBH$_4$ (4 eq.) was added portionwise. The reaction mixture was stirred at 0° C. for further 15 min and then at RT for 1 h. Then reaction was quenched with water, the methanol was evaporated and the residue extracted with Et$_2$O (3×). The organic phases were collected, washed with brine, dried (Na$_2$SO$_4$) and evaporated under reduced pressure. The resulting crude was used directly in the next step. MS (ES) $C_{15}H_{28}N_2O_3$ requires: 284, found: 307 (M+Na$^+$).

Step 4: tert-Butyl {(1S)-7-hydroxy-1-[(hydroxyamino)(imino)methyl]nonyl}carbamate (T4)

A solution of NH$_2$OH.HCl (1.5 eq) in MeOH was added to a solution of KOH (1.5 eq) in MeOH. The mixture was stirred for 20 min, then the solid was filtered off and the resulting solution was added to the nitrile (T3) (1 eq.). The mixture was then heated at refluxed, and after 16 hours the solvent was removed under reduced pressure and the resulting crude was used as such in the next step. MS (ES) $C_{15}H_{31}N_3O_4$ requires: 317, found: 318 (M+H$^+$).

Step 5: tert-Butyl {(1S)-7-hydroxy-1-[5-(2-naphthyl)-1,2,4-oxadiazol-3-yl]nonyl}carbamate (T5)

A mixture of 2-naphthoic acid (0.9 eq), TBTU (1 eq), HOBt (0.2 eq) and DIPEA (5 eq) in DMF was stirred at RT for 5 min; then added the aldoxime (T4) was added and the mixture was stirred for 1 h at RT. The mixture was then warmed to 110° C. for 4 h. The solvent was removed under reduced pressure and the resulting crude used as such in the next step. MS (ES) $C_{26}H_{35}N_3O_4$ requires: 453, found: 454 (M+H$^+$).

Step 6: tert-Butyl {(1S)-1-[5-(2-naphthyl)-1,2,4-oxadiazol-3-yl]-7-oxononyl}carbamate (T6)

To a solution of the oxadiazole (1 eq.) in DCM was added the Dess-Martin periodinane (1.1 eq.). The mixture was stirred for 2 hr at RT and then a sat. aq. NaHCO$_3$ (containing Na$_2$S$_2$O$_3$ (6 eq.)) was added and the mixture was stirred for 15 min. The phases were separated and the H$_2$O phase was extracted with DCM. The combined organic phases were dried (Na$_2$SO$_4$) and concentrated under reduced pressure.

The obtained product was used in the next step without further purification. MS (ES) $C_{26}H_{33}N_3O_4$ requires: 451, found: 452 (M+H$^+$).

Step 7: 2-(5-Methoxy-2-methyl-1H-indol-3-yl)-N-{(1S)-1-[5-(2-naphthyl)-1,2,4-oxadiazol-3-yl]-7-oxononyl}acetamide (T7)

The ketone (T6) (1 eq.) was dissolved in a mixture of DCM and TFA (1:1) and stirred at RT. After 20 min, the solvents were removed under reduced pressure and the residue was partitioned between DCM and sat. aq. NaHCO$_3$ solution. The organic phase was separated, dried (Na$_2$SO$_4$) and concentrated under reduced pressure.

To the residue was added a solution of (5-methoxy-2-methyl-1H-indol-3-yl)acetic acid (1.05 eq.), HOBt (1.05 eq.) and EDC.HCl (1.05 eq.) in DCM (premixed for 3 min), followed by DIPEA (1.05 eq.). The mixture was left stirring at room temperature for 4 hr. The product was isolated by preparative RP-HPLC, using water (0.1% TFA) and acetonitrile (0.1% TFA) as eluents (column: C18), the desired fractions were lyophilized to afford the final product as a white fluffy compound. $^1$H NMR (300 MHz, d6-DMSO) δ: 10.57 (1H, s), 8.75 (1H, s), 8.60 (1H, d, J=8.2 Hz), 8.18-7.18 (4H, m), 7.65-7.49 (2H, m), 7.16-6.98 (2H, m), 6.63-6.54 (1H, m), 5.11-4.98 (1H, m), 3.68 (3H, s), 3.58-3.42 (2H, m), 2.42-2.22 (7H, m), 1.97-1.75 (2H, m), 1.50-1.12 (6H, m), 0.89 (3H, t, J=7.2 Hz). MS (ES) $C_{33}H_{36}N_4O_4$ requires: 552, found: 553 (M+H$^+$).

Example 146

2-(5-Methoxy-2-methyl-1H-indol-3-yl)-N-{(1S)-1-[3-(2-naphthyl)-1,2,4-oxadiazol-5-yl]-7-oxononyl}acetamide (U2)

Step 1: tert-Butyl {(1S)-1-[3-(2-naphthyl)-1,2,4-oxadiazol-5-yl]-7-oxononyl}carbamate (U1)

A mixture of (2S)-2-[(tert-butoxycarbonyl)amino]-8-oxodecanoic acid (1 eq), TBTU (1.2 eq), HOBt (0.2 eq) and DIPEA (5 eq) in DMF was stirred at RT for 5 min; then added N-hydroxynaphthalene-2-carboximidamide was added and the mixture was stirred at RT for 20 min, after which time the mixture was warmed to 110° C. for 2 h. The solvent was removed under reduced pressure and the resulting crude used as such in the next step. MS (ES) $C_{26}H_{33}N_3O_4$ requires: 451, found: 452 (M+H$^+$).

Step 2: 2-(5-Methoxy-2-methyl-1H-indol-3-yl)-N-{(1S)-1-[3-(2-naphthyl)-1,2,4-oxadiazol-5-yl]-7-oxononyl}acetamide (U2)

The oxadiazole was converted into titled compound by deprotection and coupling as described in Example 145 step 7. $^1$H NMR (400 MHz, d6-DMSO) δ: 10.60 (1H, s), 8.80 (1H, d, J=7.8 Hz), 8.58 (1H, s), 8.16-7.98 (4H, m), 7.68-7.60 (2H, m), 7.10 (1H, d, J=8.6 Hz), 7.05 (1H, d, J=2.5 Hz), 6.60 (1H, dd, J$_1$=8.6 Hz, J$_2$=2.5 Hz), 5.18-5.10 (1H, m), 3.71 (3H, s), 3.58-3.47 (2H, m), 2.41-2.30 (7H, m), 2.02-1.86 (2H, m), 1.46-1.17 (6H, m), 0.90 (3H, t, J=7.3 Hz). MS (ES) $C_{33}H_{36}N_4O_4$ requires: 552, found: 553 (M+H$^+$).

Example 147

2-{(1S)-1-[(Methoxycarbonyl)amino]-7-oxononyl}-5-(2-naphthyl)-1H-imidazol-1-ium trifluoroacetate (V3)

Step 1: tert-Butyl[(1S)-7-oxo-1-(5-(2-naphthyl)-1H-imidazol-2-yl)nonyl]carbamate (V1)

The product was obtained as a pale yellow solid from (2S)-2-[(tert-butoxycarbonyl)amino]-8-oxodecanoic acid and 2-bromo-1-(2-naphthyl)ethanone following the procedure described for tert-butyl [(1S)-7-oxo-1-(5-phenyl-1H-imidazol-2-yl)octyl]carbamate from Example 1, Step 2. $^1$H NMR (300 MHz, d6-DMSO) δ: 12.30-11.70 (1H, m), 8.30-8.07 (1H, m), 7.95-7.72 (4H, m), 7.62 (1H, s), 7.50-7.31 (2H, m), 7.12-6.90 (1H, m), 4.70-4.50 (1H, m), 2.245-2.30 (4H, m), 1.92-1.65 (2H, m), 1.55-1.15 (15H, m), 0.89 (3H, t, J=7.1 Hz). MS (ES) $C_{27}H_{35}N_3O_3$ requires: 449, found: 450 (M+H)$^+$.

Step 2: (9S)-9-Amino-9-[5-(2-naphthyl)-1H-imidazol-2-yl]nonan-3-one (V2)

The carbamate (V1) (1 eq.) was dissolved in TFA/DCM (1:1) at 0° C. The cooling bath was removed and the mixture was stirred for 60 min at RT. The solvents were removed under reduced pressure and the remaining oil was partitioned between DCM and sat. aq. NaHCO$_3$ solution. The organic phase was dried (Na$_2$SO$_4$) and concentrated to dryness under reduced pressure. The obtained crude product was used without purification in the next step. MS (ES) $C_{22}H_{27}N_3O$ requires: 349, found: 350 (M+H)$^+$.

Step 3: 2-{(1S)-1-[(Methoxycarbonyl)amino]-7-oxononyl}-5-(2-naphthyl)-1H-imidazol-1-ium trifluoroacetate (V3)

To a solution of the amine (V2) and Et$_3$N (2.2 eq.) in DCM was added methyl chloridocarbonate (2.2 eq.). The reaction mixture was stirred at RT until consumption of the starting material. The product was isolated by preparative RP-HPLC, using H$_2$O (+0.1% TFA) and MeCN (+0.1% TFA) as eluents (column: C18). The desired fractions were lyophilized to afford the titled compound as colourless oil. $^1$H NMR (400 MHz, CD$_3$CN) δ: 8.37 (1H, s), 8.03 (1H, d, J=8.7 Hz), 8.00-7.95 (2H, m), 7.81 (1H, dd, J$_1$=8.7 Hz, J$_2$=1.8 Hz), 7.72-7.65 (2H, m), 7.64-7.58 (2H, m), 5.14-5.05 (1H, m), 3.66 (3H, s), 2.46-2.38 (4H, m), 2.07-1.99 (2H, m), 1.59-1.28 (6H, m), 0.98 (3H, t, J=7.2 Hz). MS (ES) $C_{24}H_{29}N_3O_3$ requires: 407, found: 408 (M+H$^+$).

Example 148

2-((1S)-1-{[(Dimethylamino)carbonyl]amino}-7-oxononyl)-5-(2-naphthyl)-1H-imidazol-1-ium trifluoroacetate (W1)

To a solution of the amine (V2) and Et$_3$N (2.2 eq.) in DCM was added dimethylcarbamyl chloride (2.2 eq.). The reaction mixture was stirred at RT until consumption of the starting material. The product was isolated by preparative RP-HPLC, using H$_2$O (+0.1% TFA) and MeCN (+0.1% TFA) as eluents (column: C18). The desired fractions were lyophilized to afford the titled compound as colourless oil. $^1$H NMR (300 MHz, CD$_3$CN) δ: 7.80-7.65 (5H, m), 7.56-7.44 (2H, m), 7.42-7.35 (2H, m), 7.33 (1H, s), 5.37-5.24 (1H, m), 3.01 (6H, s), 2.46-2.32 (4H, m), 2.24-2.01 (2H, m), 1.61-1.24 (6H, m), 0.97 (3H, t, J=7.4 Hz). MS (ES) $C_{25}H_{32}N_4O_2$ requires: 407, found: 421 (M+H$^+$).

Example 149

3-Nitro-N-[7-oxo-1-(4-phenyl-2-furyl)octyl]benzenesulfonamide (X5)

Step 1: 1-(4-Phenyl-2-furyl)oct-7-en-1-ol (X1)

To a stirred mixture of Mg (2.5 eq.) in anhydrous THF under Ar was added 12 (>5 mol %) and the mixture heated at reflux until the solution became colourless. Then 7-bromohept-1-ene (2.2 eq.) was added dropwise, and upon complete addition the mixture was heated at reflux for 2.5 hr. The resulting Grignard reagent obtained was used immediately for the next step.

The resulting Grignard solution was added to a solution of 4-phenyl-2-furaldehyde (1 eq.) in THF at 0° C. under Ar and the mixture was stirred for 30 min. The reaction was quenched by slow addition of sat. aq. NH$_4$Cl solution and the desired product was extracted with EtOAc. The organic layer was washed with brine, dried (Na$_2$SO$_4$) and concentrated under reduced pressure. The crude was purified by column chromatography eluting with 5% EtOAc/Petroleum ether to afford the desired alcohol. $^1$H NMR (300 MHz, CD$_3$Cl3) δ: 7.65 (2H, d, J=7.3 Hz), 7.42 (2H, t, J=7.2 Hz), 7.25-7.15 (1H, m), 6.60 (1H, d, J=5.3 Hz), 6.30 (1H, d, J=5.3 Hz), 5.87-5.75 (1H, m), 5.05-4.89 (2H, m), 4.75-4.65 (1H, m), 2.15-2.05 (2H, m), 1.87-1.75 (2H, m), 1.45-1.35 (6H, m). MS (ES) $C_{18}H_{22}O_2$ requires: 270 found: 271 (M+H)$^+$.

Step 2: 1-(4-Phenyl-2-furyl)oct-7-en-1-yl azide (X2)

The alcohol (X1) (1 eq.) was dissolved in toluene, to give a solution of 0.5 M, together with DPPA (1.2 eq.) and then DBU (1.2 eq.) was added and the mixture was heated with stirring at 50° C. overnight. After cooling to RT, EtOAc was added and the mixture was washed with H$_2$O and then with 5% HCl solution. The organic layer was washed with brine, dried (Na$_2$SO$_4$) and concentrated under reduced pressure. The residue was purified by column chromatography eluting with 10% EtOAc/Petroleum ether to afford the azide. $^1$H NMR (300 MHz, CD$_3$Cl3) δ: 7.65 (2H, d, J=7.3 Hz), 7.42 (2H, t, J=7.2 Hz), 7.25-7.15 (1H, m), 6.60 (1H, d, J=5.3 Hz), 6.30 (1H, d, J=5.3 Hz), 5.87-5.75 (1H, m), 5.05-4.89 (2H, m), 4.45-4.35 (1H, m), 2.15-2.05 (2H, m), 1.87-1.75 (2H, m), 1.45-1.35 (6H, m). MS (ES) $C_{18}H_{21}N_3O$ requires: 295 found: 296 (M+H)$^+$.

Step 3: [1-(4-Phenyl-2-furyl)oct-7-en-1-yl]amine (X3)

The azide (X2) was dissolved in THF under Ar and PPh$_3$ (1.2 eq.) was added and the solution was stirred overnight at RT. Water was added and the mixture was stirred other 24 hours, and then the solution concentrated under reduced pressure and the crude purified by SCX cartridge, washing first with MeOH and then eluting the desired amine with methanolic ammonia solution, the desired fractions were concentrated under reduced pressure. $^1$H NMR (300 MHz, CD$_3$Cl3) δ: 7.65 (2H, d, J=7.3 Hz), 7.42 (2H, t, J=7.2 Hz), 7.25-7.15 (1H, m), 6.60 (1H, d, J=5.3 Hz), 6.30 (1H, d, J=5.3 Hz), 5.87-5.75 (1H, m), 5.05-4.89 (2H, m), 3.95-3.85 (1H, m), 2.15-2.05 (2H, m), 1.87-1.75 (2H, m), 1.45-1.35 (6H, m). MS (ES) $C_{18}H_{23}NO$ requires: 269 found: 270 (M+H)$^+$.

Step 4: 3-Nitro-N-[1-(4-phenyl-2-furyl)oct-7-en-1-yl]benzenesulfonamide (X4)

To a stirred solution of the amine (X3) (1 eq.) in DCM was added 3-nitrobenzenesulfonyl chloride (1.2 eq.) and the mixture was stirred at RT for 2 hr. The reaction mixture was washed successively with 0.25 M HCl solution, 0.25 M NaOH solution and brine, dried (Na$_2$SO$_4$) and concentrated under reduced pressure. The mixture was purified by column chromatography eluting with 50% EtOAc/Petroleum ether to afford the sulfonamide. $^1$H NMR (300 MHz, d6-DMSO) δ: 8.70 (1H, d, J=7.3 Hz), 8.40 (1H, s) 8.15-8.05 (2H, m), 7.60 (1H, t, J=7.2 Hz), 7.45-7.25 (4H, m), 6.60 (1H, d, J=5.3 Hz), 6.30 (1H, d, J=5.3 Hz), 5.87-5.75 (1H, br, m), 5.05-4.89 (2H, t, J=8.3 Hz), 4.45-4.35 (1H, m), 2.15-2.05 (2H, m), 1.87-1.75 (2H, m), 1.45-1.35 (6H, m). MS (ES) $C_{24}H_{26}N_2O_5S$ requires: 454 found: 455 (M+H)$^+$.

Step 5: 3-Nitro-N-[7-oxo-1-(4-phenyl-2-furyl)octyl]benzenesulfonamide (X5)

To a stirred mixture of DMF-H$_2$O (5:1) were added CuCl (1 eq.) and PdCl$_2$ (0.1 eq.) under the mixture was stirred under an O$_2$ atmosphere for 1 hour and then the sulfonamide (X3) (1 eq.) was added. The final solution was left stirring under an O$_2$ atmosphere at RT for 18 h. The solution was then concentrated under reduced pressure and the residue taken up in DCM, washed with sat. aq. NH$_4$Cl solution and brine. The organics were dried (Na$_2$SO$_4$) and concentrated under reduced pressure. The mixture was purified by preparative RP-HPLC, using H$_2$O (+0.1% TFA) and MeCN (+0.1% TFA) as eluents (column: C18). The desired fractions were lyophilized to afford the titled compound. $^1$H NMR (300 MHz, 6-DMSO) δ: 8.70 (1H, d, J=7.3 Hz), 8.40 (1H, s) 8.15-8.05 (2H, m), 7.65-7.55 (1H, t, J=7.2 Hz), 7.45-7.25 (4H, m), 6.60 (1H, d, J=5.3 Hz), 6.30 (1H, d, J=5.3 Hz), 4.45-4.35 (1H, m), 2.40 (2H, t, J=7.2 Hz), 2.15-2.05 (3H, s), 1.87-1.75 (2H, m), 1.45-1.45 (6H, m). MS (ES) $C_{24}H_{26}N_2O_6S$ requires: 470 found: 471 (M+H)$^+$.

Example 150

2-((1M)-7-[(Ethylsulfonyl)amino]-1-{[(5-methoxy-2-methyl-1H-indol-3-yl)acetyl]amino}-7-oxoheptyl)-5-(2-naphthyl)-1H-imidazol-1-ium trifluoroacetate (Y1)

To a solution of (7S)-7-{[(5-methoxy-2-methyl-1H-indol-3-yl)acetyl]amino}-7-[5-(2-naphthyl)-1H-imidazol-2-yl]heptanoic acid (Free base of Example 107) (1 eq.) in DCM (0.2 M solution) was added EDCI (1.5 eq.), DMAP (1.5 eq.) and, after one hour under stirring at RT, ethanesulfonamide (1.5 eq.). The mixture was stirred overnight then the solvent removed under reduced pressure and crude purified by preparative RP-HPLC, using H$_2$O (0.1% TFA) and MeCN (+0.1% TFA) as eluents (column: C18). The desired fractions were lyophilized to afford the titled compound as a white powder. $^1$H NMR (400 MHz, DMSO) δ: 14.44 (1H, br. s), 11.51 (1H, s), 10.62 (1H, s), 8.60 (1H, d, J=6.6 Hz), 8.32 (1H, s), 8.16 (1H, s), 8.06 (1H, d, J=8.7 Hz), 8.00-7.92 (2H, m), 7.88 (1H, d, J=8.7 Hz) 7.66-7.54 (2H, m), 7.09 (1H, d, J=8.7 Hz), 6.96 (1H, s), 6.59 (1H, d, J=8.7 Hz), 5.08-5.00 (1H, m), 3.67 (3H, s), 3.54 (2H, app. quart.), 3.33 (2H, q, J=7.4 Hz), 2.31 (3H, s), 2.24 (2H, t, J=7.5 Hz), 2.03-1.83 (2H, m), 1.53-1.12 (6H, m), 1.18 (3H, t, J=7.4 Hz). MS (ES) $C_{34}H_{39}N_5O_5S$ requires: 629, found: 630 (M+H)+.

Example 151

5-(2-Naphthyl)-2-((1S)-8,8,8-trifluoro-1-{[(5-methoxy-2-methyl-1H-indol-3-yl)acetyl]amino}-7-oxooctyl)-1H-imidazol-1-ium trifluoroacetate (Z1)

To a solution of (7S)-7-{[(5-methoxy-2-methyl-1H-indol-3-yl)acetyl]amino}-7-[5-(2-naphthyl)-1H-imidazol-2-yl] heptanoic acid (Free base of Example 107) (1 eq.) in EtOH (0.5 M solution) was added $Na_2CO_3$ (1 eq.). The heterogeneous mixture was stirred 40 min at RT then the solvent was removed under reduced pressure. DCM was added (0.14 M solution), the mixture was cooled at 0° C. with an ice-bath then TFAA (6 eq.) was added followed by pyridine (8 eq.). After 40 min at the same temperature some water was added and the product extracted with DCM. The collected organic phase were treated with brine and dried ($Na_2SO_4$) and after removing the solvent under reduced pressure the crude was purified by preparative RP-HPLC, using $H_2O$ (+0.1% TFA) and MeCN (+0.1% TFA) as eluents (column: C18). The desired fractions were lyophilized to afford the titled compound as a white powder as a mixture of the ketone and hydrated form $^1$H NMR (500 MHz, pyridine) δ: 11.65-11.55 (0.5H, m), 11.50-11.38 (0.5H, m), 9.21-9.12 (0.5H, m), 8.71-8.63 (2H, m), 8.30-8.10 (1.5H, m), 8.00-7.79 (4.5H, m), 7.56-7.30 (4H, m), 7.09-6.97 (1H, m), 5.76-5.62 (1H, m), 4.11-3.96 (1.5, m), 3.85-3.71 (2.5H, m) 2.71-2.58 (1H, m), 2.55-2.41 (3.5H, m), 2.40-2.23 (2H, m), 2.21-2.03 (2H, m), 2.10-1.79 (1.5H, m), 1.70-1.00 (6H, m). MS (ES) $C_{33}H_{33}F_3N_4O_3$ requires: 590, found: 609 (M+H$_2$O+H)+.

Examples 152-298 were made according to the reaction schemes and the processes given in Example 14, 32, 33, 87-89, 107, 108 and 136 to 151.

| Example | Name | (M + H)+ | Procedure from Example Number |
|---|---|---|---|
| 152 | 3-Nitro-N-[7-oxo-1-(4-phenyl-1,3-thiazol-2-yl)octyl]benzenesulfonamide | 488 | 149 |
| 153 | 2-((1S)-7-Amino-1-{[(5-methoxy-2-methyl-1H-indol-3-yl)acetyl]amino}-7-oxoheptyl)-5-(2-naphthyl)-1H-imidazol-1-ium trifluoroacetate | 538 | 325 |
| 154 | 2-((1S)-7-(Dimethylamino)-1-{[(5-methoxy-2-methyl-1H-indol-3-yl)acetyl]amino}-7-oxoheptyl)-5-(2-naphthyl)-1H-imidazol-1-ium trifluoroacetate | 566 | 108 |
| 155 | 2-((1S)-7-(Isopropylamino)-1-{[(5-methoxy-2-methyl-1H-indol-3-yl)acetyl]amino}-7-oxoheptyl)-5-(2-naphthyl)-1H-imidazol-1-ium trifluoroacetate | 580 | 108 |
| 156 | 2-((1S)-7-Anilino-1-{[(5-methoxy-2-methyl-1H-indol-3-yl)acetyl]amino}-7-oxoheptyl)-5-(2-naphthyl)-1H-imidazol-1-ium trifluoroacetate | 614 | 108 |
| 157 | 2-((1S)-7-(Benzylamino)-1-{[(5-methoxy-2-methyl-1H-indol-3-yl)acetyl]amino}-7-oxoheptyl)-5-(2-naphthyl)-1H-imidazol-1-ium trifluoroacetate | 628 | 108 |
| 158 | 2-{(1S)-1-{[(5-Methoxy-2-methyl-1H-indol-3-yl)acetyl]amino}-7-[(methylsulfonyl)amino]-7-oxoheptyl}-5-(2-naphthyl)-1H-imidazol-1-ium trifluoroacetate | 616 | 108 |
| 159 | 1-Methyl-4-[({(1S)-1-[5-(2-naphthyl)-4H-1,2,4-triazol-3-yl]-7-oxononyl}amino)carbonyl]piperidinium trifluoroacetate | 476 | 88 |
| 160 | (3S)-1-Methyl-3-[({(1S)-1-[5-(2-naphthyl)-4H-1,2,4-triazol-3-yl]-7-oxononyl}amino)carbonyl]pyrrolidinium trifluoroacetate | 462 | 88 |
| 161 | (3S)-1-Methyl-3-[({(1S)-1-[5-(2-naphthyl)-4H-1,2,4-triazol-3-yl]-7-oxononyl}amino)carbonyl]piperidinium trifluoroacetate | 476 | 88 |
| 162 | N-{(1S)-1-[5-(2-Naphthyl)-4H-1,2,4-triazol-3-yl]-7-oxononyl}-1,3-thiazole-5-carboxamide | 462 | 88 |
| 163 | 4-Cyano-N-{(1S)-1-[3-(2-naphthyl)-1H-1,2,4-triazol-5-yl]-7-oxononyl}benzenesulfonamide | 516 | 88 |
| 164 | 2-((1S)-7-[Methoxy(methyl)amino]-1-{[(5-methoxy-2-methyl-1H-indol-3-yl)acetyl]amino}-7-oxoheptyl)-5-(2-naphthyl)-1H-imidazol-1-ium trifluoroacetate | 582 | 108 |
| 165 | 1-Methyl-4-[({(1S)-7-(methylamino)-1-[5-(2-naphthyl)-1H-imidazol-1-ium-2-yl]-7-oxoheptyl}amino)carbonyl]piperidinium bis(trifluoroacetate) | 476 | 108 |
| 166 | 4-[({(1S)-7-(Hydroxyamino)-1-[5-(2-naphthyl)-1H-imidazol-1-ium-2-yl]-7-oxoheptyl}amino)carbonyl]-1-methylpiperidinium bis(trifluoroacetate) | 478 | 108 |
| 167 | 2-{(1S)-6-Carboxy-1-[(1,3-thiazol-5-ylcarbonyl)amino]hexyl}-5-(2-naphthyl)-1H-imidazol-1-ium trifluoroacetate | 449 | 107 |

-continued

| Example | Name | (M + H)⁺ | Procedure from Example Number |
|---|---|---|---|
| 168 | 4-[({(1S)-7-[(2-Aminophenyl)amino]-1-[5-(2-naphthyl)-1H-imidazol-1-ium-2-yl]-7-oxoheptyl}amino)carbonyl]-1-methylpiperidinium bis(trifluoroacetate) | 553 | 108 |
| 169 | 2-[(1S)-6-Carboxy-1-({[(3R)-1-methylpyrrolidinium-3-yl]carbonyl}amino)hexyl]-5-(2-naphthyl)-1H-imidazol-1-ium bis(trifluoroacetate) | 449 | 107 |
| 170 | 2-[(1S)-6-Carboxy-1-({[(3S)-1-methylpyrrolidinium-3-yl]carbonyl}amino)hexyl]-5-(2-naphthyl)-1H-imidazol-1-ium bis(trifluoroacetate) | 449 | 107 |
| 171 | 2-((1S)-6-Carboxy-1-{[(dimethylamino)sulfonyl]amino}hexyl)-5-(2-naphthyl)-1H-imidazol-1-ium trifluoroacetate | 445 | 326 |
| 172 | 4-[({(1S)-7-[Methoxy(methyl)amino]-1-[5-(2-naphthyl)-1H-imidazol-1-ium-2-yl]-7-oxoheptyl}amino)carbonyl]-1-methylpiperidinium bis(trifluoroacetate) | 506 | 108 |
| 173 | 2-((1S)-1-{[(5-Methoxy-2-methyl-1H-indol-3-yl)acetyl]amino}-7-oxo-7-{[(trifluoromethyl)sulfonyl]amino}heptyl)-5-(2-naphthyl)-1H-imidazol-1-ium trifluoroacetate | 670 | 150 |
| 174 | 2-((1S)-7-(Ethylamino)-1-{[(5-methoxy-2-methyl-1H-indol-3-yl)acetyl]amino}-7-oxoheptyl)-5-(2-naphthyl)-1H-imidazol-1-ium trifluoroacetate | 566 | 108 |
| 175 | (3S)-3-[({(1S)-1-[3-(3,5-Dichlorophenyl)-1H-1,2,4-triazol-5-yl]-7-oxononyl}amino)carbonyl]-1-methylpyrrolidinium trifluoroacetate | 480 | 88 |
| 176 | 4-[({(1S)-1-[3-(3,5-Dichlorophenyl)-1H-1,2,4-triazol-5-yl]-7-oxononyl}amino)carbonyl]-1-azoniabicyclo[2.2.2]octane trifluoroacetate | 506 | 88 |
| 177 | N-{(1S)-1-[3-(3,5-Dichlorophenyl)-1H-1,2,4-triazol-5-yl]-7-oxononyl}-2-(5-methoxy-2-methyl-1H-indol-3-yl)acetamide | 570 | 88 |
| 178 | 2-(5-Methoxy-2-methyl-1H-indol-3-yl)-N-{(1S)-1-[3-(3-methoxyphenyl)-1H-1,2,4-triazol-5-yl]-7-oxononyl}acetamide | 532 | 88 |
| 179 | 2-(5-Methoxy-2-methyl-1H-indol-3-yl)-N-[7-oxo-1-(4-phenyl-1,3-thiazol-2-yl)octyl]acetamide | 504 | 149 |
| 180 | 2-((1S)-1-{[(5-Methoxy-2-methyl-1H-indol-3-yl)acetyl]amino}-7-oxononyl)-5-(2-naphthyl)-1H-imidazol-3-ium trifluoroacetate | 551 | 1 |
| 181 | 2-{(1S)-1-[(1H-indol-3-ylacetyl)amino]-7-oxononyl}-5-(2-naphthyl)-1H-imidazol-3-ium trifluoroacetate | 507 | 1 |
| 182 | 2-((1S)-1-{[(2-Methyl-1H-indol-3-yl)acetyl]amino}-7-oxononyl)-5-(2-naphthyl)-1H-imidazol-3-ium trifluoroacetate | 521 | 1 |
| 183 | 2-((1S)-1-{[(5-Methoxy-1H-indol-3-yl)acetyl]amino}-7-oxononyl)-5-(2-naphthyl)-1H-imidazol-3-ium trifluoroacetate | 537 | 1 |
| 184 | 2-((1S)-1-{[(5-Bromo-1H-indol-3-yl)acetyl]amino}-7-oxononyl)-5-(2-naphthyl)-1H-imidazol-3-ium trifluoroacetate | 587 | 1 |
| 185 | 2-((1S)-1-{[(5-Fluoro-1H-indol-3-yl)acetyl]amino}-7-oxononyl)-5-(2-naphthyl)-1H-imidazol-3-ium trifluoroacetate | 525 | 1 |
| 186 | 1-[2-({(1S)-1-[5-(2-Naphthyl)-1H-imidazol-3-ium-2-yl]-7-oxononyl}amino)-2-oxoethyl]-1H-benzimidazol-3-ium bis(trifluoroacetate) | 508 | 1 |
| 187 | 2-((1S)-1-{[(7-Methoxy-1-benzofuran-2-yl)carbonyl]amino}-7-oxononyl)-5-(2-naphthyl)-1H-imidazol-3-ium trifluoroacetate | 524 | 1 |
| 188 | 2-((1S)-1-{[(5-Methoxy-1H-indol-2-yl)carbonyl]amino}-7-oxononyl)-5-(2-naphthyl)-1H-imidazol-3-ium trifluoroacetate | 523 | 1 |
| 189 | 2-((1S)-1-{[(5-Fluoro-1H-indol-2-yl)carbonyl]amino}-7-oxononyl)-5-(2-naphthyl)-1H-imidazol-3-ium trifluoroacetate | 511 | 1 |
| 190 | 6-[2-({(1S)-1-[5-(2-Naphthyl)-1H-imidazol-3-ium-2-yl]-7-oxononyl}amino)-2-oxoethyl][1,2,4]triazolo[1,5-a]pyrimidin-4-ium bis(trifluoroacetate) | 510 | 1 |

-continued

| Example | Name | (M + H)⁺ | Procedure from Example Number |
|---|---|---|---|
| 191 | 5-(2-Naphthyl)-2-((1S)-7-oxo-1-{[(4-phenyl-1,3-thiazol-2-yl)acetyl]amino}nonyl)-1H-imidazol-3-ium trifluoroacetate | 551 | 1 |
| 192 | 2-((1S)-1-{[(5-Chloro-1-benzothien-3-yl)acetyl]amino}-7-oxononyl)-5-(2-naphthyl)-1H-imidazol-3-ium trifluoroacetate | 558 | 1 |
| 193 | 2-((1S)-1-{[(4-Chloro-1H-indol-3-yl)acetyl]amino}-7-oxononyl)-5-(2-naphthyl)-1H-imidazol-3-ium trifluoroacetate | 541 | 1 |
| 194 | 5-(2-Naphthyl)-2-((1S)-7-oxo-1-{[(2-oxo-1,3-benzoxazol-3(2H)-yl)acetyl]amino}nonyl)-1H-imidazol-3-ium trifluoroacetate | 525 | 1 |
| 195 | 2-((1S)-1-{[(5-Methoxy-2-oxo-2,3-dihydro-1H-indol-3-yl)acetyl]amino}-7-oxononyl)-5-(2-naphthyl)-1H-imidazol-3-ium trifluoroacetate | 553 | 1 |
| 196 | 2-((1S)-1-{[(6-Methoxy-2-oxo-2,3-dihydro-1H-indol-3-yl)acetyl]amino}-7-oxononyl)-5-(2-naphthyl)-1H-imidazol-3-ium trifluoroacetate | 553 | 1 |
| 197 | 2-Ethyl-1-[3-({(1S)-1-[5-(2-naphthyl)-1H-imidazol-3-ium-2-yl]-7-oxononyl}amino)-3-oxopropyl]-1H-benzimidazol-3-ium bis(trifluoroacetate) | 550 | 1 |
| 198 | 5-(2-Naphthyl)-2-{(1S)-1-[(1-naphthylacetyl)amino]-7-oxononyl}-1H-imidazol-3-ium trifluoroacetate | 518 | 1 |
| 199 | 5-(2-Naphthyl)-2-{(1S)-1-[(2-naphthylacetyl)amino]-7-oxononyl}-1H-imidazol-3-ium trifluoroacetate | 518 | 1 |
| 200 | 5-(2-Naphthyl)-2-((1S)-7-oxo-1-{[(2-oxoquinazolin-1(2H)-yl)acetyl]amino}nonyl)-1H-imidazol-3-ium trifluoroacetate | 536 | 1 |
| 201 | 2-((1S)-1-{[(4-Methyl-1-oxophthalazin-2(1H)-yl)acetyl]amino}-7-oxononyl)-5-(2-naphthyl)-1H-imidazol-3-ium trifluoroacetate | 550 | 1 |
| 202 | 5-(2-Naphthyl)-2-{(1S)-7-oxo-1-[(phenylacetyl)amino]nonyl}-1H-imidazol-3-ium trifluoroacetate | 468 | 1 |
| 203 | 2-((1S)-1-{[(2,6-Dichlorophenyl)acetyl]amino}-7-oxononyl)-5-(2-naphthyl)-1H-imidazol-3-ium trifluoroacetate | 536 | 1 |
| 204 | 2-((1S)-1-{[(2,4-Dichlorophenyl)acetyl]amino}-7-oxononyl)-5-(2-naphthyl)-1H-imidazol-3-ium trifluoroacetate | 536 | 1 |
| 205 | 2-[(1S)-1-({[2-Fluoro-6-(trifluoromethyl)phenyl]acetyl}amino)-7-oxononyl]-5-(2-naphthyl)-1H-imidazol-3-ium trifluoroacetate | 554 | 1 |
| 206 | 2-[(1S)-1-({[2-Fluoro-3-(trifluoromethyl)phenyl]acetyl}amino)-7-oxononyl]-5-(2-naphthyl)-1H-imidazol-3-ium trifluoroacetate | 554 | 1 |
| 207 | 2-[(1S)-1-{[(5-methoxy-2-methyl-1H-indol-3-yl)acetyl]amino}-7-oxo-7-(1,3-thiazol-2-ylamino)heptyl]-5-(2-naphthyl)-1H-imidazol-3-ium trifluoroacetate | 621 | 150 |
| 208 | 2-[(1S)-1-{[(5-methoxy-2-methyl-1H-indol-3-yl)acetyl]amino}-7-oxo-7-(1,3,4-thiadiazol-2-ylamino)heptyl]-5-(2-naphthyl)-1H-imidazol-3-ium trifluoroacetate | 622 | 150 |
| 209 | 2-Methyl-1-[2-({(1S)-1-[5-(2-naphthyl)-1H-imidazol-1-ium-2-yl]-7-oxononyl}amino)-2-oxoethyl]-1H-benzimidazol-3-ium bis(trifluoroacetate) | 522 | 1 |
| 210 | 1-[2-({(1S)-1-[5-(2-Naphthyl)-1H-imidazol-1-ium-2-yl]-7-oxononyl}amino)-2-oxoethyl]-2-(trifluoromethyl)-1H-benzimidazol-3-ium bis(trifluoroacetate) | 576 | 1 |
| 211 | 2-{(1S)-1-[(1H-Indazol-1-ylacetyl)amino]-7-oxononyl}-5-(2-naphthyl)-1H-imidazol-1-ium trifluoroacetate | 508 | 1 |
| 212 | 3-[2-({(1S)-1-[5-(2-Naphthyl)-1H-imidazol-1-ium-2-yl]-7-oxononyl}amino)-2-oxoethyl]quinolinium bis(trifluoroacetate) | 519 | 1 |
| 213 | 2-((1S)-1-{[(Dimethylamino)(oxo)acetyl]amino}-7-oxononyl)-5-(2-naphthyl)-1H-imidazol-1-ium trifluoroacetate | 449 | 1 |

-continued

| Example | Name | (M + H)⁺ | Procedure from Example Number |
|---|---|---|---|
| 214 | 2-{(1S)-1-[(1,2-Benzisoxazol-3-ylacetyl)amino]-7-oxononyl}-5-(2-naphthyl)-1H-imidazol-1-ium trifluoroacetate | 509 | 1 |
| 215 | 2-((1S)-1-{[(2-Methyl-1H-indol-1-yl)acetyl]amino}-7-oxononyl)-5-(2-naphthyl)-1H-imidazol-1-ium trifluoroacetate | 521 | 1 |
| 216 | 2-{(1S)-1-[(1H-1,2,3-Benzotriazol-1-ylacetyl)amino]-7-oxononyl}-5-(2-naphthyl)-1H-imidazol-1-ium trifluoroacetate | 509 | 1 |
| 217 | 2-((1S)-1-{[(5-Cyano-1H-indol-1-yl)acetyl]amino}-7-oxononyl)-5-(2-naphthyl)-1H-imidazol-1-ium trifluoroacetate | 532 | 1 |
| 218 | 2-((1S)-1-{[(Dimethylammonio)acetyl]amino}-7-oxononyl)-5-(2-naphthyl)-1H-imidazol-1-ium bis(trifluoroacetate) | 436 | 1 |
| 219 | 1-Methyl-4-[({(1S)-1-[5-(2-naphthyl)-1H-imidazol-1-ium-2-yl]-7-oxononyl}amino)carbonyl]piperidinium bis(trifluoroacetate) | 475 | 1 |
| 220 | 4-[({(1S)-1-[5-(2-Naphthyl)-1H-imidazol-1-ium-2-yl]-7-oxononyl}amino)carbonyl]-1-azoniabicyclo[2.2.2]octane bis(trifluoroacetate) | 487 | 1 |
| 221 | (7S)-7-{[(5-Methoxy-2-methyl-1H-indol-3-yl)acetyl]amino}-N-methyl-7-[5-(2-naphthyl)-4H-1,2,4-triazol-3-yl]heptanamide | 553 | 144 |
| 222 | 4-[({(1S)-1-[5-(2-Naphthyl)-1,3,4-oxadiazol-2-yl]-7-oxononyl}amino)carbonyl]-1-azoniabicyclo[2.2.2]octane trifluoroacetate | 489 | 136 |
| 223 | 2-Ethyl-1-[3-({(1S)-1-[5-(2-naphthyl)-1,3,4-oxadiazol-2-yl]-7-oxononyl}amino)-3-oxopropyl]-1H-benzimidazol-3-ium trifluoroacetate | 552 | 136 |
| 224 | 6-[2-({(1S)-1-[5-(2-Naphthyl)-1,3,4-oxadiazol-2-yl]-7-oxononyl}amino)-2-oxoethyl][1,2,4]triazolo[1,5-a]pyrimidin-3-ium trifluoroacetate | 512 | 136 |
| 225 | 1-Methyl-4-[({(1S)-1-[5-(2-naphthyl)-1,3,4-oxadiazol-2-yl]-7-oxononyl}amino)carbonyl]piperidinium trifluoroacetate | 477 | 136 |
| 226 | (3R)-1-Methyl-3-[({(1S)-1-[5-(2-naphthyl)-1,3,4-oxadiazol-2-yl]-7-oxononyl}amino)carbonyl]pyrrolidinium trifluoroacetate | 463 | 136 |
| 227 | (4R)-4-[({(1S)-1-[5-(2-Naphthyl)-1H-imidazol-3-ium-2-yl]-7-oxononyl}amino)carbonyl]-2,3,4,9-tetrahydro-1H-beta-carbolin-2-ium bis(trifluoroacetate) | 548 | 1 |
| 228 | (7S)-7-{[(5-Methoxy-2-methyl-1H-indol-3-yl)acetyl]amino}-N-methyl-7-[5-(2-naphthyl)-1,3,4-oxadiazol-2-yl]heptanamide | 554 | 142 |
| 229 | 4-[({(1S)-6-Carboxy-1-[5-(2-naphthyl)-1,3,4-oxadiazol-2-yl]hexyl}amino)carbonyl]-1-methylpiperidinium trifluoroacetate | 465 | 141 |
| 230 | (7S)-7-[5-(2-Naphthyl)-1,3,4-oxadiazol-2-yl]-7-[(1,3-thiazol-4-ylcarbonyl)amino]heptanoic acid | 451 | 141 |
| 231 | 4-[({(1S)-1-[5-(2,3-Dihydro-1,4-benzodioxin-6-yl)-1H-imidazol-3-ium-2-yl]-7-oxononyl}amino)carbonyl]-1-methylpiperidinium bis(trifluoroacetate) | 483 | 1 |
| 232 | 2-(5-Methoxy-2-methyl-1H-indol-3-yl)-N-{(1S)-1-[4-(2-naphthyl)-1,3-oxazol-2-yl]-7-oxononyl}acetamide | 552 | 33 |
| 233 | 2-((1S)-7-(Methylamino)-7-oxo-1-{[(1-pyridin-2-ylpiperidin-3-yl)carbonyl]amino}heptyl)-5-(2-naphthyl)-1H-imidazol-1-ium trifluoroacetate | 539 | 327 |
| 234 | 2-[2-({(1S)-7-(Methylamino)-1-[5-(2-naphthyl)-1H-imidazol-1-ium-2-yl]-7-oxoheptyl}amino)-2-oxoethyl]-2,3-dihydro-1H-isoindolium bis(trifluoroacetate) | 510 | 327 |
| 235 | 2-{(1S)-7-(Methylamino)-7-oxo-1-[(piperidin-1-ylacetyl)amino]heptyl}-5-(2-naphthyl)-1H-imidazol-1-ium trifluoroacetate | 476 | 327 |
| 236 | 4-[({(1S)-7-(Methylamino)-1-[5-(2-naphthyl)-1H-imidazol-1-ium-2-yl]-7-oxoheptyl}amino)carbonyl]-1-azoniabicyclo[2.2.2]octane bis(trifluoroacetate) | 488 | 327 |

-continued

| Example | Name | (M + H)⁺ | Procedure from Example Number |
|---|---|---|---|
| 237 | 5-[({(1S)-7-(Methylamino)-1-[5-(2-naphthyl)-1H-imidazol-1-ium-2-yl]-7-oxoheptyl}amino)carbonyl]-1,2,3,4-tetrahydro-1,8-naphthyridin-1-ium bis(trifluoroacetate) | 511 | 327 |
| 238 | 2-((1S)-7-(Methylamino)-7-oxo-1-{[(5-pyrrolidin-1-yl-2H-tetrazol-2-yl)acetyl]amino}heptyl)-5-(2-naphthyl)-1H-imidazol-1-ium trifluoroacetate | 530 | 327 |
| 239 | 2-{(1S)-7-(Methylamino)-7-oxo-1-[(1,3-thiazol-5-ylcarbonyl)amino]heptyl}-5-(2-naphthyl)-1H-imidazol-1-ium trifluoroacetate | 462 | 327 |
| 240 | 2-((1S)-7-(Methylamino)-1-{[(4-methyl-1,2,3-thiadiazol-5-yl)carbonyl]amino}-7-oxoheptyl)-5-(2-naphthyl)-1H-imidazol-1-ium trifluoroacetate | 477 | 327 |
| 241 | 2-{(1S)-7-(Methylamino)-7-oxo-1-[(pyridin-3-ylcarbonyl)amino]heptyl}-5-(2-naphthyl)-1H-imidazol-1-ium trifluoroacetate | 456 | 327 |
| 242 | 2-{(1S)-7-(Methylamino)-7-oxo-1-[(phenylacetyl)amino]heptyl}-5-(2-naphthyl)-1H-imidazol-1-ium trifluoroacetate | 469 | 327 |
| 243 | (7S)-7-({[(3S)-1-Methylpyrrolidin-3-yl]carbonyl}amino)-7-[5-(2-naphthyl)-1,3,4-oxadiazol-2-yl]heptanoic acid | 451 | 141 |
| 244 | (3S)-3-[({(1S)-6-Carboxy-1-[5-(2-naphthyl)-4H-1,2,4-triazol-3-yl]hexyl}amino)carbonyl]-1-methylpyrrolidinium trifluoroacetate | 450 | 143 |
| 245 | (3S)-3-[({(1S)-7-amino-1-[5-(2-naphthyl)-4H-1,2,4-triazol-3-yl]-7-oxoheptyl}amino)carbonyl]-1-methylpyrrolidinium trifluoroacetate | 449 | 144 |
| 246 | 4-[({(1S)-1-[5-(2,3-Dihydro-1,4-benzodioxin-5-yl)-1H-imidazol-3-ium-2-yl]-7-oxononyl}amino)carbonyl]-1-methylpiperidinium bis(trifluoroacetate) | 483 | 304 |
| 247 | 4-[({(1S)-1-[5-(1,3-Benzothiazol-2-yl)-1H-imidazol-3-ium-2-yl]-7-oxononyl}amino)carbonyl]-1-methylpiperidinium bis(trifluoroacetate) | 482 | 304 |
| 248 | 4-[({(1S)-1-[5-(1-Benzothien-2-yl)-1H-imidazol-3-ium-2-yl]-7-oxononyl}amino)carbonyl]-1-methylpiperidinium bis(trifluoroacetate) | 481 | 304 |
| 249 | 2-[(1S)-1-{[(Benzylamino)carbonyl]amino}-7-(methylamino)-7-oxoheptyl]-5-(2-naphthyl)-1H-imidazol-1-ium trifluoroacetate | 484 | 328 |
| 250 | 2-[(1S)-1-({[(4-Methoxyphenyl)amino]carbonyl}amino)-7-(methylamino)-7-oxoheptyl]-5-(2-naphthyl)-1H-imidazol-1-ium trifluoroacetate | 500 | 328 |
| 251 | 2-[(1S)-1-{[(Cyclopentylamino)carbonyl]amino}-7-(methylamino)-7-oxoheptyl]-5-(2-naphthyl)-1H-imidazol-1-ium trifluoroacetate | 462 | 328 |
| 252 | 2-((1S)-7-(Methylamino)-1-{[(3-nitrophenyl)sulfonyl]amino}-7-oxoheptyl)-5-(2-naphthyl)-1H-imidazol-1-ium trifluoroacetate | 536 | 328 |
| 253 | 2-[(1S)-1-{[(4-Cyanophenyl)sulfonyl]amino}-7-(methylamino)-7-oxoheptyl]-5-(2-naphthyl)-1H-imidazol-1-ium trifluoroacetate | 516 | 328 |
| 254 | 2-[(1S)-7-(Methylamino)-1-({[(3S)-1-methylpyrrolidinium-3-yl]carbonyl}amino)-7-oxoheptyl]-5-(2-naphthyl)-1H-imidazol-1-ium bis(trifluoroacetate) | 462 | 328 |
| 255 | 2-[(1S)-7-(Methylamino)-1-({[(3R)-1-methylpyrrolidinium-3-yl]carbonyl}amino)-7-oxoheptyl]-5-(2-naphthyl)-1H-imidazol-1-ium bis(trifluoroacetate) | 462 | 328 |
| 256 | 2-[(1S)-1-{[(Benzyloxy)carbonyl]amino}-7-(methylamino)-7-oxoheptyl]-5-(2-naphthyl)-1H-imidazol-1-ium trifluoroacetate | 485 | 328 |
| 257 | 1-Methyl-4-[({(1R)-1-[5-(2-naphthyl)-1H-imidazol-1-ium-2-yl]-7-oxononyl}amino)carbonyl]piperidinium bis(trifluoroacetate) | 475 | 1 |
| 258 | (3R)-3-[({(1S)-6-Carboxy-1-[5-(2-naphthyl)-1,3,4-oxadiazol-2-yl]hexyl}amino)carbonyl]-1-methylpyrrolidinium trifluoroacetate | 451 | 141 |
| 259 | 5-Methoxy-N-{(1S)-7-(methylamino)-1-[5-(2-naphthyl)-1,3,4-oxadiazol-2-yl]-7-oxoheptyl}-1H-indole-2-carboxamide | 526 | 142 |

-continued

| Example | Name | (M + H)+ | Procedure from Example Number |
|---|---|---|---|
| 260 | (7S)-7-{[(Benzylamino)carbonyl]amino}-N-methyl-7-[5-(2-naphthyl)-1,3,4-oxadiazol-2-yl]heptanamide | 486 | 142 |
| 261 | 2-((1R)-1-{[(5-Methoxy-2-methyl-1H-indol-3-yl)acetyl]amino}-7-oxononyl)-5-(2-naphthyl)-1H-imidazol-1-ium trifluoroacetate | 551 | 1 |
| 262 | 4-[({(1S)-1-[5-(4-Methoxyquinolin-2-yl)-1H-imidazol-3-ium-2-yl]-7-oxononyl}amino)carbonyl]-1-methylpiperidinium bis(trifluoroacetate) | 506 | 1 |
| 263 | 3-[2-((1S)-1-{[(1-Methylpiperidinium-4-yl)carbonyl]amino}-7-oxononyl)-1H-imidazol-1-ium-5-yl]quinolinium tris(trifluoroacetate) | 476 | 1 |
| 264 | 6-[2-((1S)-1-{[(1-Methylpiperidinium-4-yl)carbonyl]amino}-7-oxononyl)-1H-imidazol-1-ium-5-yl]quinolinium tris(trifluoroacetate) | 476 | 1 |
| 265 | 1-Methyl-4-({[(1S)-7-oxo-1-(5-quinolin-2-yl-1H-imidazol-1-ium-2-yl)nonyl]amino}carbonyl)piperidinium bis(trifluoroacetate) | 476 | 1 |
| 266 | 4-({[(1S)-1-(5-Isoquinolin-3-yl-1H-imidazol-1-ium-2-yl)-7-oxononyl]amino}carbonyl)-1-methylpiperidinium bis(trifluoroacetate) | 476 | 1 |
| 267 | 1-Methyl-N-{1-[2-(2-naphthyl)-1H-imidazol-5-yl]-7-oxononyl}piperidine-4-carboxamide | 475 | 138 |
| 268 | 1-Methyl-N-[7-oxo-1-(3-phenyl-1H-pyrazol-5-yl)nonyl]piperidine-4-carboxamide | 425 | 89 |
| 269 | 2-[(1S)-1-(Acetylamino)-7-oxononyl]-5-(2-naphthyl)-1H-imidazol-1-ium trifluoroacetate | 392 | 1 |
| 270 | 2-((1S)-1-{[(1,3-Dimethylpyrrolidinium-3-yl)carbonyl]amino}-7-oxononyl)-5-(2-naphthyl)-1H-imidazol-1-ium bis(trifluoroacetate) | 475 | 1 |
| 271 | 4-[3-({(1S)-1-[5-(2-Naphthyl)-1H-imidazol-1-ium-2-yl]-7-oxononyl}amino)-3-oxopropyl]thiomorpholin-4-ium 1,1-dioxide bis(trifluoroacetate) | 539 | 1 |
| 272 | 5-(2-Naphthyl)-2-{(1S)-7-oxo-1-[(trifluoroacetyl)amino]nonyl}-1H-imidazol-1-ium trifluoroacetate | 446 | 302 |
| 273 | 2-((1S)-1-{[2-(Dimethylammonio)-2-methylpropanoyl]amino}-7-oxononyl)-5-(2-naphthyl)-1H-imidazol-1-ium bis(trifluoroacetate) | 463 | 1 |
| 274 | 2-((1S)-1-{[(1-Methylazetidinium-3-yl)carbonyl]amino}-7-oxononyl)-5-(2-naphthyl)-1H-imidazol-1-ium bis(trifluoroacetate) | 447 | 1 |
| 275 | 2-[(1S)-1-{[3-(2-Ethyl-1H-benzimidazol-1-yl)propanoyl]amino}-7-(methylamino)-7-oxoheptyl]-5-(2-naphthyl)-1H-imidazol-1-ium trifluoroacetate | 551 | 327 |
| 276 | 6-[2-({(1S)-7-(Methylamino)-1-[5-(2-naphthyl)-1H-imidazol-1-ium-2-yl]-7-oxoheptyl}amino)-2-oxoethyl][1,2,4]triazolo[1,5-a]pyrimidin-3-ium bis(trifluoroacetate) | 511 | 327 |
| 277 | 2-((1S)-7-(Methylamino)-7-oxo-1-{[(2-oxoquinazolin-1(2H)-yl)acetyl]amino}heptyl)-5-(2-naphthyl)-1H-imidazol-1-ium trifluoroacetate | 537 | 327 |
| 278 | 2-((1S)-7-(Methylamino)-7-oxo-1-{[(2-oxo-1,3-benzoxazol-3(2H)-yl)acetyl]amino}heptyl)-5-(2-naphthyl)-1H-imidazol-1-ium trifluoroacetate | 526 | 327 |
| 279 | 1-ethyl-3-[({(1S)-7-(methylamino)-1-[5-(2-naphthyl)-1H-imidazol-1-ium-2-yl]-7-oxoheptyl}amino)carbonyl]piperidinium bis(trifluoroacetate) | 490 | 327 |
| 280 | 2-((1S)-1-{[Methoxy(oxo)acetyl]amino}-7-oxononyl)-5-(2-naphthyl)-1H-imidazol-1-ium trifluoroacetate | 436 | 147 |
| 281 | 2-((1S)-1-{[2-Methyl-2-(methylammonio)propanoyl]amino}-7-oxononyl)-5-(2-naphthyl)-1H-imidazol-1-ium bis(trifluoroacetate) | 449 | 1 |
| 282 | 2-(5-Methoxy-2-methyl-1H-indol-3-yl)-N-[7-oxo-1-(3-phenyl-1H-pyrazol-5-yl)nonyl]acetamide | 501 | 89 |
| 283 | 1-Methyl-4-({[(1S)-7-oxo-1-(5-quinolin-2-yl-1H-imidazol-1-ium-2-yl)nonyl]amino}carbonyl)piperidinium dichloride | 476 | 1 |

-continued

| Example | Name | (M + H)+ | Procedure from Example Number |
|---|---|---|---|
| 284 | 1-Methyl-4-[({(1S)-1-[5-(2-naphthyl)-1H-imidazol-1-ium-2-yl]-7-oxononyl}amino)(oxo)acetyl]piperazin-1-ium bis(trifluoroacetate) | 504 | 1 |
| 285 | 2-((1S)-1-{[Morpholin-4-yl(oxo)acetyl]amino}-7-oxononyl)-5-(2-naphthyl)-1H-imidazol-1-ium trifluoroacetate | 491 | 301 |
| 286 | 2-((1S)-1-{[Amino(oxo)acetyl]amino}-7-oxononyl)-5-(2-naphthyl)-1H-imidazol-1-ium trifluoroacetate | 421 | 1 |
| 287 | 2-((1S)-1-{[3-(Diethylammonio)propanoyl]amino}-7-oxononyl)-5-(2-naphthyl)-1H-imidazol-1-ium bis(trifluoroacetate) | 477 | 1 |
| 288 | 2-((1S)-1-{[3-(Dimethylammonio)propanoyl]amino}-7-oxononyl)-5-(2-naphthyl)-1H-imidazol-1-ium bis(trifluoroacetate) | 449 | 1 |
| 289 | 2-((1S)-1-{[(5-Cyano-1H-indol-3-yl)acetyl]amino}-7-oxooctyl)-5-phenyl-1H-imidazol-1-ium trifluoroacetate | 468 | 1 |
| 290 | 2-{(1S)-1-[(Carboxycarbonyl)amino]-7-oxononyl}-5-(2-naphthyl)-1H-imidazol-1-ium trifluoroacetate | 422 | 300 |
| 291 | 2-{(1S)-1-[(Methylsulfonyl)amino]-7-oxononyl}-5-(2-naphthyl)-1H-imidazol-1-ium trifluoroacetate | 428 | 2 |
| 292 | 2-((1S)-1-{[(Dimethylamino)sulfonyl]amino}-7-oxononyl)-5-(2-naphthyl)-1H-imidazol-1-ium trifluoroacetate | 457 | 3 |
| 293 | 5-methoxy-2-methyl-3-(2-oxo-2-{[(1S)-7-oxo-1-(4-phenylpyridinium-2-yl)nonyl]amino}ethyl)-1H-indolium bis(trifluoroacetate) | 512 | 140 |
| 294 | 2-ethyl-1-(3-oxo-3-{[(1S)-7-oxo-1-(4-phenylpyridinium-2-yl)nonyl]amino}propyl)-1H-3,1-benzimidazol-1-ium bis(trifluoroacetate) | 511 | 140 |
| 295 | 1-Methyl-N-{(1S)-1-[5-(2-naphthyl)-1,3,4-oxadiazol-2-yl]-7-oxononyl}piperidine-4-carboxamide | 477 | 308 |
| 296 | 6-[2-((1S)-1-{[(1-Methylpiperidinium-4-yl)carbonyl]amino}-7-oxononyl)-1H-imidazol-1-ium-5-yl]quinolinium trichloride | 476 | 1 |
| 297 | N-{(1S)-1-[5-(2-Naphthyl)-1,3,4-oxadiazol-2-yl]-7-oxononyl}quinuclidine-4-carboxamide | 489 | 308 |
| 298 | 4-Methoxy-2-[2-((1S)-1-{[(1-methylpiperidinium-4-yl)carbonyl]amino}-7-oxononyl)-1H-imidazol-3-ium-5-yl]quinolinium trichloride | 506 | 1 |

Particular intermediates of the present invention are given in Example 299.

Example 299

| Intermediate 1 | 2-[(1S)-1-Ammonio-6-carboxyhexyl]-5-(2-naphthyl)-1H-imidazol-1-ium bis(trifluoroacetate) | 338 (M + H)+ |
|---|---|---|
| Intermediate 2 | (1S)-1-[3-(2-Naphthyl)-1H-1,2,4-triazol-5-yl]-7-oxononan-1-aminium trifluoroacetate | 351 (M + H)+ |
| Intermediate 3 | tert-Butyl {(1S)-1-[5-(2-naphthyl)-1H-imidazol-2-yl]-7-oxononyl}carbamate | 448 (M + H)+ |
| Intermediate 4 | (1S)-7-Oxo-1-(4-phenylpyridin-2-yl)nonan-1-aminium trifluoroacetate | 311 (M + H)+ |
| Intermediate 5 | 2-[(1S)-1-Ammonio-7-oxooctyl]-5-(2-naphthyl)-1H-imidazol-3-ium bis(trifluoroacetate) | 336 (M + H)+ |
| Intermediate 6 | 2-[(1S)-1-Ammonio-7-oxooctyl]-5-phenyl-1H-imidazol-3-ium bis(trifluoroacetate) | 286 (M + H)+ |

Example 300

2-{(1S)-1-[(Carboxycarbonyl)amino]-7-oxononyl}-5-(2-naphthyl)-1H-imidazol-1-ium trifluoroacetate (AA1)

Methyl ({(1S)-1-[5-(2-naphthyl)-1H-imidazol-2-yl]-7-oxononyl}amino)(oxo)acetate (Prepared as in example 147) was dissolved in THF and a solution of LiOH.H$_2$O (1.05 eq.) in H$_2$O was added and the mixture was then stirred for 1 hr at RT. The reaction was quenched with 1M HCl until pH 5 was reached and then the THF was removed under reduced pressure. The aqueous phase was extracted with DCM (3×); the combined organic phases were washed with brine and then dried (Na$_2$SO$_4$) and concentrated under reduced pressure. The resulting crude was purified by preparative RP-HPLC, using H$_2$O (0.1% TFA) and MeCN (+0.1% TFA) as eluents (column: C18). The desired fractions were lyophilized to afford the titled compound as colorless oil. $^1$H NMR (300 MHz, DMSO-d6) δ: 9.39 (1H, d, J=8.2 Hz), 8.30 (1H, s), 8.11-7.85 (6H, m), 7.58-7.47 (2H, m), 6.88-6.18 (1H, bs), 5.15-5.02 (1H, m), 2.45-2.36 (4H, m), 2.13-1.87 (2H, m), 1.55-1.41 (2H, m), 1.40-1.20 (4H, m), 0.90 (3H, t, J=7.3 Hz). MS (ES) $C_{24}H_{27}N_3O_4$ requires: 421, found: 422 $(M+H)^+$.

Example 301

2-((1S)-1-{[Morpholin-4-yl(oxo)acetyl]amino}-7-oxononyl)-5-(2-naphthyl)-1H-imidazol-1-ium trifluoroacetate (BB1)

A solution of EDC-HCl (1.1 eq.), HOBt (1.1 eq.) and Example 300, AA1 (1 eq.) in DMF was premixed at RT for 1 hr, and then this was added to a solution of morpholine (1 eq.) and $^iPrNEt_2$ (1 eq.) in DMF. The mixture was stirred at RT and the crude was directly purified by preparative RP-HPLC, using $H_2O$ (0.1% TFA) and MeCN (+0.1% TFA) as eluents (column: C18). The desired fractions were lyophilized to afford the titled compound as colorless oil. $^1H$ NMR (400 MHz, DMSO-d6) δ: 9.40 (1H, bs), 8.31 (1H, s), 8.06-7.88 (2H, m), 7.97-7.88 (3H, m), 7.61-7.50 (2H, m), 6.89-6.01 (1H, bs), 5.13-5.04 (1H, m), 3.65-3.58 (4H, m), 3.54-3.48 (4H, m), 2.44-2.36 (4H, m), 2.05-1.89 (2H, m), 1.52-1.41 (2H, m), 1.40-1.21 (4H, m), 0.89 (3H, t, J=7.3 Hz). MS (ES) $C_{28}H_{34}N_4O_4$ requires: 490, found: 491 $(M+H)^+$.

Example 302

5-(2-Naphthyl)-2-{(1S)-7-oxo-1-[(trifluoroacetyl)amino]nonyl}-1H-imidazol-1-ium trifluoroacetate (CC1)

To a solution of Example 147, V2 and $Et_3N$ (1 eq.) in DCM at 0° C. was added TFAA (1 eq.). The reaction mixture was stirred at RT for 1 hr. After removal of the solvent under reduced pressure the resulting crude was purified by preparative RP-HPLC, using $H_2O$ (0.1% TFA) and MeCN (+0.1% TFA) as eluents (column: C18). The desired fractions were lyophilized to afford the titled compound as colorless oil. $^1H$ NMR (400 MHz, CD3CN) δ: 10.67 (1H, d, J=8.0 Hz), 8.42 (1H, s), 8.07-8.01 (1H, m), 8.00-7.93 (2H, m), 7.88-7.81 (1H, m), 7.74 (1H, s), 7.67-7.58 (2H, m), 5.49-5.39 (1H, m), 2.48-2.37 (4H, m), 2.26-2.18 (2H, m), 1.61-1.42 (3H, m), 1.41-1.29 (3H, m), 0.99 (3H, t, J=7.3 Hz). MS (ES) $C_{24}H_{26}F_3N_3O_2$ requires: 445, found: 446 $(M+H)^+$.

Example 303

2-((1S)-1-{[(1-Methylazetidinium-3-yl)carbonyl]amino}-7-oxononyl)-5-(2-naphthyl)-1H-imidazol-3-ium dichloride (DD3)

Step 1: tert-Butyl 3-[({(1S)-1-[5-(2-naphthyl)-1H-imidazol-2-yl]-7-oxononyl}amino)-carbonyl]azetidine-1-carboxylate (DD1)

1-(tert-Butoxycarbonyl)azetidine-3-carboxylic acid (1.2 eq.), EDC-HCl (1.45 eq.) and HOBt (1.4 eq.) were stirred for 5 min in DMF. The resulting clear solution was added to Example 147,V2 and left stirring at RT for 1 hr. The mixture was diluted with DCM and washed with saturated aqueous $NaHCO_3$ solution. The organic phase was separated, dried ($Na_2SO_4$) and concentrated under reduced pressure. The residue was purified by flash chromatography on silica gel, eluting with 1:1 petroleum ether/EtOAc. The combined product fractions were concentrated under reduced pressure and the title compound was obtained as a colourless oil. MS (ES) $C_{31}H_{40}N_4O_4$ requires: 532, found: 533 $(M+H)^+$.

Step 2: N-{(1S)-1-[5-(2-Naphthyl)-1H-imidazol-2-yl]-7-oxononyl}azetidine-3-carboxamide (DD2)

DD1 was dissolved in a 1:1 mixture of DCM and TFA. The mixture was stirred at RT for 20 min then diluted with DCM. The mixture was neutralized with 1M NaOH solution, the organic phase was separated, washed with brine, dried ($Na_2SO_4$), filtered and concentrated to dryness under reduced pressure. The crude title compound was obtained as a colourless oil. MS (ES) $C_{26}H_{32}N_4O_2$ requires: 432, found: 433 $(M+H)^+$.

Step 3: 2-((1S)-1-{[(1-Methylazetidinium-3-yl)carbonyl]amino}-7-oxononyl)-5-(2-naphthyl)-1H-imidazol-3-ium dichloride (DD3)

DD2 was dissolved in MeOH and formaldehyde (15 eq., 37% aq. solution) was added and the mixture was stirred for 4 minutes. NaOAc (3.2 eq.) and $NaBH_3(CN)$ (3.2 eq.) were added and the mixture was stirred for 25 min at RT. The mixture was diluted with DCM and washed with sat. aq. $NaHCO_3$ solution (5x) and brine. The organic phase was dried ($Na_2SO_4$) and concentrated under reduced pressure. The residue was purified by preparative RP-HPLC, using $H_2O$ (0.1% TFA) and MeCN (0.1% TFA) as eluents (column: C18). The desired fractions were concentrated under the reduced pressure in order to remove the MeCN and sat. aq. $NaHCO_3$ solution was added. The solution was extracted with DCM (2x) and the combined organic phases were concentrated under reduced pressure. The residue was lyophilized from 0.1 M aq. HCl/MeCN to yield the title compound as a pale yellow oil. $^1H$ NMR (400 MHz, DMSO-d6) δ: 15.50-14.20 (2H, br, m), 10.61 (0.6H, br. s), 10.09 (0.4H, br. s), 9.21-9.00 (1H, m), 8.59-8.44 (1H, m), 8.17 (1H, s), 8.10-7.86 (4H, m), 7.68-7.50 (2H, m), 5.40-5.20 (1H, m), 4.40-4.16 (2H, m), 4.15-4.03 (1H, m), 4.01-3.84 (1H, m), 3.78-3.65 (1H, m), 2.86-2.71 (3H, m), 2.45-2.34 (4H, m), 2.11-1.83 (2H, m), 1.56-1.18 (6H, m), 0.90 (3H, t, J=7.3 Hz). MS (ES) $C_{27}H_{34}N_4O_2$ requires: 446, found: 447 $(M+H)^+$.

Example 304

2-((1S)-1-{[(5-Methoxy-2-methyl-1H-indol-3-yl)acetyl]amino}-7-oxononyl)-5-[4-(1H-pyrazol-1-yl)phenyl]-1H-imidazol-3-ium trifluoroacetate (EE7)

Step 1: 2,4-Dibromo-1-{[2-(trimethylsilyl)ethoxy]methyl}-1H-imidazole (EE1)

NaH (60%, 1.2 eq) was added portionwise to a solution of 2,4-dibromoimidazole (1 eq.) in THF at 0° C. After 1 hr, SEM-Cl (1.2 eq.) was added and the mixture was stirred at RT for 12 hr. The reaction was carefully quenched with $H_2O$ and the aqueous phase was extracted with EtOAc (3x). The combined organic phase was dried ($MgSO_4$) and concentrated under reduced pressure. Purification by flash chromatography on silica gel eluting with 5-33% EtOAc/pentane yielded the title compound as an oil. $^1H$ NMR (300 MHz, $CDCl_3$) δ: 7.09 (1H, s), 5.22 (2H, s), 3.54 (2H, t, J=8.1 Hz), 0.92 (2H, t, J=8.1 Hz), 0.00 (9H, s). MS (ES) $C_9H_{16}Br_2N_2OSi$ requires: 354/356/358, found: 355/357/359 $(M+H)^+$.

Step 2: (−)-(R)—N-[(1S)-1-(4-bromo-1-{[2-(trimethylsilyl)ethoxy]methyl}-1H-imidazol-2-yl)-6-(2-ethyl-1,3-dioxolan-2-yl)hexyl]-2-methylpropane-2-sulfinamide (EE2)

To solution of EE1 (1 eq) in dry THF at 78° C. under an Ar atmosphere was slowly added a solution of n-BuLi (1.1 eq).

After 30 min a solution of Example 140, O1 in THF was added and the reaction mixture was stirred for 3 hr at −78° C. and then slowly warmed to RT over 2 hr. The reaction was carefully quenched with $H_2O$ (25 mL) and the aqueous phase was extracted with EtOAc (3×). The combined organic phase was dried ($MgSO_4$) and evaporated to dryness under reduced pressure. The analysis of the crude by LC-MS showed a diastereomeric excess of 77%. Purification by flash chromatography on silica gel 1-25% EtOAc/pentane yielded two fractions, the first fraction was a mixture of diastereomers (37% de), while the second fraction was the desired the (R,S)-diastereomer (>95% de). $[\alpha]_D^{25° C.}=-19.0$ (c=2.05 in DCM). $^1$H NMR (300 MHz, CDCl$_3$) δ: 6.88 (1H, s), 5.39 (1H, d, J=11.0 Hz), 5.12 (1H, d, J=11.0 Hz), 4.49 (1H, m), 3.91 (4H, s), 3.74 (1H, d, J=7.5 Hz), 3.50 (2H, t, J=8.3 Hz), 2.06 (2H, m), 1.65-1.51 (6H, m), 1.36-1.19 (4H, m), 1.15 (9H, s), 0.90 (5H, m), 0.00 (9H, s); MS (ES) $C_{24}H_{45}BrN_3O_4SSi$ requires: 579/581, found: 580/582 (M+H)$^+$.

Step 3: (9S)-9-Amino-9-(4-bromo-1-{[2-(trimethyl-silyl)ethoxy]methyl}-1H-imidazol-2-yl)nonan-3-one (EE3)

EE2 was dissolved in 1.2 M HCl in MeOH (ca. 12 eq.) and the mixture was stirred for 30 min at RT and then quenched with sat. aq. $NaHCO_3$ solution. The mixture was extracted with DCM (2×) and the combined organic phases were dried ($Na_2SO_4$), filtered and concentrated to dryness under reduced pressure to yield the crude product as a colourless oil. MS (ES) $C_{18}H_{34}BrN_3O_2Si$ requires: 433, found: 434 (M+H)$^+$.

Step 4: tert-Butyl 5-methoxy-3-(2-methoxy-2-oxoethyl)-2-methyl-1H-indole-1-carboxylate (EE4)

(5-Methoxy-2-methyl-1H-indol-3-yl)acetic acid was dissolved in dry MeOH, amberlyst 15 resin (2.8 parts in weight) was added and the mixture was stirred overnight at RT. The mixture was centrifuged, the supernatant was separated and concentrated to dryness under reduced pressure. The residue was dissolved in DCM and washed with sat. aq. $NaHCO_3$ solution, dried ($Na_2SO_4$) and concentrated to dryness under reduced pressure. The resulting oil was dissolved in MeCN and DMAP (0.2 eq.) and $Boc_2O$ (1.2 eq.) were added and the mixture was stirred for 2 h at RT. The solvent was removed under reduced pressure and the residue was used in the next step without purification. MS (ES) $C_{18}H_{23}NO_5$ requires: 333, found: 334 (M+H)$^+$.

Step 5: [1-(tert-Butoxycarbonyl)-5-methoxy-2-methyl-1H-indol-3-yl]acetic acid (EE5)

EE4 was dissolved in THF/water mixture (1:1) and LiOH (3 eq.) was added and the mixture was stirred for 2 hr. The mixture was acidified with 0.1 M HCl and extracted with DCM. The organic phase was washed with brine, dried ($Na_2SO_4$), filtered and concentrated to dryness under reduced pressure to yield a white solid. $^1$H NMR (300 MHz, DMSO-d6) δ: 12.29 (1H, s), 7.90 (1H, d, J=9.1 Hz), 6.99 (1H, d, J=2.4 Hz), 6.84 (1H, dd, $J_1$=2.4 Hz, $J_2$=9.1 Hz), 3.77 (3H, s), 3.62 (2H, s), 2.46 (3H, s), 1.62 (9H, s). MS (ES) $C_{17}H_{21}NO_5$ requires: 319, found: 320 (M+H)$^+$.

Step 6: tert-Butyl 3-(2-{[(1S)-1-(4-bromo-1-{[2-(trimethylsilyl)ethoxy]methyl}-1H-imidazol-2-yl)-7-oxononyl]amino}-2-oxoethyl)-5-methoxy-2-methyl-1H-indole-1-carboxylate (EE6)

EE5 (1.2 eq.), EDC.HCl (1.3 eq.) and HOBt (1.3 eq.) in DMF were shaken for 5 min and this mixture and DIPEA (1 eq.) was added to EE3. The mixture was left stirring overnight and was then partitioned between DCM and sat. aq. $NaHCO_3$ solution. The organic phase was dried ($Na_2SO_4$), concentrated to dryness under reduced pressure and the residue was purified by flash chromatography on silica gel, eluting with petroleum ether/EtOAc, 3:1. The combined product fractions were concentrated under reduced pressure and the title compound was obtained as a colourless solid. $^1$H NMR (300 MHz, CDCl$_3$) δ: 7.97 (1H, d, J=9.1 Hz), 6.89-6.80 (2H, m), 6.73 (1H, m), 5.99 (1H, d, J=8.85 Hz), 5.58 (1H, d, J=10.8 Hz), 5.17-4.98 (2H, m), 3.78 (3H, s), 3.58-3.42 (4H, m), 2.46 (3H, s), 2.41-2.21 (4H, m), 1.85-1.69 (2H, m), 1.67 (9H, s), 1.50-1.34 (2H, m), 1.25-1.06 (4H, m), 1.01 (3H, t, J=7.5 Hz), 0.94-0.81 (2H, m), −0.02 (9H, s). MS (ES) $C_{35}H_{53}BrN_4O_6Si$ requires: 734, found: 735 (M+H)$^+$.

Step 7: 2-((1S)-1-{[(5-Methoxy-2-methyl-1H-indol-3-yl)acetyl]amino}-7-oxononyl)-5-[4-(1H-pyrazol-1-yl)phenyl]-1H-imidazol-3-ium trifluoroacetate (EE7)

EE6, [4-(1H-pyrazol-1-yl)phenyl]boronic acid (1.5 eq.), dicyclohexyl-(2',6'-dimethoxybiphenyl-2-yl)phosphine (0.25 eq.), Pd(OAc)$_2$ (0.1 eq.) and $K_3PO_4$ (3 eq.) were placed in a chromacoll tube and suspended in degassed n-BuOH. The air was replaced by an argon atmosphere and the closed tube was stirred and heated to 90° C. for 16 hr. The mixture was diluted with DCM, washed with 120 and 1M NaOH, then dried ($Na_2SO_4$) and concentrated to dryness under reduced pressure. The residue was treated with 0.33 M TBAF in THF (3 eq.) and the mixture was heated at 70° C. for 5 hr. It was diluted with DCM and washed with $H_2O$ (3×). After centrifugation for 3 min at 3000 rpm the water phase was removed and the organic phase was concentrated under reduced pressure and the residue was dissolved in DCM/TFA (1:1) and was stirred for 45 min at RT. The solvents were removed under reduced pressure and the residue was partitioned between DCM and sat. aq. $NaHCO_3$ solution. After centrifugation for 3 min at 3000 rpm the aqueous phase was removed and the residue was concentrated to dryness under reduced pressure. The crude deprotected product was purified by preparative RP-HPLC, using $H_2O$ (0.1% TFA) and MeCN (0.1% TFA) as eluents (column: C18). The pooled product fractions were lyophilized and the title compound was obtained as a white solid. $^1$H NMR (300 MHz, CDCl$_3$) δ: 14.23 (1H, br. s), 10.62 (1H, s), 8.59 (1H, d, J=2.2 Hz), 8.54 (1H, d, J=6.6 Hz), 8.06-7.94 (3H, m), 7.93-7.84 (2H, m), 7.79 (1H, s), 7.10 (1H, d, J=11.5 Hz), 7.00-6.95 (1H, m), 6.64-6.56 (2H, m), 5.05-4.94 (1H, m), 3.69 (3H, s), 3.57 (1H, d, J=15.0 Hz), 3.48 (1H, d, J=15.0 Hz), 2.42-2.28 (7H, m), 2.01-1.79 (2H, m), 1.47-1.12 (6H, m), 0.90 (3H, t, J=7.3 Hz). MS (ES) $C_{33}H_{38}N_6O_3$ requires: 566, found: 567 (M+H)$^+$.

Example 305

5-(2-Methoxyquinolin-3-yl)-2-((1S)-1-{[(1-methylazetidinium-3-yl)carbonyl]amino}-7-oxononyl)-1H-imidazol-3-ium bis(trifluoroacetate) (FF5)

Step 1: tert-Butyl 3-({[(1S)-1-(4-bromo-1-{[2-(trimethylsilyl)ethoxy]methyl}-1H-imidazol-2-yl)-7-oxononyl]amino}carbonyl)azetidine-1-carboxylate (FF1)

1-(tert-Butoxycarbonyl)azetidine-3-carboxylic acid (1.2 eq.), EDC HCl (1.45 eq.) and HOBt (1.4 eq.) were stirred for 5 min in DMF. The clear solution was added to Example 304, EE3 and left stirring for 1 hr at RT. The mixture was diluted with DCM and washed with sat. aq. NaHCO$_3$ solution. The organic phase was separated, dried (Na$_2$SO$_4$) and concentrated under reduced pressure. The residue was purified by flash chromatography on silica gel, eluting with 55% EtOAc/petroleum ether, to yield the titled compound as a colourless oil. $^1$H NMR (300 MHz, CDCl$_3$) δ: 6.87 (1H, s), 6.43 (1H, d, J=7.3 Hz), 5.54 (1H, d, J=10.6 Hz), 5.19-5.01 (2H, m), 4.06-3.85 (4H, m), 3.57-3.42 (2H, m), 3.15-3.02 (1H, m), 2.44-2.28 (4H, m), 1.97-1.76 (2H, m), 1.58-1.45 (2H, m), 1.40 (9H, s), 1.33-1.14 (4H, m), 1.01 (3H, t, J=7.3 Hz), 0.96-0.81 (2H, m), −0.02 (9H, s). MS (ES) C$_{27}$H$_{47}$BrN$_4$O$_5$Si requires: 616, found: 617 (M+H)$^+$.

Step 2: N-[(1S)-1-(4-Bromo-1-{[2-(trimethylsilyl)ethoxy]methyl}-1H-imidazol-2-yl)-7-oxononyl]azetidine-3-carboxamide (FF2)

The carbamate (FF1) was dissolved in 20% TFA/DCM and after 20 min toluene was added and the mixture was concentrated under reduced pressure. The residue was diluted with DCM and washed with sat. aq. NaHCO$_3$ solution. The aqueous phase was extracted with DCM and the combined organics were dried (Na$_2$SO$_4$) and concentrated to dryness under reduced pressure to yield the amine as a colourless oil. MS (ES) C$_{22}$H$_{39}$BrN$_4$O$_3$Si requires: 516, found: 517 (M+H)$^+$.

Step 3: N-[(1S)-1-(4-Bromo-1-{[2-(trimethylsilyl)ethoxy]methyl}-1H-imidazol-2-yl)-7-oxononyl]-1-methylazetidine-3-carboxamide (FF3)

The title compound was prepared according to the procedure in Example 303, step 3 to yield the crude product which was used without purification by preparative RP-HPLC. MS (ES) C$_{23}$H$_{41}$BrN$_4$O$_3$Si requires: 530, found: 531 (M+H)$^+$.

Step 4: (2-Methoxyquinolin-3-yl)boronic acid (FF4)

(2-Fluoroquinolin-3-yl)boronic acid was dissolved in 1.25M HCl in MeOH and stirred for 1 hr at RT. The mixture was quenched with sat. aq. NaHCO$_3$ solution and the mixture was extracted with DCM (3×). The organics were dried (Na$_2$SO$_4$) and concentrated under reduced pressure to yield the crude product as a pale yellow solid which was used in the next step without further purification. MS (ES) C$_{10}$H$_{10}$BNO$_3$ requires: 203, found: 204 (M+H)$^+$.

Step 5: 5-(2-Methoxyquinolin-3-yl)-2-((1S)-1-{[(1-methylazetidinium-3-yl)carbonyl]amino}-7-oxononyl)-1H-imidazol-3-ium bis(trifluoroacetate) (FF5)

A mixture of the bromide (FF3) and the boronic acid (FF4) (1.5 eq.), dicyclohexyl-(2',6'-dimethoxybiphenyl-2-yl)phosphine (0.25 eq.), Pd(OAc)$_2$ (0.1 eq.) and K$_3$PO$_4$ (3 eq.) in n-BuOH in a chromacoll tube was degassed. The air was replaced by an Ar atmosphere and the closed tube was heated with stirring at 90° C. for 2 hr. The mixture was diluted with DCM, washed with sat. aq. NaHCO$_3$ solution, dried (Na$_2$SO$_4$) and concentrated to dryness under reduced pressure. The residue was dissolved in DCM/TFA (1:1) and the mixture was stirred for 5 hr at RT. Toluene was added and the mixture was concentrated under reduced pressure, the residue was diluted with DCM and washed with sat. aq. NaHCO$_3$ solution. The aqueous phase was extracted with DCM and the organics were dried (Na$_2$SO$_4$), filtered and concentrated to dryness under reduced pressure. The residue was purified by preparative RP-HPLC, using H$_2$O (0.1% TFA) and MeCN (0.1% TFA) as eluents (column: C18) and the desired fractions were lyophilized to yield the title compound was obtained as a colourless oil. $^1$H NMR (400 MHz, DMSO-d6) δ: 9.78 (1H, br. s), 8.80 (1H, br. s), 8.70 (1H, s), 7.93 (1H, d, J=7.6 Hz), 7.81 (2H, d, J=8.1 Hz), 7.72-7.64 (1H, m), 7.51-7.44 (1H, m), 5.08-4.98 (1H, m), 4.41-4.27 (1H, m), 4.26-4.17 (1H, m), 4.14 (3H, s), 4.13-4.04 (1H, m), 3.97-3.87 (1H, m), 3.67-3.55 (1H, m), 2.81 (3H, s), 2.43-2.35 (4H, m), 2.03-1.77 (2H, m), 1.52-1.41 (2H, m), 1.40-1.19 (4H, m), 0.89 (3H, t, J=7.2 Hz). MS (ES) C$_{27}$H$_{35}$N$_5$O$_3$ requires: 477, found: 478 (M+H)$^+$.

Example 306

2-((1S)-1-{[3-(Dimethylammonio)propanoyl]amino}-7-oxononyl)-5-(2-naphthyl)-1H-imidazol-3-ium dichloride (GG1)

A solution of N,N-dimethyl-β-alanine hydrochloride (1.25 eq.), TBTU (1.25 eq.) and DIPEA (2.5 eq.) in DCM was added to Example 147, V2 and was stirred at RT for 1 hr. The mixture was diluted with DCM and washed with sat. aq. NaHCO$_3$ solution, the organic phase was dried (Na$_2$SO$_4$) and concentrated to dryness under reduced pressure. The resulting residue was dissolved in THF, polymer-bound tetralkylammonium carbonate (2.5 mmol/g, 10 eq.) was added and the mixture was shaken for 12 hr. After filtration of the polymer and evaporation of the solvent under reduced pressure the desired material was isolated by preparative RP-HPLC, using H$_2$O (+0.1% TFA) and MeCN (+0.1% TFA) as eluents (C18 column). The desired fractions were concentrated under reduced pressure to remove the MeCN and sat. aq. NaHCO$_3$ solution was added. The aqueous phase was extracted with DCM (2×) and the combined organic phases were concentrated under reduced pressure. The residue was lyophilized from 0.1 M aq. HCl/MeCN to obtain the desired compound as a pale yellow hydroscopic solid. $^1$H NMR (400 MHz, DMSO-d6) δ: 15.70-14.60 (1H, br. m), 10.53 (1H, br. s), 9.09 (1H, d, J=6.4 Hz), 8.58 (1H, s), 8.19 (1H, s), 8.07-7.90 (4H, m), 7.63-7.54 (2H, m), 5.19-5.10 (1H, m), 3.37-3.26 (2H, m), 2.94-2.73 (3H, m), 2.74 (6H, s), 2.44-2.36 (4H, m), 2.09-1.88 (2H, m), 1.51-1.21 (6H, m), 0.89 (3H, t, J=7.3 Hz). $^{13}$C NMR (100 MHz, DMSO-d6) δ: 211.3, 170.3, 149.5, 133.1, 133.0, 129.2, 128.4, 128.2, 127.5, 127.3, 124.9, 124.7, 123.6, 115.6, 52.8, 46.8, 42.5, 41.7, 35.3, 33.2, 30.1, 28.4, 25.4, 23.4, 8.1. MS (ES) C$_{27}$H$_{36}$N$_4$O$_2$ requires: 448, found: 449 (M+H)$^+$.

Example 307

4-Methoxy-2-[2-((1S)-1-{[(1-methylazetidinium-3-yl)carbonyl]amino}-7-oxononyl)-1H-imidazol-1-ium-5-yl]quinolinium trichloride (HH7)

Step 1: 2-Chloro-1-(4-methoxyquinolin-2-yl)ethanone (HH1)

To a solution of 4-methoxyquinoline-2-carboxylic acid and DMF (50 µL) in DCM at 0° C. was added dropwise oxalyl chloride (1.2 eq). The cooling bath was removed and the mixture was stirred for 2 hr at RT, then the solvent was removed under reduced pressure. The residue was dissolved in THF/MeCN (1:1) and cooled to 0° C., a pre-cooled solution (0° C.) of TMSCHN$_2$ (1.2 eq) and Et$_3$N (1.2 eq) was added dropwise and the resulting mixture was stirred for 2 hr at 0° C.

An excess of 2M HCl solution in Et₂O was added and the reaction was stirred for further hour at 0° C. and then partitioned between sat. aq. NaHCO₃ solution and DCM. The organic phase was separated, dried (Na₂SO₄), and concentrated under reduced pressure to afford a dark brown solid which was used as such in the next step. ¹H NMR (300 MHz, CDCl₃) δ: 8.47 (1H, d, J=8.0 Hz), 8.09 (1H, d, J=8.4 Hz), 7.81-7.73 (1H, m), 7.66-7.58 (1H, m), 7.51 (1H, s), 5.31 (2H, s), 4.13 (3H, s). MS (ES) C$_{12}$H$_{10}$ClNO$_2$ requires: 235, found: 236 (M+H)⁺.

Step 2: 2-(4-Methoxyquinolin-2-yl)-2-oxoethyl (2S)-2-[(tert-butoxycarbonyl)amino]-8-oxodecanoate (HH2)

A solution of (2S)-2-[(tert-butoxycarbonyl)amino]-8-oxodecanoic acid (1 eq.) and Cs₂CO₃ (0.5 eq) in EtOH was stirred for 30 min at RT and then concentrated under reduced pressure. The resulting residue was diluted in DMF and HH1 (1 eq.) was slowly added during a period of 15 min. The mixture was stirred for 1 h at RT and then the solvent was evaporated under reduced pressure. The resulting crude was purified by chromatography on silica gel eluting with 80% EtOAc/petroleum ether to obtain the product as orange oil. MS (ES) C$_{27}$H$_{36}$N$_2$O$_7$ requires: 500, found: 501 (M+H)⁺.

Step 3: tert-Butyl {(1S)-1-[5-(4-methoxyquinolin-2-yl)-1H-imidazol-2-yl]-7-oxononyl}carbamate (HH3)

A mixture of the ester (HH2) and NH₄OAc (20 eq) were suspended in xylene and heated in a microwave oven at 160° C. for 180 sec. The mixture was diluted with DCM and washed with sat. aq. NaHCO₃ solution. The organic phase was dried (Na₂SO₄), filtered and concentrated under reduced pressure and the resulting brown oil was purified by chromatography on silica gel eluting with 2.5% MeOH/DCM to obtain the imidazole as orange oil. MS (ES) C$_{27}$H$_{36}$N$_4$O$_4$ requires: 480, found: 481 (M+H)⁺.

Step 4: (9S)-9-Amino-9-[5-(4-methoxyquinolin-2-yl)-1H-imidazol-2-yl]nonan-3-one (HH4)

The imidazole (HH3) was dissolved in TFA/DCM (1:1) and the mixture was stirred for an hour at RT. The solvents were removed under reduced pressure and the residue was partitioned between sat. aq. NaHCO₃ solution and DCM. The organic phase was separated, dried (Na₂SO₄) and concentrated under reduced pressure to yield the amine which was used without further purification. MS (ES) C$_{22}$H$_{28}$N$_4$O$_2$ requires: 380, found: 381 (M+H)⁺.

Step 5: tert-Butyl 3-[({(1S)-1-[5-(4-methoxyquinolin-2-yl)-1H-imidazol-2-yl]-7-oxononyl}amino)carbonyl]azetidine-1-carboxylate (HH5)

The amine (HH4) (1 eq.) was added to a clear solution of EDC-HCl (1.45 eq), HOBt (1.41 eq) and 1-(tert-butoxycarbonyl)azetidine-3-carboxylic acid (1.24 eq) in DMF. The mixture was stirred at RT for 30 min and was diluted with DCM and washed with 1N NaOH solution (2×). The organic phase was dried (Na₂SO₄), filtered and concentrated under reduced pressure and the resulting crude was used without further purification. MS (ES) C$_{31}$H$_{41}$N$_5$O$_5$ requires: 563, found: 564 (M+H)⁺.

Step 6: N-{(1S)-1-[5-(4-methoxyquinolin-2-yl)-1H-imidazol-2-yl]-7-oxononyl}azetidine-3-carboxamide (HH6)

The amide (HH5) was dissolved in a mixture of DCM/TFA (1:1) and the mixture was stirred at RT for 1 hr and was then diluted with DCM and the solvents were removed under reduced pressure. The residue was partitioned between sat. aq. NaHCO₃ solution and DCM, then separated and the organic phase was dried (Na₂SO₄), filtered and concentrated under reduced pressure to afford the crude amine was used without further purification. MS (ES) C$_{26}$H$_{33}$N$_5$O$_3$ requires: 463, found: 464 (M+H)⁺.

Step 7: 4-Methoxy-2-[2-((1S)-1-{[(1-methylazetidinium-3-yl)carbonyl]amino}-7-oxononyl)-1H-imidazol-1-ium-5-yl]quinolinium trichloride (HH7)

The amine (HH6) was dissolved in MeOH, formaldehyde (15 eq., 37% aq. solution) was added and the mixture was stirred for 4 min. NaOAc (3.2 eq.) and NaBH₃(CN) (3.2 eq.) were added and the mixture was stirred for 25 min at RT. The mixture was diluted with DCM and washed sat. aq. NaHCO₃ solution (5×) and brine. The organic phase was dried (Na₂SO₄) and concentrated under reduced pressure. The residue was purified by preparative RP-HPLC, using H₂O (0.1% TFA) and MeCN (0.1% TFA) as eluents (column: C18). After lyophilization of the pooled product fractions, the resulting TFA salt was dissolved in some drops of water and was partitioned between sat. aq. NaHCO₃ solution and DCM; the aqueous phase was extracted with DCM (2×) and the combined organic extracts were dried (Na₂SO₄) and concentrated under reduced pressure. The residue was then lyophilized from 0.1N HCl (aq.) and MeCN to yield the title compound was as a pale yellow hydroscopic solid. ¹H NMR (400 MHz, D₂O) δ: 8.39 (1H, d, J=8.3 Hz), 8.28 (1H, s), 8.12-8.01 (2H, m), 7.84-7.77 (1H, m), 7.59 (1H, s), 5.14-5.08 (1H, m), 4.68-4.55 (1H, m), 4.54-4.46 (1H, m), 4.37 (3H, s), 4.32-4.20 (1H, m), 4.18-4.09 (1H, m), 3.88-3.78 (1H, m), 3.02-2.98 (3H, m), 2.59-2.50 (4H, m), 2.11-1.97 (2H, m), 1.63-1.53 (2H, m), 1.50-1.28 (4H, m), 0.97 (3H, t, J=7.3 Hz). MS (ES) C$_{27}$H$_{35}$N$_5$O$_3$ requires: 477, found: 478 (M+H)⁺.

Example 308

N-{(1S)-1-[5-(2-Naphthyl)-1,3,4-oxadiazol-2-yl]-5-oxoheptyl}quinuclidine-4-carboxamide (H2)

Step 1: tert-Butyl ((1S)-1-{[2-(2-naphthoyl)hydrazino]carbonyl}-7-oxononyl)carbamate (II1)

A solution of EDC.HCl (1.4 eq.), HOBt (1.4 eq.) and (2S)-2-[(tert-butoxycarbonyl)amino]-8-oxodecanoic acid in DMF (0.5 M) was premixed at RT for 10 min, and then a solution of 2-naphthohydrazide (1 eq) in DMF (1 M) was added. The mixture was stirred for 16 hr at RT and then it was diluted in DCM, washed with 0.1 M HCl solution and brine. The solution was dried (Na₂SO₄), concentrated under reduced pressure and the crude product was purified by chromatography on silica gel eluting with 1% MeOH/DCM to obtain the desired hydrazide. ¹H NMR (300 MHz, CDCl₃, 300 K) δ9.64 (1H, broad s), 9.44 (1H, broad s), 8.36 (1H, s), 7.86-7.81 (4H, m), 7.57-7.46 (2H, m), 5.36 (1H, d, J=7 Hz), 4.39-4.36 (1H, m), 2.41-2.32 (4H, m), 1.90-1.84 (1H, m), 1.72-1.66 (1H, m), 1.56-1.28 (15H, m), 1.02 (3H, t, J=7.5 Hz). MS (ES) C$_{26}$H$_{35}$N$_3$O$_5$ required: 469, found: 470 (M+H⁺).

Step 2: N-{(1S)-1-[5-(2-naphthyl)-1,3,4-oxadiazol-2-yl]-5-oxoheptyl}quinuclidine-4-carboxamide (II2)

The hydrazide (II1) was converted to the corresponding oxadiazole and the Boc-protecting group removed following procedures in Example 136, steps 3 and 4 then the resulting amine (1 eq) was treated with quinuclidine-4-carboxylic acid (2.7 eq), TBTU (3.2 eq) and DIPEA (6.3 eq) in DMF and was stirred overnight at RT. The product was isolated by preparative RP-HPLC, using $H_2O$ (+0.1% TFA) and MeCN (+0.1% TFA) as eluents (column: C18). The desired fractions were basified with a sat. aq. $NaHCO_3$ solution and extracted with EtOAc. The EtOAc phase was dried ($Na_2SO_4$) and concentrated under reduced pressure to obtain the desired product as a white powder. $^1$H NMR (400 MHz, DMSO-d6, 300 K) δ: 8.55 (1H, s), 8.16-8.13 (2H, m), 8.04-8.01 (3H, m), 7.69-6.63 (2H, m), 5.21-5.16 (1H, m), 2.76 (6H, t, J=7.5 Hz), 2.43-2.38 (4H, m), 2.05-1.90 (2H, m), 1.63 (6H, t, J=7.5 Hz), 1.51-1.23 (6H, m), 0.91 (3H, t, J=7.2 Hz). MS (ES) $C_{29}H_{36}N_4O_3$ required: 488, found: 489 (M+H)$^+$.

Example 309

N-{(1S)-1-[5-(4-Methoxyquinolin-2-yl)-1,3,4-oxadiazol-2-yl]-7-oxononyl}-1-methylazetidine-3-carboxamide (JJ3)

Step 1: 4-Methoxyquinoline-2-carbohydrazide (JJ1)

The methyl 4-methoxyquinoline-2-carboxylate (1 eq) was dissolved in i-PrOH (0.75 M) and then hydrazine monohydrate (10 eq) was added. The reaction mixture was heated at 80° C. overnight and then the solvent was evaporated under reduced pressure and the crude product was used in the next step without purification. MS (ES) $C_{11}H_{11}N_3O_2$ required: 217, found: 218 (M+H)$^+$.

Step 2: (9S)-9-Amino-9-[5-(4-methoxyquinolin-2-yl)-1,3,4-oxadiazol-2-yl]nonan-3-one (JJ2)

The title compound was prepared as described in Example 308, steps 1 and 2, starting from hydrazide (JJ1) and (2S)-2-[(tert-butoxycarbonyl)amino]-8-oxodecanoic acid and was obtained as brown oil. $^1$H NMR (300 MHz, CDCl$_3$, 300 K) δ: 8.23 (1H, d, J=8.2 Hz), 8.15 (1H, d, J=8.4 Hz), 7.77 (1H, t, J=8.4 Hz), 7.68 (1H, s), 7.59 (1H, t, J=8.2 Hz), 4.36 (1H, t, J=7 Hz), 4.15 (3H, s), 2.43-2.36 (6H, m), 2.16-1.88 (2H, m), 1.65-1.32 (6H, m), 1.03 (3H, t, J=7.3 Hz). MS (ES) $C_{21}H_{26}N_4O_3$ required: 382, found: 383 (M+H)$^+$.

Step 3: N-{(1S)-1-[5-(4-Methoxyquinolin-2-yl)-1,3,4-oxadiazol-2-yl]-7-oxononyl}-1-methylazetidine-3-carboxamide (JJ3)

The title compound was prepared as described in Example 303, steps 1-3, from crude amine (JJ2). The after preparative HPLC purification the desired fractions were basified with a sat. aq. $NaHCO_3$ solution. The aqueous phase was extracted with DCM, the organic phase was dried ($Na_2SO_4$) and concentrated under reduced pressure to obtain the desired product as a white powder. $^1$H NMR (400 MHz, DMSO-d6, 300 K) δ: 8.64 (1H, d, J=7.7 Hz), 8.21 (1H, d, J=8.1 Hz), 8.09 (1H, d, J=8.3 Hz), 7.87 (1H, t, J=7.2 Hz), 7.70 (2H, m), 5.22-5.20 (1H, m), 4.17 (3H, s), 3.50-3.00 (5H, m), 2.43-2.37 (4H, m), 2.17 (3H, s), 2.00-1.80 (2H, m), 1.50-1.20 (6H, m), 0.89 (3H, t, J=7.2 Hz). MS (ES) $C_{26}H_{33}N_5O_4$ required: 479, found: 480 (M+H)$^+$.

Example 310

5-(Hydroxymethyl)-2-(1-{[(5-methoxy-2-methyl-1H-indol-3-yl)acetyl]amino}-7-oxononyl)-1H-imidazol-1-ium trifluoroacetate (KK6)

Step 1: 4-({[tert-Butyl(dimethyl)silyl]oxy}methyl)-1-{[2-(trimethylsilyl)ethoxy]methyl}-1H-imidazole-2-carbaldehyde (KK1)

To a stirred solution of 4-({[tert-butyl(dimethyl)silyl]oxy}methyl)-1-{[2-(trimethylsilyl)ethoxy]methyl}-1H-imidazole (See WO03/022274) (1 eq) in THF at 40° C. was added dropwise a solution of BuLi (2 eq.) in hexanes and the mixture was stirred at 40° C. for a further 30 min. DMF (4 eq.) was then added and the cooling bath was removed and the reaction mixture was allowed to warm to RT and stirred for 30 min, after which time it was quenched by addition of a sat. aq. $NH_4Cl$ solution. The organics were extracted with EtOAc (2×), washed with brine, dried ($Na_2SO_4$) and concentrated under reduced pressure. The material was purified by column chromatography on silica eluting with 15% EtOAc/petroleum ether. $^1$H NMR (300 MHz, CDCl$_3$) δ: 9.81 (1H, s), 7.30 (1H, s), 5.95 (2H, s), 4.87, (2H, s), 3.58 (2H, t, J=7.7 Hz), 1.05-0.85 (20H, m), 0.05 (6H, s).

Step 2: 1-(4-({[tert-Butyl(dimethyl)silyl]oxy}methyl)-1-{[2-(trimethylsilyl)ethoxy]methyl}-1H-imidazol-2-yl)-6-(2-ethyl-1,3-dioxolan-2-yl)hexan-1-ol (KK2)

To a stirred solution of the 2-ethyl-2-(5-iodopentyl)-1,3-dioxolane (1.5 eq) in Et$_2$O at −78° C. was added dropwise a solution of tert-BuLi (3 eq.) in hexanes and the mixture was stirred at −40° C. for a further 30 min. A solution of the aldehyde (KK1) (1 eq.) in Et$_2$O was added in one portion and then after 5 min the cooling bath was removed and the reaction was allowed to warm to RT and stirred at RT for 1 hour. The reaction was quenched by addition of a sat. aq. $NH_4Cl$ solution and separated. The aqueous layer was extracted with EtOAc (2×), then the combined organic fractions were washed with brine, dried ($Na_2SO_4$) and concentrated under reduced pressure. The material was purified by column chromatography on silica eluting with 50-70% EtOAc/petroleum ether. $^1$H NMR (300 MHz, CDCl$_3$) δ: 6.85 (1H, s), 5.45 (1H, d, J=10.0 Hz), 5.38 (1H, d, J=10.0 Hz), 4.82-4.65 (4H, m), 3.98-3.85 (4H, m), 3.55 (2H, t, J=7.7 Hz), 2.00-1.88 (1H, m), 1.70-1.30 (1H, m), 0.97-0.82 (14H, m), 0.10-0.00 (15H, s).

Step 3: 1-(4-({[tert-Butyl(dimethyl)silyl]oxy}methyl)-1-{[2-(trimethylsilyl)ethoxy]methyl}-1H-imidazol-2-yl)-6-(2-ethyl-1,3-dioxolan-2-yl)hexan-1-azide (KK3)

To a stirred solution of the substrate (KK2) (1 eq.) and DBU (1.5 eq) in toluene was added DPPA (1.5 eq) and the mixture was stirred at RT for 18 hours. The mixture was diluted with Et$_2$O and washed with sat. aq. $NaHCO_3$ solution and brine, then dried ($Na_2SO_4$) and concentrated under reduced pressure. The material was purified by column chromatography on silica eluting with 25% EtOAc/petroleum ether.

$^1$H NMR (300 MHz, CDCl$_3$) δ: 6.91 (1H, s), 5.45 (1H, d, J=10.0 Hz), 5.39 (1H, d, J=10.0 Hz), 4.72 (2H, s), 4.39 (1H, t, J=5.5 Hz), 3.95 (4H, app. s), 3.58 (2H, t, J=7.7 Hz), 2.22-2.05 (2H, m), 1.70-1.30 (10H, m), 0.97-0.82 (14H, m), 0.10-0.00 (15H, s).

Step 4: N-[1-(4-({[tert-Butyl(dimethyl)silyl]oxy}methyl)-1-{[2-(trimethylsilyl)ethoxy]methyl}-1H-imidazol-2-yl)-6-(2-ethyl-1,3-dioxolan-2-yl)hexyl]-2-(5-methoxy-2-methyl-1H-indol-3-yl)acetamide (KK4)

To a solution of the azide (KK3) (1 eq.) in THF was added PPh$_3$ (1.2 eq) and the mixture was stirred at RT for 60 hours, then H$_2$O (0.25 volumes) was added and the reaction was warmed at 45° C. for 24 hours. The THF was removed under reduced pressure and then the organics were extracted with EtOAc, washed with brine and concentrated under reduced pressure to yield 1-(4-({[tert-butyl(dimethyl)silyl]oxy}methyl)-1-{[2-(trimethylsilyl)ethoxy]methyl}-1H-imidazol-2-yl)-6-(2-ethyl-1,3-dioxolan-2-yl)hexan-1-amine, MS (ES) C$_{27}$H$_{55}$N$_3$O$_4$Si$_2$ required: 541, found: 542 (M+H)$^+$.

DMF was added to the crude mixture followed by (5-methoxy-2-methyl-1H-indol-3-yl)acetic acid (1.5 eq.), EDCI (1.5 eq.), HOBt (1.5 eq) and Et$_3$N (2.5 eq) and the mixture was stirred for 24 hours. Xylene was added to the reaction and the mixture was concentrated under reduced pressure. The residue was taken up in EtOAc and was washed with sat. aq. NaHCO$_3$ solution and brine, then dried (Na$_2$SO$_4$) and concentrated under reduced pressure. The mixture was purified by column chromatography on silica eluting with 60-75% EtOAc/petroleum ether to yield the desired amide. $^1$H NMR (400 MHz, CDCl$_3$) δ: 7.88 (1H, s), 7.16 (1H, d, J=8.8 Hz), 6.85 (1H, d, J=1.5 Hz), 6.80 (2H, m), 5.60 (1H, d, J=10.4 Hz), 5.32 (1H, d, J=10.4 Hz), 5.24 (1H, q, J=8.8 Hz), 4.69 (1H, d, J=12.8 Hz), 4.65 (1H, d, J=12.8 Hz), 3.98 (4H, app. s), 3.80 (3H, s), 3.66-3.48 (4H, s), 2.31 (3H, s), 1.87-1.48 (8H, m), 1.30-1.10 (6H), 0.97-0.82 (12H), 0.08-0.00 (15H, m). MS (ES) C$_{39}$H$_{66}$N$_4$O$_6$Si$_2$ required: 742, found: 743 (M+H)$^+$.

Step 5: N-{6-(2-Ethyl-1,3-dioxolan-2-yl)-1-[5-(hydroxymethyl)-1H-imidazol-2-yl]hexyl}-2-(5-methoxy-2-methyl-1H-indol-3-yl)acetamide (KK5)

The amide (KK4) was dissolved in THF and 1 M TBAF solution in THF (2.5 eq.) was added. The mixture was heated at 65° C. overnight and then was quenched by addition of H$_2$O and the product extracted in DCM. The organic phase were washed with brine and dried (Na$_2$SO$_4$) and concentrated under reduced pressure to obtain the desired intermediate. MS (ES) C$_{27}$H$_{38}$N$_4$O$_5$ requires: 498, found: 499 (M+H)$^+$.

Step 6: 5-(Hydroxymethyl)-2-(1-{[(5-methoxy-2-methyl-1H-indol-3-yl)acetyl]amino}-7-oxononyl)-1H-imidazol-1-ium trifluoroacetate (KK6)

A solution of the alcohol (KK5) in THF was treated with 1M HCl solution (4 eq.) and was stirred at RT for 4 hr. The mixture neutralized with 1 M NaOH and concentrated under reduced pressure. The mixture was purified by preparative RP-HPLC, using H$_2$O (+0.1% TFA) and MeCN (+0.1% TFA) as eluents (column: C18) and the desired fractions were lyophilized to afford the titled compound. $^1$HNMR (300 MHz, CD$_3$CN) δ: 9.00-8.90 (1H, s), 8.15-8.00 (1H, d, J=7.0 Hz), 7.28-7.18 (1H, d, J=7.0 Hz), 7.15-7.05 (1H, s), 7.00-6.90 (1H, s), 6.70 (1H, d, J=7.0 Hz), 5.16 (1H, q, J=7.0 Hz), 4.55 (2H, s), 3.78 (3H, s), 3.67 (1H, d, J=10.0 Hz), 3.60 (1H, d, J=10.0 Hz), 2.70-2.20 (7H, m), 1.90-1.20 (8H, m), 1.00-0.75 (3H, t J=7.0 Hz). MS (ES) C$_2$H$_{34}$N$_4$O$_4$ requires: 454, found: 455 (M+H)$^+$.

Example 311

4-{[2-(1-{[(5-Methoxy-2-methyl-1H-indol-3-yl)acetyl]amino}-7-oxononyl)-1H-imidazol-1-ium-5-yl]methyl}morpholin-4-ium bis(trifluoroacetate) (LL2)

Step 1: N-[6-(2-Ethyl-1,3-dioxolan-2-yl)-1-(5-formyl-1H-imidazol-2-yl)hexyl]-2-(5-methoxy-2-methyl-1H-indol-3-yl)acetamide (LL1)

To a stirred solution of the alcohol Example 310, KK5 in DCM was added MnO$_2$ (10 eq.) and the mixture was stirred at RT overnight, then filtered through celite. The solvent was removed under reduced pressure to obtain the desired aldehyde. $^1$H NMR (300 MHz, CDCl$_3$) δ: 9.85-9.70 (1H, s), 8.05-7.90 (1H, s), 7.65-7.55 (1H, s), 7.15-7.05 (1H, d. J=6.8 Hz), 7.85-7.68 (2H, m), 4.85-4.75 (1H, m), 3.95-3.85 (4H, s), 3.85-3.75 (3H, s), 3.55-3.40 (2H, m), 2.30 (3H, s), 1.90-1.20 (8H, m), 1.00-0.75 (7H, m). MS (ES) C$_{27}$H$_{36}$N$_4$O$_5$ requires: 496, found: 497 (M+H)$^+$.

Step 2: 4-{[2-(1-{[(5-Methoxy-2-methyl-1H-indol-3-yl)acetyl]amino}-7-oxononyl)-1H-imidazol-1-ium-5-yl]methyl}morpholin-4-ium bis(trifluoroacetate) (LL2)

The aldehyde (LL1) was taken up in MeOH and morpholine (2 eq.) was added followed by AcOH (2 eq.) and NaBH$_3$(CN) (1 eq) and the mixture was stirred at RT for 4 hr. The reaction was quenched by addition of sat. aq. NH$_4$Cl solution and the mixture was concentrated under reduced pressure. Sat. aq. NaHCO$_3$ solution was added and the product was extracted with EtOAc, dried (Na$_2$SO$_4$) and concentrated under reduced pressure. The mixture was purified by preparative RP-HPLC, using H$_2$O (+0.1% TFA) and MeCN (+0.1% TFA) as eluents (column: C18). The desired fractions were collected, then allowed to stand in the acid solution until the ketal protection was removed, finally the solution was lyophilized to afford to the titled compound. $^1$H-NMR (300 MHz, CDCl$_3$) δ: 9.35 (1H, d, J=3 Hz), 9.03 (1H, s), 7.18 (1H, d, J=7.3 Hz), 7.03 (1H, s), 6.65 (1H, d, J=7.3 Hz), 5.65-5.55 (1H, br. s), 5.10 (1H, q, J=6.5 Hz), 4.10 (2H, s), 3.95-3.60 (1H, br. m), 2.95-2.60 (2H, m), 2.45-2.30 (7H, m), 2.05-1.90 (1H, m), 1.85-1.65 (1H, m), 1.55-1.15 (6H, m), 1.05 (3H, t, J=7.0 Hz). MS (ES) C$_{29}$H$_{41}$N$_5$O$_4$ requires: 523, found: 524 (M+H)$^+$.

Example 312

2-(1-{[(5-Methoxy-2-methyl-1H-indol-3-yl)acetyl]amino}-7-oxononyl)-5-[(1E)-3-methoxy-3-oxoprop-1-en-1-yl]-1H-imidazol-1-ium trifluoroacetate (MM1)

To a stirred solution of the aldehyde Example 311, LL1 in THF was added Ph$_3$P=CHCO$_2$CH$_3$ (6 eq.) portionwise and the resulting mixture was stirred at RT overnight. The reaction was quenched by addition of 0.1 M HCl solution and extracted in EtOAc. The organics were dried (Na$_2$SO$_4$) and concentrated under reduced pressure. The crude was purified by preparative RP-HPLC, using H$_2$O (+0.1% TFA) and MeCN (+0.1% TFA) as eluents (column: C18). The desired fractions were collected, left to stand in the acid solution in order to remove the ketal protection and then lyophilized to afford to the titled compound. $^1$H-NMR (300 MHz, CD$_3$CN) δ: 9.00-8.90 (2H, m), 7.45-7.35 (1H, d, J=8.3 Hz), 7.25 (1H, s), 7.12 (1H, d, J=7.3 Hz), 6.95 (1H, s), 6.70-6.55 (2H, m), 5.20 (1H, q, J=6.5 Hz), 3.95-3.65 (6H, m), 3.55-3.40 (2H, m), 2.45-2.20 (7H, m), 1.95-1.80 (2H, m), 1.45-1.00 (6H, m), 0.95 (3H, t, J=7.0 Hz). MS (ES) C$_{28}$H$_{36}$N$_4$O$_5$ requires: 508, found: 509 (M+H)$^+$.

Example 313

5-(2-Carboxyethyl)-2-(1-{[(5-methoxy-2-methyl-1H-indol-3-yl)acetyl]amino}-7-oxononyl)-1H-imidazol-1-ium trifluoroacetate (NN1)

The unsaturated ester Example 312, MM1 was dissolved in anhydrous EtOAc and stirred in the presence of 10% Pd/C under an H$_2$ atmosphere for 1 hr. The H$_2$ atmosphere was removed and N$_2$ introduced. The reaction mixture was filtered and the catalyst washed with EtOAc and the filtrates concentrated under reduced pressure. The crude was purified by preparative RP-HPLC, using H$_2$O (+0.1% TFA) and MeCN (+0.1% TFA) as eluents (column: C18). The desired fractions were collected and lyophilized to afford the titled compound. $^1$HNMR (300 MHz, (CD$_3$)$_2$SO) δ: 10.65 (1H, s), 8.65 (1H, d, J=5.0 Hz), 7.35 (1H, s), 7.18 (1H, d, J=7.3 Hz), 7.02 (1H, s), 6.65 (2H, d, J=7.3 Hz), 4.98 (1H, q, J=6.5 Hz), 3.78 (3H, s), 3.70-3.40 (2H, m), 2.90-2.80 (2H, t, J=6.7 Hz), 2.70-2.60 (2H, t, J=6.7 Hz), 2.45-2.20 (7H, m), 1.90-1.75 (2H, m), 1.40-1.10 (6H, m), 0.90 (3H, t, J=7.0 Hz). MS (ES) C$_{27}$H$_{36}$N$_4$O$_5$ requires: 496, found: 497 (M+H)$^+$.

Example 314

5-Acetyl-2-((1S)-1-{[(5-methoxy-2-methyl-1H-indol-3-yl)acetyl]amino}-7-oxononyl)-1H-imidazol-1-ium trifluoroacetate (OO1)

To a stirred solution of Example 304, EE6 in DMF under Ar was added tributyl (1-ethoxyvinyl)stannane (2 eq.) and Pd(PPh$_3$)$_4$ (10 mol %). The temperature was raised to 110° C. and heating was continued for 48 hr. The solvent was removed under reduced pressure and the residue was purified by flash chromatography on silica using 20% EtOAc/petroleum ether as eluent to give a mixture of the 5-acetyl-(MS (ES) C$_{37}$H$_{56}$N$_4$O$_7$Si requires: 696, found: 697 (M+H)$^+$) and the 5-(1-ethoxyvinyl)-imidazole (MS (ES) C$_{39}$H$_{60}$N$_4$O$_7$Si requires: 725, found: 726 (M+H)$^+$).

The purified mixture was dissolved in THF and a solution of 1 M TBAF in THF (2.5 eq.) was added and the mixture was heated at 65° C. overnight. The reaction was quenched by addition of H$_2$O and the product extracted in DCM. The collected organic phases were washed with brine, dried (Na$_2$SO$_4$) and concentrated under reduced pressure to obtain a similar mixture of acetyl- and enol ether: tert-Butyl 3-(2-{[(1S)-1-(5-acetyl-1H-imidazol-2-yl)-7-oxononyl]amino}-2-oxoethyl)-5-methoxy-2-methyl-1H-indole-1-carboxylate, MS (ES) C$_{31}$H$_{42}$N$_4$O$_7$ requires: 566, found: 567 (M+H)$^+$; tert-butyl 3-[2-({(1S)-1-[5-(1-ethoxyvinyl)-1H-imidazol-2-yl]-7-oxononyl}amino)-2-oxoethyl]-5-methoxy-2-methyl-1H-indole-1-carboxylate, MS (ES) C$_{33}$H$_{46}$N$_4$O$_6$ requires: 594, found: 595 (M+H)$^+$.

This material was then dissolved in the minimum amount of DCM/TFA (1:1) mixture and stirred 1 hr. The reaction was quenched by addition of water and the solvent removed under reduced pressure. The product was purified by preparative RP-HPLC, using H$_2$O (+0.1% TFA) and MeCN (+0.1% TFA) as eluents (column: C18) and lyophilized to afford the titled compound. $^1$H-NMR (300 MHz, CDCl$_3$) δ: 8.00 (1H, s), 7.43 (1H, s), 7.08 (1H, d, J=7.3 Hz), 6.80-6.65 (2H, m), 6.35 (1H, br. s), 4.88 (1H, q, J=5.5 Hz), 3.75 (3H, s), 3.63 (2H, s), 2.40-2.10 (10H, m), 1.90-1.10 (8H, m), 0.95 (3H, t, J=7.0 Hz). MS (ES) C$_{26}$H$_{34}$N$_4$O$_4$ requires: 466, found: 467 (M+H)$^+$.

Example 315

5-Cyclohexyl-2-((1S)-1-{[(5-methoxy-2-methyl-1H-indol-3-yl)acetyl]amino}-7-oxononyl)-1H-imidazol-1-ium trifluoroacetate (PP4)

Step 1: tert-Butyl [(1S)-1-(4-cyclohex-1-en-1-{[2-(trimethylsilyl)ethoxy]methyl}-1H-imidazol-2-yl)-7-oxononyl]carbamate (PP1)

The Suzuki coupling was carried out according to Example 304, step 7 using cyclohex-1-en-1-ylboronic acid and tert-butyl [(is)-1-(4-bromo-1-{[2-(trimethylsilyl)ethoxy]methyl}-1H-imidazol-2-yl)-7-oxononyl]carbamate to yield the desired compound. MS (ES) C$_{29}$H$_{51}$N$_3$O$_4$Si requires: 533, found: 534 (M+H)$^+$.

Step 2: tert-Butyl [(1S)-1-(5-cyclohexyl-1-{[2-(trimethylsilyl)ethoxy]methyl}-1H-imidazol-2-yl)-7-oxononyl]carbamate (PP2)

The cyclohexenylimidazole (PP1) was dissolved in EtOAc and stirred in the presence of 10% Pd/C under an H$_2$ atmosphere for 1 hr. The H$_2$ atmosphere removed and N$_2$ introduced. The reaction mixture was filtered and the catalyst washed with EtOAc and the filtrates concentrated under reduced pressure. The crude was purified by preparative RP-HPLC, using H$_2$O (+0.1% TFA) and MeCN (+0.1% TFA) as eluents (column: C18). The desired fractions were collected and lyophilized to afford the desired compound. MS (ES) C$_{29}$H$_{49}$N$_3$O$_4$Si requires: 535, found: 536 (M+H)$^+$ Step 3: (9S)-9-Amino-9-(5-cyclohexyl-1H-imidazol-2-yl)nonan-3-one (PP3)

The carbamate (PP2) was dissolved in the minimum amount of DCM/TFA (1:1) and stirred at RT for 1 hr. The reaction was quenched by addition of water and the solvent removed under reduced pressure. The product was partitioned between DCM and sat. aq. NaHCO$_3$ solution. The organic phase was separated, washed with brine, dried (Na$_2$SO$_4$) and concentrated under reduced pressure to obtain the desired amine. MS (ES). C$_{18}$H$_{31}$N$_3$O requires: 305, found: 306 (M+H)$^+$.

Step 4: 5-Cyclohexyl-2-((1S)-1-{[(5-methoxy-2-methyl-1H-indol-3-yl)acetyl]amino}-7-oxononyl)-1H-imidazol-1-ium trifluoroacetate (PP4)

The amine (PP3) was taken up in DMF and a solution of (5-methoxy-2-methyl-1H-indol-3-yl)acetic acid (1.3 eq.), HOBt (1.3 eq.) and EDC.HCl (1.3 eq.) in DMF (previously premixed for 5 min) was added, followed by DIPEA (1.3 eq.). The mixture was left stirring at RT for 3 hr and was then purified by preparative RP-HPLC, using H$_2$O (+0.1% TFA) and MeCN (+0.1% TFA) as eluents (column: C18). The desired fractions were collected and lyophilized to afford titled compound. $^1$H NMR (300 MHz, (CD$_3$)$_2$SO) δ: 10.65

(1H, s), 8.68 (1H, d, J=3.5 Hz), 7.35 (1H, s), 7.18 (1H, d, J=7.3 Hz), 7.00 (1H, s), 6.68 (1H, d, J=7.3 Hz), 4.98 (1H, q, J=5.0 Hz), 3.80 (3H, s), 3.50-3.10 (2H, m), 2.75-2.50 (1H, m), 2.50-2.30 (7H, m), 2.05-1.70 (6H, m), 1.50-1.10 (12H, m), 0.97 (3H, t, J=7.0 Hz). MS (ES) $C_{30}H_{42}N_4O_3$ requires: 506, found: 507 (M+H)$^+$.

Example 316

2-((1S)-1-{[(5-Methoxy-2-methyl-1H-indol-3-yl)acetyl]amino}-7-oxoundecyl)-5-phenyl-1H-imidazol-1-ium trifluoroacetate (QQ4)

Step 1: tert-Butyl (7S)-7-[(tert-butoxycarbonyl)amino]-7-(4-phenyl-1H-imidazol-2-yl)heptanoate (QQ1)

A solution Example 107, 13 and $Cs_2CO_3$ (0.6 eq) in EtOH was stirred for 30 min at RT and then concentrated under reduced pressure. 2-Bromo-1-phenylethanone (1.2 eq.) was added to the resulting salt in DMF and the mixture was stirred for 1.5 h at RT under $N_2$. The DMF was coevaporated with toluene. EtOAc was added, the mixture was filtered and the residue was washed with EtOAc. The combined filtrates were concentrated under reduced pressure. A solution of the resulting oil and $NH_4OAc$ (20 eq.) in toluene was heated at reflux for 2 hr whilst excess $NH_4OAc$ and $H_2O$ were removed using a Dean-Stark trap. The mixture was cooled to RT, diluted with EtOAc and washed with water (×2), sat. aq. $NaHCO_3$ solution, water (×2) and brine. The solution was dried ($Na_2SO_4$), concentrated under reduced pressure and the resulting brown oil was purified by chromatography on silica gel eluting with EtOAc/petroleum ether (9:1 to 3:2) to obtain the title compound as a pale brown foam. $^1$H NMR (400 MHz, DMSO-d6) δ: 11.75 (1H, s), 7.73 (2H, d, J=7.5 Hz), 7.76 (1H, s), 7.31, (2H, t, J=7.5 Hz), 7.18-7.11 (1H, m), 7.05 (1H, d, J=8.1 Hz), 4.63-4.51 (1H, m), 2.15 (2H, t, J=7.2 Hz), 1.87-1.75 (1H, m), 1.75-1.64 (1H, m), 1.52-1.43 (2H, m), 1.38 (18H, s), 1.33-1.18 (4H, m). MS (ES) $C_{25}H_{37}N_3O_4$ requires: 443, found: 444 (M+H)$^+$.

Step 2: 2-[(1S)-1-Ammonio-6-carboxyhexyl]-5-phenyl-1H-imidazol-3-ium bis(trifluoroacetate) (QQ2)

The imidazole (QQ1) (1 eq.) was dissolved in TFA/DCM (1:1) at 0° C., the cooling bath was removed and the mixture was stirred for 2 h at RT. The solvents were then removed under reduced pressure and the crude was used as such without any further purification. MS (ES) $C_{16}H_{21}N_3O_2$ requires: 287, found: 288 (M+H)$^+$.

Step 3: (7S)—N-methoxy-7-{[(5-methoxy-2-methyl-1H-indol-3-yl)acetyl]amino}-N-methyl-7-(5-phenyl-1H-imidazol-2-yl)heptanamide (QQ3)

A solution of EDC.HCl (1.2 eq.), HOBt (1.2 eq.) and (5-methoxy-2-methyl-1H-indol-3-yl)acetic acid (1.2 eq.) in DMF was stirred for 1 hr at RT and was then added to a solution of the amine (QQ2) (1 eq.) and DIPEA (2 eq.) in DMF. The mixture was stirred overnight then more HATU (2 eq.) was added followed after 1 h by $CH_3ON(CH_3)H.HCl$ (2 eq.). After stirring for a further 12 hours the crude was purified by preparative RP-HPLC, using $H_2O$ (0.1% TFA) and MeCN (+0.1% TFA) as eluents (column: C18). The desired fractions were lyophilized to afford the titled compound as a white solid. The compound was then extracted from sat. aq. $NaHCO_3$ solution to obtain the free base. $^1$H NMR (400 MHz, DMSO-d6) δ: 10.62 (1H, s), 8.62 (1H, d, J=6.3 Hz), 8.03 (1H, s), 7.77 (2H, d, J=7.6 Hz), 7.52 (2H, t, J=7.6 Hz), 7.48-7.39 (1H, m), 7.10 (1H, d, J=8.6 Hz), 6.96 (1H, s), 6.64-6.56 (2H, m), 5.06-4.96 (1H, m), 3.69 (3H, s), 3.62 (3H, s), 3.60-3.45 (2H, m), 3.06 (3H, s), 2.35-2.26 (2H, m), 2.36-2.26 (5H, m), 1.50-1.18 (6H, m). MS (ES) $C_{30}H_{37}N_5O_4$ requires: 531, found: 532 (M+H)$^+$.

Step 4: 2-((1S)-1-{[(5-Methoxy-2-methyl-1H-indol-3-yl)acetyl]amino}-7-oxoundecyl)-5-phenyl-1H-imidazol-1-ium trifluoroacetate (QQ4)

To a solution of QQ3 in THF (2 mL) at −78° C. was added n-BuLi (5 eq.). After 1 hr, the reaction mixture was quenched carefully with $H_2O$. After warming to RT the aqueous phase was extracted with EtOAc, the combined organic phases were dried ($MgSO_4$) and the solvent was removed under reduced pressure. The desired material was isolated by preparative RP-HPLC, using $H_2O$ (+0.1% TFA) and MeCN (+0.1% TFA) as eluents (C18 column) to yield after lyophilisation the imidazole as a white solid.
$^1$H NMR (300 MHz, CDCl$_3$) δ: 10.23 (1H, d, J=6.9 Hz), 8.25 (1H, s), 7.52-7.32 (6H, m), 7.13 (1H, d, J=8.5 Hz), 6.87 (1H, m), 6.73 (1H, d, J=8.5 Hz), 5.88 (1H, m), 5.44 (1H, m), 3.73 (2H, s), 3.62 (3H, s), 2.35 (6H, m), 2.27 (3H, s), 1.98 (2H, m), 1.60-0.94 (8H, m), 0.89 (3H, t, J=7.2 Hz). MS (ES) $C_{32}H_{40}N_4O_3$ requires: 529, found: 530 (M+H)$^+$.

Example 317

2-((1S)-7-Cyclopropyl-1-{[(5-methoxy-2-methyl-1H-indol-3-yl)acetyl]amino}-7-oxoheptyl)-5-phenyl-1H-imidazol-1-ium trifluoroacetate (RR1)

This material was obtained as described for Example 316 using QQ3 and cyclopropylmagnesium bromide. $^1$H NMR (300 MHz, CDCl$_3$) δ: 10.32 (1H, d, J=8.0 Hz), 8.31 (1H, s), 7.52-7.31 (5H, m), 7.12 (1H, d, J=8.6 Hz), 6.89 (1H, d, J=1.5 Hz), 6.73 (1H, dd, J=8.6 Hz, J=1.5 Hz), 5.88 (1H, m), 5.43 (1H, m), 3.73 (2H, s), 3.62 (3H, s), 2.48 (2H, m), 2.27 (3H, s), 2.05-1.86 (4H, m), 1.50 (2H, m), 1.24 (3H, m), 0.98 (3H, m), 0.86 (2H, m). MS (ES) $C_{31}H_{36}N_4O_3$ requires: 513, found: 514 (M+H)$^+$.

Example 318

2-((1S)-1-{[(5-Methoxy-2-methyl-1H-indol-3-yl)acetyl]amino}-9-methyl-7-oxodecyl)-5-phenyl-1H-imidazol-1-ium trifluoroacetate (SS1)

This material was obtained as described for Example 316 using QQ3 and isobutylmagnesium bromide. $^1$H NMR (300 MHz, CDCl$_3$) δ: 10.60 (1H, d, J=8.0 Hz), 8.19 (1H, s), 7.53-7.32 (5H, m), 7.14 (1H, d, J=8.6 Hz), 6.91 (1H, d, J=2.0 Hz), 6.75 (1H, dd, J=8.6 Hz, J=2.0 Hz), 5.75 (1H, br s), 5.46 (1H, m), 3.75 (2H, s), 3.62 (3H, s), 2.37-1.69 (10H, m), 1.46 (2H, m), 1.33-1.00 (5H, m), 0.90 (3H, d, J=6.6 Hz), 0.89 (3H, d, J=6.6 Hz). MS (ES) $C_{32}H_{40}N_4O_3$ requires: 529, found: 530 (M+H)$^+$.

Example 319

2-((1S)-8-hydroxy-1-{[(5-methoxy-2-methyl-1H-indol-3-yl)acetyl]amino}-7-oxooctyl)-5-phenyl-1H-imidazol-1-ium trifluoroacetate (TT1)

To a solution of chloroiodomethane (5.3 eq.) in THF at −78° C. was slowly added a solution of MeLi in Et$_2$O (5.3 eq.), after 5 min the solution was transferred via cannula to a solution of Example 316 QQ3 (1 eq.) in THF at −78° C. The reaction was stirred at −78° C. for 2 hr and was then quenched by carefully addition of water. After warning to RT the aqueous phase was extracted with EtOAc. The combined organic phase was dried (MgSO$_4$) and solvent was removed under reduced pressure.

The crude was solved in DMF (3 mL) and treated with potassium acetate (1 eq.) for 2 hr at 60° C. The reaction mixture was diluted with EtOAc and washed with brine (2×). The organic phase was dried (MgSO$_4$) and the solvents were removed under reduced pressure. The crude acetate was dissolved in MeOH (3 mL) and treated with sodium carbonate (1 eq.) for 30 min at RT. Water was added and the aqueous phase was extracted with EtOAc. The combined organic phase was dried (MgSO$_4$) and concentrated under reduced pressure. The desired material was isolated by preparative RP-HPLC, using H$_2$O (+0.1% TFA) and MeCN (+0.1% TFA) as eluents (C18 column) to yield the imidazole as a colourless oil. $^1$H NMR (300 MHz, CDCl$_3$) δ: 10.60 (1H, s), 8.56 (1H, br s), 7.99 (1H, s), 7.75 (2H, d, J=7.5 Hz), 7.53-7.37 (3H, m), 7.09 (1H, d, J=8.8 Hz), 6.95 (1H, d, J=2.0 Hz), 6.59 (1H, dd, J=2.0 Hz, J=8.8 Hz), 4.99 (1H, m), 4.00 (2H, s), 3.67 (3H, s), 3.51 (2H, m), 2.29 (5H, m), 1.88 (2H, m), 1.45-1.12 (8H, m). MS (ES) C$_{29}$H$_{34}$N$_4$O$_4$ requires: 502, found: 503 (M+H)$^+$.

Example 320

2-((1S)-7-(2-Furyl)-1-{[(5-methoxy-2-methyl-1H-indol-3-yl)acetyl]amino}-7-oxoheptyl)-5-(2-naphthyl)-1H-imidazol-1-ium trifluoroacetate (UU1)

To a solution of furan (10 eq.) in THF at −78° C. was slowly added a solution of n-BuLi in hexane (10 eq.). The solution was then warmed to 0° C. and stirred at 0° C. for 1.5 h. After cooling to −78° C. it was transferred via cannula to a solution of (7S)—N-methoxy-7-{[(5-methoxy-2-methyl-1H-indol-3-yl)acetyl]amino}-N-methyl-7-[5-(2-naphthyl)-1H-imidazol-2-yl]heptanamide (1 eq.) (Prepared in a similar manner to Example 316, QQ3) in THF at −78° C. The reaction mixture was allowed to warm up to RT overnight and then was quenched carefully with water. The aqueous phase was extracted with EtOAc. The combined organic phase was dried (MgSO$_4$) and solvent was removed under reduced pressure. The desired material was isolated by preparative RP-HPLC, using H$_2$O (+0.1% TFA) and MeCN (+0.1% TFA) as eluents (C18 column) to afford the imidazole O1 as a white solid. $^1$H NMR (300 MHz, DMSO) δ: 10.61 (1H, s), 8.64 (1H, d, J=5.8 Hz), 8.33 (1H, s), 8.14 (1H, s), 8.04 (1H, d, J=8.8 Hz), 7.99-7.86 (4H, m), 7.58 (2H, m), 7.38 (1H, dd, J=0.7 Hz, J=3.6 Hz), 7.08 (1H, d, J=8.8 Hz), 6.97 (1H, d, J=2.4 Hz), 6.67 (1H, dd, J=1.6 Hz, J=3.6 Hz), 6.57 (1H, dd, J=2.4 Hz, J=8.6 Hz), 5.04 (1H, m), 3.65 (3H, s), 3.53 (2H, dt, J=14.7 Hz, J=14 Hz), 2.74 (2H, t, J=7.3 Hz), 2.30 (3H, s), 1.94 (2H, m), 1.58-1.17 (6H, m). MS (ES) C$_{36}$H$_{36}$N$_4$O$_4$ requires: 589, found: 590 (M+H)$^+$.

Example 321

2-[(1S)-1-{[(5-Methoxy-2-methyl-1H-indol-3-yl)acetyl]amino}-8-(methylsulfinyl)-7-oxooctyl]-5-(2-naphthyl)-1H-imidazol-1-ium trifluoroacetate (VV1)

To a solution of DMSO (15 eq.) in THF at −78° C. was slowly added n-BuLi solution in hexane (15 eq.), after 30 min the solution was transferred via cannula to a solution of (7S)—N-methoxy-7-{[(5-methoxy-2-methyl-1H-indol-3-yl)acetyl]amino}-N-methyl-7-[5-(2-naphthyl)-1H-imidazol-2-yl]heptanamide (1 eq.) (Prepared in a similar manner to Example 316, QQ3) in THF at −78° C. The reaction mixture was allowed to warm up to RT overnight and was then quenched by carefully addition of water. The aqueous phase was extracted with EtOAc, dried (MgSO$_4$) and then solvent was removed under reduced pressure. The desired material was isolated by preparative RP-HPLC, using H$_2$O (+0.1% TFA) and MeCN (+0.1% TFA) as eluents (C18 column) and lyophilized to afford the imidazole as a colourless oil. $^1$H NMR (300 MHz, CDCl$_3$) δ: 10.10 (1H, br s), 8.25 (1H, s), 8.11 (1H, s), 7.88-7.73 (3H, m), 7.58-7.46 (2H, m), 7.43-7.34 (1H, m), 7.15 (1H, d, J=8.6 Hz), 6.91 (1H, d, J=1.7 Hz), 6.74 (1H, dd, J=1.7 Hz, J=8.6 Hz), 6.11 (1H, d, J=15 Hz), 5.48 (1H, m), 3.77 (4H, s), 3.62 (3H, s), 2.69 (3H, s), 2.47 (2H, m), 2.30 (3H, s), 2.15-1.92 (2H, m), 1.53 (2H, m), 1.37-1.04 (4H, m). MS (ES) C$_{34}$H$_{39}$N$_4$O$_4$S requires: 599, found: 600 (M+H)$^+$.

Example 322

2-[(1S)-1-{[(5-Methoxy-2-methyl-1H-indol-3-yl)acetyl]amino}-8-(methylsulfonyl)-7-oxooctyl]-5-(2-naphthyl)-1H-imidazol-1-ium trifluoroacetate (WW1)

This material was obtained as described for Example 321 using dimethylsulfone. $^1$H NMR (300 MHz, DMSO) δ: 10.83 (1H, s), 8.84 (1H, d, J=6.4 Hz), 8.54 (1H, s), 8.37 (1H, s), 8.26 (1H, d, J=8.6 Hz), 8.21-8.06 (4H, m), 7.80 (2H, m), 7.31 (1H, d, J=8.6 Hz), 7.18 (1H, d, J=2.0 Hz), 6.80 (1H, dd, J=2.0 Hz, J=8.6 Hz), 5.26 (1H, m), 4.64 (2H, s), 3.88 (3H, s), 3.75 (2H, m), 3.26 (3H, s), 2.77 (2H, t, J=7.0 Hz), 2.52 (3H, s), 2.15 (2H, m), 1.70-1.36 (6H, m). MS (ES) C$_{34}$H$_{38}$N$_4$O$_5$S requires: 615, found: 616 (M+H)$^+$.

Example 323

2-((1S)-8-(Aminosulfonyl)-1-{[(5-methoxy-2-methyl-1H-indol-3-yl)acetyl]amino}-7-oxooctyl)-5-(2-naphthyl)-1H-imidazol-1-ium trifluoroacetate (XX1)

To a solution of tert-butyl (methylsulfonyl)carbamate (15 eq.) in THF at −78° C. was slowly added a solution of n-BuLi in hexane (30 eq.), after 30 min the solution was transferred via cannula to a solution of (7S)—N-methoxy-7-{[(5-methoxy-2-methyl-1H-indol-3-yl)acetyl]amino}-N-methyl-7-[5-(2-naphthyl)-1H-imidazol-2-yl]heptanamide (1 eq.) (Prepared in a similar manner to Example 316, QQ3) in THF at −78° C. The reaction mixture was allowed to warm up to RT overnight and was then quenched carefully with water. The aqueous phase was extracted with EtOAc and was dried (MgSO$_4$) and solvent was removed under reduced pressure.

The crude was resolved in DCM/TFA (3:1) and stirred for 1 h. The solvents were removed under reduced pressure and the desired material was isolated by preparative RP-HPLC, using H$_2$O (+0.1% TFA) and MeCN (+0.1% TFA) as eluents (C18 column) to yield the imidazole as a white solid. $^1$H NMR (300 MHz, DMSO) δ: 10.61 (1H, s), 8.60 (1H, m), 8.32 (1H, s), 8.13 (1H, s), 8.05 (1H, d, J=8.6 Hz), 7.99-7.84 (4H, m), 7.58 (2H, m), 7.09 (3H, m), 6.96 (1H, d, J=2.4 Hz), 6.58 (1H, dd, J=2.4 Hz, J=8.6 Hz), 5.03 (1H, m), 4.15 (2H, s), 3.66 (3H, s), 3.59 (2H, m), 2.60 (2H, t, J=7.0 Hz), 2.30 (3H, s), 1.93 (2H, m), 1.48-1.15 (8H, m). MS (ES) C$_{33}$H$_{37}$N$_5$O$_5$S requires: 616, found: 617 (M+H)$^+$.

Example 324

1-Methyl-4-({[(1S)-7-oxo-1-(4-phenyl-1H-imidazol-3-ium-2-yl)-7-pyridin-2-ylheptyl]amino}carbonyl) piperidinium bis(trifluoroacetate) (YY8)

Step 1: tert-Butyl (7S)-7-[(tert-butoxycarbonyl) amino]-7-(5-phenyl-1H-imidazol-2-yl)heptanoate (YY1)

A solution (0.5 M) of [(2S)-8-tert-butoxy-2-[(tert-butoxycarbonyl)amino]-8-oxooctanoic acid in EtOH was treated with $Cs_2CO_3$ (0.5 eq.). The reaction mixture was stirred at RT for 50 min then the solvent was evaporated under reduced pressure and then the resulting salt was dissolved in DMF and was treated with 2-bromo-1-phenylethanone (1.0 eq.). The reaction mixture was stirred for 1 h at RT then the DMF was coevaporated with toluene. The residue was suspended in EtOAc and filtrate. The filtrate was concentrated under reduced pressure to give an oil that was dissolved in toluene. The resulting solution (0.14 M) was treated with $NH_4OAc$ (20 eq.) and heated at reflux with a Dean Stark trap for 2 h. The reaction mixture was cooled down to RT and diluted with EtOAc and a sat. aq. $NaHCO_3$ solution. The organic layers were washed with brine, dried and concentrated under reduced pressure to give an oil which was purified by chromatography on silica gel eluting with 20% EtOAc/petroleum ether/EtOAc to afford the title compound as a solid. $^1$H NMR (400 MHz, DMSO-$d_6$, 300 K) δ 11.77 (1H, s), 7.75 (2H, d, J=7.3 Hz), 7.48 (1H, s), 7.33 (2H, t, J=7.6 Hz), 7.17 (1H, t, J=7.3 Hz), 7.12-7.02 (1H, m), 4.70-4.50 (1H, m), 2.17 (2H, t, J=7.3 Hz), 1.93-1.63 (2H, m), 1.57-1.15 (24H, m); MS (ES) $C_{25}H_{37}N_3O_4$ requires: 443, found: 444 (M+H)$^+$.

Step 2: (7S)-7-{1-[(Benzyloxy)methyl]-5-phenyl-1H-imidazol-2-yl}-7-[(tert-butoxycarbonyl)amino] heptanoic acid (YY2)

A solution the imidazole (YY1) in MeCN was treated with [(chloromethoxy)methyl]benzene (1.2 eq.) and stirred at reflux for 3 h. The reaction mixture was cooled to RT, the solvent was evaporated under reduced pressure and the residue was diluted with $H_2O$ and extracted with EtOAc. The collected organic layers were washed with brine, dried and concentrated under reduced pressure to give an oil residue containing a mixture of the tert-butyl (7S)-7-{1-[(benzyloxy)methyl]-5-phenyl-1H-imidazol-2-yl}-7-[(tert-butoxycarbonyl)amino]heptanoate and tert-butyl (7S)-7-amino-7-{1-[(benzyloxy)methyl]-5-phenyl-1H-imidazol-2-yl}heptanoate that was used without further purification. MS (ES) $C_{33}H_{45}N_3O_5$ requires: 563, found: 564 (M+H)$^+$.

The above mixture in DCM/TFA (4:1) was stirred at 0° C. then the cooling bath was removed and the reaction mixture was stirred at RT for 1 h. The solvents were removed under reduced pressure and the residue was coevaporated with toluene to give desired compounds that was used without any further purification. MS (ES) $C_{24}H_{29}N_3O_3$ requires: 407, found: 408 (M+H)$^+$.

A solution of the above intermediate in $H_2O$/MeCN was cooled to 0° C. and treated with $NaHCO_3$ (3.0 eq.) and $Boc_2O$ (1.5 eq.). The reaction mixture was stirred at RT for 2 h. The $CH_3CN$ was removed under reduced pressure and the aqueous phase was extracted with EtOAc. The pH was adjusted to pH 4-5 with 1N HCl and was extracted again. The collected organic phases were washed with brine, dried and concentrated under reduced pressure to yield an amber oil which was purified by chromatography on silica gel eluting with 50-60% EtOAc/petroleum ether to afford the title compound (92%) as a pale amber oil. $^1$H NMR (400 MHz, DMSO-$d_6$, 300 K) δ 8.11 (1H, s), 7.81 (2H, d, J=7.5 Hz), 7.50 (2H, t, J=7.7 Hz), 7.41-7.28 (7H, m), 5.81 (1H, d, J=10.2 Hz), 5.64 (1H, d, J=10.2 Hz), 4.96-4.86 (1H, m), 4.69-4.59 (2H, m), 2.17 (2H, t, J=7.3 Hz), 1.97-1.85 (2H, m), 1.55-1.43 (15H, m); MS (ES) $C_{29}H_{37}N_3O_5$ requires: 507, found: 508 (M+H)$^+$.

Step 3: tert-Butyl ((1S)-1-{1-[(benzyloxy)methyl]-5-phenyl-1H-imidazol-2-yl}-7-hydroxyheptyl)carbamate (YY3)

A solution the above acid (YY2) in THF was treated with 4-methylmorpholine (2.0 eq.) and cooled to 0° C. The resulting solution was treated dropwise with isobutyl chloridocarbonate (2.0 eq.) and was then stirred for 15 min at 0° C., during which period a white precipitate formed. The precipitate was filtered off and the filtrate was treated dropwise at 0° C. with $NaBH_4$ (2.5 eq.) in $H_2O$ (0.6 M). The reaction mixture was stirred for 15 min at the same temperature then it was warmed up to RT and the THF was removed under reduced pressure. The residue was diluted with $H_2O$ and extracted with EtOAc. The collected organic layers were washed with brine, dried and concentrated under reduced pressure to give a yellow oil. The purification by chromatography on silica gel eluting with 30% EtOAc/petroleum ether afforded the title compound as a pale yellow solid. $^1$H NMR (400 MHz, DMSO-$d_6$, 300 K) δ 8.26 (1H, s), 7.83-7.76 (3H, m), 7.57-7.50 (2H, m), 7.49-7.43 (1H, m), 7.38-7.26 (5H, m), 5.86 (1H, d, J=10.7 Hz), 5.74 (1H, d, J=10.7 Hz), 5.04-4.94 (1H, m), 4.68 (2H, s), 3.36 (2H, t, J=6.6 Hz), 2.05-1.81 (2H, m), 1.47-1.17 (15H, m).

Step 4: tert-Butyl ((1S)-1-{1-[(benzyloxy)methyl]-5-phenyl-1H-imidazol-2-yl}-7-oxoheptyl)carbamate (YY4)

A solution the alcohol (YY3) in DCM was treated with pyridine (4.2 eq.) and the Dess-Martin Periodinane (2.0 eq.). The reaction mixture was stirred for 3 hr then the reaction mixture was diluted with sat. aq. $Na_2CO_3$ solution and extracted with DCM. The collected organic phases were washed with brine, dried and concentrated under reduced pressure to afford the title compound as a colorless oil. $^1$H NMR (400 MHz, CDCl$_3$, 300 K) δ 9.71 (1H, s), 7.80 (2H, d, J=7.5 Hz), 7.43-7.23 (8H, m), 7.20 (1H, s), 5.68 (1H, d, J=10.6 Hz), 5.38-5.24 (1H, bs), 5.28 (1H, d, J=10.6 Hz), 5.00-4.89 (1H, m), 4.54 (2H, s), 2.36 (2H, t, J=6.6 Hz), 2.08-1.89 (2H, m), 1.63-1.53 (2H, m), 1.43 (9H, s), 1.41-1.30 (4H, m); MS (ES) $C_{29}H_{37}N_3O_4$ requires: 491, found: 492 (M+H)$^+$.

Step 5: tert-Butyl ((1S)-1-{1-[(benzyloxy)methyl]-5-phenyl-1H-imidazol-2-yl}-7-hydroxy-7-pyridin-2-ylheptyl)carbamate (YY5)

A solution of 2-bromopyridine (2.05 eq.) in THF was cooled to −78° C. and treated with a 1.6 M solution of n-BuLi in hexanes (2.1 eq.) The resulting orange solution was stirred at −78° C. for 30 min then it was treated with a solution the aldehyde (YY4) in THF. The resulting pale yellow solution was left to reach RT overnight and was then cooled to 0° C. and quenched with sat. aq. $NH_4Cl$ solution and extracted with EtOAc. The collected organic phases were washed with brine, dried and evaporated under reduced pressure. The resulting yellow oil was purified by chromatography on silica gel eluting with 30-50% EtOAc/petroleum ether to afford the title compound as a pale yellow oil. $^1$H NMR (400 MHz, DMSO-d$_6$, 300 K) δ 8.46 (1H, d, J=4.6 Hz), 7.82-7.69 (4H, m), 7.45 (1H, d, J=7.9 Hz), 7.41-7.26 (8H, m), 7.25-7.16 (2H, m), 5.66 (1H, d, J=10.6 Hz), 5.42 (1H, d, J=10.6 Hz), 5.25 (1H, d, J=5.0 Hz), 4.80-4.68 (1H, m), 4.60-4.46 (2H, m), 3.36-2.28 (2H, m), 1.92-1.77 (2H, m), 1.76-1.64 (1H, m), 1.63-1.49 (1H, m), 1.35 (9H, s), 1.36-1.22 (4H, m); MS (ES) $C_{34}H_{42}N_4O_4$ requires: 570, found: 571 (M+H)$^+$.

Step 6: tert-Butyl ((1S)-1-{1-[(benzyloxy)methyl]-5-phenyl-1H-imidazol-2-yl}-7-oxo-7-pyridin-2-ylheptyl)carbamate (YY6)

A solution the alcohol (YY5) in DCM was treated with pyridine (4.2 eq.) and the Dess-Martin Periodinane (2.0 eq.). The reaction mixture was stirred for 3 h then the crude material was diluted with sat. aq. Na$_2$CO$_3$ solution and extracted with DCM. The collected organic phases were washed with brine, dried and concentrated under reduced pressure to afford a brown oil which was purified by chromatography on silica gel eluting with 20-30% EtOAc/petroleum ether to yield the desired material as a pale yellow oil.

$^1$H NMR (400 MHz, CDCl$_3$, 300 K) δ 8.67 (1H, d, J=4.6 Hz), 8.02 (1H, d, J=7.9 Hz), 7.99-7.89 (2H, m), 7.83 (1H, td, J=1.3 Hz, J=7.7 Hz), 7.53-7.30 (10H, m), 7.17 (1H, s), 5.96-5.84 (1H, m), 5.49-5.36 (1H, m), 5.13-5.01 (1H, m), 4.74-4.59 (2H, m), 3.19 (2H, t, J=7.2 Hz), 2.54-2.36 (1H, m), 2.23-2.09 (1H, m), 1.79-1.63 (2H, m), 1.50-1.22 (4H, m), 1.42 (9H, s); MS (ES) $C_{34}H_{40}N_4O_4$ requires: 568, found: 569 (M+H)$^+$.

Step 7: N-((1S)-1-{1-[(Benzyloxy)methyl]-5-phenyl-1H-imidazol-2-yl}-7-oxo-7-pyridin-2-ylheptyl)-1-methylpiperidine-4-carboxamide (YY7)

The ketone (YY6) was treated at 0° C. with a mixture TFA/DCM (1:4), then the cooling bath was removed and the reaction mixture was stirred at RT for 1 h. The solvents were removed under reduced pressure and the residue was coevaporated with toluene to give a crude material that was used without any further purification. MS (ES) $C_{29}H_{32}N_4O_2$ requires: 468, found: 469 (M+H)$^+$.

A solution of 1-methylpiperidine-4-carboxylic acid in DMF was treated at 0° C. with EDC hydrochloride (1.2 eq.), HOBt (1.2 eq.) and Et$_3$N (4.2 eq.) and the mixture was stirred at 0° C. for 30 min, then a solution of the above intermediate in DMF was added and the reaction mixture was stirred overnight at RT. The reaction mixture was diluted with 2N NaOH and extracted with EtOAc. The collected organic phases were washed with brine, dried and evaporated under reduced pressure to give the title compound as a pale yellow solid which was used in the next step without any purification. $^1$H NMR (400 MHz, DMSO-d$_6$, 300 K) δ 8.71 (1H, d, J=4.4 Hz), 8.28 (1H, d, J=8.3 Hz), 8.01 (1H, dt, J=1.5 Hz, J=7.7 Hz), 7.95 (1H, d, J=7.7 Hz), 7.81-7.72 (3H, m), 7.69-7.62 (1H, m), 7.41-7.24 (7H, m), 7.21 (1H, t, J=7.3 Hz), 5.65 (1H, d, J=10.7 Hz), 5.39 (1H, d, J=10.7 Hz), 5.12-5.01 (1H, m), 4.56 (1H, d, J=11.6 Hz), 4.51 (1H, d, J=11.6 Hz), 3.12 (2H, t, J=7.3 Hz), 3.04-2.95 (2H, m), 2.76-2.63 (2H, m), 2.22-2.16 (1H, m), 2.14-2.04 (4H, m), 2.00-1.83 (2H, m), 1.82-1.67 (2H, m), 1.67-1.42 (4H, m), 1.41-1.19 (4H, m); MS (ES) $C_{36}H_{43}N_5O_3$ requires: 593, found: 594 (M+H)$^+$.

Step 8: 1-Methyl-4-({[(1S)-7-oxo-1-(4-phenyl-1H-imidazol-3-ium-2-yl)-7-pyridin-2-ylheptyl]amino}carbonyl)piperidinium bis(trifluoroacetate) (YY8)

A solution of the amide (YY7) in toluene at 0° C. was treated with BBr$_3$ (3.0 eq.). The reaction mixture was stirred at RT overnight then it was diluted with water and concentrated under reduced pressure. The residue was purified by RP-HPLC (Waters X-TERRA MS C18, 5 micron, 19×150 mm) using H$_2$O (+0.1% TFA) and MeCN (+0.1% TFA) as eluents to afford the title compound as an oil. $^1$H NMR (400 MHz, DMSO-d$_6$, 300 K) δ 8.80-8.62 (2H, m), 8.08-7.91 (3H, m), 7.79 (2H, d, J=7.5 Hz), 7.72-7.64 (1H, m), 7.59-7.35 (3H, m), 5.07-4.95 (1H, m), 3.53-3.38 (2H, m), 3.23-3.12 (2H, m), 3.03-2.87 (2H, m), 2.79 (3H, s), 2.53-2.42 (1H, m), 2.09-1.83 (4H, m), 1.81-1.58 (4H, m), 1.48-1.21 (4H, m); MS (ES) $C_{28}H_{35}N_5O_2$ requires: 473, found: 474 (M+H)$^+$.

Example 325

2-((1S)-7-Amino-1-{[(5-methoxy-2-methyl-1H-indol-3-yl)acetyl]amino}-7-oxoheptyl)-5-(2-naphthyl)-1H-imidazol-3-ium trifluoroacetate (ZZ7)

Step 1: 8-tert-Butyl 1-methyl (2S)-2-{[(benzyloxy)carbonyl]amino}octanedioate (ZZ1)

Example 107, 11 (1 eq.) was dissolved in THF and cooled at 0° C.; 1M HCl was added (4 eq.) and the mixture was stirred 20 min. 1M NaOH was added (4 eq), the aqueous phase was extracted with EtOAc and the collected organic phases were treated with brine, dried (Na$_2$SO$_4$) and the solvent removed under reduced pressure. The pale yellow oil obtained was dissolved in DCM and Et$_3$N was added (1.5 eq.). To this mixture a solution of N-(benzyloxycarbonyloxy)succinimide (1.3 eq) in DCM was added and stirring for a 1 hr at RT the solvents were removed under reduced pressure. The yellow oil was purified by chromatography on silica gel eluting with 5-50% EtOAc/petroleum ether to obtain the title compound as a colorless oil. $^1$H NMR (400 MHz, CDCl$_3$) δ: 7.42-7.28 (5H, m), 5.24 (1H, d, J=7.7 Hz), 5.11 (2H, s), 4.41-4.32 (1H, m), 3.74 (3H, s), 2.19 (2H, t, J=7.5 Hz), 1.89-1.77 (1H, m), 1.70-1.50 (3H, m), 1.44 (9H, s), 1.38-1.24 (4H, m). MS (ES) $C_{21}H_{31}NO_6$ requires: 393, found: 394 (M+H)$^+$.

Step 2: (2S)-2-{[(Benzyloxy)carbonyl]amino}-8-tert-butoxy-8-oxooctanoic acid (ZZ2)

The above ester (ZZ1) (1 eq.) was dissolved in a THF/H$_2$O (4:1) and LiOH.H$_2$O (1.1 eq.) was added, the mixture was stirred for 1.5 hr. 1M HCl was added until pH 4-5 and the THF was removed under reduced pressure. The aqueous phase was extracted with EtOAc (3×); the collected organic phases were washed with brine and then dried (Na$_2$SO$_4$). The solvent were removed under reduced pressure to yield the title compound was as a colorless oil which solidified upon standing. MS (ES) $C_{20}H_{29}NO_6$ requires: 379, found: 380 (M+H)$^+$.

Step 3: tert-Butyl (7S)-7-{[(benzyloxy)carbonyl]amino}-7-[5-(2-naphthyl)-1H-imidazol-2-yl]heptanoate (ZZ3)

A mixture of the acid (ZZ2) (1 eq.) and Cs$_2$CO$_3$ (0.5 eq) in EtOH was stirred for 30 min at RT and then concentrated under reduced pressure. 2-2-Bromo-1-(2-naphthyl)ethanone (1 eq.) was added to the resulting salt in DMF and the mixture was stirred for 1.5 h at RT under N$_2$. The DMF was coevaporated with toluene. EtOAc was added, the mixture was filtered and the residue was washed with EtOAc. The combined filtrates were concentrated under reduced pressure. A solution of the resulting oil and NH$_4$OAc (20 eq.) in toluene was heated at reflux for 2 hr while excess NH$_4$OAc and H$_2$O were removed using a Dean-Stark trap. The mixture was cooled to RT, diluted with EtOAc and washed with water (×2), sat. aq. NaHCO$_3$ solution, water (×2) and brine. The solution was dried (Na$_2$SO$_4$), concentrated under reduced pressure and the resulting brown oil was purified by chromatography on silica gel eluting with EtOAc/petrol ether to obtain the title compound as a pale brown foam. $^1$H NMR (400 MHz, CDCl$_3$) δ: 7.95-7.70 (5H, m), 7.56-7.41 (3H, m), 7.39-7.30 (5H, m), 5.59 (1H, bs), 5.19-5.10 (2H, m), 4.83-4.72 (1H, m), 2.22 (2H, t, J=7.4 Hz), 2.09-1.97 (1H, m), 1.82-1.55 (5H, m), 1.45 (9H, s), 1.49-1.38 (2H, m). MS (ES) C$_{32}$H$_{37}$N$_3$O$_4$ requires: 528, found: 529 (M+H)$^+$.

Step 4: (7S)-7-{[(Benzyloxy)carbonyl]amino}-7-[5-(2-naphthyl)-1H-imidazol-2-yl]heptanoic acid (ZZ4)

The imidazole (ZZ3) (1 eq.) was dissolved in TFA/DCM (1:1) at 0° C., the cooling bath was removed and the mixture was stirred for 60 min at RT. The solvents were removed under reduced pressure and the residue was purified by chromatography on silica gel eluting with EtOAc/AcOH (99:1) to obtain the title compound as a pale brown foam. $^1$H NMR (400 MHz, DMSO-d6) δ: 11.99 (1H, bs), 8.34 (1H, s), 8.10-7.98 (3H, m), 7.98-7.76 (3H, m), 7.63-7.50 (2H, m), 7.43-7.28 (4H, m), 5.16-4.98 (2H, m), 4.90-4.80 (1H, m), 2.19 (2H, t, J=7.2 Hz), 2.00-1.83 (2H, m), 1.56-1.44 (2H, m), 1.42-1.24 (4H, m). MS (ES) C$_{28}$H$_{29}$N$_3$O$_4$ requires: 471, found: 472 (M+H)$^+$.

Step 5: Benzyl {(1S)-7-amino-1-[5-(2-naphthyl)-1H-imidazol-2-yl]-7-oxoheptyl}carbamate (ZZ5)

The acid (ZZ4) (1 eq.) was dissolved in DMF in an ace tube, HATU (2 eq.) and DIPEA (2 eq.) were added and the mixture was stirred 1 h at RT. A solution of NH$_3$ in dioxane (0.5 N, 5 eq.) was added and after stirring 3 h at RT solvents were removed under reduced pressure. The crude was used as such in the following reaction. MS (ES) C$_{28}$H$_{30}$N$_4$O$_3$ requires: 470, found: 471 (M+H)$^+$.

Step 6: (7S)-7-Amino-7-[5-(2-naphthyl)-1H-imidazol-2-yl]heptanamide (ZZ6)

A solution of the amide (ZZ5) (1 eq.) in MeOH was cooled at 0° C. under N$_2$, then Pd/C (10% wt) was added. After two vacuum-H$_2$ cycles the mixture was stirred 2.5 hr under an H$_2$ atmosphere. The catalyst was filtered off and washed with MeOH then the solvent was removed under reduced pressure. The crude was used as such in the following reaction. MS (ES) C$_{20}$H$_{24}$N$_4$O requires: 336, found: 337 (M+H)$^+$.

Step 7: 2-((1S)-7-Amino-1-{[(5-methoxy-2-methyl-1H-indol-3-yl)acetyl]amino}-7-oxoheptyl)-5-(2-naphthyl)-1H-imidazol-3-ium trifluoroacetate (ZZ7)

A solution of EDC.HCl (1.2 eq.), HOBt (1.2 eq.) and (5-methoxy-2-methyl-1H-indol-3-yl)acetic acid (1.2 eq.) in DCM was stirred for 1 hr at RT then it was added to a solution of the amine (ZZ6) in DMF. The mixture was stirred overnight at RT then the crude was directly purified by preparative RP-HPLC, using H$_2$O (0.1% TFA) and MeCN (+0.1% TFA) as eluents (column: C18). The desired fractions were lyophilized to afford the titled compound as a white solid. $^1$H NMR (400 MHz, DMSO-d6) δ: 10.62 (1H, s), 8.61 (1H, d, J=6.3 Hz), 8.34 (1H, s), 8.16 (1H, s), 8.07 (1H, d, J=8.8 Hz), 8.01-7.93 (2H, m), 7.90 (1H, dd J=8.6, J$_2$=1.8 Hz), 7.66-7.55 (2H, m), 7.19 (1H, s), 7.10 (1H, d, J=8.6 Hz), 6.97 (1H, d, J=2.3 Hz), 6.67 (1H, s), 6.62 (1H, dd J=8.6, J$_2$=2.3 Hz), 5.10-5.00 (1H, m), 3.68 (3H, s), 3.64-3.48 (2H, m), 2.32 (3H, s), 2.00 (2H, t, J=7.3 Hz), 2.05-1.87 (2H, m), 1.52-1.32 (3H, m), 1.32-1.20 (3H, m). MS (ES) C$_{32}$H$_{35}$N$_5$O$_3$ requires: 537, found: 538 (M+H)$^+$.

Example 326

2-((1S)-6-Carboxy-1-{[(dimethylamino)sulfonyl]amino}hexyl)-5-(2-naphthyl)-1H-imidazol-3-ium trifluoroacetate (AAA1)

A solution of Example 107, 15 (1 eq.), DIPEA (2 eq.) and dimethylsulfamoyl chloride (2 eq.) in DMF was stirred overnight at RT. The crude was purified by preparative RP-HPLC, using H$_2$O (0.1% TFA) and MeCN (+0.1% TFA) as eluents (column: C18) and the desired fractions were lyophilized to afford the titled compound as a white solid. $^1$H NMR (400 MHz, DMSO-d6) δ: 12.04 (1H, bs), 8.33 (1H, s), 8.12 (1H, bs), 8.09-8.00 (2H, m), 7.99-7.87 (3H, m), 7.63-7.52 (2H, m), 4.62-4.51 (1H, m), 2.63 (6H, s), 2.19 (2H, t, J=7.2 Hz), 2.02-1.84 (2H, m), 1.55-1.44 (2H, m), 1.44-1.35 (1H, m), 1.35-1.16 (3H, m). MS (ES) C$_{22}$H$_{28}$N$_4$O$_4$S requires: 444, found: 445 (M+H)$^+$.

Example 327

2-((1S)-7-(Methylamino)-7-oxo-1-{[(1-pyridin-2-ylpiperidin-3-yl)carbonyl]amino}heptyl)-5-(2-naphthyl)-1H-imidazol-3-ium trifluoroacetate (BBB1)

Step 1: Benzyl {(1S)-7-(methylamino)-1-[5-(2-naphthyl)-1H-imidazol-2-yl]-7-oxoheptyl}carbamate (BBB1)

Example 325, ZZ4 (1 eq.) was dissolved in DMF and HATU (2 eq.) and DIPEA (2 eq.) were added and the mixture was stirred 1 h at RT. A solution of MeNH$_2$ in THF (2 N, 5 eq.) was added and after stirring 3 h at RT solvents were removed under reduced pressure. The crude was used as such in the following reaction. MS (ES) C$_{29}$H$_{32}$N$_4$O$_3$ requires: 484, found: 485 (M+H)$^+$.

Step 2: (7S)-7-Amino-N-methyl-7-[5-(2-naphthyl)-1H-imidazol-2-yl]heptanamide (BBB2)

A solution of the amide (BBB1) (1 eq.) in MeOH was cooled at 0° C. under N$_2$, then Pd/C (10% wt) was added. After two vacuum-H$_2$ cycles the mixture was stirred 2.5 hr under an H$_2$ atmosphere. The catalyst was filtered off and washed with MeOH then the solvent was removed under reduced pressure. The crude was used as such in the following reaction. MS (ES) C$_{21}$H$_{26}$N$_4$O requires: 350, found: 351 (M+H)$^+$.

Step 3: 2-((1S)-7-(Methylamino)-7-oxo-1-{[(1-pyridin-2-ylpiperidin-3-yl)carbonyl]amino}heptyl)-5-(2-naphthyl)-1H-imidazol-3-ium trifluoroacetate (BBB3)

1-Pyridin-2-ylpiperidine-3-carboxylic acid (1.1 eq.) was suspended in DCM and DIPEA (1.1 eq.) and HATU (1.1 eq.)

were added and the mixture was stirred at RT for 1 hour. A solution of the above amine (BBB2) in DMF (0.1 M solution) was added and stirred overnight. The crude was directly purified by preparative RP-HPLC, using $H_2O$ (0.1% TFA) and MeCN (+0.1% TFA) as eluents (column: C18). The desired fractions were lyophilized to afford the titled compound as a white solid. $^1$H NMR (400 MHz, DMSO-d6) δ: 8.72-8.64 (1H, m), 8.36 (1H, s), 8.20-8.14 (1H, m), 8.11-8.01 (2H, m), 8.01-7.88 (3H, m), 7.80-7.65 (2H, m), 7.64-7.56 (2H, m), 7.19-7.08 (1H, m), 6.80-6.71 (1H, m), 5.08-4.98 (1H, m), 4.28-4.20 (2H, m), 4.14-4.02 (2H, m), 3.23-2.98 (2H, m), 2.54 (3H, d, J=7.3 Hz), 2.04 (2H, t, J=7.2 Hz), 1.99-1.88 (2H, m), 1.82-1.60 (2H, m), 1.57-1.44 (3H, m), 1.42-1.21 (4H, m). MS (ES) $C_{32}H_{38}N_6O_2$ requires: 538, found: 538 (M+H)$^+$.

Example 328

2-[(1S)-1-{[(Benzylamino)carbonyl]amino}-7-(methylamino)-7-oxoheptyl]-5-(2-naphthyl)-1H-imidazol-3-ium trifluoroacetate (CCC1)

The amine from Example 327, BB2 (1 eq.) was dissolved in DCM, then DIPEA (1 eq.) and benzyl isocyanate were added. After stirring for 1 hr at RT the solvent were removed under reduced pressure and the crude was purified by preparative RP-HPLC, using $H_2O$ (0.1% TFA) and MeCN (+0.1% TFA) as eluents (column: C18). The desired fractions were lyophilized to afford the titled compound as a white solid. $^1$H NMR (400 MHz, DMSO-d6) δ: 8.36 (1H, s), 8.16 (1H, s), 8.07 (1H, d, J=8.6 Hz), 8.02-7.93 (2H, m), 7.91 (1H, dd, J=8.6 Hz, $J_2$=1.5 Hz), 7.71-7.55 (3H, m), 7.35-7.19 (5H, m), 6.75-6.67 (2H, m), 4.97-4.87 (1H, m), 4.30-4.15 (2H, m), 2.53 (3H, d, J=4.6 Hz), 2.04 (2H, t, J=7.4 Hz), 1.97-1.83 (2H, m), 1.55-1.44 (2H, m), 1.42-1.22 (4H, m). MS (ES) $C_{29}H_{33}N_5O_2$ requires: 483, found: 484 (M+H)$^+$.

Example 329

5-(2-Methoxyquinolin-3-yl)-2-((1S)-1-{[(1-methylazetidinium-3-yl)carbonyl]amino}-7-oxononyl)-1H-imidazol-3-ium-L-tartrate (DDD1)

Example 305 was partitioned between EtOAc and saturated aqueous $NaHCO_3$ solution. The aqueous phase was further extracted with EtOAc and the combined organic phases were dried ($Na_2SO_4$), filtered and concentrated under reduced pressure. The remaining colourless oil was dissolved in a mixture of $H_2O$ and MeCN and L-tartaric acid (1 eq.) was added. The mixture was lyophilized to afford a white powder. $^1$H NMR (400 MHz, DMSO-d6) δ: 12.16 (1H, br. s), 8.71 (1H, br. s), 8.52 (1H, d, J=8.2 Hz), 8.13 (1H, d, J=7.7 Hz), 7.84 (1H, d, J=8.2 Hz), 7.66-7.54 (2H, m), 7.42 (1H, m), 5.05-4.91 (1H, m), 4.13 (3H, s), 4.04 (2H, s), 3.99-3.85 (2H, m), 3.81-3.65 (2H, m), 3.54-3.37 (1H, m), 2.59 (3H, s), 2.44-2.32 (4H, m), 2.04-1.66 (2H, m), 1.54-1.38 (2H, m), 1.36-1.16 (4H, m), 0.89 (3H, t, J=7.2 Hz). MS (ES) $C_{27}H_{35}N_5O_3$ requires: 477, found: 478 (M+H$^+$).

| Example | Name | [M + H]$^+$ Observed | M Expected | Procedure from Example Number |
|---|---|---|---|---|
| 330 | 2-((1S)-1-{[(1-methyl-1H-indol-3-yl)carbonyl]amino}-7-oxooctyl)-5-phenyl-1H-imidazol-3-ium trifluoroacetate | 443 | 442 | 1 |
| 331 | 2-((1S)-1-{[(5-methoxy-1H-indol-2-yl)carbonyl]amino}-7-oxooctyl)-5-phenyl-1H-imidazol-3-ium trifluoroacetate | 459 | 458 | 1 |
| 332 | 2-((1S)-1-{[(6-fluoro-1H-indol-3-yl)acetyl]amino}-7-oxooctyl)-5-phenyl-1H-imidazol-3-ium trifluoroacetate | 461 | 460 | 1 |
| 333 | 2-((1S)-1-{[(2-methyl-1H-indol-3-yl)acetyl]amino}-7-oxooctyl)-5-phenyl-1H-imidazol-3-ium trifluoroacetate | 457 | 456 | 1 |
| 334 | 2-{(1S)-1-[(1H-indol-3-ylacetyl)amino]-7-oxooctyl}-5-phenyl-1H-imidazol-3-ium trifluoroacetate | 443 | 442 | 1 |
| 335 | 2-{(1S)-1-[(1H-indol-3-ylcarbonyl)amino]-7-oxooctyl}-5-phenyl-1H-imidazol-3-ium trifluoroacetate | 429 | 428 | 1 |
| 336 | 2-((1S)-1-{[(5-bromo-1H-indol-3-yl)acetyl]amino}-7-oxooctyl)-5-phenyl-1H-imidazol-3-ium trifluoroacetate | 521 523 | 520 522 | 1 |
| 337 | 2-((1S)-1-{[(7-methoxy-6,7-dihydro-1-benzofuran-2-yl)carbonyl]amino}-7-oxooctyl)-5-phenyl-1H-imidazol-3-ium trifluoroacetate | 460 | 461 | 1 |
| 338 | 2-{(1S)-1-[(1-naphthylacetyl)amino]-7-oxooctyl}-5-phenyl-1H-imidazol-3-ium trifluoroacetate | 454 | 453 | 1 |
| 339 | 2-((1S)-1-{[(5-fluoro-1H-indol-3-yl)acetyl]amino}-7-oxooctyl)-5-phenyl-1H-imidazol-3-ium trifluoroacetate | 461 | 460 | 1 |
| 340 | 2-((1S)-1-{[(5-chloro-1H-indol-3-yl)acetyl]amino}-7-oxooctyl)-5-phenyl-1H-imidazol-3-ium trifluoroacetate | 477 | 477 | 1 |
| 341 | 2-{(1S)-1-[(1H-indol-2-ylcarbonyl)amino]-7-oxooctyl}-5-phenyl-1H-imidazol-3-ium trifluoroacetate | 429 | 428 | 1 |

| Example | Name | [M + H]+ Observed | M Expected | Procedure from Example Number |
|---|---|---|---|---|
| 342 | 2-((1S)-1-{[(5-fluoro-1H-indol-2-yl)carbonyl]amino}-7-oxooctyl)-5-phenyl-1H-imidazol-3-ium trifluoroacetate | 448 | 446 | 1 |
| 343 | 2-((1S)-1-{[(5-methoxy-1H-indol-3-yl)acetyl]amino}-7-oxooctyl)-5-phenyl-1H-imidazol-3-ium trifluoroacetate | 473 | 472 | 1 |
| 344 | 2-((1S)-1-{[(5-hydroxy-1H-indol-3-yl)acetyl]amino}-7-oxooctyl)-5-phenyl-1H-imidazol-3-ium trifluoroacetate | 459 | 458 | 1 |
| 345 | 2-((1S)-1-{[(6-methoxy-2-oxo-2,3-dihydro-1H-indol-3-yl)acetyl]amino}-7-oxooctyl)-5-phenyl-1H-imidazol-3-ium trifluoroacetate | 489 | 488 | 1 |
| 346 | 2-((1S)-1-{[(5-methoxy-2-oxo-2,3-dihydro-1H-indol-3-yl)acetyl]amino}-7-oxooctyl)-5-phenyl-1H-imidazol-3-ium trifluoroacetate | 489 | 488 | 1 |
| 347 | 6-(2-oxo-2-{[(1S)-7-oxo-1-(5-phenyl-1H-imidazol-3-ium-2-yl)octyl]amino}ethyl)[1,2,4]triazolo[1,5-a]pyrimidin-3-ium bis(trifluoroacetate) | 446 | 445 | 1 |
| 348 | 3-({[(1S)-7-oxo-1-(5-phenyl-1H-imidazol-3-ium-2-yl)octyl]amino}carbonyl)-3,4-dihydrospiro[isochromene-1,4'-piperidinium] bis(trifluoroacetate) | 515 | 514 | 1 |
| 349 | 4-({[(1S)-7-oxo-1-(5-phenyl-1H-imidazol-3-ium-2-yl)octyl]amino}carbonyl)-3,4-dihydrospiro[chromene-2,4'-piperidinium] bis(trifluoroacetate) | 515 | 514 | 1 |
| 350 | 5-chloro-2-(2-oxo-2-{[(1S)-7-oxo-1-(5-phenyl-1H-imidazol-3-ium-2-yl)octyl]amino}ethyl)-1H-3,1-benzimidazol-3-ium bis(trifluoroacetate) | 478 | 477 | 1 |
| 351 | 2-((1S)-7-oxo-1-{[(2-oxoquinazolin-1(2H)-yl)acetyl]amino}octyl)-5-phenyl-1H-imidazol-3-ium trifluoroacetate | 472 | 471 | 1 |
| 352 | 2-((1S)-7-oxo-1-{[(2-oxo-1,3-benzoxazol-3(2H)-yl)acetyl]amino}octyl)-5-phenyl-1H-imidazol-3-ium trifluoroacetate | 461 | 460 | 1 |
| 353 | 2-{(1S)-1-[(2H-indazol-2-ylacetyl)amino]-7-oxooctyl}-5-phenyl-1H-imidazol-3-ium trifluoroacetate | 444 | 443 | 1 |
| 354 | 3-({[(1S)-7-oxo-1-(5-phenyl-1H-imidazol-3-ium-2-yl)octyl]amino}carbonyl)-2,3-dihydrospiro[indene-1,4'-piperidinium] bis(trifluoroacetate) | 499 | 498 | 1 |
| 355 | 2-((1S)-7-oxo-1-{[(2-oxo-1,2,3,4-tetrahydroquinolin-4-yl)carbonyl]amino}octyl)-5-phenyl-1H-imidazol-3-ium trifluoroacetate | 459 | 458 | 1 |
| 356 | 2-((1S)-1-{[(5-cyano-1H-indol-1-yl)acetyl]amino}-7-oxooctyl)-5-phenyl-1H-imidazol-3-ium trifluoroacetate | 468 | 467 | 1 |
| 357 | 2-{(1S)-1-[(2-naphthylacetyl)amino]-7-oxooctyl}-5-phenyl-1H-imidazol-3-ium trifluoroacetate | 454 | 453 | 1 |
| 358 | 2-((1S)-1-{[(5-chloro-1-benzothien-3-yl)acetyl]amino}-7-oxooctyl)-5-phenyl-1H-imidazol-3-ium trifluoroacetate | 494 | 494 | 1 |
| 359 | 2-((1S)-1-{[(5-chloro-1H-indazol-3-yl)acetyl]amino}-7-oxooctyl)-5-phenyl-1H-imidazol-3-ium trifluoroacetate | 478 | 477 | 1 |
| 360 | 2-(2-{(1S)-1-[(1-Azoniabicyclo[2.2.2]oct-4-ylcarbonyl)amino]-7-oxononyl}-1H-imidazol-1-ium-5-yl)-4-methoxyquinolinium tris(trifluoroacetate) | 518 | 517 | 307 |
| 361 | 4-Methoxy-2-[2-((1S)-1-{[(5-methoxy-2-methyl-1H-indol-3-yl)acetyl]amino}-7-oxononyl)-1H-imidazol-1-ium-5-yl]quinolinium bis(trifluoroacetate) | 582 | 581 | 307 |
| 362 | 5-Methoxy-N-{(1S)-1-[5-(2-naphthyl)-1,3-oxazol-2-yl]-7-oxononyl}-1H-indole-2-carboxamide | 524 | 523 | 137 |

-continued

| Example | Name | [M + H]+ Observed | M Expected | Procedure from Example Number |
|---|---|---|---|---|
| 363 | 1-Methyl-4-[({(1S)-1-[5-(2-naphthyl)-1,3-oxazol-2-yl]-7-oxononyl}amino)carbonyl]piperidinium trifluoroacetate | 476 | 475 | 137 |
| 364 | 4-[({(1S)-1-[5-(2-Naphthyl)-1,3-oxazol-2-yl]-7-oxononyl}amino)carbonyl]-1-azoniabicyclo[2.2.2]octane trifluoroacetate | 488 | 487 | 137 |
| 365 | N,N,2-Trimethyl-1-({(1S)-1-[5-(2-naphthyl)-1,3-oxazol-2-yl]-7-oxononyl}amino)-1-oxopropan-2-aminium trifluoroacetate | 464 | 463 | 137 |
| 366 | 1-Methyl-3-[({(1S)-1-[5-(2-naphthyl)-1,3-oxazol-2-yl]-7-oxononyl}amino)carbonyl]azetidinium trifluoroacetate | 448 | 447 | 137 |
| 367 | N-{(1S)-1-[5-(2-Naphthyl)-1,3-oxazol-2-yl]-7-oxononyl}acetamide | 393 | 392 | 137 |
| 368 | N,N-Dimethyl-N'-{(1S)-1-[5-(2-naphthyl)-1,3-oxazol-2-yl]-7-oxononyl}ethanediamide | 450 | 449 | 137 |
| 369 | 8-[2-(1-{[(1-Methylpiperidinium-4-yl)carbonyl]amino}-7-oxononyl)-1H-imidazol-1-ium-5-yl]quinolinium tris(trifluoroacetate) | 476 | 475 | 1 |
| 370 | 2-((1S)-1-{[(1-Methylpiperidinium-4-yl)carbonyl]amino}-7-oxononyl)-6-phenylpyridinium bis(trifluoroacetate) | 436 | 435 | 140 |
| 371 | N-{(1S)-1-[5-(2-Naphthyl)-1,3-oxazol-2-yl]-7-oxononyl}-2-(2-oxoquinazolin-1(2H)-yl)acetamide | 537 | 536 | 137 |
| 372 | 3-(2-Ethyl-1H-benzimidazol-1-yl)-N-{(1S)-1-[5-(2-naphthyl)-1,3-oxazol-2-yl]-7-oxononyl}propanamide | 551 | 550 | 137 |
| 373 | N,N-Dimethyl-2-({(1S)-1-[5-(2-naphthyl)-1,3-oxazol-2-yl]-7-oxononyl}amino)-2-oxoethanaminium trifluoroacetate | 436 | 435 | 137 |
| 374 | 2-Ethyl-1-(3-oxo-3-{[(1S)-7-oxo-1-(6-phenylpyridinium-2-yl)nonyl]amino}propyl)-1H-3,1-benzimidazol-1-ium bis(trifluoroacetate) | 511 | 510 | 140 |
| 375 | 4-({[(1S)-7-Oxo-1-(6-phenylpyridinium-2-yl)nonyl]amino}carbonyl)-1-azoniabicyclo[2.2.2]octane bis(trifluoroacetate) | 448 | 447 | 140 |
| 376 | 2-((1S)-1-{[(Benzylamino)carbonyl]amino}-7-oxononyl)-6-phenylpyridinium trifluoroacetate | 444 | 443 | 140 |
| 377 | 2-((1S)-7-[Methoxy(methyl)amino]-1-{[(5-methoxy-2-methyl-1H-indol-3-yl)acetyl]amino}-7-oxoheptyl)-5-phenyl-1H-imidazol-1-ium trifluoroacetate | 532 | 531 | 108 |
| 378 | 2-((1S)-1-{[(5-Methoxy-2-methyl-1H-indol-3-yl)acetyl]amino}-7-oxononyl)-5-quinoxalin-2-yl-1H-imidazol-1-ium trifluoroacetate | 553 | 552 | 1 |
| 379 | 2-((1S)-1-{[(5-Methoxy-2-methyl-1H-indol-3-yl)acetyl]amino}-7-oxononyl)-5-(3-methoxy-2-naphthyl)-1H-imidazol-1-ium trifluoroacetate | 581 | 580 | 1 |
| 380 | 5-{[Benzyl(methyl)ammonio]methyl}-2-(1-{[(5-methoxy-2-methyl-1H-indol-3-yl)acetyl]amino}-7-oxononyl)-1H-imidazol-1-ium bis(trifluoroacetate) | 558 | 557 | 311 |
| 381 | 2-{[2-(1-{[(5-Methoxy-2-methyl-1H-indol-3-yl)acetyl]amino}-7-oxononyl)-1H-imidazol-1-ium-5-yl]methyl}-1,2,3,4-tetrahydroisoquinolinium bis(trifluoroacetate) | 570 | 569 | 311 |
| 382 | 2-((1S)-1-{[(5-Methoxy-2-methyl-1H-indol-3-yl)acetyl]amino}-7-oxodecyl)-5-phenyl-1H-imidazol-1-ium trifluoroacetate | 515 | 514 | 316 |

-continued

| Example | Name | [M + H]+ Observed | M Expected | Procedure from Example Number |
|---|---|---|---|---|
| 383 | 2-(1-{[(5-Methoxy-2-methyl-1H-indol-3-yl)acetyl]amino}-7-oxononyl)-5-(2-methoxyphenyl)-1H-imidazol-3-ium trifluoroacetate | 531 | 530 | 304 |
| 384 | 2-(1-{[(5-Methoxy-2-methyl-1H-indol-3-yl)acetyl]amino}-7-oxononyl)-5-(3-methoxyphenyl)-1H-imidazol-3-ium trifluoroacetate | 531 | 530 | 304 |
| 385 | 6-[2-(1-{[(5-Methoxy-2-methyl-1H-indol-3-yl)acetyl]amino}-7-oxononyl)-1H-imidazol-3-ium-5-yl]quinolinium bis(trifluoroacetate) | 552 | 551 | 304 |
| 386 | 5-[2-(1-{[(5-Methoxy-2-methyl-1H-indol-3-yl)acetyl]amino}-7-oxononyl)-1H-imidazol-3-ium-5-yl]-2-methylquinolinium bis(trifluoroacetate) | 566 | 565 | 304 |
| 387 | 5-[2-(1-{[(5-Methoxy-2-methyl-1H-indol-3-yl)acetyl]amino}-7-oxononyl)-1H-imidazol-3-ium-5-yl]quinolinium bis(trifluoroacetate) | 552 | 551 | 304 |
| 388 | 5-[2-(1-{[(5-Methoxy-2-methyl-1H-indol-3-yl)acetyl]amino}-7-oxononyl)-1H-imidazol-3-ium-5-yl]-8-methylquinolinium bis(trifluoroacetate) | 566 | 565 | 304 |
| 389 | 8-Methoxy-5-[2-(1-{[(5-methoxy-2-methyl-1H-indol-3-yl)acetyl]amino}-7-oxononyl)-1H-imidazol-3-ium-5-yl]quinolinium bis(trifluoroacetate) | 582 | 581 | 304 |
| 390 | 5-(1-Benzothien-7-yl)-2-(1-{[(5-methoxy-2-methyl-1H-indol-3-yl)acetyl]amino}-7-oxononyl)-1H-imidazol-3-ium trifluoroacetate | 557 | 556 | 304 |
| 391 | 5-(1H-Indol-5-yl)-2-(1-{[(5-methoxy-2-methyl-1H-indol-3-yl)acetyl]amino}-7-oxononyl)-1H-imidazol-3-ium trifluoroacetate | 540 | 539 | 304 |
| 392 | 5-[3-(3,5-Dimethyl-1H-pyrazol-1-yl)phenyl]-2-(1-{[(5-methoxy-2-methyl-1H-indol-3-yl)acetyl]amino}-7-oxononyl)-1H-imidazol-3-ium trifluoroacetate | 595 | 594 | 304 |
| 393 | 5-(3-Methoxy-2-naphthyl)-2-((1S)-1-{[(1-methylazetidinium-3-yl)carbonyl]amino}-7-oxononyl)-1H-imidazol-1-ium bis(trifluoroacetate) | 477 | 476 | 1 |
| 394 | 2-((1S)-1-{[(2-Ethyl-5-methyl-1H-indol-3-yl)acetyl]amino}-7-oxononyl)-5-phenyl-1H-imidazol-1-ium trifluoroacetate | 499 | 498 | 1 |
| 395 | 2-((1S)-1-{[(1-Methylazetidinium-3-yl)carbonyl]amino}-7-oxononyl)-5-quinoxalin-2-yl-1H-imidazol-1-ium bis(trifluoroacetate) | 449 | 448 | 1 |
| 396 | 2-((1S)-1-{[(2-Ethyl-6-methyl-1H-indol-3-yl)acetyl]amino}-7-oxononyl)-5-phenyl-1H-imidazol-1-ium trifluoroacetate | 499 | 498 | 1 |
| 397 | 5-[4-(Dimethylammonio)phenyl]-2-1-{[(5-methoxy-2-methyl-1H-indol-3-yl)acetyl]amino}-7-oxononyl)-1H-imidazol-1-ium bis(trifluoroacetate) | 544 | 543 | 304 |
| 398 | 5-(2-Fluoro-4-methoxyphenyl)-2-(1-{[(5-methoxy-2-methyl-1H-indol-3-yl)acetyl]amino}-7-oxononyl)-1H-imidazol-1-ium trifluoroacetate | 549 | 548 | 304 |
| 399 | 5-(3-Fluoro-4-methoxyphenyl)-2-(1-{[(5-methoxy-2-methyl-1H-indol-3-yl)acetyl]amino}-7-oxononyl)-1H-imidazol-1-ium trifluoroacetate | 549 | 548 | 304 |
| 400 | 5-(3-Carboxyphenyl)-2-(1-{[(5-methoxy-2-methyl-1H-indol-3-yl)acetyl]amino}-7-oxononyl)-1H-imidazol-1-ium trifluoroacetate | 545 | 544 | 304 |
| 401 | 5-Biphenyl-2-yl-2-(1-{[(5-methoxy-2-methyl-1H-indol-3-yl)acetyl]amino}-7-oxononyl)-1H-imidazol-1-ium trifluoroacetate | 577 | 576 | 304 |

-continued

| Example | Name | [M + H]+ Observed | M Expected | Procedure from Example Number |
|---|---|---|---|---|
| 402 | 5-Dibenzo[b,d]furan-4-yl-2-(1-{[(5-methoxy-2-methyl-1H-indol-3-yl)acetyl]amino}-7-oxononyl)-1H-imidazol-1-ium trifluoroacetate | 591 | 590 | 304 |
| 403 | 2-(1-{[(5-Methoxy-2-methyl-1H-indol-3-yl)acetyl]amino}-7-oxononyl)-5-[3-(piperidin-1-ylcarbonyl)phenyl]-1H-imidazol-1-ium trifluoroacetate | 612 | 611 | 304 |
| 404 | 2-(1-{[(5-Methoxy-2-methyl-1H-indol-3-yl)acetyl]amino}-7-oxononyl)-5-quinoxalin-6-yl-1H-imidazol-1-ium trifluoroacetate | 553 | 552 | 304 |
| 405 | 5-[(Dimethylammonio)methyl]-2-(1-{[(5-methoxy-2-methyl-1H-indol-3-yl)acetyl]amino}-7-oxononyl)-1H-imidazol-1-ium bis(trifluoroacetate) | 482 | 481 | 311 |
| 406 | 5-(1,4-Dimethoxy-2-naphthyl)-2-((1S)-1-{[(5-methoxy-2-methyl-1H-indol-3-yl)acetyl]amino}-7-oxononyl)-1H-imidazol-1-ium trifluoroacetate | 611 | 610 | 1 |
| 407 | 2-((1S)-1-{[(5-Methoxy-2-methyl-1H-indol-3-yl)acetyl]amino}-7-{[2-(methylthio)ethyl]amino}-7-oxoheptyl)-5-(2-naphthyl)-1H-imidazol-1-ium trifluoroacetate | 613 | 611 | 108 |
| 408 | 2-((1S)-7-(Methoxyamino)-1-{[(5-methoxy-2-methyl-1H-indol-3-yl)acetyl]amino}-7-oxoheptyl)-5-(2-naphthyl)-1H-imidazol-1-ium trifluoroacetate | 569 | 567 | 108 |
| 409 | 2-((1S)-7-(Ethoxyamino)-1-{[(5-methoxy-2-methyl-1H-indol-3-yl)acetyl]amino}-7-oxoheptyl)-5-(2-naphthyl)-1H-imidazol-1-ium trifluoroacetate | 583 | 581 | 108 |
| 410 | 2-((1S)-1-{[(2-Methyl-5-nitro-1H-indol-3-yl)acetyl]amino}-7-oxononyl)-5-phenyl-1H-imidazol-1-ium trifluoroacetate | 516 | 515 | 1 |
| 411 | 2-((1S)-1-{[(5-Methoxy-2-methyl-1H-inden-3-yl)acetyl]amino}-7-oxononyl)-5-phenyl-1H-imidazol-1-ium trifluoroacetate | 500 | 499 | 1 |
| 412 | 2-((1S)-1-{[(5-Hydroxy-2-methyl-1H-indol-3-yl)acetyl]amino}-7-oxononyl)-5-phenyl-1H-imidazol-1-ium trifluoroacetate | 487 | 486 | 1 |
| 413 | 2-((1S)-1-{[3-(5-Methoxy-1H-benzimidazol-2-yl)propanoyl]amino}-7-oxononyl)-5-phenyl-1H-imidazol-1-ium trifluoroacetate | 502 | 501 | 1 |
| 414 | 2-{(1S)-1-[(1-Benzothien-3-ylacetyl)amino]-7-oxononyl}-5-phenyl-1H-imidazol-1-ium trifluoroacetate | 474 | 473 | 1 |
| 415 | 2-((1S)-1-{[(2,5-Dimethyl-1H-indol-3-yl)acetyl]amino}-7-oxononyl)-5-phenyl-1H-imidazol-1-ium trifluoroacetate | 485 | 484 | 1 |
| 416 | 2-((1S)-1-{[3-(1H-Benzimidazol-2-yl)propanoyl]amino}-7-oxononyl)-5-phenyl-1H-imidazol-1-ium trifluoroacetate | 472 | 471 | 1 |
| 417 | 2-((1S)-1-{[(6-Methoxy-1H-indol-3-yl)acetyl]amino}-7-oxononyl)-5-phenyl-1H-imidazol-1-ium trifluoroacetate | 487 | 486 | 1 |
| 418 | 2-{(1S)-1-[(1H-Indol-6-ylacetyl)amino]-7-oxononyl}-5-phenyl-1H-imidazol-1-ium trifluoroacetate | 457 | 456 | 1 |
| 419 | 2-((1S)-1-{[(2-Methyl-1,3-benzothiazol-5-yl)acetyl]amino}-7-oxononyl)-5-phenyl-1H-imidazol-1-ium trifluoroacetate | 489 | 488 | 1 |
| 420 | 2-((1S)-1-{[3-(5-Methoxy-2-oxo-1,3-benzoxazol-3(2H)-yl)propanoyl]amino}-7-oxononyl)-5-phenyl-1H-imidazol-1-ium trifluoroacetate | 519 | 518 | 1 |
| 421 | 2-((1S)-1-{[3-(7-Methoxy-1H-indol-3-yl)propanoyl]amino}-7-oxononyl)-5-phenyl-1H-imidazol-1-ium trifluoroacetate | 501 | 500 | 1 |
| 422 | 2-((1S)-1-{[3-(1,3-Benzothiazol-2-yl)propanoyl]amino}-7-oxononyl)-5-phenyl-1H-imidazol-1-ium trifluoroacetate | 489 | 488 | 1 |

| Example | Name | [M + H]+ Observed | M Expected | Procedure from Example Number |
|---|---|---|---|---|
| 423 | 2-((1S)-1-{[(5-Methoxy-2-oxo-2,3-dihydro-1H-indol-3-yl)acetyl]amino}-7-oxononyl)-5-phenyl-1H-imidazol-1-ium trifluoroacetate | 503 | 502 | 1 |
| 424 | 2-((1S)-1-{[(6-Methoxy-2-oxo-2,3-dihydro-1H-indol-3-yl)acetyl]amino}-7-oxononyl)-5-phenyl-1H-imidazol-1-ium trifluoroacetate | 503 | 502 | 1 |
| 425 | 2-((1S)-1-{[(Benzylamino)carbonyl]amino}-7-oxononyl)-4-phenylpyridinium trifluoroacetate | 444 | 443 | 140 |
| 426 | 4-({[(1S)-7-Oxo-1-(4-phenylpyridinium-2-yl)nonyl]amino}carbonyl)-1-azoniabicyclo[2.2.2]octane bis(trifluoroacetate) | 448 | 447 | 140 |
| 427 | 2-((1S)-1-{[2-(Dimethylammonio)-2-methylpropanoyl]amino}-7-oxononyl)-4-phenylpyridinium bis(trifluoroacetate) | 424 | 423 | 140 |
| 428 | 5-(3,5-Dimethoxy-2-naphthyl)-2-((1S)-1-{[(5-methoxy-2-methyl-1H-indol-3-yl)acetyl]amino}-7-oxononyl)-1H-imidazol-1-ium trifluoroacetate | 611 | 610 | 1 |
| 429 | 2-((1S)-1-{[(Benzyloxy)carbonyl]amino}-7-oxononyl)-4-phenylpyridinium trifluoroacetate | 445 | 444 | 140 |
| 430 | 2-((1S)-1-{[(1-Methyl-1H-indol-3-yl)acetyl]amino}-7-oxononyl)-5-phenyl-1H-imidazol-1-ium trifluoroacetate | 471 | 470 | 1 |
| 431 | 2-((1S)-1-{[(7-Fluoro-2-methyl-1H-indol-3-yl)acetyl]amino}-7-oxononyl)-5-phenyl-1H-imidazol-1-ium trifluoroacetate | 489 | 488 | 1 |
| 432 | 2-((1S)-1-{[(5-Ethyl-2-methyl-1H-indol-3-yl)acetyl]amino}-7-oxononyl)-5-phenyl-1H-imidazol-1-ium trifluoroacetate | 499 | 498 | 1 |
| 433 | 2-(5-tert-Butyl-2-methyl-1H-indol-3-yl)-N-[(1S)-7-oxo-1-(5-phenyl-1H-imidazol-2-yl)nonyl]acetamide | 527 | 526 | 1 |
| 434 | 2-((1S)-1-{[(5-Ethoxy-2-methyl-1H-indol-3-yl)acetyl]amino}-7-oxononyl)-5-phenyl-1H-imidazol-1-ium trifluoroacetate | 515 | 514 | 1 |
| 435 | 2-[5-(Benzyloxy)-2-methyl-1H-indol-3-yl]-N-[(1S)-7-oxo-1-(5-phenyl-1H-imidazol-2-yl)nonyl]acetamide | 577 | 576 | 1 |
| 436 | 3-(1H-Indol-1-yl)-N-[(1S)-7-oxo-1-(5-phenyl-1H-imidazol-2-yl)nonyl]propanamide | 471 | 470 | 1 |
| 437 | 2-((1S)-1-{[(5-Methoxy-1H-indol-3-yl)acetyl]amino}-7-oxononyl)-5-phenyl-1H-imidazol-1-ium trifluoroacetate | 487 | 486 | 1 |
| 438 | 2-((1S)-7-Oxo-1-{[3-(2-oxo-1,3-benzothiazol-3(2H)-yl)propanoyl]amino}nonyl)-5-phenyl-1H-imidazol-1-ium trifluoroacetate | 505 | 504 | 1 |
| 439 | 2-{(1S)-7-Oxo-1-[(quinolin-3-ylacetyl)amino]nonyl}-5-phenyl-1H-imidazol-1-ium trifluoroacetate | 469 | 468 | 1 |
| 440 | 2-{(1S)-7-Oxo-1-[(quinolin-5-ylacetyl)amino]nonyl}-5-phenyl-1H-imidazol-1-ium trifluoroacetate | 469 | 468 | 1 |
| 441 | 2-((1S)-1-{[3-(6-Chloro-1H-benzimidazol-2-yl)propanoyl]amino}-7-oxononyl)-5-phenyl-1H-imidazol-1-ium trifluoroacetate | 507<br>509 | 506<br>508 | 1 |
| 442 | 2-((1S)-1-{[3-(6-Fluoro-1H-benzimidazol-2-yl)propanoyl]amino}-7-oxononyl)-5-phenyl-1H-imidazol-1-ium trifluoroacetate | 490 | 489 | 1 |
| 443 | N-[(1S)-7-Oxo-1-(5-phenyl-1H-imidazol-2-yl)nonyl]-2-(5,6,7,8-tetrahydronaphthalen-1-yl)acetamide | 472 | 471 | 1 |
| 444 | 2-((1S)-1-{[(5-Methoxy-2-methyl-1H-indol-3-yl)acetyl]amino}-8-methyl-7-oxononyl)-5-phenyl-1H-imidazol-1-ium trifluoroacetate | 515 | 514 | 316 |
| 445 | 2-((1S)-6-Carboxy-1-{[(5-methoxy-2-methyl-1H-indol-3- | 409 | 488 | 107 |

| Example | Name | [M + H]+ Observed | M Expected | Procedure from Example Number |
|---|---|---|---|---|
| | yl)acetyl]amino}hexyl)-5-phenyl-1H-imidazol-1-ium trifluoroacetate | | | |
| 446 | 2-((1S)-1-{[(5-Methoxy-2-methyl-1H-indol-3-yl)acetyl]amino}-7-oxononyl)-5-(2-thienyl)-1H-imidazol-3-ium trifluoroacetate | 507 | 506 | 304 |
| 447 | 2-((1S)-1-{[(5-Methoxy-2-methyl-1H-indol-3-yl)acetyl]amino}-7-oxononyl)-5-(1-naphthyl)-1H-imidazol-3-ium trifluoroacetate | 551 | 550 | 304 |
| 448 | 2-((1S)-1-{[(5-Methoxy-2-methyl-1H-indol-3-yl)acetyl]amino}-7-oxononyl)-5-quinolin-8-yl-1H-imidazol-3-ium trifluoroacetate | 552 | 551 | 304 |
| 449 | 2-((1S)-1-{[(5-Methoxy-2-methyl-1H-indol-3-yl)acetyl]amino}-7-oxononyl)-5-(2-morpholin-4-ylphenyl)-1H-imidazol-3-ium trifluoroacetate | 586 | 585 | 304 |
| 450 | 2-((1S)-1-{[(5-Methoxy-2-methyl-1H-indol-3-yl)acetyl]amino}-7-oxononyl)-5-(3-nitrophenyl)-1H-imidazol-3-ium trifluoroacetate | 546 | 545 | 304 |
| 451 | 3-[2-((1S)-1-{[(5-Methoxy-2-methyl-1H-indol-3-yl)acetyl]amino}-7-oxononyl)-1H-imidazol-3-ium-5-yl]pyridinium bis(trifluoroacetate) | 502 | 501 | 304 |
| 452 | 5-(3-Cyanophenyl)-2-((1S)-1-{[(5-methoxy-2-methyl-1H-indol-3-yl)acetyl]amino}-7-oxononyl)-1H-imidazol-3-ium trifluoroacetate | 526 | 525 | 304 |
| 453 | 2-((1S)-1-{[(5-Methoxy-2-methyl-1H-indol-3-yl)acetyl]amino}-7-oxononyl)-5-[3-(trifluoromethoxy)phenyl]-1H-imidazol-3-ium trifluoroacetate | 585 | 584 | 304 |
| 454 | 2-((1S)-1-{[(5-Methoxy-2-methyl-1H-indol-3-yl)acetyl]amino}-7-oxononyl)-5-[4-(trifluoromethoxy)phenyl]-1H-imidazol-3-ium trifluoroacetate | 585 | 584 | 304 |
| 455 | 2-((1S)-1-{[(5-Methoxy-2-methyl-1H-indol-3-yl)acetyl]amino}-7-oxononyl)-5-[4-(trifluoromethyl)phenyl]-1H-imidazol-3-ium trifluoroacetate | 569 | 568 | 304 |
| 456 | 2-((1S)-1-{[(5-Methoxy-2-methyl-1H-indol-3-yl)acetyl]amino}-7-oxononyl)-5-[3-(trifluoromethyl)phenyl]-1H-imidazol-3-ium trifluoroacetate | 569 | 568 | 304 |
| 457 | 2-((1S)-1-{[(5-Methoxy-2-methyl-1H-indol-3-yl)acetyl]amino}-7-oxononyl)-5-[2-(trifluoromethyl)phenyl]-1H-imidazol-3-ium trifluoroacetate | 569 | 568 | 304 |
| 458 | 2-((1S)-1-{[(5-Methoxy-2-methyl-1H-indol-3-yl)acetyl]amino}-7-oxononyl)-5-[2-fluoro-phenyl]-1H-imidazol-3-ium trifluoroacetate | 519 | 518 | 304 |
| 459 | 2-((1S)-1-{[(5-Methoxy-2-methyl-1H-indol-3-yl)acetyl]amino}-7-oxononyl)-5-[3-(ethoxy)phenyl]-1H-imidazol-3-ium trifluoroacetate | 545 | 544 | 304 |
| 460 | 2-((1S)-1-{[(5-Methoxy-2-methyl-1H-indol-3-yl)acetyl]amino}-7-oxononyl)-5-[4-(ethoxy)phenyl]-1H-imidazol-3-ium trifluoroacetate | 545 | 544 | 304 |
| 461 | 5-[4-(Acetylamino)phenyl]-2-((1S)-1-{[(5-methoxy-2-methyl-1H-indol-3-yl)acetyl]amino}-7-oxononyl)-1H-imidazol-3-ium trifluoroacetate | 558 | 557 | 304 |
| 462 | 5-[2-(Methoxycarbonyl)phenyl]-2-((1S)-1-{[(5-methoxy-2-methyl-1H-indol-3-yl)acetyl]amino}-7-oxononyl)-1H-imidazol-3-ium trifluoroacetate | 559 | 558 | 304 |
| 463 | 2-((1S)-1-{[(5-Methoxy-2-methyl-1H-indol-3-yl)acetyl]amino}-7-oxononyl)-5-[4-cyano-phenyl]-1H-imidazol-3-ium trifluoroacetate | 526 | 525 | 304 |

-continued

| Example | Name | [M + H]+ Observed | M Expected | Procedure from Example Number |
|---|---|---|---|---|
| 464 | 2-((1S)-1-{[5-(3-Methyl-5,6,7,8-tetrahydro-1,8-naphthyridin-2-yl)pentanoyl]amino}-7-oxononyl)-5-phenyl-1H-imidazol-1-ium trifluoroacetate | 530 | 529 | 1 |
| 465 | 6-(2-Oxo-2-{[(1S)-7-oxo-1-(5-phenyl-1H-imidazol-1-ium-2-yl)nonyl]amino}ethyl)imidazo[2,1-b][1,3]thiazol-4-ium bis(trifluoroacetate) | 464 | 463 | 1 |
| 466 | 2-{(1S)-1-[(1-Benzofuran-5-ylacetyl)amino]-7-oxononyl}-5-phenyl-1H-imidazol-1-ium trifluoroacetate | 458 | 457 | 1 |
| 467 | 2-{(1S)-1-[(1-Benzothien-2-ylacetyl)amino]-7-oxononyl}-5-phenyl-1H-imidazol-1-ium trifluoroacetate | 474 | 473 | 1 |
| 468 | 2-((1S)-1-{[(2-Ethyl-1H-benzimidazol-1-yl)acetyl]amino}-7-oxononyl)-5-phenyl-1H-imidazol-1-ium trifluoroacetate | 486 | 485 | 1 |
| 469 | 2-(1-{[(5-methoxy-2-methyl-1H-indol-3-yl)acetyl]amino}-7-oxononyl)-1H-imidazol-1-ium trifluoroacetate | 425 | 424 | 304 then hydrogenated |
| 470 | 2-[2-((1S)-1-{[3-(Dimethylammonio)propanoyl]amino}-7-oxononyl)-1H-imidazol-1-ium-5-yl]-4-methoxyquinolinium tris(trifluoroacetate) | 480 | 479 | 307 |
| 471 | 5-(4-Chlorophenyl)-2-((1S)-1-{[(5-methoxy-2-methyl-1H-indol-3-yl)acetyl]amino}-7-oxononyl)-1H-imidazol-1-ium trifluoroacetate | 535<br>537<br>539 | 534<br>536<br>538 | 1 |
| 472 | 5-(3,4-Dichlorophenyl)-2-((1S)-1-{[(5-methoxy-2-methyl-1H-indol-3-yl)acetyl]amino}-7-oxononyl)-1H-imidazol-1-ium trifluoroacetate | 569<br>571<br>573 | 568<br>570<br>572 | 1 |
| 473 | 5-(3-Bromophenyl)-2-((1S)-1-{[(5-methoxy-2-methyl-1H-indol-3-yl)acetyl]amino}-7-oxononyl)-1H-imidazol-1-ium trifluoroacetate | 579<br>581 | 578<br>580 | 1 |
| 474 | 2-((1S)-7-Methoxy-1-{[(5-methoxy-2-methyl-1H-indol-3-yl)acetyl]amino}-7-oxoheptyl)-5-phenyl-1H-imidazol-1-ium trifluoroacetate | 504 | 503 | 107 |
| 475 | 2-(1-{[(5-Methoxy-2-methyl-1H-indol-3-yl)acetyl]amino}-7-oxononyl)-5-(2-phenylethyl)-1H-imidazol-1-ium trifluoroacetate | 529 | 528 | 315 |
| 476 | 7-(3-Oxo-3-{[(1S)-7-oxo-1-(5-phenyl-1H-imidazol-1-ium-2-yl)nonyl]amino}propyl)-1,8-naphthyridin-1-ium bis(trifluoroacetate) | 484 | 483 | 1 |
| 477 | 7-(3-Oxo-3-{[(1S)-7-oxo-1-(5-phenyl-1H-imidazol-1-ium-2-yl)nonyl]amino}propyl)-1,2,3,4-tetrahydro-1,8-naphthyridin-1-ium bis(trifluoroacetate) | 488 | 487 | 1 |
| 478 | N3,N3-Dimethyl-N-[{(1S)-1-[5-(2-naphthyl)-1,3,4-oxadiazol-2-yl]-7-oxononyl}-α-alaninamide | 451 | 450 | 308 |
| 479 | 2-{(1S)-7-Oxo-1-[(4,5,6,7-tetrahydro-1H-indazol-3-ylcarbonyl)amino]nonyl}-5-phenyl-1H-imidazol-1-ium trifluoroacetate | 448 | 447 | 1 |
| 480 | 2-{(1S)-7-Oxo-1-[(4,5,6,7-tetrahydro-1-benzothien-3-ylcarbonyl)amino]nonyl}-5-phenyl-1H-imidazol-1-ium trifluoroacetate | 464 | 463 | 1 |
| 481 | 2-((1S)-7-Oxo-1-{[3-(1-oxo-1,3-dihydro-2H-isoindol-2-yl)propanoyl]amino}nonyl)-5-phenyl-1H-imidazol-1-ium trifluoroacetate | 487 | 486 | 1 |
| 482 | 2-{(1S)-1-[({2-[2-(Dimethylammonio)ethyl]-3-oxo-2,3-dihydro-1H-isoindol-4-yl}carbonyl)amino]-7-oxononyl}-5-phenyl-1H-imidazol-1-ium bis(trifluoroacetate) | 530 | 529 | 1 |

| Example | Name | [M + H]+ Observed | M Expected | Procedure from Example Number |
|---|---|---|---|---|
| 483 | 6-Benzyl-2-oxo-3-({[(1S)-7-oxo-1-(5-phenyl-1H-imidazol-1-ium-2-yl)nonyl]amino}carbonyl)-1,2,5,6,7,8-hexahydro-1,6-naphthyridin-6-ium bis(trifluoroacetate) | 566 | 565 | 1 |
| 484 | 7-(4-Oxo-4-{[(1S)-7-oxo-1-(5-phenyl-1H-imidazol-1-ium-2-yl)nonyl]amino}butanoyl)-6,7,8,9-tetrahydropyrido[2,3-b]-1,6-naphthyridin-1-ium bis(trifluoroacetate) | 567 | 566 | 1 |
| 485 | 2-((1S)-1-{[(2-Acetyl-1,2,3,4-tetrahydroisoquinolin-1-yl)acetyl]amino}-7-oxononyl)-5-phenyl-1H-imidazol-1-ium trifluoroacetate | 515 | 514 | 1 |
| 486 | 2-Methyl-3-({[(1S)-7-oxo-1-(5-phenyl-1H-imidazol-1-ium-2-yl)nonyl]amino}carbonyl)-1,2,3,4-tetrahydroisoquinolinium bis(trifluoroacetate) | 473 | 472 | 1 |
| 487 | 2-(2-Oxo-2-{[(1S)-7-oxo-1-(5-phenyl-1H-imidazol-1-ium-2-yl)nonyl]amino}ethyl)-1,2,3,4-tetrahydroisoquinolinium bis(trifluoroacetate) | 473 | 472 | 1 |
| 488 | 4-[2-((1S)-1-{[(5-Methoxy-2-methyl-1H-indol-3-yl)acetyl]amino}-7-oxononyl)-1H-imidazol-3-ium-5-yl]pyridinium bis(trifluoroacetate) | 502 | 501 | 304 |
| 489 | 2-((1S)-1-{[(5-Methoxy-2-methyl-1H-indol-3-yl)acetyl]amino}-7-oxononyl)-5-(2-nitrophenyl)-1H-imidazol-3-ium trifluoroacetate | 546 | 545 | 304 |
| 490 | 5-(3-Ammoniophenyl)-2-((1S)-1-{[(5-methoxy-2-methyl-1H-indol-3-yl)acetyl]amino}-7-oxononyl)-1H-imidazol-3-ium bis(trifluoroacetate) | 516 | 515 | 304 |
| 491 | 5-(2,3-Dihydro-1,4-benzodioxin-6-yl)-2-((1S)-1-{[(5-methoxy-2-methyl-1H-indol-3-yl)acetyl]amino}-7-oxononyl)-1H-imidazol-3-ium trifluoroacetate | 559 | 558 | 304 |
| 492 | 5-(2,4-Dimethoxyphenyl)-2-((1S)-1-{[(5-methoxy-2-methyl-1H-indol-3-yl)acetyl]amino}-7-oxononyl)-1H-imidazol-3-ium trifluoroacetate | 561 | 560 | 304 |
| 493 | 5-[2-Fluoro-5-(trifluoromethyl)phenyl]-2-((1S)-1-{[(5-methoxy-2-methyl-1H-indol-3-yl)acetyl]amino}-7-oxononyl)-1H-imidazol-3-ium trifluoroacetate | 587 | 586 | 304 |
| 494 | 5-[3-(Ammoniomethyl)phenyl]-2-((1S)-1-{[(5-methoxy-2-methyl-1H-indol-3-yl)acetyl]amino}-7-oxononyl)-1H-imidazol-3-ium bis(trifluoroacetate) | 530 | 529 | 304 |
| 495 | 5-[2-(Ammoniomethyl)-4-fluorophenyl]-2-((1S)-1-{[(5-methoxy-2-methyl-1H-indol-3-yl)acetyl]amino}-7-oxononyl)-1H-imidazol-3-ium bis(trifluoroacetate) | 548 | 547 | 304 |
| 496 | 5-Biphenyl-3-yl-2-((1S)-1-{[(5-methoxy-2-methyl-1H-indol-3-yl)acetyl]amino}-7-oxononyl)-1H-imidazol-3-ium trifluoroacetate | 577 | 576 | 304 |
| 497 | 3-[2-((1S)-1-{[(5-Methoxy-2-methyl-1H-indol-3-yl)acetyl]amino}-7-oxononyl)-1H-imidazol-3-ium-5-yl]quinolinium bis(trifluoroacetate) | 552 | 551 | 304 |
| 498 | 5-(3-Carboxyphenyl)-2-((1S)-1-{[(5-methoxy-2-methyl-1H-indol-3-yl)acetyl]amino}-7-oxononyl)-1H-imidazol-3-ium trifluoroacetate | 545 | 544 | 304 |
| 499 | 2-((1S)-1-{[(5-Methoxy-2-methyl-1H-indol-3-yl)acetyl]amino}-7-oxononyl)-5-[3-(1H-tetrazol-5-yl)phenyl]-1H-imidazol-3-ium trifluoroacetate | 569 | 568 | 304 |

-continued

| Example | Name | [M + H]+ Observed | M Expected | Procedure from Example Number |
|---|---|---|---|---|
| 500 | 2-((1S)-1-{[(5-Methoxy-2-methyl-1H-indol-3-yl)acetyl]amino}-7-oxononyl)-5-(3-{[(methylsulfonyl)amino]carbonyl}phenyl)-1H-imidazol-3-ium trifluoroacetate | 622 | 621 | 304 |
| 501 | 2-((1R)-1-{[(1-Methylazetidinium-3-yl)carbonyl]amino}-7-oxononyl)-5-(2-naphthyl)-1H-imidazol-1-ium bis(trifluoroacetate) | 447 | 446 | 1 |
| 502 | 2-[(1S)-1-({[1-(2-tert-Butoxy-2-oxoethyl)-5-methoxy-2-methyl-1H-indol-3-yl]acetyl}amino)-7-oxononyl]-5-phenyl-1H-imidazol-1-ium trifluoroacetate | 615 | 614 | 1 |
| 503 | 2-[(1S)-1-({[5-Methoxy-2-methyl-1-(pyridin-3-ylmethyl)-1H-indol-3-yl]acetyl}amino)-7-oxononyl]-5-phenyl-1H-imidazol-1-ium trifluoroacetate | 592 | 591 | 1 |
| 504 | 2-((1S)-1-{[(5-Methoxy-1,2-dimethyl-1H-indol-3-yl)acetyl]amino}-7-oxononyl)-5-phenyl-1H-imidazol-1-ium trifluoroacetate | 515 | 514 | 1 |
| 505 | 2-[(1S)-1-({[5-Methoxy-2-methyl-1-(2-pyrrolidinium-1-ylethyl)-1H-indol-3-yl]acetyl}amino)-7-oxononyl]-5-phenyl-1H-imidazol-1-ium bis(trifluoroacetate) | 598 | 597 | 1 |
| 506 | 4-{2-[5-Methoxy-2-methyl-3-(2-oxo-2-{[(1S)-7-oxo-1-(5-phenyl-1H-imidazol-1-ium-2-yl)nonyl]amino}ethyl)-1H-indol-1-yl]ethyl}morpholin-4-ium bis(trifluoroacetate) | 614 | 613 | 1 |
| 507 | 2-((1S)-1-{[(5-Methyl-1,2-benzisoxazol-3-yl)acetyl]amino}-7-oxononyl)-5-phenyl-1H-imidazol-1-ium trifluoroacetate | 473 | 472 | 1 |
| 508 | 2-[(1S)-1-({[5-(Dimethylammonio)-2-methyl-1H-indol-3-yl]acetyl}amino)-7-oxononyl]-5-phenyl-1H-imidazol-1-ium bis(trifluoroacetate) | 514 | 513 | 1 |
| 509 | 1-Methyl-4-[({(1S)-1-[5-(2-naphthyl)-1H-imidazol-1-ium-2-yl]-7-oxoundecyl}amino)carbonyl]piperidinium bis(trifluoroacetate) | 503 | 502 | 316 |
| 510 | 1-Methyl-4-[({(1S)-1-[5-(2-naphthyl)-1H-imidazol-1-ium-2-yl]-7-oxodecyl}amino)carbonyl]piperidinium bis(trifluoroacetate) | 489 | 488 | 316 |
| 511 | N-[1-(5-Acetyl-1H-imidazol-2-yl)-7-oxononyl]-2-(5-methoxy-2-methyl-1H-indol-3-yl)acetamide | 467 | 466 | 314 |
| 512 | 2-[2-((1S)-1-{[3-(Dimethylammonio)propanoyl]amino}-7-oxononyl)-1H-imidazol-1-ium-5-yl]-4-methoxyquinolinium trichloride | 480 | 479 | 307 |
| 513 | 2-((1S)-1-{[(6-Methoxy-1-benzofuran-3-yl)acetyl]amino}-7-oxononyl)-5-phenyl-1H-imidazol-1-ium trifluoroacetate | 488 | 487 | 1 |
| 514 | 6-({[(1S)-7-Oxo-1-(5-phenyl-1H-imidazol-1-ium-2-yl)nonyl]amino}carbonyl)quinolinium bis(trifluoroacetate) | 455 | 454 | 1 |
| 515 | 6-({[(1S)-7-Oxo-1-(5-phenyl-1H-imidazol-1-ium-2-yl)nonyl]amino}carbonyl)isoquinolinium bis(trifluoroacetate) | 455 | 454 | 1 |
| 516 | 5-Methyl-6-({[(1S)-7-oxo-1-(5-phenyl-1H-imidazol-1-ium-2-yl)nonyl]amino}carbonyl)-4,5,6,7-tetrahydro-3H-imidazo[4,5-c]pyridine-3,5-diium tris(trifluoroacetate) | 463 | 462 | 1 |
| 517 | 2-(5-Methyl-1-benzothien-3-yl)-N-[(1S)-7-oxo-1-(5-phenyl-1H-imidazol-2-yl)nonyl]acetamide | 488 | 487 | 1 |
| 518 | 2-[(1S)-1-({[1-(Carboxymethyl)-5-methoxy-2-methyl-1H-indol-3-yl]acetyl}amino)-7-oxononyl]-5-phenyl-1H-imidazol-1-ium trifluoroacetate | 559 | 558 | 1 |

-continued

| Example | Name | [M + H]+ Observed | M Expected | Procedure from Example Number |
|---|---|---|---|---|
| 519 | 4-{[5-Methoxy-2-methyl-3-(2-oxo-2-{[(1S)-7-oxo-1-(5-phenyl-1H-imidazol-1-ium-2-yl)nonyl]amino}ethyl)-1H-indol-1-yl]acetyl}-1-methylpiperazin-1-ium bis(trifluoroacetate) | 641 | 640 | 1 |
| 520 | 7-Methyl-2-({[(1S)-7-oxo-1-(5-phenyl-1H-imidazol-1-ium-2-yl)nonyl]amino}carbonyl)-5,6,7,8-tetrahydroimidazo[1,2-a]pyrazine-4,7-diium tris(trifluoroacetate) | 463 | 462 | 1 |
| 521 | 2-{(1S)-1-[({5-[(Dimethylammonio)methyl]-2-methyl-1H-indol-3-yl}acetyl)amino]-7-oxononyl}-5-phenyl-1H-imidazol-1-ium bis(trifluoroacetate) | 528 | 527 | 1 |
| 522 | 5-Bromo-2-((1S)-1-{[(5-methoxy-2-methyl-1H-indol-3-yl)acetyl]amino}-7-oxononyl)-1H-imidazol-3-ium trifluoroacetate | 503<br>505 | 502<br>504 | 304 |
| 523 | 5-(4-Carboxyphenyl)-2-((1S)-1-{[(5-methoxy-2-methyl-1H-indol-3-yl)acetyl]amino}-7-oxononyl)-1H-imidazol-3-ium trifluoroacetate | 544 | 544 | 304 |
| 524 | 5-(3-Hydroxyphenyl)-2-((1S)-1-{[(5-methoxy-2-methyl-1H-indol-3-yl)acetyl]amino}-7-oxononyl)-1H-imidazol-1-ium trifluoroacetate | 517 | 516 | 304 |
| 525 | 5-[2-((1S)-1-{[(5-Methoxy-2-methyl-1H-indol-3-yl)acetyl]amino}-7-oxononyl)-1H-imidazol-1-ium-5-yl]isoquinolinium bis(trifluoroacetate) | 552 | 551 | 304 |
| 526 | 5-{4-[(Dimethylammonio)methyl]phenyl}-2-((1S)-1-{[(5-methoxy-2-methyl-1H-indol-3-yl)acetyl]amino}-7-oxononyl)-1H-imidazol-1-ium bis(trifluoroacetate) | 558 | 557 | 304 |
| 527 | 4-Methoxy-2-[2-((1S)-1-{[(1-methylazetidinium-3-yl)carbonyl]amino}-7-oxononyl)-1H-imidazol-1-ium-5-yl]quinolinium tris(trifluoroacetate) | 478 | 477 | 307 |
| 528 | 5-(2-Carboxyphenyl)-2-((1S)-1-{[(5-methoxy-2-methyl-1H-indol-3-yl)acetyl]amino}-7-oxononyl)-1H-imidazol-1-ium trifluoroacetate | 545 | 544 | 304 |
| 529 | 5-[4-(Dimethylammonio)phenyl]-2-((1S)-1-{[(5-methoxy-2-methyl-1H-indol-3-yl)acetyl]amino}-7-oxononyl)-1H-imidazol-1-ium bis(trifluoroacetate) | 544 | 543 | 304 |
| 530 | 2-((1S)-7-Oxo-1-{[(4,5,6,7-tetrafluoro-1H-indol-3-yl)acetyl]amino}nonyl)-5-phenyl-1H-imidazol-1-ium trifluoroacetate | 529 | 528 | 1 |
| 531 | 2-((1S)-1-{[(5-Fluoro-2-methyl-1H-indol-3-yl)acetyl]amino}-7-oxononyl)-5-phenyl-1H-imidazol-1-ium trifluoroacetate | 489 | 488 | 1 |
| 532 | 1-Methyl-N-{(1S)-1-[5-(2-naphthyl)-1,3,4-oxadiazol-2-yl]-7-oxononyl}azetidine-3-carboxamide | 449 | 448 | 308 |
| 533 | 2-{(1S)-7-Oxo-1-[(1H-pyrrolo[2,3-b]pyridin-3-ylacetyl)amino]nonyl}-5-phenyl-1H-imidazol-1-ium trifluoroacetate | 458 | 457 | 1 |
| 534 | 4-({[(1S)-6-Carboxy-1-(5-phenyl-1H-imidazol-1-ium-2-yl)hexyl]amino}carbonyl)-1-azoniabicyclo[2.2.2]octane bis(trifluoroacetate) | 425 | 424 | 107 |
| 535 | 4-({[(1S)-7-(Methoxyamino)-7-oxo-1-(5-phenyl-1H-imidazol-1-ium-2-yl)heptyl]amino}carbonyl)-1-azoniabicyclo[2.2.2]octane bis(trifluoroacetate) | 454 | 453 | 108 |
| 536 | 1-Methyl-4-({[(1S)-7-oxo-1-(4-phenyl-1H-imidazol-3-ium-2-yl)-7-(2-thienyl)heptyl]amino}carbonyl)piperidinium bis(trifluoroacetate) | 479 | 478 | 320 |

-continued

| Example | Name | [M + H]+ Observed | M Expected | Procedure from Example Number |
|---|---|---|---|---|
| 537 | 2-{(1S)-7-Oxo-1-[(1H-pyrrolo[3,2-c]pyridin-3-ylacetyl)amino]nonyl}-5-phenyl-1H-imidazol-1-ium trifluoroacetate | 458 | 457 | 1 |
| 538 | 2-((1S)-1-{[(5-Methoxy-1H-pyrrolo[2,3-c]pyridin-3-yl)acetyl]amino}-7-oxononyl)-5-phenyl-1H-imidazol-1-ium trifluoroacetate | 488 | 487 | 1 |
| 539 | 5-(2-Fluoroquinolin-3-yl)-2-((1S)-1-{[(1-methylazetidinium-3-yl)carbonyl]amino}-7-oxononyl)-1H-imidazol-3-ium bis(trifluoroacetate) | 466 | 465 | 305 |
| 540 | 2-((1S)-1-{[(1-Methylazetidinium-3-yl)carbonyl]amino}-7-oxononyl)-5-quinoxalin-6-yl-1H-imidazol-3-ium bis(trifluoroacetate) | 449 | 448 | 305 |
| 541 | 8-Methoxy-5-[2-((1S)-1-{[(1-methylazetidinium-3-yl)carbonyl]amino}-7-oxononyl)-1H-imidazol-3-ium-5-yl]quinolinium tris(trifluoroacetate) | 478 | 477 | 305 |
| 542 | 5-[4-(Dimethylamino)phenyl]-2-((1S)-1-{[(1-methylazetidinium-3-yl)carbonyl]amino}-7-oxononyl)-1H-imidazol-3-ium bis(trifluoroacetate) | 440 | 439 | 305 |
| 543 | 2-Methyl-1-({[((1S)-7-oxo-1-(5-phenyl-1H-imidazol-1-ium-2-yl)nonyl]amino}carbonyl)-1,2,3,4-tetrahydroisoquinolinium bis(trifluoroacetate) | 473 | 472 | 1 |
| 544 | 5-(3-Carboxyphenyl)-2-{(1S)-7-oxo-1-[(2-thienylcarbonyl)amino]nonyl}-1H-imidazol-3-ium trifluoroacetate | 453 | 454 | 307 |
| 545 | 4-Methoxy-2-(2-{(1S)-1-[(3-morpholin-4-ium-4-ylpropanoyl)amino]-7-oxononyl}-1H-imidazol-1-ium-5-yl)quinolinium trichloride | 521 | 522 | 307 |
| 546 | 2-[2-((1S)-1-{[3-(1H-Imidazol-1-ium-1-yl)propanoyl]amino}-7-oxononyl)-1H-imidazol-1-ium-5-yl]-4-methoxyquinolinium trichloride | 502 | 503 | 307 |
| 547 | 2-[2-((1S)-1-{[(4-Acetylpiperazin-1-ium-1-yl)acetyl]amino}-7-oxononyl)-1H-imidazol-1-ium-5-yl]-4-methoxyquinolinium trichloride | 548 | 549 | 307 |
| 548 | 2-[2-((1S)-1-{[(Dimethylammonio)acetyl]amino}-7-oxononyl)-1H-imidazol-1-ium-5-yl]-4-methoxyquinolinium trichloride | 465 | 466 | 307 |
| 549 | 4-Methoxy-2-(2-{(1S)-7-oxo-1-[(piperidinium-1-ylacetyl)amino]nonyl}-1H-imidazol-1-ium-5-yl)quinolinium trichloride | 505 | 506 | 307 |
| 550 | 4-Methoxy-2-[2-((1S)-1-{[(4-methylpiperazin-4-ium-1-yl)acetyl]amino}-7-oxononyl)-1H-imidazol-1-ium-5-yl]quinolinium trichloride | 520 | 521 | 307 |
| 551 | 4-Methoxy-2-[2-((1S)-1-{[(4-methylmorpholin-4-ium-2-yl)carbonyl]amino}-7-oxononyl)-1H-imidazol-1-ium-5-yl]quinolinium tris(trifluoroacetate) | 507 | 508 | 307 |
| 552 | 4-Methoxy-2-[2-((1S)-1-{[3-(4-methylpiperazin-4-ium-1-yl)propanoyl]amino}-7-oxononyl)-1H-imidazol-1-ium-5-yl]quinolinium tris(trifluoroacetate) | 534 | 535 | 307 |
| 553 | 4-Methoxy-2-[2-((1S)-1-{[(4-methylpiperazin-4-ium-1-yl)(oxo)acetyl]amino}-7-oxononyl)-1H-imidazol-1-ium-5-yl]quinolinium tris(trifluoroacetate) | 534 | 535 | 307 |

-continued

| Example | Name | [M + H]+ Observed | M Expected | Procedure from Example Number |
|---|---|---|---|---|
| 554 | 2-[(1S)-1-({[1-(N,N-Dimethylglycyl)azetidin-3-yl]carbonyl}amino)-7-oxononyl]-5-(4-methoxyquinolin-2-yl)-1H-imidazol-1-ium trifluoroacetate | 548 | 549 | 307 |
| 555 | 2-[(1S)-1-({[1-(2-Methoxyethyl)azetidinium-3-yl]carbonyl}amino)-7-oxononyl]-5-(4-methoxyquinolin-2-yl)-1H-imidazol-1-ium bis(trifluoroacetate) | 521 | 522 | 307 |
| 556 | 1-Methyl-3-[({(1S)-1-[5-(1,8-naphthyridin-2-yl)-1,3,4-oxadiazol-2-yl]-7-oxononyl}amino)carbonyl]azetidinium formate | 450 | 451 | 309 |
| 557 | 1-Methyl-3-[({(1S)-1-[5-(1,6-naphthyridin-2-yl)-1,3,4-oxadiazol-2-yl]-7-oxononyl}amino)carbonyl]azetidinium formate | 450 | 451 | 309 |
| 558 | 1-Methyl-3-[({(1S)-1-[5-(1,6-naphthyridin-8-yl)-1,3,4-oxadiazol-2-yl]-7-oxononyl}amino)carbonyl]azetidinium formate | 450 | 451 | 309 |
| 559 | 3-({(1S)-1-[5-(4-Methoxyquinolin-2-yl)-1,3,4-oxadiazol-2-yl]-7-oxononyl}amino)-N,N-dimethyl-3-oxopropan-1-aminium formate | 481 | 482 | 309 |
| 560 | 4-[({(1S)-1-[5-(4-Methoxyquinolin-2-yl)-1,3,4-oxadiazol-2-yl]-7-oxononyl]amino)carbonyl]-1-azoniabicyclo[2.2.2]octane formate | 519 | 520 | 309 |
| 561 | 2-((1S)-1-{[(1-methylazetidinium-3-yl)carbonyl]amino}-7-oxononyl)-5-(2-oxo-1,2-dihydroquinolin-3-yl)-1H-imidazol-3-ium bis(trifluoroacetate) | 463 | 464 | 305 |
| 562 | N-{(1S)-1-[5-(4-Methoxyquinolin-2-yl)-1,3,4-oxadiazol-2-yl]-7-oxononyl}-2-(1H-pyrrolo[3,2-c]pyridin-3-yl)acetamide | 540 | 541 | 307 |
| 563 | 5-(4-Methoxyquinolin-2-yl)-2-{(1S)-7-oxo-1-[(1H-pyrrolo[3,2-c]pyridin-3-ylacetyl)amino]nonyl}-1H-imidazol-1-ium trifluoroacetate | 538 | 539 | 307 |
| 564 | 5-(3-Carboxyphenyl)-2-((1S)-1-{[(1-methylpiperidin-4-yl)carbonyl]amino}-7-oxononyl)-1H-imidazol-3-ium trifluoroacetate | 468 | 470 | 307 |
| 565 | 5-(3-Carboxyphenyl)-2-{(1S)-1-[(morpholin-4-ylacetyl)amino]-7-oxononyl}-1H-imidazol-3-ium trifluoroacetate | 470 | 471 | 307 |
| 566 | 5-(3-Carboxyphenyl)-2-{(1S)-1-[(N,N-dimethylglycyl)amino]-7-oxononyl}-1H-imidazol-3-ium trifluoroacetate | 428 | 429 | 307 |
| 567 | 2-((1S)-1-{[(1-Methylpiperidin-4-yl)carbonyl]amino}-7-oxononyl)-5-(3-{[(methylsulfonyl)amino]carbonyl}phenyl)-1H-imidazol-3-ium trifluoroacetate | 545 | 546 | 307 |
| 568 | 2-((1S)-1-{[3-(3-Methoxyazetidinium-1-yl)propanoyl]amino}-7-oxononyl)-5-quinoxalin-6-yl-1H-imidazol-1-ium bis(trifluoroacetate) | 492 | 493 | 305 |
| 569 | 3-({[(1S)-7-Oxo-1-(5-quinoxalin-6-yl-1H-imidazol-3-ium-2-yl)nonyl]amino}carbonyl)-1-azoniabicyclo[2.2.2]octane bis(trifluoroacetate) | 488 | 489 | 305 |
| 570 | 4-({[(1S)-7-Oxo-1-(5-quinoxalin-6-yl-1H-imidazol-1-ium-2-yl)nonyl]amino}carbonyl)-1-azoniabicyclo[2.2.2]octane bis(trifluoroacetate) | 488 | 489 | 305 |
| 571 | 5-(2-Methoxyquinolin-3-yl)-2-((1S)-1-{[(1-methylazetidinium-3-yl)carbonyl]amino}-7-oxononyl)-1H-imidazol-3-ium dichloride | 477 | 478 | 305 |

| Example | Name | [M + H]+ Observed | M Expected | Procedure from Example Number |
|---|---|---|---|---|
| 572 | 2-((1S)-1-{[(Dimethylammonio)acetyl]amino}-7-oxononyl)-5-(4-methoxyquinolin-2-yl)-1H-imidazol-1-ium dichloride | 465 | 466 | 307 |
| 573 | 3-[({(1S)-1-[5-(2-Methoxyquinolin-3-yl)-1H-imidazol-2-yl]-7-oxononyl}amino)carbonyl]-1-methylazetidinium chloride | 477 | 478 | 305 |
| 574 | N-{(1S)-1-[5-(2-methoxyquinolin-3-yl)-1H-imidazol-2-yl]-7-oxononyl}-1-methylazetidine-3-carboxamide | 477 | 478 | 329 |
| 575 | N-{(1S)-7-[Methoxy(methyl)amino]-1-[5-(2-methoxyquinolin-3-yl)-1H-imidazol-2-yl]-7-oxoheptyl}-1-methylazetidine-3-carboxamide | 508 | 509 | 316 |

What is claimed is:

1. A compound of formula (I):

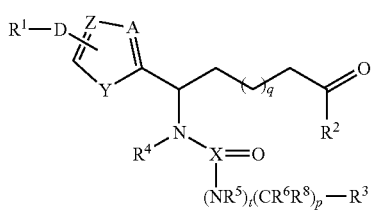

wherein:
p is 0, 1, 2, 3, 4 or 5;
q is 2, 3 or 4;
t is 0 or 1;
D is absent, $(CH_2)_b$ or $(CH=CH)_c$;
b is 1, 2 or 3;
c is 1, 2 or 3;
A represents CH or N;
Y represents $NR^e$, O or S;
Z represents N or $CR^f$;
X is C or S=O;
$R^1$ is hydrogen, hydroxy, halogen, $C_{1-6}$alkylcarbonyl, $C_{1-6}$alkoxycarbonyl, $C_{1-6}$alkyl, halo$C_{1-6}$alkyl, $N(R^h)_2$ wherein $R^h$ is independently selected from hydrogen, $C_{1-6}$alkyl, $C_{6-10}$aryl and $C_{6-10}$aryl$C_{1-6}$alkyl; $C_{3-10}$cycloalkyl, $C_{6-10}$aryl, 5 or 6 membered saturated or partially saturated heterocycle containing 1, 2 or 3 heteroatoms independently selected from N, O and S, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-13 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkylN$(R^a)_2$ and $(CO)_dR^k$ wherein d is 0 or 1 and $R^k$ is as defined below;

$R^2$ is $C_{1-6}$alkyl,
$R^3$ is hydrogen, halogen, hydroxy, cyano, $C_{1-6}$alkyl, halo$C_{1-6}$alkyl, hydroxy$C_{1-6}$alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, amino, $C_{1-6}$alkylamino, di($C_{1-6}$ alkyl)amino, $C_{6-10}$aryl, $C_{6-10}$aryl$C_{1-6}$alkyl, $C_{6-10}$aryl$C_{1-6}$alkoxy; 6-13 membered partially saturated hydrocarbon ring; 4, 5 or 6 membered saturated or partially saturated heterocycle containing 1, 2 or 3 heteroatoms independently selected from N, O and S, optionally bridged by a $C_1$-$C_4$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-15 membered saturated, partially saturated or unsaturated heterocycle containing heteroatoms independently selected from N, O or S; any of which rings being optionally substituted by one or more groups independently chosen from $(CH_2)_m(CO)_nR^d$;
m is 0, 1, 2 or 3;
n is 0, 1 or 2;
$R^4$ and $R^5$ are independently selected from hydrogen and $C_{1-6}$alkyl;
$R^6$ and $R^8$ are independently hydrogen, $C_{1-6}$alkyl, a 5 or 6 membered saturated or partially saturated heterocycle containing 1, 2 or 3 heteroatoms independently selected from N, O and S or a 6 membered unsaturated heterocycle containing 1, 2 or 3 nitrogen atoms; each of which rings being optionally substituted by one or more groups independently chosen from halogen, nitro, amino, cyano, oxo, hydroxy, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl and $C_{2-6}$alkynyl; or
$R^6$ and $R^8$ together represent an oxo group;
$R^g$ is $C_{1-6}$alkyl, halo$C_{1-6}$alkyl, amino, $C_{1-6}$alkylamino or di($C_{1-6}$alkyl)amino;
each $R^d$ is halogen, hydroxy, cyano, $C_{1-6}$alkyl, halo$C_{1-6}$alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, oxo, $SO_2N(R^e)_2$, $N(R^e)_2$ wherein $R^e$ is independently selected from hydrogen, $C_{1-6}$alkyl, $C_{1-6}$alkylcarbonyl, carboxy and $C_{1-6}$alkyloxycarbonyl; $C_{1-6}$alkylN$(R^e)_2$, $C_{6-10}$aryl;

$C_{6-10}$aryl$C_{1-6}$alkoxy, 5 or 6 membered saturated or partially saturated heterocycle containing 1, 2 or 3 heteroatoms independently selected from N, O or S, optionally bridged by a $C_{1-4}$-alkyl group; 5 membered unsaturated heterocycle containing 1, 2, 3 or 4 heteroatoms independently selected from N, O and S, but not more than one of which is O or S; a 5 or 6 membered spiro ring containing zero, one or two heteroatoms independently selected from N, O or S, or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy;

$R^e$ represents hydrogen or $C_{1-6}$alkyl;

$R^f$ represents hydrogen, $C_{1-6}$alkyl or $C_{6-10}$aryl optionally substituted by up to two groups selected from halogen, cyano, $C_{1-6}$alkyl, $C_{1-6}$alkoxy, halo$C_{1-6}$alkyl or halo$C_{1-6}$alkoxy;

$R^k$ is $NHSO_2R^g$, 5 or 6 membered saturated or partially saturated heterocycle containing 1, 2 or 3 heteroatoms independently selected from N, O and S or a 5 membered unsaturated heterocycle containing 1, 2, 3 or 4 heteroatoms independently selected from N, O and S, but not more than one of which is O or S; any of which rings being optionally substituted by one or more groups independently selected from halogen and $C_{1-6}$alkyl;

or a pharmaceutically acceptable salt or tautomer thereof.

2. The compound according to claim 1 wherein:

$R^1$ is a 5 or 6 membered saturated or partially saturated heterocycle containing 1, 2 or 3 heteroatoms independently selected from N, O and S, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-13 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkyl$N(R^a)_2$ and $(CO)_dR^k$ wherein d is 0 or 1 and $R^k$ is as defined in claim 1.

3. The compound according to claim 1 wherein:

$R^3$ is azoniabicyclo[2.2.1]heptanyl, azoniabicyclo[2.2.2]octanyl, thiazolyl, pyrazolyl, isoxazolyl, thiadiazolyl, benzothienyl, benzothiadiazolyl, benzoxadiazolyl, dihydrobenzofuryl, dihydrothiazolopyrimidinyl, dihydrobenzodioxinyl, dihydrobenzoxazinyl, benzimidazolyl, triazolopyrimidinyl, dihydrobenzoxazolyl, dihydroindolyl, dihydroquinazolinyl, dihydrophthalazinyl, indazolyl, benzisoxazolyl, benzotriazolyl, tetrahydrobetacarbolinyl, dihydroisoindolyl, tetrahydronaphthyridinyl, tetrazolyl, thiomorpholinyl, azetidinyl, dihydroisochromenyl, dihydrochromenyl, tetrahydroquinolinyl, indenyl, dihydrobenzothiazolyl, imidazothiazolyl, naphthyridinyl, tetrahydroindazolyl, tetrahydrobenzothienyl, hexahydronaphthyridinyl, tetrahydropyridonaphthyridinyl, tetrahydroisoquinolinyl, tetrahydroimidazopyridinyl, tetrahydroimidazopyrazinyl or pyrrolopyridinyl; any of which rings being optionally substituted by one or more groups independently chosen from $(CH_2)_m(CO)_nR^d$, wherein m, n and $R^d$ are as defined in claim 1.

4. The compound of claim 1 of formula II:

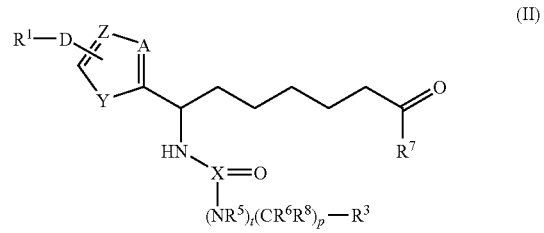

(II)

wherein:

$R^1$, $R^3$, $R^5$, $R^6$, $R^8$, X, p and t are as defined in any one of claim 1, 3 or 4;

D is absent, $CH_2$, $CH_2CH_2$ or $CH=CH$;

A represents CH or N;

Y represents $NR^e$, O or S;

Z represents N or $CR^f$;

$R^7$ represents $C_{1-6}$alkyl $R^e$ represents hydrogen or $C_{1-6}$alkyl;

$R^f$ represents hydrogen, $C_{1-6}$alkyl or $C_{6-10}$aryl optionally substituted by up to two groups selected from halogen, cyano, $C_{1-6}$alkyl, $C_{1-6}$alkoxy, halo$C_{1-6}$alkyl or halo$C_{1-6}$alkoxy;

$R^g$ is $C_{1-6}$alkyl, halo$C_{1-6}$alkyl, amino, $C_{1-6}$alkylamino or di($C_{1-6}$alkyl)amino;

m is 0, 1, 2 or 3;

or a pharmaceutically acceptable salt or tautomer thereof.

5. The compound according to claim 1 of formula IB:

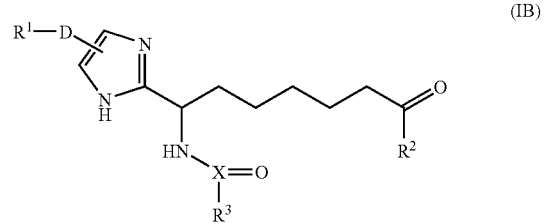

(IB)

wherein D, $R^2$ and X are as defined in claim 1;

$R^1$ is a 8-13 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkyl$N(R^a)_2$ and $(CO)_dR^k$ wherein d is 0 or 1;

$R^k$ is $NHSO_2R^g$, 5 or 6 membered saturated or partially saturated heterocycle containing 1, 2 or 3 heteroatoms independently selected from N, O and S or a 5 membered unsaturated heterocycle containing 1, 2, 3 or 4 heteroatoms independently selected from N, O and S, but not more than one of which is O or S; any of which rings being optionally substituted by one or more groups independently selected from halogen and $C_{1-6}$alkyl;

R^g is C$_{1-6}$alkyl, haloC$_{1-6}$alkyl, amino, C$_{1-6}$alkylamino or di(C$_{1-6}$alkyl)amino;

R$^3$ is azoniabicyclo[2.2.1]heptanyl, azoniabicyclo[2.2.2]octanyl, thiazolyl, pyrazolyl, isoxazolyl, thiadiazolyl, benzothienyl, benzothiadiazolyl, benzoxadiazolyl, dihydrobenzofuryl, dihydrothiazolopyrimidinyl, dihydrobenzodioxinyl, dihydrobenzoxazinyl, benzimidazolyl, triazolopyrimidinyl, dihydrobenzoxazolyl, dihydroindolyl, dihydroquinazolinyl, dihydrophthalazinyl, indazolyl, benzisoxazolyl, benzotriazolyl, tetrahydrobetacarbolinyl, dihydroisoindolyl, tetrahydronaphthyridinyl, tetrazolyl, thiomorpholinyl, azetidinyl, dihydroisochromenyl, dihydrochromenyl, tetrahydroquinolinyl, dihydrobenzothiazolyl, imidazothiazolyl, naphthyridinyl, tetrahydroindazolyl, tetrahydrobenzothienyl, hexahydronaphthyridinyl, tetrahydropyridonaphthyridinyl, tetrahydroisoquinolinyl, tetrahydroimidazopyridinyl, tetrahydroimidazopyrazinyl or pyrrolopyridinyl; any of which rings being optionally substituted by one or more groups independently chosen from (CH$_2$)$_m$(CO)$_n$R$^d$;

m is 0, 1, 2 or 3;

n is 0, 1 or 2;

R$^d$ is halogen, cyano, C$_{1-6}$alkyl, C$_{1-6}$alkoxy, haloC$_{1-6}$alkoxy, carboxy, C$_{1-6}$alkoxycarbonyl, nitro, aminosulfonyl, (C$_{1-6}$alkylcarbonyl)amino, morpholinyl, piperazinyl, thiazolyl, pyrazolyl, isoxazolyl, pyridinyl, oxo, haloC$_{1-6}$alkyl, phenyl or pyrrolidinyl, hydroxy, piperidinespiro, C$_{6-10}$arylC$_{1-6}$alkoxy, di(C$_{1-6}$alkyl)amino, C$_{1-6}$alkylcarbonyl or di(C$_{1-6}$alkylamino)C$_{1-6}$alkyl; any of which rings being optionally substituted by one or more groups independently chosen from C$_{1-6}$alkyl and haloC$_{1-6}$alkyl;

or a pharmaceutically acceptable salt or tautomer thereof.

6. A compound selected from:

2-{(1S)-1-[(carboxycarbonyl)amino]-7-oxononyl}-5-(2-naphthyl)-1H-imidazol-1-ium trifluoroacetate;

2-((1S)-1-{[morpholin-4-yl(oxo)acetyl]amino}-7-oxononyl)-5-(2-naphthyl)-1H-imidazol-1-ium trifluoroacetate;

5-(2-naphthyl)-2-{(1S)-7-oxo-1-[(trifluoroacetyl)amino]nonyl}-1H-imidazol-1-ium trifluoroacetate;

2-((1S)-1-{[(1-methylazetidinium-3-yl)carbonyl]amino}-7-oxononyl)-5-(2-naphthyl)-1H-imidazol-3-ium dichloride;

2-((1S)-1-{[(5-methoxy-2-methyl-1H-indol-3-yl)acetyl]amino}-7-oxononyl)-5-[4-(1H-pyrazol-1-yl)phenyl]-1H-imidazol-3-ium trifluoroacetate;

5-(2-methoxyquinolin-3-yl)-2-((1S)-1-{[(1-methylazetidinium-3-yl)carbonyl]amino}-7-oxononyl)-1H-imidazol-3-ium bis(trifluoroacetate);

2-((1S)-1-{[3-(dimethylammonio)propanoyl]amino}-7-oxononyl)-5-(2-naphthyl)-1H-imidazol-3-ium dichloride;

4-methoxy-2-[2-((1S)-1-{[(1-methylazetidinium-3-yl)carbonyl]amino}-7-oxononyl)-1H-imidazol-1-ium-5-yl]quinolinium trichloride;

N-{(1S)-1-[5-(2-naphthyl)-1,3,4-oxadiazol-2-yl]-5-oxoheptyl}quinuclidine-4-carboxamide;

N-{(1S)-1-[5-(4-methoxyquinolin-2-yl)-1,3,4-oxadiazol-2-yl]-7-oxononyl}-1-methylazetidine-3-carboxamide;

5-(hydroxymethyl)-2-(1-{[(5-methoxy-2-methyl-1H-indol-3-yl)acetyl]amino}-7-oxononyl)-1H-imidazol-1-ium trifluoroacetate;

4-{[2-(1-{[(5-methoxy-2-methyl-1H-indol-3-yl)acetyl]amino}-7-oxononyl)-1H-imidazol-1-ium-5-yl]methyl}morpholin-4-ium bis(trifluoroacetate);

2-(1-{[(5-methoxy-2-methyl-1H-indol-3-yl)acetyl]amino}-7-oxononyl)-5-[(1E)-3-methoxy-3-oxoprop-1-en-1-yl]-1H-imidazol-1-ium trifluoroacetate;

5-(2-carboxyethyl)-2-(1-{[(5-methoxy-2-methyl-1H-indol-3-yl)acetyl]amino}-7-oxononyl)-1H-imidazol-1-ium trifluoroacetate;

5-acetyl-2-((1S)-1-{[(5-methoxy-2-methyl-1H-indol-3-yl)acetyl]amino}-7-oxononyl)-1H-imidazol-1-ium trifluoroacetate;

5-cyclohexyl-2-((1S)-1-{[(5-methoxy-2-methyl-1H-indol-3-yl)acetyl]amino}-7-oxononyl)-1H-imidazol-1-ium trifluoroacetate;

2-((1S)-1-{[(5-methoxy-2-methyl-1H-indol-3-yl)acetyl]amino}-7-oxoundecyl)-5-phenyl-1H-imidazol-1-ium trifluoroacetate;

2-((1S)-7-cyclopropyl-1-{[(5-methoxy-2-methyl-1H-indol-3-yl)acetyl]amino}-7-oxoheptyl)-5-phenyl-1H-imidazol-1-ium trifluoroacetate;

2-((1S)-1-{[(5-methoxy-2-methyl-1H-indol-3-yl)acetyl]amino}-9-methyl-7-oxodecyl)-5-phenyl-1H-imidazol-1-ium trifluoroacetate;

2-((1S)-8-hydroxy-1-{[(5-methoxy-2-methyl-1H-indol-3-yl)acetyl]amino}-7-oxooctyl)-5-phenyl-1H-imidazol-1-ium trifluoroacetate;

2-((1S)-7-(2-furyl)-1-{[(5-methoxy-2-methyl-1H-indol-3-yl)acetyl]amino}-7-oxoheptyl)-5-(2-naphthyl)-1H-imidazol-1-ium trifluoroacetate;

2-[(1S)-1-{[(5-methoxy-2-methyl-1H-indol-3-yl)acetyl]amino}-8-(methylsulfinyl)-7-oxooctyl]-5-(2-naphthyl)-1H-imidazol-1-ium trifluoroacetate;

2-[(1S)-1-{[(5-methoxy-2-methyl-1H-indol-3-yl)acetyl]amino}-8-(methylsulfonyl)-7-oxooctyl]-5-(2-naphthyl)-1H-imidazol-1-ium trifluoroacetate;

2-((1S)-8-(aminosulfonyl)-1-{[(5-methoxy-2-methyl-1H-indol-3-yl)acetyl]amino}-7-oxooctyl)-5-(2-naphthyl)-1H-imidazol-1-ium trifluoroacetate;

1-methyl-4-({[((1S)-7-oxo-1-(4-phenyl-1H-imidazol-3-ium-2-yl)-7-pyridin-2-ylheptyl]amino}carbonyl)piperidinium bis(trifluoroacetate);

2-((1S)-7-amino-1-{[(5-methoxy-2-methyl-1H-indol-3-yl)acetyl]amino}-7-oxoheptyl)-5-(2-naphthyl)-1H-imidazol-3-ium trifluoroacetate;

2-((1S)-6-carboxy-1-{[(dimethylamino)sulfonyl]amino}hexyl)-5-(2-naphthyl)-1H-imidazol-3-ium trifluoroacetate;

2-((1S)-7-(methylamino)-7-oxo-1-{[(1-pyridin-2-ylpiperidin-3-yl)carbonyl]amino}heptyl)-5-(2-naphthyl)-1H-imidazol-3-ium trifluoroacetate;

2-[(1S)-1-{[(benzylamino)carbonyl]amino}-7-(methylamino)-7-oxoheptyl]-5-(2-naphthyl)-1H-imidazol-3-ium trifluoroacetate; and 5-(2-methoxyquinolin-3-yl)-2-415)-1-{[(1-methylazetidinium-3-yl)carbonyl]amino}-7-oxononyl)-1H-imidazol-3-ium-L-tartrate;

and the pharmaceutically acceptable free bases, salts, alternative salts and stereoisomers thereof.

7. A tartrate salt of a compound of claim 1.

8. A pharmaceutical composition comprising a compound of claim 1 or a pharmaceutically acceptable salt thereof and a pharmaceutically acceptable carrier.

9. The compound of claim 1 that is 5-(2-Methoxyquinolin-3-yl)-2-((1S)-1-{[(1-methylazetidinium-3-yl)carbonyl]amino}-7-oxononyl)-1H-imidazol-3-ium-L-tartrate or a stereoisomer thereof.

10. The compound of claim 1 that is 5-(2-Methoxyquinolin-3-yl)-2-((1S)-1-{[(1-methylazetidinium-3-yl)carbonyl]amino}-7-oxononyl)-1H-imidazol-3-ium-L-tartrate.

11. The compound of claim 1 that is (N-{(1S)-1-[5-(2-methoxyquinolin-3-yl)-1H-imidazol-2-yl]-7-oxononyl}-1-methylazetidine-3-carboxamide) or a pharmaceutically acceptable salt thereof or stereoisomer thereof.

12. The compound of claim 1 that is (N-{(1S)-1-[5-(2-methoxyquinolin-3-yl)-1H-imidazol-2-yl]-7-oxononyl}-1-methylazetidine-3-carboxamide) or a pharmaceutically acceptable salt thereof.

13. A pharmaceutical composition comprising a compound of claim 9 and a pharmaceutically acceptable carrier.

14. A pharmaceutical composition comprising a compound of claim 10 and a pharmaceutically acceptable carrier.

15. A pharmaceutical composition comprising a compound of claim 11 and a pharmaceutically acceptable carrier.

16. A pharmaceutical composition comprising a compound of claim 12 and a pharmaceutically acceptable carrier.

17. The compound of claim 1,

Wherein D, $R^2$ and X are as defined in claim 1;

$R^1$ is quinolinyl, isoquinolinyl, quinoxalinyl, tetrahydroisoquinolinyl, naphthyridinyl or dihydroquinolinyl, optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl, $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl; $C_{1-6}$alkylN$(R^a)_2$ and $(CO)_d R^k$ wherein d is 0 or 1;

$R^k$ is NHSO$_2$R$^g$, 5 or 6 membered saturated or partially saturated heterocycle containing 1, 2 or 3 heteroatoms independently selected from N, O and S or a 5 membered unsaturated heterocycle containing 1, 2, 3 or 4 heteroatoms independently selected from N, O and S, but not more than one of which is O or S; any of which rings being optionally substituted by one or more groups independently selected from halogen and $C_{1-6}$alkyl;

$R^g$ is $C_{1-6}$alkyl, halo$C_{1-6}$alkyl, amino, $C_{1-6}$alkylamino or di($C_{1-6}$alkyl)amino;

$R^3$ is an azetidinyl optionally substituted by one or more groups independently chosen from $(CH_2)_m(CO)_n R^d$;

m is 0, 1, 2 or 3;

n is 0, 1 or 2;

$R^d$ is halogen, cyano, $C_{1-6}$alkyl, $C_{1-6}$alkoxy, halo$C_{1-6}$alkoxy, carboxy, $C_{1-6}$alkoxycarbonyl, nitro, aminosulfonyl, ($C_{1-6}$alkylcarbonyl)amino, morpholinyl, piperazinyl, thiazolyl, pyrazolyl, isoxazolyl, pyridinyl, oxo, halo$C_{1-6}$alkyl, phenyl or pyrrolidinyl, hydroxy, piperidinespiro, $C_{6-10}$aryl$C_{1-6}$alkoxy, di($C_{1-6}$alkyl)amino, $C_{1-6}$alkylcarbonyl or di($C_{1-6}$alkylamino)$C_{1-6}$alkyl; any of which rings being optionally substituted by one or more groups independently chosen from $C_{1-6}$alkyl and halo$C_{1-6}$alkyl.

18. The compound of claim 17,

Wherein $R^1$ is as defined in claim 17;

$R^2$ is $C_{1-6}$alkyl;

$R^3$ is 1-methylazetidin-3-yl;

D is a direct bond;

X is C.

* * * * *